(12) United States Patent
Kragh et al.

(10) Patent No.: US 11,473,073 B2
(45) Date of Patent: Oct. 18, 2022

(54) AMINOPEPTIDASES FOR PROTEIN HYDROLYZATES

(71) Applicant: DUPONT NUTRITION BIOSCIENCES APS, Copenhagen K (DK)

(72) Inventors: Karsten Matthias Kragh, Hoejbjerg (DK); Ernst Meinjohanns, Frederiksberg C (DK); Thomas Eisele, Copenhagen K (DK); Peter Edvard Degn, Egå (DK); Steffen Yde Bak, Aarhus N (DK)

(73) Assignee: Dupont Nutrition Biosciences APS, Copenhagen K (DK)

( * ) Notice: Subject to any disclaimer, the term of this patent is extended or adjusted under 35 U.S.C. 154(b) by 112 days.

(21) Appl. No.: 15/574,323

(22) PCT Filed: Jun. 27, 2016

(86) PCT No.: PCT/US2016/039494
§ 371 (c)(1),
(2) Date: Nov. 15, 2017

(87) PCT Pub. No.: WO2016/210395
PCT Pub. Date: Dec. 29, 2016

(65) Prior Publication Data
US 2018/0291360 A1    Oct. 11, 2018

Related U.S. Application Data

(60) Provisional application No. 62/235,937, filed on Oct. 1, 2015, provisional application No. 62/185,503, filed on Jun. 26, 2015.

(51) Int. Cl.
*C12N 9/48* (2006.01)
*C12P 21/06* (2006.01)
*C12N 15/80* (2006.01)
*C12C 1/047* (2006.01)
*C12C 5/00* (2006.01)
*C12C 11/00* (2006.01)
*C12N 1/14* (2006.01)

(52) U.S. Cl.
CPC .............. *C12N 9/485* (2013.01); *C12C 1/047* (2013.01); *C12C 5/004* (2013.01); *C12C 11/003* (2013.01); *C12N 1/14* (2013.01); *C12N 15/80* (2013.01); *C12P 21/06* (2013.01); *C12Y 304/11* (2013.01); *C07K 2319/02* (2013.01)

(58) Field of Classification Search
None
See application file for complete search history.

(56) References Cited

U.S. PATENT DOCUMENTS 6,800,467 B1 * 10/2004 Blinkovsky ............ A21D 2/267
                                                             435/183
7,354,734 B2 * 4/2008 Monod .................. C07K 14/37
                                                             435/212

FOREIGN PATENT DOCUMENTS

WO   WO 2005/019251    * 3/2005

* cited by examiner

*Primary Examiner* — Suzanne M Noakes

(57) ABSTRACT

The present disclosure provides polypeptides having aminopeptidase activity and isolated nucleic acid sequences encoding the polypeptides. In some embodiments, the disclosure also provides to nucleic acid constructs, vectors, and host cells comprising the nucleic acid sequences as well as methods for producing the polypeptides. In some embodiments, the present disclosure further provides to methods of obtaining protein hydrolysates useful as flavor improving agents.

6 Claims, 17 Drawing Sheets

Specification includes a Sequence Listing.

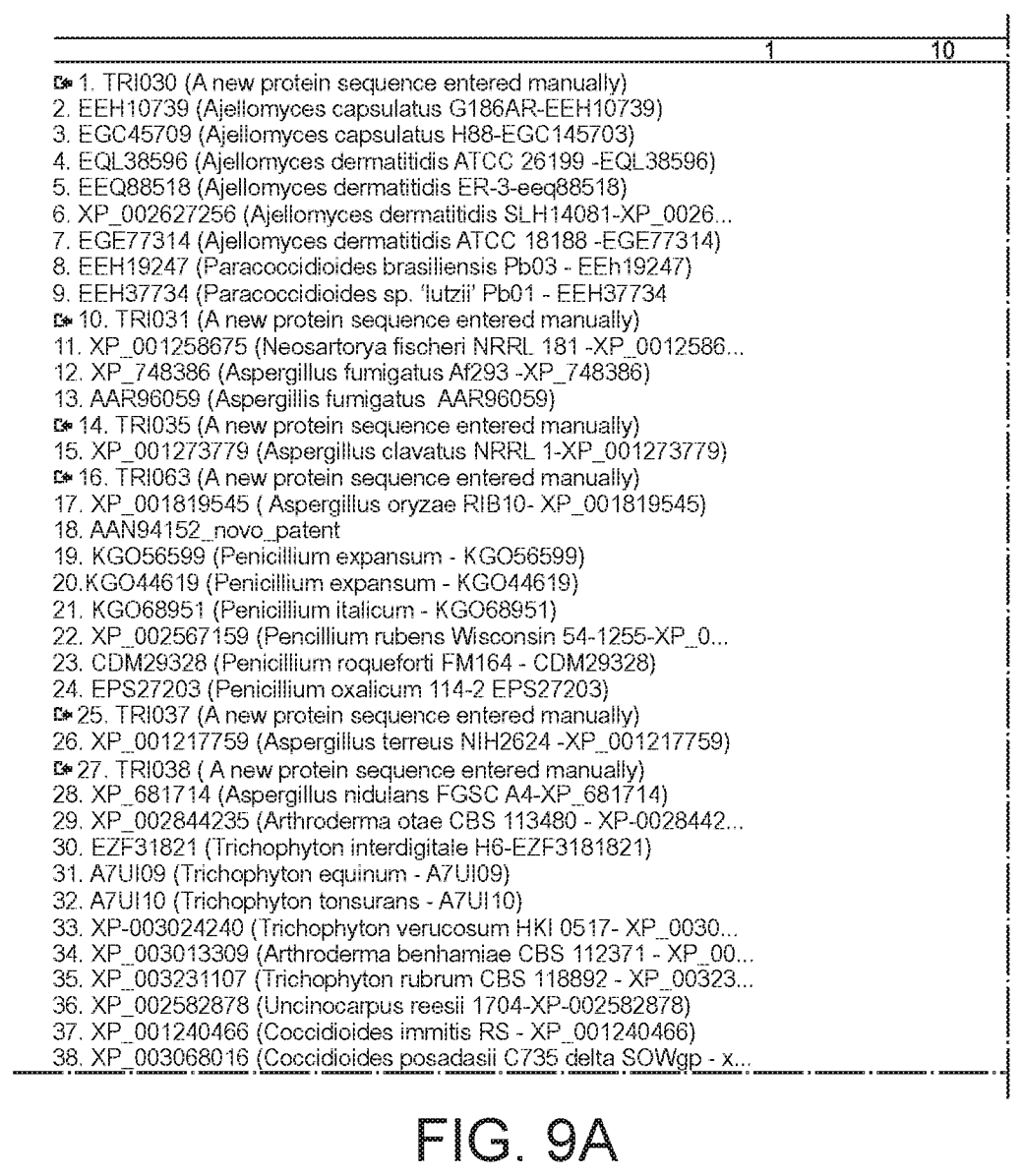

1. TRI030 (A new protein sequence entered manually)
2. EEH10739 (Ajellomyces capsulatus G186AR-EEH10739)
3. EGC45709 (Ajellomyces capsulatus H88-EGC145703)
4. EQL38596 (Ajellomyces dermatitidis ATCC 26199

FIG. 9B

39. TRI032 (A new protein sequence entered manually)
40. XP_003667354 (Myceliophthora thermophila ATCC 42464 - XP...
41. TRI036 (A new protein sequence entered manually)
42. Chaetomium thermophilum var. thermophilum DSM 1495 - EG...
43. XP_006690644 (Chaetomium thermophilum var.thermophilum...
44. XP_001903523 (Podospora anserina S mat+ - XP_001903523)
45. TRI033 (A new protein sequence entered manually)
46. EGU74500 (Fusarium oxysporum Fo5176 - EGU74500)
47. CCT71037 (Fusarium fujikuroi IMI 58289 - CCT71037)
48. EWG46123 (Fusarium verticillioides 7600 - EWG46723)
49. XP_009255336 (Fusarium pseudograminearum CS3096-XP...
50. XP_385112 (Fusarium graminearum PH-1 - XP_385112)
51. XP_003047139 (Nectria haematococca mpVI 77-13-4-XP_003...
52. KEZ45562 (Scedosporium apiospermum - KEZ44562)
53. XP_009648975 (Verticillium dahliae VdLs.17-XP_009648975)
54. XP_003005085 (Verticillium alfalfae VaMs.102-XP_003005085)
55. XP_003350285 (Sordaria macrospora l-hell- XP_003350285)
56. XP_009849609 (Neurospora tetrasperma FGSC 2508-XP_00...
57. XP_957507 ( Neurospora crassa OR74A- XP_957507)
58. KFH45625 (Acremonium chrysogenum ATCC 11550 - KFH456...
59. XP_007788830 (Eutypa lata UCREL1-XP_007788830)
60. XP_0007839968 (Pestalotiopsis fici W106-1-XP_007839968)
61. KFA80591 (Stachybotrys chartarum IBT 40288 - KFA80591)
62. KEY68187 (Stachybotrys chartarum IBT 7711-KEY68187)
63. KFA60290 (Stachybotrys chlorohalonata IBT 40285 - KFA60290)
64. XP_007286350 (Colletotrichum gloesporioides Nara gc5- XP_...
65. KDN67073 (Colletotrichum sublineola - KDN67073)
66. EFQ32028 (Colletotrichum graminicola M1.001-EFQ32028)
67. XP_008712303 (Cyphellophora europaea CBS 101466-XP_00...
68. KEF52078 (Exophiala aquamarina CBS 119948- KEF52078)
69. XP_007756804 (Cladophialophora yegresii CBS 114405-XP_...

FIG. 9C

```
GGHGGSS-GLGCDSQRPLWSSEKIQSLWNELKIQKDWNIKDWMAGAQHIMKKEDWLAGSQEL
GGHGGSS-GLGCDSQRPLWSSEKIQSLWNELKIQKDWNIKDWMAGAQHIMKKEDWLAGSQEL
GGPHGF--GLPKIDLRPMWSSNRIQSMWTLKDWMDGAKHIMKKEDWLAGSAKEL
GGPHGF--GLPKIDLRPMWSSNRIQSMWTLKDWMDGAKHIMKKEDWMDGAKHI
GGPHGF--GLPKIDLRPMWSSAKIQSYWNKRWLNDANHIMKKEDWMDGAKHI
GDGKGK--GKDKTPKKPLWSSAKIQSYWNKRWLNDANHI
         TKKPLWNELKIQKDWTLKGWMAGAQHIMKKEDWMAGAQHI
         TKKPLWNELKIQKDWTLKGWMAGAQHIMKKEDWMAGAQHI
         TKKPLWNELKIQKDWNIKDWMAGAQHIMKKEDWMAGAQHI
         TKKPLWNELKIQKDWNIKGWMEGAQHIMKKEDWMEGAQHI
         TPKKKPLWNELKIQKDWTLKGWMAGAQHI
         TPKKKPLWNSLKIQKLWNIDGWLAGSQHI
         GSSKKKPLWNSSKKIQQHWKLKDWLAGSQKL
GGKGGKG-GHGGQCSKPLWSSEAIQELWKIEDWMAGSQAL
         AKCKPYWSSEAIQELWKIEDWMRAGAQTH
         AKCKPYWSSDALQQHLWTEKDWMRAGAQTH
ST-SQGGPTRKPYWCSDALQQHLWTEKDWMRAGAQTH
AT-IQGGPTRKPYWCSDALQYQWTEQDWRAGAQNH
AT-IQGGPTRKPYWCSDALQYQWTEKDWRAGAQNH
KG-PVPFPGKHKYWTSEALQQHWTLDSWLAGSQHI
         YNTQPLWTSEQSQELWTIEDWLAGSQHI
         SSEEQSKPAWTSEAIQELWLIEDWLAGSQHI
         QECLEHWTSEAIQELWTLEDWLAGSQHI
         QECLEHWTSEAIQELWTLEDWLAGSQHI
         QECLEHWTSEAIQELWTLEDWLAGSQHI
         AKCKPYWDSESIQELWTIEDWLAGSQHI
NKTYVENKTYWESDKIQALWTIDDWLAGSQHI
         FDVKPYWESDKIQALWNIDDWLAGSQHI
QDWDSDLPPWSSETWVDLWTLEDWQAGAEHI
         NDLPPWTTEALQALWALDEWLSARNQL
         TETELPPWTSEAIQALWSIDGWTSGAQQL
```

70. XP_008726648 (Cladophialophora carrionii CBS 160.54-XP_0...
71. XP_003302914 (Pyrenophora teres f.teres 0-1- XP_003302914)
72. XP_001939352 (Pyrenophora tritici-repentis Pt-1C-BFP- XP_00...
73. XP_007711902 (Bipolaris zeicola 26-R-13 - XP_007711902)
74. EUN32952 (Bipolaris victoriae FI3 -EUN32952)
75. XP_007693445 (Bipolaris oryzae ATCC 44560-XP_007693445)
76. EMD95569 (Bipolaris maydis C5 - EMD95569)
77. XP_007694276 (Bipolaris sorokiniana ND90Pr-XP_007694276)
78. XP_008025353 (Setosphaeria turcica ET28A - XP_008025353)
79. XP_007799086 (Phaeosphaeria nodorum SN15 - XP_017990...
80. XP_003837343 (Leptopaeria maculans JN3 - XP+003837343)
81. XP_007584460 (Neofusicoccum parvum UCRNP2 - XP_00758... TPAHHAVRPA
82. EKG22544 (Macrophomina phaseolina MS6 - EKG22544) VRPA
83. XP_007779904 (Coniosporium apollinis CBS 100218 - XP_007... SSPS
84. XP_007877829 (Pseusozyma flocculosa PF-1 - XP_007877829)
85. GAC92761 (Pseudozyma hubeiensis SY62 - GAC92761)
86. EST06929 (Pseudosyma brasiliensis GHG001 - EST06929)
87. CBQ71642 (Sporisorium reilianum SRZ2 - CBQ71642)
88. XP_762603 (Ustilago maydis 521- XP_762603)
89. GAC71207 (Pseudozyma antarctica T-34 - GAC71207)
90. XP_003856003 (Zymoseptoria tritici IPO323 - XP_003856003) NVDPEIIEVR
91. EMF10676 (Sphaerulina musiva SO2202 - EMF10676)
92. XP_007580302 (Neofusicoccum parvum UCRNP2 - XP_00785...
93. EKG11208 (Macrophomina phaseolina MS6-EKG11208)
94. XP_007777605 (Coniosporium apollinis CBS 100218 - XP_007...
95. XP_008000916 (Endocarpon pusillum Z07020 - XP_007800916)
96. XP_001791850 (Phaeosphaeria nodorum SN15-XP_0017918...
97. XP_008086247 (Glarea lozoyensis ATCC 20868 - XP_0080862...
98. XP_008081131 (Glarea lozoyensis ATCC 20868 - XP_0080811...
99. XP_001833866 (Caprinopsis cinerea okayama7#130 - XP_001...
100. XP_002840011 (Tuber melanosporum Mel28 - XP_28400011)
101. XP_007799116 (Eutypa lata UCREL1 - XP_007799116)
102. TRI034 (A new protein sequence entered manually)
103. Fusarium oxysporum f. sp. cubense race 1 - ENH69875 (Modi...

FIG. 9F

SEQUENCE LISTING

<160> NUMBER OF SEQ ID NOS: 134

<210> SEQ ID NO 1
<211> LENGTH: 503
<212> TYPE: PRT
<213> ORGANISM: Artificial Sequence
<220> FEATURE:
<223> OTHER INFORMATION: Synthetic peptide with leader sequence

<400> SEQUENCE: 1

Met Gln Thr Phe Gly Ala Phe Leu Val Ser Phe Leu Ala Ala Ser Gly
1               5                   10                  15

Leu Ala Ala Ala Asn Gly Pro Gly Trp Asp Trp Lys Pro Val His
            20                  25                  30

Pro Lys Val Leu Pro Gln Met Ile His Leu Trp Asp Leu Met His Gly
            35                  40                  45

Ala Gln Lys Leu Glu Asp Phe Ala Tyr Ala Tyr Pro Glu Arg Asn Arg
        50                  55                  60

Val Phe Gly Gly Pro Ala His Glu Asp Thr Val Asn Tyr Leu Tyr Arg
65                  70                  75                  80

Glu Leu Lys Lys Thr Gly Tyr Tyr Asp Val Tyr Lys Gln Pro Gln Val
                85                  90                  95

His Gln Trp Thr Arg Ala Asp Gln Ala Leu Thr Val Asp Gly Lys Ser
            100                 105                 110

Tyr Val Ala Thr Thr Met Thr Tyr Ser Pro Ser Val Asn Val Thr Ala
            115                 120                 125

Pro Leu Ala Val Val Asn Asn Leu Gly Cys Val Glu Ser Asp Tyr Pro
    130                 135                 140

Ala Asp Leu Lys Gly Lys Ile Ala Leu Val Ser Arg Gly Glu Cys Pro
145                 150                 155                 160

Phe Ala Thr Lys Ser Val Leu Ser Ala Lys Ala Gly Ala Ala Ala
                165                 170                 175

Leu Val Tyr Asn Asn Ile Glu Gly Ser Met Ala Gly Thr Leu Gly Gly
            180                 185                 190

Pro Thr Ser Glu Leu Gly Pro Tyr Ala Pro Ile Ala Gly Ile Ser Leu
        195                 200                 205

Ala Asp Gly Gln Ala Leu Ile Gln Met Ile Gln Ala Gly Thr Val Thr
    210                 215                 220

Ala Asn Leu Trp Ile Asp Ser Lys Val Glu Asn Arg Thr Thr Tyr Asn
225                 230                 235                 240

Val Ile Ala Gln Thr Lys Gly Gly Asp Pro Asn Asn Val Val Ala Leu
                245                 250                 255

Gly Gly His Thr Asp Ser Val Glu Ala Gly Pro Gly Ile Asn Asp Asp
            260                 265                 270

Gly Ser Gly Ile Ile Ser Asn Leu Val Val Ala Lys Ala Leu Thr Arg
        275                 280                 285

Phe Ser Val Lys Asn Ala Val Arg Phe Cys Phe Trp Thr Ala Glu Glu
    290                 295                 300

Phe Gly Leu Leu Gly Ser Ser Tyr Tyr Val Asn Ser Leu Asn Ala Thr
305                 310                 315                 320

Glu Lys Ala Lys Ile Arg Leu Tyr Leu Asn Phe Asp Met Ile Ala Ser
                325                 330                 335

Pro Asn Tyr Ala Leu Met Ile Tyr Asp Gly Asp Gly Ser Ala Phe Asn
            340                 345                 350

Leu Thr Gly Pro Ala Gly Ser Ala Gln Ile Glu Arg Leu Phe Glu Asp

```
                355                 360                 365
Tyr Tyr Lys Ser Ile Arg Lys Pro Phe Val Pro Thr Glu Phe Asn Gly
370                 375                 380

Arg Ser Asp Tyr Glu Ala Phe Ile Leu Asn Gly Ile Pro Ala Gly Gly
385                 390                 395                 400

Ile Phe Thr Gly Ala Glu Ala Ile Lys Thr Glu Gln Ala Lys Leu
                405                 410                 415

Phe Gly Gly Gln Ala Gly Val Ala Leu Asp Ala Asn Tyr His Ala Lys
                420                 425                 430

Gly Asp Asn Met Thr Asn Leu Asn Arg Glu Ala Phe Leu Ile Asn Ser
                435                 440                 445

Lys Ala Thr Ala Phe Ala Val Ala Thr Tyr Ala Asn Ser Leu Asp Ser
                450                 455                 460

Ile Pro Ser Arg Asn Met Ser Thr Val Val Lys Arg Ser Gln Leu Glu
465                 470                 475                 480

Gln Ala Lys Lys Ser Thr Pro His Thr His Thr Gly Gly Thr Gly Cys
                485                 490                 495

Tyr Lys Asp Arg Val Glu Gln
                500

<210> SEQ ID NO 2
<211> LENGTH: 512
<212> TYPE: PRT
<213> ORGANISM: Artificial Sequence
<220> FEATURE:
<223> OTHER INFORMATION: Synthetic peptide with leader sequence

<400> SEQUENCE: 2

Met Gln Thr Phe Gly Ala Phe Leu Val Ser Phe Leu Ala Ala Ser Gly
1               5                   10                  15

Leu Ala Ala Ala Gly Gly His Gly Gly Ser Ser Gly Leu Gly Cys Asp
                20                  25                  30

Ser Gln Arg Pro Leu Val Ser Ser Glu Lys Leu Gln Ser Leu Ile Lys
            35                  40                  45

Lys Glu Asp Leu Leu Ala Gly Ser Gln Glu Leu Gln Asp Ile Ala Thr
50                  55                  60

Ala His Gly Gly His Arg Ala Phe Gly Ser Ser Gly His Asn Ala Thr
65                  70                  75                  80

Val Asp Phe Leu Tyr Tyr Thr Leu Lys Ala Leu Asp Tyr Tyr Asn Val
                85                  90                  95

Thr Lys Gln Pro Phe Lys Glu Ile Phe Ser Ser Gly Thr Gly Ser Leu
                100                 105                 110

Thr Val Asp Gly Glu Asp Ile Glu Ala Glu Thr Leu Thr Tyr Thr Pro
                115                 120                 125

Ser Gly Ser Ala Thr Asp Lys Pro Val Val Val Ala Asn Val Gly
            130                 135                 140

Cys Asp Ala Ala Asp Tyr Pro Ala Glu Val Ala Gly Asn Ile Ala Leu
145                 150                 155                 160

Ile Lys Arg Gly Thr Cys Thr Phe Ser Gln Lys Ser Val Asn Ala Lys
                165                 170                 175

Ala Ala Gly Ala Val Ala Ile Ile Tyr Asn Asn Ala Glu Gly Lys
                180                 185                 190

Leu Ser Gly Thr Leu Gly Gln Pro Phe Leu Asp Tyr Ala Pro Val Leu
            195                 200                 205

Gly Ile Thr Leu Glu Ala Gly Glu Ala Leu Leu Ala Lys Leu Ala Gly
```

```
                210                 215                 220
Gly Pro Val Thr Ala Thr Leu Gln Ile Asp Ala Leu Val Glu Glu Arg
225                 230                 235                 240

Val Thr Tyr Asn Val Ile Ala Glu Thr Lys Glu Gly Asp His Ser Asn
                245                 250                 255

Val Leu Val Leu Gly Gly His Thr Asp Ser Val Pro Ala Gly Pro Gly
                260                 265                 270

Ile Asn Asp Asp Gly Ser Gly Thr Ile Gly Met Leu Thr Val Ala Lys
                275                 280                 285

Ala Leu Thr Lys Phe Arg Val Lys Asn Ala Val Arg Phe Ala Phe Trp
                290                 295                 300

Ser Ala Glu Glu Tyr Gly Leu Leu Gly Ser Tyr Ala Tyr Ile Lys Ser
305                 310                 315                 320

Ile Asn Ser Ser Ala Ala Glu Leu Ser Lys Ile Arg Ala Tyr Leu Asn
                325                 330                 335

Phe Asp Met Ile Ala Ser Pro Asn Tyr Ile Tyr Gly Ile Tyr Asp Gly
                340                 345                 350

Asp Gly Asn Ala Phe Asn Leu Thr Gly Pro Ala Gly Ser Asp Val Ile
                355                 360                 365

Glu Arg Asn Phe Glu Asn Phe Phe Lys Arg Lys His Thr Pro Ser Val
                370                 375                 380

Pro Thr Glu Phe Ser Gly Arg Ser Asp Tyr Ala Ala Phe Ile Glu Asn
385                 390                 395                 400

Gly Ile Pro Ser Gly Gly Leu Phe Thr Gly Ala Glu Val Leu Lys Thr
                405                 410                 415

Glu Arg Glu Ala Glu Leu Phe Gly Gly Arg Ala Gly Val Ala Tyr Asp
                420                 425                 430

Val Asn Tyr His Gln Ala Gly Asp Thr Val Asp Asn Leu Ala Leu Asp
                435                 440                 445

Ala Phe Leu Leu Asn Thr Lys Ala Ile Ala Asp Ser Val Ala Thr Tyr
450                 455                 460

Ala Leu Ser Phe Asp Gly Leu Pro Arg Val Asp Gly Lys Lys Arg Arg
465                 470                 475                 480

Trp Asp Ala His Arg Ala Arg Met Leu Lys Arg Ser Ala Gly Ser His
                485                 490                 495

Gly His Ala His Leu His Ser Gly Pro Cys Gly Gly Gly Ala Ser Ile
                500                 505                 510

<210> SEQ ID NO 3
<211> LENGTH: 494
<212> TYPE: PRT
<213> ORGANISM: Artificial Sequence
<220> FEATURE:
<223> OTHER INFORMATION: Synthetic peptide with leader sequence

<400> SEQUENCE: 3

Met Gln Thr Phe Gly Ala Phe Leu Val Ser Phe Leu Ala Ala Ser Gly
1               5                   10                  15

Leu Ala Ala Ala Thr Lys Lys Pro Leu Val Asn Glu Leu Lys Leu Gln
                20                  25                  30

Lys Asp Ile Asn Ile Lys Asp Leu Met Ala Gly Ala Gln Lys Leu Gln
                35                  40                  45

Asp Ile Ala Glu Ala Asn Gly Asn Thr Arg Val Phe Gly Gly Ala Gly
                50                  55                  60

His Asn Ala Thr Val Asp Tyr Leu Tyr Lys Thr Leu Lys Ala Thr Gly
```

```
                65                  70                  75                  80
Tyr Tyr Asn Val Lys Lys Gln Pro Phe Thr Glu Leu Tyr Ser Ala Gly
                    85                  90                  95
Thr Ala Ser Leu Lys Val Asp Gly Asp Ile Thr Ala Ala Ile Met
                100                 105                 110
Thr Tyr Thr Pro Ala Gly Glu Ala Thr Gly Pro Leu Val Ala Glu
                115                 120                 125
Asn Leu Gly Cys Glu Ala Ser Asp Phe Pro Ala Glu Ser Gly Lys
            130                 135                 140
Val Val Leu Val Leu Arg Gly Glu Cys Pro Phe Ser Gln Lys Ser Thr
145                 150                 155                 160
Asn Gly Lys Thr Ala Gly Ala Ala Val Ile Val Tyr Asn Asn Val
                165                 170                 175
Pro Gly Glu Leu Ala Gly Thr Leu Gly Glu Pro Phe Gly Glu Phe Ala
                180                 185                 190
Pro Ile Val Gly Ile Ser Gln Glu Asp Gly Gln Ala Ile Leu Ala Lys
                195                 200                 205
Thr Lys Ala Gly Glu Val Thr Val Asp Leu Lys Val Asp Ala Thr Val
            210                 215                 220
Glu Asn Arg Val Thr Phe Asn Val Ile Ala Glu Thr Lys Glu Gly Asp
225                 230                 235                 240
His Asp Asn Val Leu Val Val Gly Gly His Ser Asp Ser Val Ala Ala
                245                 250                 255
Gly Pro Gly Ile Asn Asp Asp Gly Ser Gly Ile Ile Gly Ile Leu Lys
                260                 265                 270
Val Ala Gln Ala Leu Thr Lys Tyr Arg Val Lys Asn Ala Val Arg Phe
            275                 280                 285
Gly Phe Trp Ser Ala Glu Glu Phe Gly Leu Leu Gly Ser Tyr Ala Tyr
            290                 295                 300
Met Lys Ser Ile Asn Gly Ser Asp Ala Glu Val Ala Lys Ile Arg Ala
305                 310                 315                 320
Tyr Leu Asn Phe Asp Met Ile Ala Ser Pro Asn Tyr Val Tyr Gly Ile
                325                 330                 335
Tyr Asp Gly Asp Gly Ser Ala Phe Asn Leu Thr Gly Pro Ala Gly Ser
            340                 345                 350
Asp Ala Ile Glu Lys Asp Phe Glu Arg Phe Lys Thr Lys Arg Leu
            355                 360                 365
Gly Tyr Val Pro Ser Glu Phe Ser Gly Arg Ser Asp Tyr Ala Ala Phe
            370                 375                 380
Ile Glu Asn Gly Ile Pro Ser Gly Leu Phe Thr Gly Ala Glu Gln
385                 390                 395                 400
Leu Lys Thr Glu Glu Ala Lys Lys Phe Gly Gly Glu Ala Gly Val
                405                 410                 415
Ala Tyr Asp Ile Asn Tyr His Lys Ile Gly Asp Ile Asn Asn Leu
            420                 425                 430
Asn Lys Glu Ala Phe Leu Val Asn Thr Gln Ala Ile Ala Asn Ser Val
            435                 440                 445
Ala Arg Tyr Ala Lys Thr Trp Lys Ser Leu Pro Lys Val Thr His Asn
            450                 455                 460
Thr Arg Arg Trp Asp Ala Glu Val Ala Ser Val Leu Lys Arg Ser Ser
465                 470                 475                 480
Gly His Ser His Ala Gly Gly Pro Cys Gly Ser Val Ser Val
            485                 490
```

<210> SEQ ID NO 4
<211> LENGTH: 508
<212> TYPE: PRT
<213> ORGANISM: Artificial Sequence
<220> FEATURE:
<223> OTHER INFORMATION: Synthetic peptide with leader sequence

<400> SEQUENCE: 4

```
Met Gln Thr Phe Gly Ala Phe Leu Val Ser Phe Leu Ala Ala Ser Gly
1               5                   10                  15

Leu Ala Ala Leu Gln Ile Pro Leu Asn Leu Gln Val Pro Lys Leu
            20                  25                  30

Ser Trp Asn Leu Phe Gly Asp Asp Leu Pro Leu Val Asp Thr Lys Glu
        35                  40                  45

Leu Gln Lys Ser Ile Lys Pro Glu Asn Leu Glu Ala Arg Ala Lys Asp
    50                  55                  60

Leu Tyr Glu Ile Ala Lys Asn Gly Glu Glu Tyr Gly His Pro Thr
65                  70                  75                  80

Arg Val Ile Gly Ser Glu Gly His Leu Gly Thr Leu Ser Tyr Ile His
                85                  90                  95

Ala Glu Leu Ala Lys Leu Gly Gly Tyr Tyr Ser Val Ser Asn Gln Gln
            100                 105                 110

Phe Pro Ala Val Ser Gly Asn Val Phe Glu Ser Arg Leu Val Ile Gly
        115                 120                 125

Asp Ser Val Pro Lys Gln Ala Ser Pro Met Gly Leu Thr Pro Pro Thr
    130                 135                 140

Lys Asn Lys Glu Pro Val His Gly Thr Leu Val Leu Val Asp Asn Glu
145                 150                 155                 160

Gly Cys Asp Ala Ser Asp Tyr Pro Glu Ala Val Lys Gly Asn Ile Ala
                165                 170                 175

Leu Ile Leu Arg Gly Thr Cys Pro Phe Gly Thr Lys Ser Gly Asn Ala
            180                 185                 190

Gly Lys Ala Gly Ala Val Ala Ala Val Val Tyr Asn Tyr Glu Lys Asp
        195                 200                 205

Glu Val His Gly Thr Leu Gly Thr Pro Ser Pro Asp His Val Ala Thr
    210                 215                 220

Phe Gly Leu Gly Gly Glu Glu Gly Lys Ala Val Ala Lys Lys Leu Lys
225                 230                 235                 240

Asp Gly Glu Lys Val Asp Ala Ile Ala Tyr Ile Asp Ala Glu Val Lys
                245                 250                 255

Thr Ile Ser Thr Thr Asn Ile Ile Ala Gln Thr Arg Gly Gly Asp Pro
            260                 265                 270

Asp Asn Cys Val Met Leu Gly Gly His Ser Asp Ser Val Ala Glu Gly
        275                 280                 285

Pro Gly Ile Asn Asp Asp Gly Ser Gly Ser Ile Ser Val Leu Glu Val
    290                 295                 300

Ala Val Gln Leu Thr Lys Tyr Arg Val Asn Asn Cys Val Arg Phe Ala
305                 310                 315                 320

Trp Trp Ala Ala Glu Glu Glu Gly Leu Leu Gly Ser Asp His Tyr Val
                325                 330                 335

Ser Val Leu Pro Glu Asp Glu Asn Arg Lys Ile Arg Leu Phe Met Asp
            340                 345                 350

Tyr Asp Met Met Ala Ser Pro Asn Phe Ala Tyr Gln Ile Tyr Asn Ala
        355                 360                 365
```

```
Thr Asn Ala Glu Asn Pro Lys Gly Ser Glu Glu Leu Arg Asp Leu Tyr
        370                 375                 380

Val Asn Trp Tyr Glu Glu Gln Gly Leu Asn Tyr Thr Phe Ile Pro Phe
385                 390                 395                 400

Asp Gly Arg Ser Asp Tyr Asp Gly Phe Ile Arg Gly Gly Ile Pro Ala
                405                 410                 415

Gly Gly Ile Ala Thr Gly Ala Glu Gly Val Lys Thr Glu Asp Glu Val
        420                 425                 430

Glu Met Phe Gly Gly Glu Ala Gly Val Trp Tyr Asp Lys Asn Tyr His
            435                 440                 445

Gln Ile Gly Asp Asp Leu Thr Asn Val Asn Tyr Thr Ala Trp Glu Val
        450                 455                 460

Asn Thr Lys Leu Ile Ala His Ser Val Ala Thr Tyr Ala Lys Ser Phe
465                 470                 475                 480

Lys Gly Phe Pro Glu Arg Glu Ile Glu Thr Ser Val Gln Thr Tyr Ser
                485                 490                 495

Asp Lys Thr Lys Tyr His Gly Ser Lys Leu Phe Ile
                500                 505
```

<210> SEQ ID NO 5
<211> LENGTH: 506
<212> TYPE: PRT
<213> ORGANISM: Artificial Sequence
<220> FEATURE:
<223> OTHER INFORMATION: Synthetic peptide with leader sequence

<400> SEQUENCE: 5

```
Met Gln Thr Phe Gly Ala Phe Leu Val Ser Phe Leu Ala Ala Ser Gly
1               5                   10                  15

Leu Ala Ala Ala Asn Ala Pro Gly Gly Pro Gly Gly His Gly Arg Lys
            20                  25                  30

Leu Pro Val Asn Pro Lys Thr Phe Pro Asn Glu Ile Arg Leu Lys Asp
        35                  40                  45

Leu Leu His Gly Ser Gln Lys Leu Glu Asp Phe Ala Tyr Ala Tyr Pro
    50                  55                  60

Glu Arg Asn Arg Val Phe Gly Gly Gln Ala His Leu Asp Thr Val Asn
65                  70                  75                  80

Tyr Leu Tyr Arg Glu Leu Lys Lys Thr Gly Tyr Tyr Asp Val Tyr Lys
                85                  90                  95

Gln Pro Gln Val His Gln Trp Thr Arg Ala Asp Gln Ser Leu Thr Leu
            100                 105                 110

Gly Gly Asp Ser Ile Gln Ala Ser Thr Met Thr Tyr Ser Pro Ser Val
        115                 120                 125

Asn Val Thr Ala Pro Leu Ser Leu Val Ser Lys Leu Gly Cys Ala Glu
    130                 135                 140

Gly Asp Tyr Ser Ala Asp Val Lys Gly Lys Ile Ala Leu Val Ser Arg
145                 150                 155                 160

Gly Glu Cys Ser Phe Ala Gln Lys Ser Val Leu Ser Ala Lys Ala Gly
                165                 170                 175

Ala Val Ala Thr Ile Val Tyr Asn Asn Val Asp Gly Ser Leu Ala Gly
            180                 185                 190

Thr Leu Gly Gly Ala Thr Ser Glu Leu Gly Pro Tyr Ser Pro Ile Ile
        195                 200                 205

Gly Ile Thr Leu Ala Ala Gly Gln Asp Leu Val Ala Arg Leu Gln Ala
        210                 215                 220
```

```
Ala Pro Thr Glu Val Ser Leu Trp Ile Asp Ser Lys Val Glu Asn Arg
225                 230                 235                 240

Thr Thr Tyr Asn Val Ile Ala Gln Thr Lys Gly Gly Asp Pro Asn Asn
            245                 250                 255

Val Val Ala Leu Gly Gly His Thr Asp Ser Val Glu Asn Gly Pro Gly
                260                 265                 270

Ile Asn Asp Asp Gly Ser Gly Val Ile Ser Asn Leu Val Ala Lys
                275                 280                 285

Ala Leu Thr Arg Tyr Ser Val Lys Asn Ala Val Arg Phe Cys Phe Trp
        290                 295                 300

Thr Ala Glu Glu Phe Gly Leu Leu Gly Ser Asn Tyr Tyr Val Asp Asn
305                 310                 315                 320

Leu Ser Pro Ala Glu Leu Ala Lys Ile Arg Leu Tyr Leu Asn Phe Asp
                325                 330                 335

Met Ile Ala Ser Pro Asn Tyr Ala Leu Met Ile Tyr Asp Gly Asp Gly
                340                 345                 350

Ser Ala Phe Asn Leu Thr Gly Pro Pro Gly Ser Ala Gln Ile Glu Ser
            355                 360                 365

Leu Phe Glu Asn Tyr Tyr Lys Ser Ile Lys Gln Gly Phe Val Pro Thr
    370                 375                 380

Ala Phe Asp Gly Arg Ser Asp Tyr Glu Gly Phe Ile Leu Lys Gly Ile
385                 390                 395                 400

Pro Ala Gly Gly Val Phe Thr Gly Ala Glu Ser Leu Lys Thr Glu Glu
                405                 410                 415

Gln Ala Arg Leu Phe Gly Gly Gln Ala Gly Val Ala Leu Asp Ala Asn
            420                 425                 430

Tyr His Ala Lys Gly Asp Asn Met Thr Asn Leu Asn His Lys Ala Phe
        435                 440                 445

Leu Ile Asn Ser Arg Ala Thr Ala Phe Ala Val Ala Thr Tyr Ala Asn
    450                 455                 460

Asn Leu Ser Ser Ile Pro Pro Arg Asn Ala Thr Val Val Lys Arg Glu
465                 470                 475                 480

Ser Met Lys Trp Thr Lys Arg Glu Glu Pro His Thr His Gly Ala Asp
                485                 490                 495

Thr Gly Cys Phe Ala Ser Arg Val Lys Glu
                500                 505

<210> SEQ ID NO 6
<211> LENGTH: 514
<212> TYPE: PRT
<213> ORGANISM: Artificial Sequence
<220> FEATURE:
<223> OTHER INFORMATION: Synthetic peptide with leader sequence

<400> SEQUENCE: 6

Met Gln Thr Phe Gly Ala Phe Leu Val Ser Phe Leu Ala Ala Ser Gly
1               5                   10                  15

Leu Ala Ala Ala Gly Gly Pro His Gly Phe Gly Leu Pro Lys Ile Asp
                20                  25                  30

Leu Arg Pro Met Val Ser Ser Asn Arg Leu Gln Ser Met Ile Thr Leu
            35                  40                  45

Lys Asp Leu Met Asp Gly Ala Lys Lys Leu Gln Asp Ile Ala Thr Lys
    50                  55                  60

Asn Gly Gly Asn Arg Ala Phe Gly Gly Ala Gly His Asn Ala Thr Val
65                  70                  75                  80
```

```
Asp Tyr Leu Tyr Lys Thr Leu Thr Ser Leu Gly Gly Tyr Tyr Thr Val
                85                  90                  95

Lys Lys Gln Pro Phe Lys Glu Ile Phe Ser Ser Gly Ser Gly Ser Leu
            100                 105                 110

Ile Val Asp Gly Gln Gly Ile Asp Ala Gly Ile Met Thr Tyr Thr Pro
            115                 120                 125

Gly Gly Ser Ala Thr Ala Asn Leu Val Gln Val Ala Asn Leu Gly Cys
        130                 135                 140

Glu Asp Glu Asp Tyr Pro Ala Glu Val Ala Gly Asn Ile Ala Leu Ile
145                 150                 155                 160

Ser Arg Gly Ser Cys Thr Phe Ser Lys Ser Leu Lys Ala Lys Ala
                165                 170                 175

Ala Gly Ala Val Gly Ala Ile Val Tyr Asn Asn Val Pro Gly Glu Leu
            180                 185                 190

Ser Gly Thr Leu Gly Thr Pro Phe Leu Asp Tyr Ala Pro Ile Val Gly
                195                 200                 205

Ile Ser Gln Glu Asp Gly Gln Val Ile Leu Glu Lys Leu Ala Ala Gly
            210                 215                 220

Pro Val Thr Ala Thr Leu Asn Ile Asp Ala Ile Val Glu Glu Arg Thr
225                 230                 235                 240

Thr Tyr Asn Val Ile Ala Glu Thr Lys Glu Gly Asp His Asn Asn Val
                245                 250                 255

Leu Ile Val Gly Gly His Ser Asp Ser Val Ala Ala Gly Pro Gly Ile
                260                 265                 270

Asn Asp Asp Gly Ser Gly Thr Ile Gly Ile Leu Thr Val Ala Lys Ala
            275                 280                 285

Leu Ala Lys Ala Asn Val Arg Ile Lys Asn Ala Val Arg Phe Ala Phe
            290                 295                 300

Trp Ser Ala Glu Glu Phe Gly Leu Leu Gly Ser Tyr Ala Tyr Met Lys
305                 310                 315                 320

Ser Leu Asn Glu Ser Glu Ala Glu Val Ala Lys Ile Arg Ala Tyr Leu
                325                 330                 335

Asn Phe Asp Met Ile Ala Ser Pro Asn Tyr Ile Tyr Gly Ile Tyr Asp
            340                 345                 350

Gly Asp Gly Asn Ala Phe Asn Leu Thr Gly Pro Ala Gly Ser Asp Ile
        355                 360                 365

Ile Glu Lys Asp Phe Glu Asp Phe Lys Lys Lys Thr Pro Ser
370                 375                 380

Val Pro Thr Glu Phe Ser Gly Arg Ser Asp Tyr Ala Ala Phe Ile Glu
385                 390                 395                 400

Asn Gly Ile Pro Ser Gly Gly Leu Phe Thr Gly Ala Glu Val Leu Lys
            405                 410                 415

Thr Glu Glu Glu Ala Lys Leu Phe Gly Gly Lys Ala Gly Val Ala Tyr
                420                 425                 430

Asp Val Asn Tyr His Lys Ala Gly Asp Thr Val Asp Asn Leu Ala Lys
            435                 440                 445

Asp Ala Phe Leu Leu Asn Thr Lys Ala Ile Ala Asn Ser Val Ala Lys
450                 455                 460

Tyr Ala Ala Ser Trp Ala Gly Phe Pro Lys Pro Ser Ala Val Arg Arg
465                 470                 475                 480

Arg Tyr Asp Ala Asp Met Ala Gln Leu Leu Lys Arg Ser Gly Gly Val
            485                 490                 495
```

His Gly His Gly Pro His Thr His Ser Gly Pro Cys Gly Gly Gly Asp
            500                 505                 510

Leu Leu

<210> SEQ ID NO 7
<211> LENGTH: 508
<212> TYPE: PRT
<213> ORGANISM: Artificial Sequence
<220> FEATURE:
<223> OTHER INFORMATION: Synthetic peptide with leader sequence

<400> SEQUENCE: 7

Met Gln Thr Phe Gly Ala Phe Leu Val Ser Phe Leu Ala Ala Ser Gly
1               5                   10                  15

Leu Ala Ala Glu Gly Leu Gly Asn His Gly Arg Lys Leu Asp Pro
                20                  25                  30

Asn Lys Phe Thr Lys Asp Ile Lys Leu Lys Asp Leu Leu Lys Gly Ser
            35                  40                  45

Gln Lys Leu Glu Asp Phe Ala Tyr Ala Tyr Pro Glu Arg Asn Arg Val
    50                  55                  60

Phe Gly Gly Lys Ala His Gln Asp Thr Val Asn Trp Ile Tyr Asn Glu
65                  70                  75                  80

Leu Lys Lys Thr Gly Tyr Tyr Asp Val Tyr Lys Gln Pro Gln Val His
                85                  90                  95

Leu Trp Ser Asn Ala Glu Gln Ser Leu Thr Val Asp Gly Glu Ala Ile
            100                 105                 110

Asp Ala Thr Thr Met Thr Tyr Ser Pro Ser Leu Lys Glu Thr Thr Ala
        115                 120                 125

Glu Val Val Val Pro Gly Leu Gly Cys Thr Ala Ala Asp Tyr Pro
130                 135                 140

Ala Asp Val Ala Gly Lys Ile Ala Leu Ile Gln Arg Gly Ser Cys Thr
145                 150                 155                 160

Phe Gly Glu Lys Ser Val Tyr Ala Ala Ala Asn Ala Ala Ala Ala
                165                 170                 175

Ile Val Tyr Asn Asn Val Asp Gly Ser Leu Ser Gly Thr Leu Gly Ala
            180                 185                 190

Ala Thr Ser Glu Leu Gly Pro Tyr Ala Pro Ile Val Gly Ile Ser Leu
        195                 200                 205

Ala Asp Gly Gln Asn Leu Val Ser Leu Ala Gln Ala Gly Pro Leu Thr
    210                 215                 220

Val Asp Leu Tyr Ile Asn Ser Gln Met Glu Asn Arg Thr Thr His Asn
225                 230                 235                 240

Val Ile Ala Lys Ser Lys Gly Gly Asp Pro Asn Asn Val Ile Val Ile
                245                 250                 255

Gly Gly His Ser Asp Ala Val Asn Gln Gly Pro Gly Val Asn Asp Asp
            260                 265                 270

Gly Ser Gly Ile Ile Ser Asn Leu Val Ile Ala Lys Ala Leu Thr Lys
        275                 280                 285

Tyr Ser Leu Lys Asn Ser Val Thr Trp Ala Phe Trp Thr Ala Glu Glu
    290                 295                 300

Phe Gly Leu Leu Gly Ser Glu Phe Tyr Val Asn Ser Leu Ser Ala Ala
305                 310                 315                 320

Glu Lys Asp Lys Ile Lys Leu Tyr Leu Asn Phe Asp Met Ile Ala Ser
                325                 330                 335

Pro Asn Tyr Ala Leu Met Ile Tyr Asp Gly Asp Gly Ser Thr Phe Asn

Met Thr Gly Pro Ala Gly Ser Ala Glu Ile Glu His Leu Phe Glu Asp
        340                 345                 350

Tyr Tyr Lys Ser Arg Gly Leu Ser Tyr Ile Pro Thr Ala Phe Asp Gly
355                 360                 365

Arg Ser Asp Tyr Glu Ala Phe Ile Leu Asn Gly Ile Pro Ala Gly Gly
370                 375                 380

Leu Phe Thr Gly Ala Glu Gln Ile Lys Thr Glu Glu Gln Val Ala Met
385                 390                 395                 400

Phe Gly Gly Gln Ala Gly Val Ala Tyr Asp Pro Asn Tyr His Ala Ala
        405                 410                 415

Gly Asp Asn Met Thr Asn Leu Ser Glu Glu Ala Phe Leu Ile Asn Ser
        420                 425                 430

Lys Ala Thr Ala Phe Ala Val Ala Thr Tyr Ala Asn Ser Leu Glu Ser
        435                 440                 445

Ile Pro Pro Arg Asn Ala Thr Met Ser Ile Gln Thr Arg Ser Ala Ser
        450                 455                 460

Arg Arg Ala Ala Ala His Arg Ala Ala Lys Pro His Ser His Ser
465                 470                 475                 480

Gly Gly Thr Gly Cys Trp His Thr Arg Val Glu Leu
        485                 490                 495

500                 505

<210> SEQ ID NO 8
<211> LENGTH: 506
<212> TYPE: PRT
<213> ORGANISM: Artificial Sequence
<220> FEATURE:
<223> OTHER INFORMATION: Synthetic peptide with leader sequence

<400> SEQUENCE: 8

Met Gln Thr Phe Gly Ala Phe Leu Val Ser Phe Leu Ala Ala Ser Gly
1               5                   10                  15

Leu Ala Ala Ala Gly Lys His Lys Pro Leu Val Thr Pro Glu Ala Leu
            20                  25                  30

Gln Asp Leu Ile Thr Leu Asp Asp Leu Leu Ala Gly Ser Gln Gln Leu
        35                  40                  45

Gln Asp Phe Ala Tyr Ala Tyr Pro Glu Arg Asn Arg Val Phe Gly Gly
    50                  55                  60

Arg Ala His Asp Asp Thr Val Asn Trp Leu Tyr Arg Glu Leu Lys Arg
65                  70                  75                  80

Thr Gly Tyr Tyr His Val Tyr Lys Gln Pro Gln Val His Leu Tyr Ser
                85                  90                  95

Asn Ala Glu Glu Ser Leu Thr Val Asn Gly Glu Ala Ile Glu Ala Thr
            100                 105                 110

Thr Met Thr Tyr Ser Pro Ser Ala Asn Ala Ser Ala Glu Leu Ala Val
        115                 120                 125

Ile Ser Gly Leu Gly Cys Ser Pro Ala Asp Phe Ala Ser Asp Val Ala
    130                 135                 140

Gly Lys Val Val Leu Val Gln Arg Gly Asn Cys Thr Phe Gly Glu Lys
145                 150                 155                 160

Ser Val Tyr Ala Ala Ala Asp Ala Ala Thr Ile Val Tyr Asn
                165                 170                 175

Asn Val Glu Gly Ser Leu Ser Gly Thr Leu Gly Ala Ala Gln Ser Glu
            180                 185                 190

Gln Gly Pro Tyr Ser Gly Ile Val Gly Ile Ser Leu Ala Asp Gly Glu

```
                195                 200                 205
Ala Leu Leu Ala Leu Ala Glu Glu Gly Pro Val His Val Asp Leu Trp
    210                 215                 220

Ile Asp Ser Val Met Glu Asn Arg Thr Thr Tyr Asn Val Ile Ala Gln
225                 230                 235                 240

Thr Lys Gly Gly Asp Pro Asp Asn Val Val Thr Leu Gly Gly His Ser
                245                 250                 255

Asp Ser Val Glu Ala Gly Pro Gly Ile Asn Asp Asp Gly Ser Gly Ile
            260                 265                 270

Ile Ser Asn Leu Val Ile Ala Arg Ala Leu Thr Lys Phe Ser Thr Lys
        275                 280                 285

His Ala Val Arg Phe Phe Trp Thr Ala Glu Glu Phe Gly Leu Leu
    290                 295                 300

Gly Ser Asp Tyr Tyr Val Ser Ser Leu Ser Pro Ala Glu Leu Ala Lys
305                 310                 315                 320

Ile Arg Leu Tyr Leu Asn Phe Asp Met Ile Ala Ser Pro Asn Tyr Gly
                325                 330                 335

Leu Leu Leu Tyr Asp Gly Asp Gly Ser Ala Phe Asn Leu Thr Gly Pro
            340                 345                 350

Ala Gly Ser Asp Ala Ile Glu Lys Leu Phe Tyr Asp Tyr Phe Gln Ser
        355                 360                 365

Ile Gly Gln Ala Thr Val Glu Thr Glu Phe Asp Gly Arg Ser Asp Tyr
    370                 375                 380

Glu Ala Phe Ile Leu Asn Gly Ile Pro Ala Gly Val Phe Thr Gly
385                 390                 395                 400

Ala Glu Glu Ile Lys Ser Glu Glu Val Ala Leu Trp Gly Gly Glu
                405                 410                 415

Ala Gly Val Ala Tyr Asp Ala Asn Tyr His Gln Val Gly Asp Thr Ile
            420                 425                 430

Asp Asn Leu Asn Thr Glu Ala Tyr Leu Leu Asn Ser Lys Ala Thr Ala
        435                 440                 445

Phe Ala Val Ala Thr Tyr Ala Asn Asp Leu Ser Thr Ile Pro Lys Arg
    450                 455                 460

Glu Met Thr Thr Ala Val Lys Arg Ala Asn Val Asn Gly His Met His
465                 470                 475                 480

Arg Arg Thr Met Pro Lys Lys Arg Gln Thr Ala His Arg His Ala Ala
                485                 490                 495

Lys Gly Cys Phe His Ser Arg Val Glu Gln
            500                 505

<210> SEQ ID NO 9
<211> LENGTH: 7138
<212> TYPE: DNA
<213> ORGANISM: Artificial Sequence
<220> FEATURE:
<223> OTHER INFORMATION: Expression construct

<400> SEQUENCE: 9
ctagagttgt gaagtcggta atcccgctgt atagtaatac gagtcgcatc taaatactcc      60
gaagctgctg cgaaccccgga gaatcgagat gtgctggaaa gcttctagcg agcggctaaa    120
ttagcatgaa aggctatgag aaattctgga gacggcttgt tgaatcatgg cgttccattc    180
ttcgacaagc aaagcgttcc gtcgcagtag caggcactca ttcccgaaaa aactcggaga    240
ttcctaagta gcgatggaac cggaataata taataggcaa tacattgagt tgcctcgacg    300
```

```
gttgcaatgc agggtactg agcttggaca taactgttcc gtaccccacc tcttctcaac    360
ctttggcgtt tccctgattc agcgtacccg tacaagtcgt aatcactatt aacccagact    420
gaccggacgt gttttgccct tcatttggag aaataatgtc attgcgatgt gtaatttgcc    480
tgcttgaccg actggggctg ttcgaagccc aatgtagga ttgttatccg aactctgctc     540
gtagaggcat gttgtgaatc tgtgtcgggc aggacacgcc tcgaaggttc acggcaaggg    600
aaaccaccga tagcagtgtc tagtagcaac ctgtaaagcc gcaatgcagc atcactggaa    660
aatacaaacc aatggctaaa agtacataag ttaatgccta aagaagtcat ataccagcgg    720
ctaataattg tacaatcaag tggctaaacg taccgtaatt tgccaacggc ttgtggggtt    780
gcagaagcaa cggcaaagcc ccacttcccc acgtttgttt cttcactcag tccaatctca    840
gctggtgatc ccccaattgg gtcgcttgtt tgttccggtg aagtgaaaga agacagaggt    900
aagaatgtct gactcggagc gttttgcata caaccaaggg cagtgatgga agacagtgaa    960
atgttgacat tcaaggagta tttagccagg gatgcttgag tgtatcgtgt aaggaggttt   1020
gtctgccgat acgacgaata ctgtatagtc acttctgatg aagtggtcca tattgaaatg   1080
taagtcggca ctgaacaggc aaaagattga gttgaaactg cctaagatct cgggccctcg   1140
ggccttcggc ctttgggtgt acatgtttgt gctccgggca aatgcaaagt gtggtaggat   1200
cgaacacact gctgccttta ccaagcagct gagggtatgt gataggcaaa tgttcagggg   1260
ccactgcatg gtttcgaata aaagagaag cttagccaag aacaatagcc gataaagata    1320
gcctcattaa acggaatgag ctagtaggca aagtcagcga atgtgtatat ataaaggttc   1380
gaggtccgtg cctccctcat gctctcccca tctactcatc aactcagatc ctccaggaga   1440
cttgtacacc atcttttgag gcacagaaac ccaatagtca accatcacaa gtttgtacaa   1500
aaaagcaggc ttcaccatgc agaccttcgg tgctttctc gtttccttcc tcgccgccag    1560
gtaagttggc cttgatgaac catatcatat atcgccgaga agtggaccgc gtgctgagac   1620
tgagacagcg gcctggccgc ggccaacgga cctggatggg attggaagcc ccccgtccac   1680
cccaaggtcc tccccagat gatccacctc tgggacctca tgcacggcgc ccagaagctc    1740
gaagatttcg cctacgccta ccccgagcgc aaccgcgtct ttggcggccc tgcccacgag   1800
gacaccgtca actacctcta ccgcgagctg aagaagaccg gctactacga cgtctacaag   1860
cagccccagg tccaccagtg gacccgagcc gatcaggccc tcaccgtcga cggcaagagc   1920
tacgtcgcca ccaccatgac ctacagcccc agcgtcaacg tcaccgcccc tctcgccgtc   1980
gtcaacaacc tcggctgcgt cgagagcgac taccccgccg acctcaaggg caagatcgcc   2040
ctcgtttctc gcggcgagtg ccccttcgcc accaagtctg tcctcagcgc caaggctggc   2100
gccgctgccg ctctcgtcta caacaacatc gagggcagca tggccggcac cctcggcgga   2160
cctacttctg agctgggccc ctacgccccc attgccggca tttctctcgc cgacggccag   2220
gccctcatcc agatgattca ggccggcacc gtcaccgcca acctctggat cgacagcaag   2280
gtcgagaacc gcaccaccta caacgtcatt gcccagacca agggcggcga ccccaacaac   2340
gtcgtcgctc tcggcggcca caccgactct gttgaggctg gccctggcat caacgacgac   2400
ggcagcggca tcatcagcaa cctcgtcgtc gccaaggccc tcaccgcttt cagcgtcaag   2460
aacgccgtcc gcttctgctt ctggaccgcc gaagagttcg gcctcctcgg cagcagctac   2520
tacgtcaaca gcctcaacgc caccgagaag gccaagatcc gcctctacct caacttcgac   2580
atgatcgcca gccccaacta cgccctcatg atctacgacg cgacggcag cgccttcaac    2640
ctcactggcc ctgctggcag cgcccagatc gagcgcctct tcgaggacta ctacaagagc   2700
```

```
atccgcaagc ccttcgtccc caccgagttc aacggccgca gcgactacga ggccttcatc    2760
ctcaacggca tccccgctgg cggcatcttc actggcgccg aggccatcaa gaccgaggaa    2820
caggccaagc tgttcggcgg ccaggctggc gtcgccctcg atgccaacta ccacgccaag    2880
ggcgacaaca tgaccaacct caaccgcgag gccttcctca tcaacagcaa ggccaccgcc    2940
ttcgccgtcg ccacctacgc caactccctc gacagcatcc ccagccgcaa catgagcacc    3000
gtcgtcaagc gcagccagct tgagcaggcc aagaagtcca ccccccacac ccacactggc    3060
ggcaccggct gctacaagga ccgcgtcgaa cagtaagacc cagctttctt gtacaaagtg    3120
gtgatcgcgc cagctccgtg cgaaagcctg acgcaccggt agattcttgg tgagcccgta    3180
tcatgacggc ggcgggagct acatggcccc gggtgattta ttttttttgt atctacttct    3240 gaccctttc aaatatacgg tcaactcatc tttcactgga gatgcggcct gcttggtatt    3300
gcgatgttgt cagcttggca aattgtggct ttcgaaaaca caaaacgatt ccttagtagc    3360
catgcatttt aagataacgg aatagaagaa agaggaaatt aaaaaaaaaa aaaaaacaaa    3420
catcccgttc ataaccgta gaatcgccgc tcttcggcta gctagttacg cttgtttatt    3480
tacgacaaga tctagaagat tcgagataga ataataataa taacaacaat ttgcctcttc    3540
tttccacctt ttcagtctta ctctcccttc tgacattgaa cgcctcaatc agtcagtcgc    3600
cttgtacttg gcacggtaat cctccgtgtt cttgatatcc tcaggggtag caaagccctt    3660
catgccatcg ataatgtcat ccagagtgag gatggcaaag atggggatgc cgtactcctt    3720
cctcagctcg ccaatggcac tcggtccagg cttggagtcg tcgccatccg cagcggggag    3780
cttctccatg cggtccaggg ccacgacgat gccggcgacg atgccgccct ccttggtgat    3840
cttctcaatg gcgtccctct tggcggtgcc ggcggtgatg acgtcgtcga caatcaggac    3900
cctcttgccc ttgagcgaag cgccgacgat gttgccgccc tcgccgtggt ccttggcctc    3960
cttgcggtca aacgagtagg agacgcggtc caggttctgg ggcgccagct cgccgagctt    4020
gatggtgatg gcggagcaca gcgggatgcc cttgtaggcc gggccgaaga cgatgtcgaa    4080
ctctaggccg gccttctcct gggcctcgat gatggtcttt gcaaaggcgg aggcgatggc    4140
gccggcgagg cgcgccgtgt ggaattcgcc cgcgttgaag aagtaggggg atatccgctt    4200
ggacttgagc tcgaagctgc caaacttgag gacgccgccg tcgatggcgg atttgaggaa    4260
gtcctgcttg taggcaggca gctgggaggt ggtagccatt ctgttggatt tggatagtgt    4320
ccttattctc tgatttgaac agtagatcag gacgagtgag agggatgcag aggttggatt    4380
ggagtggttg agctataaaa tttagaggcg cgccgtatcg agttttcaca tggaagtcaa    4440
agcgtacagt gcgagcttgt acgttggtct tagtatccca caagcttctg tctaggtatg    4500
atgatggcta taagtcaccc aaggcagaac tcatcttgaa gattgtctag agtgatttta    4560
ccgctgatga aatgactgga ctccctcctc ctgctcttat acgaaaaatt gcctgactct    4620
gcaaaggttt tttgtcttgg aagatgatgt gcccccccat cgctcttatc tcataccccg    4680
ccatctttct agattctcat cttcaacaag agggcaatc catgatctgc gatccagatg    4740
tgcttctggc ctcatactct gccttcaggt tgatgttcac ttaattggtg acgaattcag    4800
ctgatttgct gcagtatgct ttgtgttggt tctttccagg cttgtgccag ccatgagcgc    4860
tttgagagca tgttgtcacc tataaactcg agtaacggcc acatattgtt cactacttga    4920
atcacatacc taattttgat agaattgaca tgtttaaaga gctgaggtag ctttaatgcc    4980
tctgaagtat tgtgacacag cttctcacag agtgagaatg aaaagttgga ctcccctaa    5040
```

```
tgaagtaaaa gtttcgtctc tgaacggtga agagcataga tccggcatca actacctggc    5100
tagactacga cgtcaattct gcggccttt gacctttata tatgtccatt aatgcaatag    5160
attctttttt tttttttttt tttttttttt tttttttttt tttttgccca atttcgcaga    5220
tcaaagtgga cgttatagca tcataactaa gctcagttgc tgagggaagc cgtctactac    5280
cttagcccat ccatccagct ccataccttg atactttaga cgtgaagcaa ttcacactgt    5340
acgtctcgca gctctccttc ccgctcttgc ttccccactg gggtccatgg tgcgtgtatc    5400
gtcccctcct taattaaggc catttaggcc gttgctggcg ttttttccata ggctccgccc    5460
ccctgacgag catcacaaaa atcgacgctc aagtcagagg tggcgaaacc cgacaggact    5520
ataaagatac caggcgtttc ccctggaag ctccctcgtg cgctctcctg ttccgaccct    5580
gccgcttacc ggatacctgt ccgcctttct cccttcggga agcgtggcgc tttctcatag    5640
ctcacgctgt aggtatctca gttcggtgta ggtcgttcgc tccaagctgg gctgtgtgca    5700
cgaaccccc gttcagcccg accgctgcgc cttatccggt aactatcgtc ttgagtccaa    5760
cccggtaaga cacgacttat cgccactggc agcagccact ggtaacagga ttagcagagc    5820
gaggtatgta ggcggtgcta cagagttctt gaagtggtgg cctaactacg gctacactag    5880
aaggacagta tttggtatct gcgctctgct gaagccagtt accttcggaa aaagagttgg    5940
tagctcttga tccggcaaac aaaccaccgc tggtagcggt ggttttttg tttgcaagca    6000
gcagattacg cgcagaaaaa aaggatctca agaagatcct ttgatctttt ctacggggtc    6060
tgacgctcag tggaacgaaa actcacgtta aggcctgcag ggccgatttt ggtcatgaga    6120
ttatcaaaaa ggatcttcac ctagatcctt taaattaaa atgaagttt taaatcaatc    6180
taaagtatat atgagtaaac ttggtctgac agttaccaat gcttaatcag tgaggcacct    6240
atctcagcga tctgtctatt tcgttcatcc atagttgcct gactcccgt cgtgtagata    6300
actacgatac gggagggctt accatctggc cccagtgctg caatgatacc gcgagaccca    6360
cgctcaccgg ctccagattt atcagcaata aaccagccag ccggaagggc cgagcgcaga    6420
agtggtcctg caactttatc cgcctccatc cagtctatta attgttgccg ggaagctaga    6480
gtaagtagtt cgccagttaa tagtttgcgc aacgttgttg ccattgctac aggcatcgtg    6540
gtgtcacgct cgtcgtttgg tatggcttca ttcagctccg gttcccaacg atcaaggcga    6600
gttacatgat cccccatgtt gtgcaaaaaa gcggttagct ccttcggtcc tccgatcgtt    6660
gtcagaagta agttggccgc agtgttatca ctcatggtta tggcagcact gcataattct    6720
cttactgtca tgccatccgt aagatgcttt tctgtgactg gtgagtactc aaccaagtca    6780
ttctgagaat agtgtatgcg gcgaccgagt tgctcttgcc cggcgtcaat acgggataat    6840
accgcgccac atagcagaac tttaaaagtg ctcatcattg gaaaacgttc ttcggggcga    6900
aaactctcaa ggatcttacc gctgttgaga tccagttcga tgtaacccac tcgtgcaccc    6960
aactgatctt cagcatcttt tactttcacc agcgtttctg ggtgagcaaa aacaggaagg    7020
caaaatgccg caaaaaaggg aataagggcg acacggaaat gttgaatact catactcttc    7080
cttttcaat attattgaag catttatcag ggttattgtc tcatgccat ttaggcct     7138
```

<210> SEQ ID NO 10
<211> LENGTH: 7165
<212> TYPE: DNA
<213> ORGANISM: Artificial Sequence
<220> FEATURE:
<223> OTHER INFORMATION: Expression construct

<400> SEQUENCE: 10

```
ctagagttgt gaagtcggta atcccgctgt atagtaatac gagtcgcatc taaatactcc      60
gaagctgctg cgaacccgga gaatcgagat gtgctggaaa gcttctagcg agcggctaaa     120
ttagcatgaa aggctatgag aaattctgga gacggcttgt tgaatcatgg cgttccattc     180
ttcgacaagc aaagcgttcc gtcgcagtag caggcactca ttcccgaaaa aactcggaga     240
ttcctaagta gcgatggaac cggaataata taataggcaa tacattgagt tgcctcgacg     300
gttgcaatgc aggggtactg agcttggaca taactgttcc gtaccccacc tcttctcaac     360
ctttggcgtt tccctgattc agcgtacccg tacaagtcgt aatcactatt aacccagact     420
gaccggacgt gttttgccct tcatttggag aaataatgtc attgcgatgt gtaatttgcc     480
tgcttgaccg actggggctg ttcgaagccc gaatgtagga ttgttatccg aactctgctc     540
gtagaggcat gttgtgaatc tgtgtcgggc aggacacgcc tcgaaggttc acggcaaggg     600
aaaccaccga tagcagtgtc tagtagcaac ctgtaaagcc gcaatgcagc atcactggaa     660
aatacaaacc aatggctaaa agtacataag ttaatgccta aagaagtcat ataccagcgg     720
ctaataattg tacaatcaag tggctaaacg taccgtaatt tgccaacggc ttgtggggtt     780
gcagaagcaa cggcaaagcc ccacttcccc acgtttgttt cttcactcag tccaatctca     840
gctggtgatc ccccaattgg gtcgcttgtt tgttccggtg aagtgaaaga agacagaggt     900
aagaatgtct gactcggagc gttttgcata caaccaaggg cagtgatgga agacagtgaa     960
atgttgacat tcaaggagta tttagccagg gatgcttgag tgtatcgtgt aaggaggttt    1020
gtctgccgat acgacgaata ctgtatagtc acttctgatg aagtggtcca tattgaaatg    1080
taagtcggca ctgaacaggc aaaagattga gttgaaactg cctaagatct cgggccctcg    1140
ggccttcggc ctttgggtgt acatgtttgt gctccgggca aatgcaaagt gtggtaggat    1200
cgaacacact gctgccttta ccaagcagct gagggtatgt gataggcaaa tgttcagggg    1260
ccactgcatg gtttcgaata gaaagagaag cttagccaag aacaatagcc gataaagata    1320
gcctcattaa acggaatgag ctagtaggca aagtcagcga atgtgtatat ataaaggttc    1380
gaggtccgtg cctccctcat gctctcccca tctactcatc aactcagatc ctccaggaga    1440
cttgtacacc atcttttgag gcacagaaac ccaatagtca accatcacaa gtttgtacaa    1500
aaaagcaggc ttcaccatgc agaccttcgg tgcttttctc gtttccttcc tcgccgccag    1560
gtaagttggc cttgatgaac catatcatat atcgccgaga agtggaccgc gtgctgagac    1620
tgagacagcg gcctggccgc ggccggtgga catggtggat cttcaggcct cggctgcgac    1680
agccagcgcc ctcttgtcag cagcgagaag ctccagagcc tgatcaagaa ggaagatctc    1740
ctcgccggca gccaagagct tcaggacatt gccactgccc acggcggcca ccgagccttt    1800
ggaagctctg ccacaacgc caccgtcgac tttctctact acaccctcaa ggccctcgac    1860
tactacaacg tcaccaagca gcccttcaag gaaatcttca gcagcggcac cggcagcctc    1920
accgtggacg cgaggacat cgaggccgag actctcacct acaccccag cggcagcgcc     1980
accgacaagc ctgtcgtcgt cgtcgccaac gtcggctgcg acgccgccga ttaccctgct    2040
gaggtcgccg caacattgc cctcatcaag cgcggcacgt gcaccttcag ccagaagtcc    2100
gtcaacgcca aggccgctgg cgccgtcgcc gccatcatct acaacaacgc cgagggcaag    2160
ctcagcggaa ccctcggcca gcccttcctc gactacgctc ccgtcctcgg catcaccctt    2220
gaggccggcg aggccctcct cgccaagctc gctggtggcc ctgtcaccgc caccctccag    2280
attgacgccc tcgtcgagga acgcgtcacc tacaacgtca ttgccgagac taaggaaggc    2340
```

-continued

```
gaccacagca acgtcctcgt cctcggcggc cacaccgata gcgtccctgc tggccctggc    2400
atcaacgacg acggcagcgg caccatcggc atgctcactg tcgccaaggc cctcaccaag    2460
ttccgcgtca agaacgccgt ccgcttcgcc ttctggtccg ccgaggaata cggcctcctc    2520
ggcagctacg cctacatcaa gagcatcaac agctctgccg ccgagctgag caagatccgc    2580
gcctacctca acttcgacat gatcgccagc cccaactaca tctacggcat ctacgacggc    2640
gacggcaacg ccttcaacct cactggccct gccggcagcg acgtcatcga gcgcaacttc    2700
gagaacttct tcaagcgcaa gcacaccccc tccgtcccca ccgagtttag cggccgatct    2760
gactacgccg ccttcatcga gaacggcatc cccagcggcg gactcttcac tggcgccgag    2820
gtcctcaaga ccgagcgcga ggctgagctg tttggcggcc gagctggcgt cgcctacgac    2880
gtcaactacc accaggccgg cgacaccgtc gacaacctcg ccctcgacgc cttcctgctc    2940
aacaccaagg ccattgccga cagcgtcgcc acctacgccc tcagctttga cggcctccct    3000
cgcgtcgacg gcaagaagcg acgttgggac gctcaccgag cccgcatgct caagcgatct    3060
gctggctctc acggccacgc ccaccttcac tctggccctt gtggcggcgg agccagcatc    3120
taagacccag cttctcttgta caaagtggtg atcgcgccag ctccgtgcga aagcctgacg    3180
caccggtaga ttcttggtga gcccgtatca tgacggcggc gggagctaca tggccccggg    3240
tgatttattt tttttgtatc tacttctgac ccttttcaaa tatacggtca actcatcttt    3300
cactggagat gcggcctgct tggtattgcg atgttgtcag cttggcaaat tgtggctttc    3360
gaaaacacaa aacgattcct tagtagccat gcattttaag ataacggaat agaagaaaga    3420
ggaaattaaa aaaaaaaaaa aaacaaacat cccgttcata acccgtagaa tcgccgctct    3480
tcggctagct agttacgctt gtttatttac gacaagatct agaagattcg agatagaata    3540
ataataataa caacaatttg cctcttcttt ccaccttttc agtcttactc tcccttctga    3600
cattgaacgc ctcaatcagt cagtcgcctt gtacttggca cggtaatcct ccgtgttctt    3660
gatatcctca ggggtagcaa agcccttcat gccatcgata atgtcatcca gagtgaggat    3720
ggcaaagatg gggatgccgt actccttcct cagctcgcca atggcactcg gtccaggctt    3780
ggagtcgtcg ccatccgcag cggggagctt ctccatgcgg tccagggcca cgacgatgcc    3840
ggcgacgatg ccgccctcct tggtgatctt ctcaatggcg tccctcttgg cggtgccggc    3900
ggtgatgacg tcgtcgacaa tcaggaccct cttgcccttg agcgaagcgc cgacgatgtt    3960
gccgccctcg ccgtggtcct tggcctcctt gcggtcaaac gagtaggaga cgcggtccag    4020
gttctggggc gccagctcgc cgagcttgat ggtgatggcg gagcacagcg ggatgccctt    4080
gtaggccggg ccgaagacga tgtcgaactc taggccggcc ttctcctggg cctcgatgat    4140
ggtctttgca aaggcggagg cgatggcgcc ggcgaggcgc gccgtgtgga attcgcccgc    4200
gttgaagaag taggggata tccgcttgga cttgagctcg aagctgccaa acttgaggac    4260
gccgccgtcg atggcggatt tgaggaagtc ctgcttgtag gcaggcagct gggaggtggt    4320
agccattctg ttggatttgg atagtgtcct tattctctga tttgaacagt agatcaggac    4380
gagtgagagg gatgcagagg ttggattgga gtggttgagc tataaaattt agaggcgcgc    4440
cgtatcgagt tttcacatgg aagtcaaagc gtacagtgcg agcttgtacg ttggtcttag    4500
tatcccacaa gcttctgtct aggtatgatg atggctataa gtcacccaag gcagaactca    4560
tcttgaagat tgtctagagt gatttttaccg ctgatgaaat gactggactc cctcctcctg    4620
ctcttatacg aaaaattgcc tgactctgca aaggttgttt gtcttggaag atgatgtgcc    4680
cccccatcgc tcttatctca taccccgcca tctttctaga ttctcatctt caacaagagg    4740
```

```
ggcaatccat gatctgcgat ccagatgtgc ttctggcctc atactctgcc ttcaggttga    4800
tgttcactta attggtgacg aattcagctg atttgctgca gtatgctttg tgttggttct    4860
ttccaggctt gtgccagcca tgagcgcttt gagagcatgt tgtcacctat aaactcgagt    4920
aacggccaca tattgttcac tacttgaatc acatacctaa ttttgataga attgacatgt    4980
ttaaagagct gaggtagctt taatgcctct gaagtattgt gacacagctt ctcacagagt    5040
gagaatgaaa agttggactc cccctaatga agtaaaagtt tcgtctctga acggtgaaga    5100
gcatagatcc ggcatcaact acctggctag actacgacgt caattctgcg gccttttgac    5160
ctttatatat gtccattaat gcaatagatt cttttttttt ttttttttt ttttttttt    5220 tttttttttt ttgcccaatt tcgcagatca agtggacgt tatagcatca taactaagct    5280
cagttgctga gggaagccgt ctactacctt agcccatcca tccagctcca taccttgata    5340
ctttagacgt gaagcaattc acactgtacg tctcgcagct ctccttcccg ctcttgcttc    5400
cccactgggg tccatggtgc gtgtatcgtc ccctccttaa ttaaggccat ttaggccgtt    5460
gctggcgttt ttccataggc tccgcccccc tgacgagcat cacaaaaatc gacgctcaag    5520
tcagaggtgg cgaaacccga caggactata aagataccag gcgtttcccc ctggaagctc    5580
cctcgtgcgc tctcctgttc cgaccctgcc gcttaccgga tacctgtccg cctttctccc    5640
ttcgggaagc gtggcgcttt ctcatagctc acgctgtagg tatctcagtt cggtgtaggt    5700
cgttcgctcc aagctgggct gtgtgcacga accccccgtt cagcccgacc gctgcgcctt    5760
atccggtaac tatcgtcttg agtccaaccc ggtaagacac gacttatcgc cactggcagc    5820
agccactggt aacaggatta gcagagcgag gtatgtaggc ggtgctacag agttcttgaa    5880
gtggtggcct aactacggct acactagaag gacagtattt ggtatctgcg ctctgctgaa    5940
gccagttacc ttcggaaaaa gagttggtag ctcttgatcc ggcaaacaaa ccaccgctgg    6000
tagcggtggt ttttttgttt gcaagcagca gattacgcgc agaaaaaaag gatctcaaga    6060
agatcctttg atcttttcta cggggtctga cgctcagtgg aacgaaaact cacgttaagg    6120
cctgcagggc cgattttggt catgagatta tcaaaaagga tcttcaccta gatcctttta    6180
aattaaaaat gaagttttaa atcaatctaa agtatatatg agtaaacttg gtctgacagt    6240
taccaatgct taatcagtga ggcacctatc tcagcgatct gtctatttcg ttcatccata    6300
gttgcctgac tccccgtcgt gtagataact acgatacggg agggcttacc atctggcccc    6360
agtgctgcaa tgataccgcg agacccacgc tcaccggctc cagatttatc agcaataaac    6420
cagccagccg aagggccga gcgcagaagt ggtcctgcaa ctttatccgc ctccatccag    6480
tctattaatt gttgccggga agctagagta gtagttcgc cagttaatag tttgcgcaac    6540
gttgttgcca ttgctacagg catcgtggtg tcacgctcgt cgtttggtat ggcttcattc    6600
agctccggtt cccaacgatc aaggcgagtt acatgatccc ccatgttgtg caaaaaagcg    6660
gttagctcct tcggtcctcc gatcgttgtc agaagtaagt tggccgcagt gttatcactc    6720
atggttatgg cagcactgca taattctctt actgtcatgc catccgtaag atgcttttct    6780
gtgactggtg agtactcaac caagtcattc tgagaatagt gtatgcggcg accgagttgc    6840
tcttgcccgg cgtcaatacg ggataatacc gcgccacata gcagaacttt aaaagtgctc    6900
atcattggaa aacgttcttc ggggcgaaaa ctctcaagga tcttaccgct gttgagatcc    6960
agttcgatgt aacccactcg tgcacccaac tgatcttcag catctttac tttcaccagc    7020 gtttctgggt gagcaaaaac aggaaggcaa aatgccgcaa aaaagggaat aagggcgaca    7080
```

-continued

```
cggaaatgtt gaatactcat actcttcctt tttcaatatt attgaagcat ttatcagggt      7140
tattgtctca tggccattta ggcct                                            7165

<210> SEQ ID NO 11
<211> LENGTH: 7111
<212> TYPE: DNA
<213> ORGANISM: Artificial Sequence
<220> FEATURE:
<223> OTHER INFORMATION: Expression construct

<400> SEQUENCE: 11
ctagagttgt gaagtcggta atcccgctgt atagtaatac gagtcgcatc taaatactcc        60
gaagctgctg cgaacccgga gaatcgagat gtgctggaaa gcttctagcg agcggctaaa       120
ttagcatgaa aggctatgag aaattctgga gacggcttgt tgaatcatgg cgttccattc       180
ttcgacaagc aaagcgttcc gtcgcagtag caggcactca ttcccgaaaa aactcggaga       240
ttcctaagta gcgatggaac cggaataata taataggcaa tacattgagt tgcctcgacg       300
gttgcaatgc aggggtactg agcttggaca taactgttcc gtaccccacc tcttctcaac       360
ctttggcgtt tccctgattc agcgtacccg tacaagtcgt aatcactatt aacccagact       420
gaccggacgt gttttgccct tcatttggag aaataatgtc attgcgatgt gtaatttgcc       480
tgcttgaccg actggggctg ttcgaagccc gaatgtagga ttgttatccg aactctgctc       540
gtagaggcat gttgtgaatc tgtgtcgggc aggacacgcc tcgaaggttc acggcaaggg       600
aaaccaccga tagcagtgtc tagtagcaac ctgtaaagcc gcaatgcagc atcactggaa       660
aatacaaacc aatggctaaa agtacataag ttaatgccta agaagtcat ataccagcgg        720 ctaataattg tacaatcaag tggctaaacg taccgtaatt tgccaacggc ttgtggggtt       780
gcagaagcaa cggcaaagcc ccacttcccc acgtttgttt cttcactcag tccaatctca       840
gctggtgatc ccccaattgg gtcgcttgtt tgttccggtg aagtgaaaga agacagaggt       900
aagaatgtct gactcggagc gttttgcata caaccaaggg cagtgatgga agacagtgaa       960
atgttgacat tcaaggagta tttagccagg gatgcttgag tgtatcgtgt aaggaggttt      1020
gtctgccgat acgacgaata ctgtatagtc acttctgatg aagtggtcca tattgaaatg      1080
taagtcggca ctgaacaggc aaaagattga gttgaaactg cctaagatct cgggccctcg      1140
ggccttcggc ctttgggtgt acatgttgt gctccgggca aatgcaaagt gtggtaggat       1200
cgaacacact gctgccttta ccaagcagct gagggtatgt gataggcaaa tgttcagggg      1260
ccactgcatg gtttcgaata gaaagagaag cttagccaag aacaatagcc gataaagata      1320
gcctcattaa acggaatgag ctagtaggca aagtcagcga atgtgtatat ataaaggttc      1380
gaggtccgtg cctccctcat gctctcccca tctactcatc aactcagatc ctccaggaga      1440
cttgtacacc atcttttgag gcacagaaac ccaatagtca accatcacaa gtttgtacaa      1500
aaaagcaggc ttcaccatgc agaccttcgg tgcttttctc gtttccttcc tcgccgccag      1560
gtaagttggc cttgatgaac catatcatat atcgccgaga agtggaccgc gtgctgagac      1620
tgagacagcg gcctggccgc ggccaccaag aagcccctcg tcaacgagct gaagctccag      1680
aaggacatca acatcaagga cctcatggct ggcgcccaga gctccaggg cattgccgag       1740 gccaacggca cacccgcgt cttggcggc gctggccaca acgccaccgt cgactacctc        1800
tacaagaccc tcaaggccac cggctactac aacgtcaaga agcagccctt caccgagctg      1860
tacagcgccg gcaccgccag cctcaaggtc gacggcgacg acatcaccgc cgccatcatg      1920
acctacaccc tgccggcga ggccaccggc cctcttgtcg tcgctgagaa ccttggctgc      1980
```

```
gaggccagcg acttccccgc tgagtctgag ggcaaggtcg tcctcgtcct ccgcggcgag    2040
tgccccttca gccagaagtc caccaacggc aagactgccg gcgctgccgc cgtcatcgtc    2100
tacaacaacg tccccggcga gctggccggc actctcggcg aacccttttgg cgagttcgcc   2160 cccatcgtcg gcatcagcca agaggacggc caggccatcc tcgccaagac caaggccggc    2220
gaggtcacgg tcgacctgaa ggtcgacgcc acggtcgaga accgcgtcac cttcaacgtc    2280
attgccgaga ctaaggaagg cgaccacgac aacgtcctcg tcgtcggcgg ccactctgat    2340
agcgtcgctg ccggccctgg catcaacgac gacggcagcg gcatcatcgg catcctcaag    2400
gtcgcccagg ccctcaccaa gtaccgcgtc aagaacgccg tccgcttcgg cttctggtcc    2460
gccgaagagt tcggcctcct cggcagctac gcctacatga agtcgatcaa cggctccgac    2520
gccgaggtcg ccaagatccg cgcctacctc aacttcgaca tgatcgccag ccccaactac    2580
gtctacggca tctacgacgg cgacggcagc gccttcaacc tcactggccc tgccggctcg    2640
gacgccatcg agaaggactt cgagcgcttc ttcaagacca agcgcctcgg ctacgtcccc    2700
agcgagttta gcggccgctc tgactacgcc gccttcatcg agaacggcat ccccagcggc    2760
ggactcttca ctggcgccga gcagctcaag accgaggaag aggccaagaa gttcggcggc    2820
gaggccggcg tcgcctacga catcaactac cacaagatcg gcgacgatat caacaacctc    2880
aacaaggaag ccttcctcgt caacacccag gccattgcca acagcgtcgc ccgctacgcc    2940
aagacctgga agtccctgcc caaggtcacc cacaacaccc gccgatggga cgccgaggtt    3000
gcctccgtcc tcaagcgaag cagcggccac tctcacgctg gcggcccttg tggctctgtc    3060
agcgtctaag acccagcttt cttgtacaaa gtggtgatcg cgccagctcc gtgcgaaagc    3120
ctgacgcacc ggtagattct tggtgagccc gtatcatgac ggcggcggga gctacatggc    3180
cccgggtgat ttattttttt tgtatctact tctgacccct ttcaaatata cggtcaactc    3240
atctttcact ggagatgcgg cctgcttggt attgcgatgt tgtcagcttg gcaaattgtg    3300
gctttcgaaa acacaaaacg attccttagt agccatgcat tttaagataa cggaatagaa    3360
gaaagaggaa attaaaaaaa aaaaaaaaac aaacatcccg ttcataaccc gtagaatcgc    3420
cgctcttcgg ctagctagtt acgcttgttt atttacgaca agatctagaa gattcgagat    3480
agaataataa taataacaac aatttgcctc ttctttccac cttttcagtc ttactctccc    3540
ttctgacatt gaacgcctca atcagtcagt cgccttgtac ttggcacggt aatcctccgt    3600
gttcttgata tcctcagggg tagcaaagcc cttcatgcca tcgataatgt catccagagt    3660
gaggatggca aagatgggga tgccgtactc cttcctcagc tcgccaatgg cactcggtcc    3720
aggcttggag tcgtcgccat ccgcagcggg gagcttctcc atgcggtcca gggccacgac    3780
gatgccggca cgatgccgc cctccttggt gatcttctca atgcgtccc tcttggcggt     3840 gccggcggtg atgacgtcgt cgacaatcag gaccctcttg cccttgagcg aagcgccgac    3900
gatgttgccg ccctcgccgt ggtccttggc ctccttgcgg tcaaacgagt aggagacgcg    3960
gtccaggttc tggggcgcca gctcgccgag cttgatggtg atggcggagc acagcgggat    4020
gcccttgtag gccgggccga agacgatgtc gaactctagg ccggccttct cctgggcctc    4080
gatgatggtc tttgcaaagg cggaggcgat ggcgccggca aggcgcgccg tgtggaattc    4140
gcccgcgttg aagaagtagg gggatatccg cttggacttg agctcgaagc tgccaaactt    4200
gaggacgccg ccgtcgatgg cggatttgag gaagtcctgc ttgtaggcag gcagctggga    4260
ggtggtagcc attctgttgg atttggatag tgtccttatt ctctgatttg aacagtagat    4320
```

```
caggacgagt gagagggatg cagaggttgg attggagtgg ttgagctata aaatttagag    4380
gcgcgccgta tcgagttttc acatggaagt caaagcgtac agtgcgagct tgtacgttgg    4440
tcttagtatc ccacaagctt ctgtctaggt atgatgatgg ctataagtca cccaaggcag    4500
aactcatctt gaagattgtc tagagtgatt ttaccgctga tgaaatgact ggactccctc    4560
ctcctgctct tatacgaaaa attgcctgac tctgcaaagg ttgtttgtct tggaagatga    4620
tgtgccccc catcgctctt atctcatacc ccgccatctt tctagattct catcttcaac    4680
aagagggca atccatgatc tgcgatccag atgtgcttct ggcctcatac tctgccttca    4740
ggttgatgtt cacttaattg gtgacgaatt cagctgattt gctgcagtat gctttgtgtt    4800
ggttctttcc aggcttgtgc cagccatgag cgctttgaga gcatgttgtc acctataaac    4860
tcgagtaacg ccacatatt gttcactact tgaatcacat acctaatttt gatagaattg    4920
acatgtttaa agagctgagg tagctttaat gcctctgaag tattgtgaca cagcttctca    4980
cagagtgaga atgaaaagtt ggactccccc taatgaagta aaagtttcgt ctctgaacgg    5040
tgaagagcat agatccggca tcaactacct ggctagacta cgacgtcaat tctgcggcct    5100
tttgaccttt atatatgtcc attaatgcaa tagattcttt tttttttttt tttttttttt    5160
tttttttttt tttttttgc ccaatttcgc agatcaaagt ggacgttata gcatcataac    5220
taagctcagt tgctgaggga agccgtctac taccttagcc catccatcca gctccatacc    5280
ttgatacttt agacgtgaag caattcacac tgtacgtctc gcagctctcc ttcccgctct    5340
tgcttcccca ctggggtcca tggtgcgtgt atcgtcccct ccttaattaa ggccatttag    5400
gccgttgctg gcgttttttcc ataggctccg ccccccctgac gagcatcaca aaaatcgacg    5460
ctcaagtcag aggtggcgaa acccgacagg actataaaga taccaggcgt ttcccctgg    5520
aagctccctc gtgcgctctc ctgttccgac cctgccgctt accggatacc tgtccgcctt    5580
tctcccttcg ggaagcgtgg cgctttctca tagctcacgc tgtaggtatc tcagttcggt    5640
gtaggtcgtt cgctccaagc tgggctgtgt gcacgaaccc cccgttcagc ccgaccgctg    5700
cgccttatcc ggtaactatc gtcttgagtc caacccggta agacacgact tatcgccact    5760
ggcagcagcc actggtaaca ggattagcag agcgaggtat gtaggcggtg ctacagagtt    5820
cttgaagtgg tggcctaact acggctacac tagaaggaca gtatttggta tctgcgctct    5880
gctgaagcca gttaccttcg gaaaaagagt tggtagctct tgatccggca acaaaccac    5940
cgctggtagc ggtggttttt tgtttgcaa gcagcagatt acgcgcagaa aaaaggatc    6000
tcaagaagat cctttgatct ttctacgggg tctgacgct cagtggaacg aaaactcacg    6060
ttaaggcctg cagggccgat tttggtcatg agattatcaa aaaggatctt cacctagatc    6120
cttttaaatt aaaatgaag ttttaaatca atctaaagta tatatgagta aacttggtct    6180
gacagttacc aatgcttaat cagtgaggca cctatctcag cgatctgtct atttcgttca    6240
tccatagttg cctgactccc cgtcgtgtag ataactacga tacggagggg cttaccatct    6300
ggccccagtg ctgcaatgat accgcgagac ccacgctcac cggctccaga tttatcagca    6360
ataaaccagc cagccggaag ggccgagcgc agaagtggtc ctgcaacttt atccgcctcc    6420
atccagtcta ttaattgttg ccgggaagct agagtaagta gttcgccagt taatagtttg    6480
cgcaacgttg ttgccattgc tacaggcatc gtggtgtcac gctcgtcgtt tggtatggct    6540
tcattcagct ccggttccca acgatcaagg cgagttacat gatcccccat gttgtgcaaa    6600
aaagcggtta gctccttcgg tcctccgatc gttgtcagaa gtaagttggc cgcagtgtta    6660
tcactcatgg ttatggcagc actgcataat tctcttactg tcatgccatc cgtaagatgc    6720
```

```
ttttctgtga ctggtgagta ctcaaccaag tcattctgag aatagtgtat gcggcgaccg   6780
agttgctctt gcccggcgtc aatacgggat aataccgcgc cacatagcag aactttaaaa   6840
gtgctcatca ttggaaaacg ttcttcgggg cgaaaactct caaggatctt accgctgttg   6900
agatccagtt cgatgtaacc cactcgtgca cccaactgat cttcagcatc ttttactttc   6960
accagcgttt ctgggtgagc aaaaacagga aggcaaaatg ccgcaaaaaa gggaataagg   7020
gcgacacgga aatgttgaat actcatactc ttcctttttc aatattattg aagcatttat   7080
cagggttatt gtctcatggc catttaggcc t                                  7111
```

<210> SEQ ID NO 12
<211> LENGTH: 7153
<212> TYPE: DNA
<213> ORGANISM: Artificial Sequence
<220> FEATURE:
<223> OTHER INFORMATION: Expression construct

<400> SEQUENCE: 12

```
ctagagttgt gaagtcggta atcccgctgt atagtaatac gagtcgcatc taaatactcc     60
gaagctgctg cgaacccgga gaatcgagat gtgctggaaa gcttctagcg agcggctaaa    120
ttagcatgaa aggctatgag aaattctgga gacggcttgt tgaatcatgg cgttccattc    180
ttcgacaagc aaagcgttcc gtcgcagtag caggcactca ttcccgaaaa aactcggaga    240
ttcctaagta gcgatggaac cggaataata taataggcaa tacattgagt tgcctcgacg    300
gttgcaatgc aggggtactg agcttggaca taactgttcc gtaccccacc tcttctcaac    360 cttttggcgtt tccctgattc agcgtacccg tacaagtcgt aatcactatt aacccagact    420
gaccggacgt gttttgccct tcatttggag aaataatgtc attgcgatgt gtaatttgcc    480
tgcttgaccg actgggctg ttcgaagccc gaatgtagga ttgttatccg aactctgctc    540
gtagaggcat gttgtgaatc tgtgtcgggc aggacacgcc tcgaaggttc acggcaaggg    600
aaaccaccga tagcagtgtc tagtagcaac ctgtaaagcc gcaatgcagc atcactggaa    660
aatacaaacc aatggctaaa agtacataag ttaatgccta agaagtcat ataccagcgg    720 ctaataattg tacaatcaag tggctaaacg taccgtaatt tgccaacggc ttgtgggtt    780 gcagaagcaa cggcaaagcc ccacttcccc acgtttgttt cttcactcag tccaatctca    840
gctggtgatc ccccaattgg gtcgcttgtt tgttccggtg aagtgaaaga agacagaggt    900
aagaatgtct gactcggagc gttttgcata caaccaaggg cagtgatgga agacagtgaa    960
atgttgacat tcaaggagta tttagccagg gatgcttgag tgtatcgtgt aaggaggttt   1020
gtctgccgat acgacgaata ctgtatagtc acttctgatg aagtggtcca tattgaaatg   1080
taagtcggca ctgaacaggc aaaagattga gttgaaactg cctaagatct cgggccctcg   1140
ggccttcggc ctttgggtgt acatgtttgt gctccgggca aatgcaaagt gtggtaggat   1200
cgaacacact gctgcccttta ccaagcagct gagggtatgt gataggcaaa tgttcagggg   1260
ccactgcatg gtttcgaata gaaagagaag cttagccaag aacaatagcc gataaagata   1320
gcctcattaa acggaatgag ctagtaggca aagtcagcga atgtgtatat ataaaggttc   1380
gaggtccgtg cctccctcat gctctcccca tctactcatc aactcagatc ctccaggaga   1440
cttgtacacc atcttttgag gcacagaaac ccaatagtca accatcacaa gtttgtacaa   1500
aaaagcaggc ttcaccatgc agaccttcgg tgcttttctc gttccttcc tcgccgccag   1560 gtaagttggc cttgatgaac catatcatat atcgccgaga agtggaccgc gtgctgagac   1620
```

-continued

```
tgagacagcg gcctggccgc ggccctccag attcctctca acctccaggt ccccaagctc      1680
agctggaacc tcttcggcga cgacctcccc ctggtcgaca ccaaggaact ccagaagtcc      1740
atcaagcccg agaaccttga ggcccgagcc aaggacctct acgagatcgc caagaacggc      1800
gaggaagagt acggccaccc cacccgcgtc attggctctg agggccacct cggcaccctc      1860
agctacatcc acgccgagct ggctaagctc ggcggctact acagcgtcag caaccagcag      1920
ttccccgccg tcagcggcaa cgtctttgag agccgcctcg tcatcggcga cagcgtccct      1980
aagcaggcca gccctatggg cctcaccccc cccaccaaga caaggaacc cgtccacggc       2040 accctcgtcc tcgtcgacaa cgagggctgc gacgccagcg actacccga ggctgtcaag       2100 ggcaacattg ccctcatcct ccgcggcacg tgccccttcg gcaccaagtc tggcaacgcc      2160
ggcaaggctg cgccgtcgc tgctgtcgtc tacaactacg agaaggacga ggtccacggc       2220
acgctgggca cccctagccc tgatcacgtc gccacctttg gcctcggcgg cgaagagggc      2280
aaggccgtcg ccaagaagct caaggacggc gagaaggtcg acgccattgc ctacattgac      2340
gccgaggtca agaccatcag caccaccaac atcattgccc agacccgagg cggcgacccc      2400
gacaactgcg ttatgcttgg cggccacagc gacagcgtcg ctgagggccc tggcatcaac      2460
gacgatggca gcggcagcat cagcgtcctt gaggtcgccg tccagctcac caagtaccgc      2520
gtcaacaact gcgtccgctt cgcctggtgg gccgctgagg aagagggcct ccttggcagc      2580
gaccactacg tcagcgtcct ccccgaggac gagaaccgca agatccgcct cttcatggac      2640
tacgacatga tggccagccc caacttcgcc taccagatct acaacgccac caacgccgag      2700
aaccccaagg gcagcgagga actccgcgac ctctacgtca actggtacga ggaacagggc      2760
ctcaactaca ccttcattcc cttcgacggc cgcagcgact acgacggctt tatccgaggc      2820
ggcatccccg ctggcggcat tgctactggc gctgagggcg tcaagaccga ggacgaggtc      2880
gagatgttcg gcggcgaggc cggcgtctgg tacgacaaga actaccacca gattggcgac      2940
gacctgacca acgtcaacta caccgcctgg gaggtcaaca ccaagctgat cgcccacagc      3000
gtcgccacct acgccaagag cttcaagggc ttccccgagc gcgagatcga gactagcgtc      3060
cagacctaca cgacaagac caagtaccac ggcagcaagc tgttcatcta agacccagct      3120 ttccttgtaca aagtggtgat cgcgccagct ccgtgcgaaa gcctgacgca ccggtagatt      3180
cttggtgagc ccgtatcatg acggcggcgg gagctacatg gccccgggtg atttattttt      3240
tttgtatcta cttctgaccc ttttcaaata tacggtcaac tcatctttca ctggagatgc      3300
ggcctgcttg gtattgcgat gttgtcagct tggcaaattg tggctttcga aaacacaaaa      3360
cgattcctta gtagccatgc attttaagat aacggaatag aagaaagagg aaattaaaaa      3420
aaaaaaaaaa acaaacatcc cgttcataac ccgtagaatc gccgctcttc ggctagctag      3480
ttacgcttgt ttatttacga caagatctag aagattcgag atagaataat aataataaca      3540
acaatttgcc tcttctttcc acctttcag tcttactctc ccttctgaca ttgaacgcct       3600
caatcagtca gtcgccttgt acttggcacg gtaatcctcc gtgttcttga tatcctcagg      3660
ggtagcaaag cccttcatgc catcgataat gtcatccaga gtgaggatgg caaagatggg     3720
gatgccgtac tccttcctca gctgccaat ggcactcggt ccaggcttgg agtcgtcgcc       3780
atccgcagcg gggagcttct ccatgcggtc cagggccacg acgatgccgg cgacgatgcc     3840
gccctccttg gtgatcttct caatggcgtc cctcttggcg gtgccggcgg tgatgacgtc     3900
gtcgacaatc aggaccctct tgcccttgag cgaagcgccg acgatgttgc cgccctcgcc     3960
gtggtccttg gcctccttgc ggtcaaacga gtaggagacg cggtccaggt tctggggcgc     4020
```

-continued

```
cagctcgccg agcttgatgg tgatggcgga gcacagcggg atgcccttgt aggccgggcc    4080
gaagacgatg tcgaactcta ggccggcctt ctcctgggcc tcgatgatgg tctttgcaaa    4140
ggcggaggcg atggcgccgg cgaggcgcgc cgtgtggaat tcgcccgcgt tgaagaagta    4200
gggggatatc cgcttggact tgagctcgaa gctgccaaac ttgaggacgc cgccgtcgat    4260
ggcggatttg aggaagtcct gcttgtaggc aggcagctgg gaggtggtag ccattctgtt    4320
ggatttggat agtgtcctta ttctctgatt tgaacagtag atcaggacga gtgagaggga    4380
tgcagaggtt ggattggagt ggttgagcta taaaatttag aggcgcgccg tatcgagttt    4440
tcacatggaa gtcaaagcgt acagtgcgag cttgtacgtt ggtcttagta tcccacaagc    4500
ttctgtctag gtatgatgat ggctataagt cacccaaggc agaactcatc ttgaagattg    4560
tctagagtga ttttaccgct gatgaaatga ctggactccc tcctcctgct cttatacgaa    4620
aaattgcctg actctgcaaa ggttgtttgt cttggaagat gatgtgcccc cccatcgctc    4680
ttatctcata ccccgccatc tttctagatt ctcatcttca acaagagggg caatccatga    4740
tctgcgatcc agatgtgctt ctggcctcat actctgcctt caggttgatg ttcacttaat    4800
tggtgacgaa ttcagctgat ttgctgcagt atgctttgtg ttggttcttt ccaggcttgt    4860
gccagccatg agcgctttga gagcatgttg tcacctataa actcgagtaa cggccacata    4920
ttgttcacta cttgaatcac ataccctaatt ttgatagaat tgacatgttt aaagagctga    4980
ggtagcttta atgcctctga agtattgtga cacagcttct cacagagtga gaatgaaaag    5040
ttggactccc cctaatgaag taaaagtttc gtctctgaac ggtgaagagc atagatccgg    5100
catcaactac ctggctagac tacgacgtca attctgcggc cttttgacct ttatatatgt    5160
ccattaatgc aatagattct tttttttttt tttttttttt tttttttttt tttttttttt    5220
gcccaatttc gcagatcaaa gtggacgtta tagcatcata actaagctca gttgctgagg    5280
gaagccgtct actaccttag cccatccatc cagctccata ccttgatact ttagacgtga    5340
agcaattcac actgtacgtc tcgcagctct ccttcccgct cttgcttccc cactggggtc    5400
catggtgcgt gtatcgtccc ctccttaatt aaggccattt aggccgttgc tggcgttttt    5460
ccataggctc cgccccctg acgagcatca caaaaatcga cgctcaagtc agaggtggcg    5520
aaacccgaca ggactataaa gataccaggc gtttccccct ggaagctccc tcgtgcgctc    5580
tcctgttccg accctgccgc ttaccggata cctgtccgcc tttctccctt cgggaagcgt    5640
ggcgctttct catagctcac gctgtaggta tctcagttcg gtgtaggtcg ttcgctccaa    5700
gctgggctgt gtgcacgaac cccccgttca gcccgaccgc tgcgccttat ccggtaacta    5760
tcgtcttgag tccaacccgg taagacacga cttatcgcca ctggcagcag ccactggtaa    5820
caggattagc agagcgaggt atgtaggcgg tgctacagag ttcttgaagt ggtggcctaa    5880
ctacggctac actagaagga cagtatttgg tatctgcgct ctgctgaagc cagttacctt    5940
cggaaaaaga gttggtagct cttgatccgg caaacaaacc accgctggta gcggtggttt    6000
ttttgtttgc aagcagcaga ttacgcgcag aaaaaaagga tctcaagaag atcctttgat    6060
cttttctacg gggtctgacg ctcagtggaa cgaaaactca cgttaaggcc tgcagggccg    6120
attttggtca tgagattatc aaaaaggatc ttcacctaga tccttttaaa ttaaaaatga    6180
agttttaaat caatctaaag tatatatgag taaacttggt ctgacagtta ccaatgctta    6240
atcagtgagg cacctatctc agcgatctgt ctatttcgtt catccatagt tgcctgactc    6300
cccgtcgtgt agataactac gatacgggag ggcttaccat ctggccccag tgctgcaatg    6360
```

```
ataccgcgag acccacgctc accggctcca gatttatcag caataaacca gccagccgga    6420
agggccgagc gcagaagtgg tcctgcaact ttatccgcct ccatccagtc tattaattgt    6480
tgccgggaag ctagagtaag tagttcgcca gttaatagtt tgcgcaacgt tgttgccatt    6540
gctacaggca tcgtggtgtc acgctcgtcg tttggtatgg cttcattcag ctccggttcc    6600
caacgatcaa ggcgagttac atgatccccc atgttgtgca aaaaagcggt tagctccttc    6660
ggtcctccga tcgttgtcag aagtaagttg gccgcagtgt tatcactcat ggttatggca    6720
gcactgcata attctcttac tgtcatgcca tccgtaagat gcttttctgt gactggtgag    6780
tactcaacca agtcattctg agaatagtgt atgcggcgac cgagttgctc ttgcccggcg    6840
tcaatacggg ataataccgc gccacatagc agaactttaa aagtgctcat cattggaaaa    6900
cgttcttcgg ggcgaaaact ctcaaggatc ttaccgctgt tgagatccag ttcgatgtaa    6960
cccactcgtg cacccaactg atcttcagca tcttttactt tcaccagcgt ttctgggtga    7020
gcaaaaacag gaaggcaaaa tgccgcaaaa aagggaataa gggcgacacg gaaatgttga    7080
atactcatac tcttcctttt tcaatattat tgaagcattt atcagggtta ttgtctcatg    7140
gccatttagg cct                                                       7153

<210> SEQ ID NO 13
<211> LENGTH: 7147
<212> TYPE: DNA
<213> ORGANISM: Artificial Sequence
<220> FEATURE:
<223> OTHER INFORMATION: Expression construct

<400> SEQUENCE: 13
ctagagttgt gaagtcggta atcccgctgt atagtaatac gagtcgcatc taaatactcc      60
gaagctgctg cgaacccgga gaatcgagat gtgctggaaa gcttctagcg agcggctaaa     120
ttagcatgaa aggctatgag aaattctgga gacggcttgt tgaatcatgg cgttccattc     180
ttcgacaagc aaagcgttcc gtcgcagtag caggcactca ttcccgaaaa aactcggaga     240
ttcctaagta gcgatggaac cggaataata taataggcaa tacattgagt tgcctcgacg     300
gttgcaatgc aggggtactg agcttggaca taactgttcc gtaccccacc tcttctcaac     360
cttttggcgtt tccctgattc agcgtacccg tacaagtcgt aatcactatt aacccagact     420
gaccggacgt gttttgccct tcatttggag aaataatgtc attgcgatgt gtaatttgcc     480
tgcttgaccg actggggctg ttcgaagccc gaatgtagga ttgttatccg aactctgctc     540
gtagaggcat gttgtgaatc tgtgtcgggc aggacacgcc tcgaaggttc acggcaaggg    600
aaaccaccga tagcagtgtc tagtagcaac ctgtaaagcc gcaatgcagc atcactggaa    660
aatacaaacc aatggctaaa agtacataag ttaatgccta aagaagtcat ataccagcgg    720
ctaataattg tacaatcaag tggctaaacg taccgtaatt tgccaacggc ttgtgggtt     780
gcagaagcaa cggcaaagcc ccacttcccc acgtttgttt cttcactcag tccaatctca    840
gctggtgatc cccaattgg gtcgcttgtt tgttccggtg aagtgaaaga agacagaggt    900
aagaatgtct gactcggagc gttttgcata caaccaaggg cagtgatgga agacagtgaa    960
atgttgacat tcaaggagta tttagccagg atgcttgagt gtatcgtgt aaggaggttt   1020
gtctgccgat acgacgaata ctgtatagtc acttctgatg aagtggtcca tattgaaatg    1080
taagtcggca ctgaacaggc aaaagattga gttgaaactg cctaagatct cgggccctcg   1140
ggccttcggc ctttgggtgt acatgttgt gctccggca aatgcaaagt gtggtaggat    1200
cgaacacact gctgccttta ccaagcagct gagggtatgt gataggcaaa tgttcagggg   1260
```

-continued

```
ccactgcatg gtttcgaata gaaagagaag cttagccaag aacaatagcc gataaagata      1320
gcctcattaa acggaatgag ctagtaggca aagtcagcga atgtgtatat ataaaggttc      1380
gaggtccgtg cctccctcat gctctcccca tctactcatc aactcagatc ctccaggaga      1440
cttgtacacc atcttttgag gcacagaaac ccaatagtca accatcacaa gtttgtacaa      1500
aaaagcaggc ttcaccatgc agaccttcgg tgcttttctc gtttccttcc tcgccgccag      1560
gtaagttggc cttgatgaac catatcatat atcgccgaga agtggaccgc gtgctgagac      1620
tgagacagcg gcctggccgc ggccaacgct cctggtggac ctggtggtca cggccgcaag      1680
ctccccgtca accccaagac cttccccaac gagatccgcc tcaaggacct cctccacggc      1740
agccagaagc tcgaagattt cgcctacgcc taccccgagc gcaaccgcgt ctttggcggc      1800
caggcccacc tcgacaccgt caactacctc taccgcgagc tgaagaagac cggctactac      1860
gacgtctaca agcagcccca ggtgcaccag tggacccgag ccgaccagtc tctcactctc      1920
ggcggcgaca gcatccaggc cagcaccatg acctacagcc cagcgtcaa cgtcaccgcc       1980
cctctcagcc tcgtcagcaa gctcggctgc gccgagggcg actacagcgc cgatgtcaag      2040
ggcaagatcg ccctcgtcag ccgaggcgag tgcagcttcg cccagaagtc cgtcctcagc      2100
gccaaggctg gcgccgtcgc caccatcgtc tacaacaacg tcgacggcag cctcgccggc      2160
acccttggcg gagctacttc tgagctgggc ccctactccc ccatcatcgg catcactctc      2220
gccgctggcc aggacctcgt cgcccgactt caggccgctc ctaccgaggt cagcctctgg      2280
atcgacagca aggtcgagaa ccgcaccacc tacaacgtca ttgcccagac caagggcggc      2340
gaccccaaca acgtcgtcgc ctcggcggc cacaccgaca gcgttgagaa cggccctggc        2400
atcaacgacg acggctccgg cgtcatcagc aacctcgtcg tcgccaaggc cctcacccgc      2460
tacagcgtca agaacgccgt ccgcttctgc ttctggaccg ccgaagagtt cggcctcctc      2520
ggcagcaact actacgtcga caacctcagc cctgccgagc tggccaagat ccgcctctac      2580
ctcaacttcg acatgatcgc cagccccaac tacgccctca tgatctacga cggcgacggc      2640
agcgccttca acctcactgg accccctggc agcgcccaga tcgagagcct cttcgagaac      2700
tactacaaga gcatcaagca gggcttcgtc cccaccgcct tcgacggccg atctgactac      2760
gagggcttca tcctcaaggg catccccgct ggcggcgtct ttactggcgc cgagagcctc      2820
aagaccgagg aacaggcccg cctgttcggc ggccaggctg gcgttgctct cgacgccaac      2880
taccacgcca agggcgacaa catgaccaac ctcaaccaca aggcctttct catcaacagc      2940
cgcgccacgg ccttcgccgt cgctacctac gccaacaacc tcagcagcat ccccctcgc       3000
aacgccaccg tcgtcaagcg cgagagcatg aagtggacca agcgcgagga accccacacc      3060
cacggcgccg acactggctg ctttgccagc cgcgtcaagg agtaagaccc agctttcttg      3120
tacaaagtgg tgatcgcgcc agctccgtgc gaaagcctga cgcaccggta gattcttggt      3180
gagcccgtat catgacggcg gcgggagcta catggcccg ggtgatttat tttttttgta        3240
tctacttctg accctttca aatatacggt caactcatct ttcactggag atgcggcctg       3300
cttggtattg cgatgttgtc agcttggcaa attgtggctt tcgaaaacac aaaacgattc      3360
cttagtagcc atgcatttta agataacgga atagaagaaa gaggaaatta aaaaaaaaaa      3420
aaaaacaaac atcccgttca taacccgtag aatcgccgct cttcggctag ctagttacgc      3480
ttgtttattt acgacaagat ctagaagatt cgagatagaa taataataat aacaacaatt      3540
tgcctcttct ttccaccttt tcagtcttac tctcccttct gacattgaac gcctcaatca      3600
```

```
gtcagtcgcc ttgtacttgg cacggtaatc ctccgtgttc ttgatatcct caggggtagc      3660
aaagcccttc atgccatcga taatgtcatc cagagtgagg atggcaaaga tggggatgcc      3720
gtactccttc ctcagctcgc caatggcact cggtccaggc ttggagtcgt cgccatccgc      3780
agcggggagc ttctccatgc ggtccagggc cacgacgatg ccggcgacga tgccgccctc      3840
cttggtgatc ttctcaatgg cgtccctctt ggcggtgccg gcggtgatga cgtcgtcgac      3900
aatcaggacc ctcttgccct tgagcgaagc gccgacgatg ttgccgccct cgccgtggtc      3960
cttggcctcc ttgcggtcaa acgagtagga gacgcggtcc aggttctggg gcgccagctc      4020
gccgagcttg atggtgatgg cggagcacag cgggatgccc ttgtaggccg ggccgaagac      4080
gatgtcgaac tctaggccgg ccttctcctg ggcctcgatg atggtctttg caaaggcgga      4140
ggcgatggcg ccggcgaggc gcgccgtgtg gaattcgccc gcgttgaaga agtaggggga      4200
tatccgcttg gacttgagct cgaagctgcc aaacttgagg acgccgccgt cgatggcgga      4260
tttgaggaag tcctgcttgt aggcaggcag ctgggaggtg gtagccattc tgttggattt      4320
ggatagtgtc cttattctct gatttgaaca gtagatcagg acgagtgaga gggatgcaga      4380
ggttggattg gagtggttga gctataaaat ttagaggcgc gccgtatcga gttttcacat      4440
ggaagtcaaa gcgtacagtg cgagcttgta cgttggtctt agtatcccac aagcttctgt      4500
ctaggtatga tgatggctat aagtcaccca aggcagaact catcttgaag attgtctaga      4560
gtgattttac cgctgatgaa atgactggac tccctcctcc tgctcttata cgaaaaattg      4620
cctgactctg caaaggttgt ttgtcttgga agatgatgtg ccccccatc gctcttatct       4680 catacccgc catctttcta gattctcatc ttcaacaaga ggggcaatcc atgatctgcg       4740
atccagatgt gcttctggcc tcatactctg ccttcaggtt gatgttcact taattggtga      4800
cgaattcagc tgatttgctg cagtatgctt tgtgttggtt cttccaggc ttgtgccagc       4860 catgagcgct ttgagagcat gttgtcacct ataaactcga gtaacggcca catattgttc      4920
actacttgaa tcacatacct aattttgata gaattgacat gtttaaagag ctgaggtagc      4980
tttaatgcct ctgaagtatt gtgacacagc ttctcacaga gtgagaatga aaagttggac      5040 tcccctaat gaagtaaaag tttcgtctct gaacggtgaa gagcatagat ccggcatcaa       5100
ctacctggct agactacgac gtcaattctg cggccttttg acctttatat atgtccatta     5160
atgcaataga ttcttttttt tttttttttt tttttttttt tttttttttt ttttgcccaa      5220
tttcgcagat caaagtggac gttatagcat cataactaag ctcagttgct gagggaagcc     5280
gtctactacc ttagcccatc catccagctc cataccttga tactttagac gtgaagcaat     5340
tcacactgta cgtctcgcag ctctccttcc cgctcttgct tccccactgg ggtccatggt      5400
gcgtgtatcg tcccctcctt aattaaggcc atttaggccg ttgctggcgt ttttccatag     5460
gctccgcccc cctgacgagc atcacaaaaa tcgacgctca agtcagaggt ggcgaaaccc     5520
gacaggacta taaagatacc aggcgtttcc cctggaagc tccctcgtgc gctctcctgt      5580
tccgaccctg ccgcttaccg gatacctgtc cgcctttctc ccttcgggaa gcgtggcgct     5640
ttctcatagc tcacgctgta ggtatctcag ttcggtgtag gtcgttcgct ccaagctggg    5700
ctgtgtgcac gaacccccg ttcagcccga ccgctgcgcc ttatccggta actatcgtct     5760
tgagtccaac ccggtaagac acgacttatc gccactggca gcagccactg gtaacaggat    5820
tagcagagcg aggtatgtag gcggtgctac agagttcttg aagtggtggc ctaactacgg    5880
ctacactaga aggacagtat ttggtatctg cgctctgctg aagccagtta ccttcggaaa    5940
aagagttggt agctcttgat ccggcaaaca aaccaccgct ggtagcggtg gtttttttgt    6000
```

```
ttgcaagcag cagattacgc gcagaaaaaa aggatctcaa gaagatcctt tgatcttttc   6060 tacgggtct gacgctcagt ggaacgaaaa ctcacgttaa ggcctgcagg gccgattttg    6120
gtcatgagat tatcaaaaag gatcttcacc tagatccttt taaattaaaa atgaagtttt   6180
aaatcaatct aaagtatata tgagtaaact tggtctgaca gttaccaatg cttaatcagt   6240
gaggcaccta tctcagcgat ctgtctattt cgttcatcca tagttgcctg actccccgtc   6300
gtgtagataa ctacgatacg ggagggctta ccatctggcc ccagtgctgc aatgataccg   6360
cgagacccac gctcaccggc tccagattta tcagcaataa accagccagc cggaagggcc   6420
gagcgcagaa gtggtcctgc aactttatcc gcctccatcc agtctattaa ttgttgccgg   6480
gaagctagag taagtagttc gccagttaat agtttgcgca acgttgttgc cattgctaca   6540
ggcatcgtgg tgtcacgctc gtcgtttggt atggcttcat tcagctccgg ttcccaacga   6600
tcaaggcgag ttacatgatc ccccatgttg tgcaaaaaag cggttagctc cttcggtcct   6660
ccgatcgttg tcagaagtaa gttggccgca gtgttatcac tcatggttat ggcagcactg   6720
cataattctc ttactgtcat gccatccgta agatgctttt ctgtgactgg tgagtactca   6780
accaagtcat tctgagaata gtgtatgcgg cgaccgagtt gctcttgccc ggcgtcaata   6840
cgggataata ccgcgccaca tagcagaact ttaaaagtgc tcatcattgg aaaacgttct   6900
tcggggcgaa aactctcaag gatcttaccg ctgttgagat ccagttcgat gtaacccact   6960
cgtgcaccca actgatcttc agcatctttt actttcacca gcgtttctgg gtgagcaaaa   7020
acaggaaggc aaaatgccgc aaaaaaggga ataagggcga cacggaaatg ttgaatactc   7080
atactcttcc ttttcaata ttattgaagc atttatcagg gttattgtct catgccatt    7140 taggcct                                                             7147
```

<210> SEQ ID NO 14
<211> LENGTH: 7171
<212> TYPE: DNA
<213> ORGANISM: Artificial Sequence
<220> FEATURE:
<223> OTHER INFORMATION: Expression construct

<400> SEQUENCE: 14

```
ctagagttgt gaagtcggta atcccgctgt atagtaatac gagtcgcatc taaatactcc     60
gaagctgctg cgaacccgga gaatcgagat gtgctggaaa gcttctagcg agcggctaaa   120
ttagcatgaa aggctatgag aaattctgga gacggcttgt tgaatcatgg cgttccattc   180
ttcgacaagc aaagcgttcc gtcgcagtag caggcactca ttcccgaaaa aactcggaga   240
ttcctaagta gcgatggaac cggaataata taataggcaa tacattgagt tgcctcgacg   300
gttgcaatgc aggggtactg agcttggaca taactgttcc gtaccccacc tcttctcaac   360
ctttggcgtt tccctgattc agcgtacccg tacaagtcgt aatcactatt aacccagact   420
gaccggacgt gttttgccct tcatttggag aaataatgtc attgcgatgt gtaatttgcc   480
tgcttgaccg actggggctg ttcgaagccc gaatgtagga ttgttatccg aactctgctc   540
gtagaggcat gttgtgaatc tgtgtcgggc aggacacgcc tcgaaggttc acggcaaggg   600
aaaccaccga tagcagtgtc tagtagcaac ctgtaaagcc gcaatgcagc atcactggaa   660
aatacaaacc aatggctaaa agtacataag ttaatgccta agaagtcat ataccagcgg    720 ctaataattg tacaatcaag tggctaaacg taccgtaatt tgccaacggc ttgtggggtt   780
gcagaagcaa cggcaaagcc ccacttcccc acgtttgttt cttcactcag tccaatctca   840
```

```
gctggtgatc ccccaattgg gtcgcttgtt tgttccggtg aagtgaaaga agacagaggt    900
aagaatgtct gactcggagc gttttgcata caaccaaggg cagtgatgga agacagtgaa    960
atgttgacat tcaaggagta tttagccagg gatgcttgag tgtatcgtgt aaggaggttt   1020
gtctgccgat acgacgaata ctgtatagtc acttctgatg aagtggtcca tattgaaatg   1080
taagtcggca ctgaacaggc aaaagattga gttgaaactg cctaagatct cgggccctcg   1140
ggccttcggc ctttgggtgt acatgtttgt gctccgggca aatgcaaagt gtggtaggat   1200
cgaacacact gctgccttta ccaagcagct gagggtatgt gataggcaaa tgttcagggg   1260
ccactgcatg gtttcgaata aaagagaag cttagccaag aacaatagcc gataaagata   1320
gcctcattaa acggaatgag ctagtaggca aagtcagcga atgtgtatat ataaaggttc   1380
gaggtccgtg cctccctcat gctctcccca tctactcatc aactcagatc ctccaggaga   1440
cttgtacacc atcttttgag gcacagaaac ccaatagtca accatcacaa gtttgtacaa   1500
aaaagcaggc ttcaccatgc agaccttcgg tgcttttctc gtttccttcc tcgccgccag   1560
gtaagttggc cttgatgaac catatcatat atcgccgaga agtggaccgc gtgctgagac   1620
tgagacagcg gcctggccgc ggccggtggc cctcatggat ttggcctccc caagatcgac   1680
ctccgcccta tggtcagcag caaccgcctc cagagcatga tcaccctcaa ggacctcatg   1740
gacggcgcca agaagctcca ggacattgcc accaagaacg gcggcaaccg gcctttggc    1800
ggcgctggcc acaacgccac tgtcgactac ctctacaaga ccctcaccag cctcggcggc   1860
tactacaccg tcaagaagca gcccttcaag gaaatcttca gcagcggcag cggcagcctc   1920
atcgtcgacg gccagggcat cgacgccggc atcatgacct ataccctgg cggcagcgcc   1980
accgccaacc tcgtccaggt tgctaacctc ggctgcgagg acgaggacta ccctgccgag   2040
gtcgccggca acattgccct cattagccgc ggcagctgca ccttcagcag caagagcctc   2100
aaggccaagg ccgctggcgc cgtcggcgct atcgtctaca caacgtcccc cggcgagctg   2160
agcggaaccc tcggcacccc ctttctcgac tacgccccca tcgtcggcat cagccaagag   2220
gacggccagg tcatccttga gaagctcgcc gctggccccg tcaccgccac cctcaacatc   2280
gacgccatcg tcgaggaacg caccacctac aacgtcattg ccgagactaa ggaaggcgac   2340
cacaacaacg tgctcattgt cggcggccac agcgacagcg ttgctgccgg ccctggcatc   2400
aacgacgacg gctctggcac catcggcatc ctcaccgtcg ccaaggccct cgccaaggcc   2460
aacgtccgca tcaagaacgc cgtccgcttc gccttctggt ccgccgaaga gttcggcctc   2520
ctcggcagct acgcctacat gaagtccctc aacgagagcg aggccgaggt ggccaagatc   2580
cgcgcctacc tcaacttcga catgatcgcc agccccaact acatctacgg catctacgac   2640
ggcgacggca acgccttcaa cctcactggc cctgccggca gcgacatcat cgagaaggac   2700
ttcgaggact tcttcaagaa gaagaagacc cccagcgtcc ccaccgagtt cagcggccga   2760
tctgactacg ccgccttcat cgagaacggc atccccagcg gcggactctt cactggcgcc   2820
gaggtcctca agaccgagga agaggccaag ctgttcggcg gcaaggccgg cgtcgcctac   2880
gacgtcaact accacaaggc cggcgacacc gtcgacaacc tcgccaagga cgccttcctg   2940
ctcaacacca aggccattgc caacagcgtc gccaagtacg ccgccagctg ggccggcttt   3000
cctaagcctt ctgccgtccg ccgacgctac gacgccgata tggcccagct cctcaagcgc   3060
tctggcggcg ttcatggcca cggccctcac actcatagcg gcccttgtgg cggcggtgac   3120
ctcctctaag acccagcttt cttgtacaaa gtggtgatcg cgccagctcc gtgcgaaagc   3180
ctgacgcacc ggtagattct tggtgagccc gtatcatgac ggcggcggga gctacatggc   3240
```

```
cccgggtgat ttattttttt tgtatctact tctgaccctt ttcaaatata cggtcaactc    3300
atctttcact ggagatgcgg cctgcttggt attgcgatgt tgtcagcttg gcaaattgtg    3360
gctttcgaaa acacaaaacg attccttagt agccatgcat tttaagataa cggaatagaa    3420
gaaagaggaa attaaaaaaa aaaaaaaaac aaacatcccg ttcataaccc gtagaatcgc    3480
cgctcttcgg ctagctagtt acgcttgttt atttacgaca agatctagaa gattcgagat    3540
agaataataa taataacaac aatttgcctc ttctttccac cttttcagtc ttactctccc    3600
ttctgacatt gaacgcctca atcagtcagt cgccttgtac ttggcacggt aatcctccgt    3660
gttcttgata tcctcagggg tagcaaagcc cttcatgcca tcgataatgt catccagagt    3720
gaggatggca agatgggga tgccgtactc cttcctcagc tcgccaatgg cactcggtcc    3780
aggcttggag tcgtcgccat ccgcagcggg gagcttctcc atgcggtcca gggccacgac    3840
gatgccggcg acgatgccgc cctccttggt gatcttctca atggcgtccc tcttggcggt    3900
gccggcggtg atgacgtcgt cgacaatcag gaccctcttg cccttgagcg aagcgccgac    3960
gatgttgccg ccctcgccgt ggtccttggc ctccttgcgg tcaaacgagt aggagacgcg    4020
gtccaggttc tggggcgcca gctcgccgag cttgatggtg atggcggagc acagcgggat    4080
gcccttgtag gccgggccga agacgatgtc gaactctagg ccggccttct cctgggcctc    4140
gatgatggtc tttgcaaagg cggaggcgat ggcgccggcg aggcgcgccg tgtgaattc    4200 gcccgcgttg aagaagtagg gggatatccg cttggacttg agctcgaagc tgccaaactt    4260
gaggacgccg ccgtcgatgg cggatttgag gaagtcctgc ttgtaggcag gcagctggga    4320
ggtggtagcc attctgttgg atttggatag tgtccttatt ctctgatttg aacagtagat    4380
caggacgagt gagagggatg cagaggttgg attggagtgg ttgagctata aaatttagag    4440
gcgcgccgta tcgagttttc acatggaagt caaagcgtac agtgcgagct tgtacgttgg    4500
tcttagtatc ccacaagctt ctgtctaggt atgatgatgg ctataagtca cccaaggcag    4560
aactcatctt gaagattgtc tagagtgatt ttaccgctga tgaaatgact ggactccctc    4620
ctcctgctct tatacgaaaa attgcctgac tctgcaaagg ttgtttgtct tggaagatga    4680
tgtgcccccc catcgctctt atctcatacc ccgccatctt tctagattct catcttcaac    4740 aagagggca atccatgatc tgcgatccag atgtgcttct ggcctcatac tctgccttca    4800
ggttgatgtt cacttaattg gtgacgaatt cagctgattt gctgcagtat gctttgtgtt    4860
ggttctttcc aggcttgtgc cagccatgag cgctttgaga gcatgttgtc acctataaac    4920
tcgagtaacg gccacatatt gttcactact tgaatcacat acctaatttt gatagaattg    4980
acatgtttaa agagctgagg tagctttaat gcctctgaag tattgtgaca cagcttctca    5040
cagagtgaga atgaaaagtt ggactccccc taatgaagta aaagtttcgt ctctgaacgg    5100
tgaagagcat agatccggca tcaactacct ggctagacta cgacgtcaat tctgcggcct    5160
tttgaccttt atatatgtcc attaatgcaa tagattcttt tttttttttt ttttttttt    5220 ttttttttt tttttttgc ccaatttcgc agatcaaagt ggacgttata gcatcataac    5280
taagctcagt tgctgaggga agccgtctac taccttagcc catccatcca gctccatacc    5340
ttgatacttt agacgtgaag caattcacac tgtacgtctc gcagctctcc ttcccgctct    5400
tgcttcccca ctggggtcca tggtgcgtgt atcgtcccct ccttaattaa ggccatttag    5460
gccgttgctg gcgttttcc ataggctccg cccccctgac gagcatcaca aaaatcgacg    5520
ctcaagtcag aggtggcgaa acccgacagg actataaaga taccaggcgt ttcccctgg    5580
```

-continued

| | |
|---|---|
| aagctccctc gtgcgctctc ctgttccgac cctgccgctt accggatacc tgtccgcctt | 5640 |
| tctcccttcg ggaagcgtgg cgctttctca tagctcacgc tgtaggtatc tcagttcggt | 5700 |
| gtaggtcgtt cgctccaagc tgggctgtgt gcacgaaccc cccgttcagc ccgaccgctg | 5760 |
| cgccttatcc ggtaactatc gtcttgagtc caacccggta agacacgact tatcgccact | 5820 |
| ggcagcagcc actggtaaca ggattagcag agcgaggtat gtaggcggtg ctacagagtt | 5880 |
| cttgaagtgg tggcctaact acggctacac tagaaggaca gtatttggta tctgcgctct | 5940 |
| gctgaagcca gttaccttcg gaaaaagagt tggtagctct tgatccggca aacaaaccac | 6000 |
| cgctggtagc ggtggttttt ttgtttgcaa gcagcagatt acgcgcagaa aaaaaggatc | 6060 |
| tcaagaagat cctttgatct tttctacggg gtctgacgct cagtggaacg aaaactcacg | 6120 |
| ttaaggcctg cagggccgat tttggtcatg agattatcaa aaaggatctt cacctagatc | 6180 |
| cttttaaatt aaaaatgaag ttttaaatca atctaaagta tatatgagta aacttggtct | 6240 |
| gacagttacc aatgcttaat cagtgaggca cctatctcag cgatctgtct atttcgttca | 6300 |
| tccatagttg cctgactccc cgtcgtgtag ataactacga tacgggaggg cttaccatct | 6360 |
| ggccccagtg ctgcaatgat accgcgagac ccacgctcac cggctccaga tttatcagca | 6420 |
| ataaaccagc cagccggaag ggccgagcgc agaagtggtc ctgcaacttt atccgcctcc | 6480 |
| atccagtcta ttaattgttg ccgggaagct agagtaagta gttcgccagt taatagtttg | 6540 |
| cgcaacgttg ttgccattgc tacaggcatc gtggtgtcac gctcgtcgtt tggtatggct | 6600 |
| tcattcagct ccggttccca acgatcaagg cgagttacat gatcccccat gttgtgcaaa | 6660 |
| aaagcggtta gctccttcgg tcctccgatc gttgtcagaa gtaagttggc cgcagtgtta | 6720 |
| tcactcatgg ttatggcagc actgcataat tctcttactg tcatgccatc cgtaagatgc | 6780 |
| ttttctgtga ctggtgagta ctcaaccaag tcattctgag aatagtgtat gcggcgaccg | 6840 |
| agttgctctt gcccggcgtc aatacgggat aataccgcgc cacatagcag aactttaaaa | 6900 |
| gtgctcatca ttggaaaacg ttcttcgggg cgaaaactct caaggatctt accgctgttg | 6960 |
| agatccagtt cgatgtaacc cactcgtgca cccaactgat cttcagcatc ttttactttc | 7020 |
| accagcgttt ctgggtgagc aaaaacagga aggcaaaatg ccgcaaaaaa gggaataagg | 7080 |
| gcgacacgga aatgttgaat actcatactc ttcctttttc aatattattg aagcatttat | 7140 |
| cagggttatt gtctcatggc catttaggcc t | 7171 |

<210> SEQ ID NO 15
<211> LENGTH: 7153
<212> TYPE: DNA
<213> ORGANISM: Artificial Sequence
<220> FEATURE:
<223> OTHER INFORMATION: Expression construct

<400> SEQUENCE: 15

| | |
|---|---|
| ctagagttgt gaagtcggta atcccgctgt atagtaatac gagtcgcatc taaatactcc | 60 |
| gaagctgctg cgaacccgga gaatcgagat gtgctggaaa gcttctagcg agcggctaaa | 120 |
| ttagcatgaa aggctatgag aaattctgga gacggcttgt tgaatcatgg cgttccattc | 180 |
| ttcgacaagc aaagcgttcc gtcgcagtag caggcactca ttcccgaaaa aactcggaga | 240 |
| ttcctaagta gcgatggaac cggaataata taataggcaa tacattgagt tgcctcgacg | 300 |
| gttgcaatgc aggggtactg agcttggaca taactgttcc gtaccccacc tcttctcaac | 360 |
| cttttggcgtt tccctgattc agcgtacccg tacaagtcg aatcactatt aacccagact | 420 |
| gaccggacgt gttttgccct tcatttggag aaataatgtc attgcgatgt gtaatttgcc | 480 |

```
tgcttgaccg actggggctg ttcgaagccc gaatgtagga ttgttatccg aactctgctc    540
gtagaggcat gttgtgaatc tgtgtcgggc aggacacgcc tcgaaggttc acggcaaggg    600
aaaccaccga tagcagtgtc tagtagcaac ctgtaaagcc gcaatgcagc atcactggaa    660
aatacaaacc aatggctaaa agtacataag ttaatgccta agaagtcat ataccagcgg     720 ctaataattg tacaatcaag tggctaaacg taccgtaatt tgccaacggc ttgtggggtt    780
gcagaagcaa cggcaaagcc ccacttcccc acgtttgttt cttcactcag tccaatctca    840
gctggtgatc ccccaattgg gtcgcttgtt tgttccggtg aagtgaaaga agacagaggt    900
aagaatgtct gactcggagc gttttgcata caaccaaggg cagtgatgga agacagtgaa    960
atgttgacat tcaaggagta tttagccagg gatgcttgag tgtatcgtgt aaggaggttt    1020
gtctgccgat acgacgaata ctgtatagtc acttctgatg aagtggtcca tattgaaatg    1080
taagtcggca ctgaacaggc aaaagattga gttgaaactg cctaagatct cgggccctcg    1140
ggccttcggc ctttgggtgt acatgtttgt gctccgggca aatgcaaagt gtggtaggat    1200
cgaacacact gctgccttta ccaagcagct gagggtatgt gataggcaaa tgttcagggg    1260
ccactgcatg gtttcgaata aaagagaag cttagccaag aacaatagcc gataaagata     1320
gcctcattaa acggaatgag ctagtaggca aagtcagcga atgtgtatat ataaaggttc    1380
gaggtccgtg cctccctcat gctctcccca tctactcatc aactcagatc ctccaggaga    1440
cttgtacacc atcttttgag gcacagaaac ccaatagtca accatcacaa gtttgtacaa    1500
aaaagcaggc ttcaccatgc agaccttcgg tgcttttctc gtttccttcc tcgccgccag    1560
gtaagttggc cttgatgaac catatcatat atcgccgaga agtggaccgc gtgctgagac    1620
tgagacagcg gcctggccgc ggccgaggga cttggaaacc acggccgaaa gctcgacccc    1680
aacaagttca ccaaggatat caagctcaag gacctcctca agggcagcca gaagctcgaa    1740
gatttcgcct acgcctaccc cgagcgcaac cgcgtctttg gcggcaaggc ccaccaggac    1800
accgtcaact ggatctacaa cgagctgaag aagaccggct actacgacgt ctacaagcag    1860
ccccaggtcc acctctggtc caacgccgag cagagcctca ccgtcgatgg cgaggccatc    1920
gacgccacca ccatgaccta cagccccagc ctcaaggaaa ccaccgccga ggtcgtcgtc    1980
gtccctggcc ttggctgcac tgccgccgac taccctgctg acgtcgccgg caagatcgcc    2040
ctcattcagc gcggcagctg caccttcggc gagaagtccg tctacgccgc tgccgccaac    2100
gccgctgctg ccatcgtcta caacaacgtc gacggcagcc tcagcggcac cctcggcgct    2160
gctacttctg agctgggccc ctacgccccc atcgtcggca tttctctcgc cgacggccag    2220
aacctcgtca gcctcgctca ggctggcccc ctgaccgtcg acctctacat caacagccag    2280
atggaaaacc gcaccaccca aacgtcatt gccaagagca agggcggcga ccctaacaac     2340
gtcatcgtca tcggcggcca cagcgacgcc gtcaaccagg acctggcgt caacgatgac     2400 ggcagcggca tcatcagcaa cctcgtgatc gccaaggccc tcaccaagta cagcctcaag    2460
aacagcgtca cctgggcctt ttggaccgcc gaagagttcg gcctcctcgg cagcgagttc    2520
tacgtcaaca gcctctctgc cgccgagaag gacaagatca gctctaccct caacttcgac    2580
atgatcgcca gccccaacta cgccctcatg atctacgacg gcgacggcag caccttcaac    2640
atgaccggcc ctgccggctc cgccgagatc gagcacctct tcgaggacta ctacaagtct    2700
cgcgccctca gctacatccc caccgccttt gacggccgca gcgactacga ggccttcatc    2760
ctcaacggca tccccgctgg cggcctcttc actggcgccg agcagatcaa gaccgaggaa    2820
```

| | |
|---|---|
| caggtcgcca tgttcggcgg ccaggctggc gtcgcctacg accccaacta tcacgccgct | 2880 |
| ggcgacaaca tgaccaacct cagcgaggaa gccttcctca tcaacagcaa ggccaccgcc | 2940 |
| ttcgccgtcg ccacctacgc caacagcctt gagagcatcc ccctcgcaa cgccaccatg | 3000 |
| agcatccaga cccgctctgc ctctcgccga gccgctgctc atcgacgagc cgccaagcct | 3060 |
| cactctcact ctggcggcac tggctgctgg cacacccgag tcgagctgta agacccagct | 3120 |
| ttcttgtaca aagtggtgat cgcgccagct ccgtgcgaaa gcctgacgca ccggtagatt | 3180 |
| cttggtgagc ccgtatcatg acggcggcgg gagctacatg gccccgggtg atttattttt | 3240 |
| tttgtatcta cttctgaccc ttttcaaata tacggtcaac tcatctttca ctggagatgc | 3300 |
| ggcctgcttg gtattgcgat gttgtcagct tggcaaattg tggctttcga aaacacaaaa | 3360 |
| cgattcctta gtagccatgc attttaagat aacggaatag aagaaagagg aaattaaaaa | 3420 |
| aaaaaaaaaa acaaacatcc cgttcataac ccgtagaatc gccgctcttc ggctagctag | 3480 |
| ttacgcttgt ttatttacga caagatctag aagattcgag atagaataat aataataaca | 3540 |
| acaatttgcc tcttctttcc accttttcag tcttactctc ccttctgaca ttgaacgcct | 3600 |
| caatcagtca gtcgccttgt acttggcacg gtaatcctcc gtgttcttga tatcctcagg | 3660 |
| ggtagcaaag cccttcatgc catcgataat gtcatccaga gtgaggatgg caaagatggg | 3720 |
| gatgccgtac tccttcctca gctcgccaat ggcactcggt ccaggcttgg agtcgtcgcc | 3780 |
| atccgcagcg gggagcttct ccatgcggtc cagggccacg acgatgccgg cgacgatgcc | 3840 |
| gccctccttg gtgatcttct caatggcgtc cctcttggcg gtgccggcgg tgatgacgtc | 3900 |
| gtcgacaatc aggaccctct tgcccttgag cgaagcgccg acgatgttgc cgccctcgcc | 3960 |
| gtggtccttg gcctccttgc ggtcaaacga gtaggagacg cggtccaggt tctggggcgc | 4020 |
| cagctcgccg agcttgatgg tgatggcgga gcacagcggg atgcccttgt aggccgggcc | 4080 |
| gaagacgatg tcgaactcta ggccggcctt ctcctgggcc tcgatgatgg tctttgcaaa | 4140 |
| ggcggaggcg atggcgccgg cgaggcgcgc cgtgtggaat tcgcccgcgt tgaagaagta | 4200 |
| gggggatatc cgcttggact tgagctcgaa gctgccaaac ttgaggacgc cgccgtcgat | 4260 |
| ggcggatttg aggaagtcct gcttgtaggc aggcagctgg gaggtggtag ccattctgtt | 4320 |
| ggatttggat agtgtcctta ttctctgatt tgaacagtag atcaggacga gtgagaggga | 4380 |
| tgcagaggtt ggattggagt ggttgagcta taaaatttag aggcgcgccg tatcgagttt | 4440 |
| tcacatggaa gtcaaagcgt acagtgcgag cttgtacgtt ggtcttagta tcccacaagc | 4500 |
| ttctgtctag gtatgatgat ggctataagt cacccaaggc agaactcatc ttgaagattg | 4560 |
| tctagagtga ttttaccgct gatgaaatga ctggactccc tcctcctgct cttatacgaa | 4620 |
| aaattgcctg actctgcaaa ggttgtttgt cttggaagat gatgtgcccc ccatcgctc | 4680 |
| ttatctcata ccccgccatc tttctagatt ctcatcttca acaagagggg caatccatga | 4740 |
| tctgcgatcc agatgtgctt ctggcctcat actctgcctt caggttgatg ttcacttaat | 4800 |
| tggtgacgaa ttcagctgat ttgctgcagt atgctttgtg ttggttcttt ccaggcttgt | 4860 |
| gccagccatg agcgctttga gagcatgttg tcacctataa actcgagtaa cggccacata | 4920 |
| ttgttcacta cttgaatcac ataccctaatt ttgatagaat tgcatgtttt aaagagctga | 4980 |
| ggtagcttta atgcctctga agtattgtga cacagcttct cacagagtga gaatgaaaag | 5040 |
| ttggactccc cctaatgaag taaaagtttc gtctctgaac ggtgaagagc atagatccgg | 5100 |
| catcaactac ctggctagac tacgacgtca attctgcggc ctttttgacct ttatatatgt | 5160 |
| ccattaatgc aatagattct tttttttttt tttttttttt tttttttttt tttttttttt | 5220 |

```
gcccaatttc gcagatcaaa gtggacgtta tagcatcata actaagctca gttgctgagg    5280
gaagccgtct actaccttag cccatccatc cagctccata ccttgatact ttagacgtga    5340
agcaattcac actgtacgtc tcgcagctct ccttcccgct cttgcttccc cactggggtc    5400
catggtgcgt gtatcgtccc ctccttaatt aaggccattt aggccgttgc tggcgttttt    5460
ccataggctc cgccccctg acgagcatca caaaaatcga cgctcaagtc agaggtggcg    5520
aaacccgaca ggactataaa gataccaggc gtttccccct ggaagctccc tcgtgcgctc    5580
tcctgttccg accctgccgc ttaccggata cctgtccgcc tttctccctt cgggaagcgt    5640
ggcgctttct catagctcac gctgtaggta tctcagttcg gtgtaggtcg ttcgctccaa    5700
gctgggctgt gtgcacgaac cccccgttca gcccgaccgc tgcgccttat ccggtaacta    5760
tcgtcttgag tccaacccgg taagacacga cttatcgcca ctggcagcag ccactggtaa    5820
caggattagc agagcgaggt atgtaggcgg tgctacagag ttcttgaagt ggtggcctaa    5880
ctacggctac actagaagga cagtatttgg tatctgcgct ctgctgaagc cagttacctt    5940
cggaaaaaga gttggtagct cttgatccgg caaacaaacc accgctggta gcggtggttt    6000
ttttgtttgc aagcagcaga ttacgcgcag aaaaaaagga tctcaagaag atcctttgat    6060
cttttctacg gggtctgacg ctcagtggaa cgaaaactca cgttaaggcc tgcagggccg    6120
attttggtca tgagattatc aaaaaggatc ttcacctaga tccttttaaa ttaaaaatga    6180
agttttaaat caatctaaag tatatatgag taaacttggt ctgacagtta ccaatgctta    6240
atcagtgagg cacctatctc agcgatctgt ctatttcgtt catccatagt tgcctgactc    6300
cccgtcgtgt agataactac gatacgggag ggcttaccat ctggccccag tgctgcaatg    6360
ataccgcgag acccacgctc accggctcca gatttatcag caataaacca gccagccgga    6420
agggccgagc gcagaagtgg tcctgcaact ttatccgcct ccatccagtc tattaattgt    6480
tgccgggaag ctagagtaag tagttcgcca gttaatagtt tgcgcaacgt tgttgccatt    6540
gctacaggca tcgtggtgtc acgctcgtcg tttggtatgg cttcattcag ctccggttcc    6600
caacgatcaa ggcgagttac atgatccccc atgttgtgca aaaaagcggt tagctccttc    6660
ggtcctccga tcgttgtcag aagtaagttg gccgcagtgt tatcactcat ggttatggca    6720
gcactgcata attctcttac tgtcatgcca tccgtaagat gcttttctgt gactggtgag    6780
tactcaacca agtcattctg agaatagtgt atgcggcgac cgagttgctc ttgcccggcg    6840
tcaatacggg ataataccgc gccacatagc agaactttaa agtgctcat cattggaaaa    6900 cgttcttcgg ggcgaaaact ctcaaggatc ttaccgctgt tgagatccag ttcgatgtaa    6960
cccactcgtg cacccaactg atcttcagca tcttttactt tcaccagcgt ttctgggtga    7020
gcaaaaacag gaaggcaaaa tgccgcaaaa aagggaataa gggcgacacg gaaatgttga    7080
atactcatac tcttcctttt tcaatattat tgaagcattt atcagggtta ttgtctcatg    7140
gccatttagg cct                                                      7153

<210> SEQ ID NO 16
<211> LENGTH: 7147
<212> TYPE: DNA
<213> ORGANISM: Artificial Sequence
<220> FEATURE:
<223> OTHER INFORMATION: Expression construct

<400> SEQUENCE: 16
ctagagttgt gaagtcggta atcccgctgt atagtaatac gagtcgcatc taaatactcc      60
```

```
gaagctgctg cgaacccgga gaatcgagat gtgctggaaa gcttctagcg agcggctaaa    120
ttagcatgaa aggctatgag aaattctgga dacggcttgt tgaatcatgg cgttccattc    180
ttcgacaagc aaagcgttcc gtcgcagtag caggcactca ttcccgaaaa aactcggaga    240
ttcctaagta gcgatggaac cggaataata taataggcaa tacattgagt tgcctcgacg    300
gttgcaatgc aggggtactg agcttggaca taactgttcc gtaccccacc tcttctcaac    360
ctttggcgtt tccctgattc agcgtacccg tacaagtcgt aatcactatt aacccagact    420
gaccggacgt gttttgccct tcatttggag aaataatgtc attgcgatgt gtaatttgcc    480
tgcttgaccg actggggctg ttcgaagccc aatgtagga ttgttatccg aactctgctc    540
gtagaggcat gttgtgaatc tgtgtcgggc aggacacgcc tcgaaggttc acggcaaggg    600
aaaccaccga tagcagtgtc tagtagcaac ctgtaaagcc gcaatgcagc atcactggaa    660
aatacaaacc aatggctaaa agtacataag ttaatgccta agaagtcat ataccagcgg    720 ctaataattg tacaatcaag tggctaaacg taccgtaatt tgccaacggc ttgtggggtt    780
gcagaagcaa cggcaaagcc ccacttcccc acgtttgttt cttcactcag tccaatctca    840
gctggtgatc ccccaattgg gtcgcttgtt tgttccggtg aagtgaaaga agacagaggt    900
aagaatgtct gactcggagc gttttgcata caaccaaggg cagtgatgga agacagtgaa    960
atgttgacat tcaaggagta tttagccagg gatgcttgag tgtatcgtgt aaggaggttt   1020
gtctgccgat acgacgaata ctgtatagtc acttctgatg aagtggtcca tattgaaatg   1080
taagtcggca ctgaacaggc aaaagattga gttgaaactg cctaagatct cgggccctcg   1140
ggccttcggc ctttgggtgt acatgtttgt gctccgggca aatgcaaagt gtggtaggat   1200
cgaacacact gctgccttta ccaagcagct gagggtatgt gataggcaaa tgttcagggg   1260
ccactgcatg gtttcgaata gaaagagaag cttagccaag aacaatagcc gataaagata   1320
gcctcattaa acggaatgag ctagtaggca aagtcagcga atgtgtatat ataaaggttc   1380
gaggtccgtg cctccctcat gctctcccca tctactcatc aactcagatc ctccaggaga   1440
cttgtacacc atcttttgag gcacagaaac ccaatagtca accatcacaa gtttgtacaa   1500
aaaagcaggc ttcaccatgc agaccttcgg tgcttttctc gtttccttcc tcgccgccag   1560
gtaagttggc cttgatgaac catatcatat atcgccgaga agtggaccgc gtgctgagac   1620
tgagacagcg gcctggccgc ggccggcaag cacaagcctc ttgtcacccc tgaggccctc   1680
caggacctga ttaccctcga cgacctcctc gccggcagcc agcagctcca ggacttcgcc   1740
tacgcctacc ccgagcgcaa ccgcgtcttt ggcggccgag cccacgacga caccgtcaac   1800
tggctctacc gcgagctgaa gcgcaccggc tactaccacg tctacaagca gccccaggtc   1860
cacctctaca gcaacgccga ggaaagcctc accgtcaacg gcgaggccat cgaggccacc   1920
accatgacct acagccccag cgccaacgcc tctgccgagc tggctgtcat cagcggcctt   1980
ggctgctctc ccgccgactt cgcctctgac gtcgccggca aggtcgtcct cgtccagcga   2040
ggcaactgca ccttcggcga gaagtccgtc tacgccgctg ccgccgatgc cgccgctacg   2100
atcgtctaca caacgtcga gggcagcctc agcggcaccc tcggcgctgc tcagtctgag   2160
caaggcccct acagcggcat cgtcggcatc agcctgctg acggcgaggc cctcctcgcc   2220
cttgctgagg aaggccctgt ccacgtcgac ctctggatcg acagcgtcat ggaaaaccgc   2280
accacctaca acgtcattgc ccagaccaag ggcggcgacc ccgacaacgt cgtcactctt   2340
ggcggccaca gcgacagcgt cgaggctggc cctggcatca acgacgacgg cagcggcatc   2400
atcagcaacc tcgtcattgc ccgagccctc accaagttca gcaccaagca cgccgtccgc   2460
```

```
tttttcttct ggaccgccga agagttcggc ctcctcggca gcgactacta cgtcagcagc    2520
ctcagccccg ctgagctggc caagatccgc ctctacctca acttcgacat gatcgccagc    2580
cccaactacg gcctcctcct ctacgatggc gacggcagcg ccttcaacct cactggccct    2640
gctggcagcg acgccatcga gaagctgttc tacgactact ccagagcat cggccaggcc    2700 accgtcgaga ctgagttcga cggccgcagc gactacgagg ccttcatcct caacggcatc    2760
cccgctggcg gcgtctttac tggcgccgag gaaatcaaga gcgaggaaga ggtcgccctc    2820
tggggcggag aggctggcgt cgcctacgac gccaactacc accaggtcgg cgacaccatc    2880
gacaacctca acaccgaggc ctacctgctc aacagcaagg ccaccgcctt cgccgtcgcc    2940
acctacgcca acgacctcag caccatcccc aagcgcgaga tgaccaccgc cgtcaagcga    3000
gccaacgtca acgccacat gcaccgccgc accatgccca agaagcgcca gactgcccac    3060
cgccacgctg ccaagggctg ctttcacagc cgcgtcgagc agtaagaccc agctttcttg    3120
tacaaagtgg tgatcgcgcc agctccgtgc gaaagcctga cgcaccggta gattcttggt    3180
gagcccgtat catgacggcg gcgggagcta catggccccg ggtgatttat ttttttttgta    3240 tctacttctg accctttca aatatacggt caactcatct ttcactggag atgcggcctg    3300
cttggtattg cgatgttgtc agcttggcaa attgtggctt tcgaaaacac aaaacgattc    3360
cttagtagcc atgcatttta agataacgga atagaagaaa gaggaaatta aaaaaaaaa    3420 aaaacaaac atcccgttca taacccgtag aatcgccgct cttcggctag ctagttacgc    3480
ttgtttattt acgacaagat ctagaagatt cgagatagaa taataataat aacaacaatt    3540
tgcctcttct ttccaccttt tcagtcttac tctcccttct gacattgaac gcctcaatca    3600
gtcagtcgcc ttgtacttgg cacggtaatc ctccgtgttc ttgatatcct caggggtagc    3660
aaagcccttc atgccatcga taatgtcatc cagagtgagg atggcaaaga tggggatgcc    3720 gtactcctc ctcagctcgc caatggcact cggtccaggc ttggagtcgt cgccatccgc    3780
agcggggagc ttctccatgc ggtccagggc cacgacgatg ccggcgacga tgccgccctc    3840
cttggtgatc ttctcaatgg cgtccctctt ggcggtgccg gcggtgatga cgtcgtcgac    3900
aatcaggacc ctcttgccct tgagcgaagc gccgacgatg ttgccgccct cgccgtggtc    3960
cttggcctcc ttgcggtcaa acgagtagga gacgcggtcc aggttctggg gcgccagctc    4020
gccgagcttg atggtgatgg cggagcacag cgggatgccc ttgtaggccg ggccgaagac    4080
gatgtcgaac tctaggccgg ccttctcctg ggcctcgatg atggtctttg caaaggcgga    4140
ggcgatggcg ccggcgaggc gcgccgtgtg gaattcgccc gcgttgaaga agtagggga    4200 tatccgcttg gacttgagct cgaagctgcc aaacttgagg acgccgccgt cgatggcgga    4260
tttgaggaag tcctgcttgt aggcaggcag ctggaggtg gtagccattc tgttggattt    4320
ggatagtgtc cttattctct gatttgaaca gtagatcagg acgagtgaga gggatgcaga    4380
ggttggattg gagtggttga gctataaaat ttagaggcgc gccgtatcga gttttcacat    4440
ggaagtcaaa gcgtacagtg cgagcttgta cgttggtctt agtatcccac aagcttctgt    4500
ctaggtatga tgatggctat aagtcaccca aggcagaact catcttgaag attgtctaga    4560
gtgattttac cgctgatgaa atgactggac tccctcctcc tgctcttata cgaaaaattg    4620
cctgactctg caaaggttgt ttgtcttgga agatgatgtg ccccccatc gctcttatct    4680 catacccgc catctttcta gattctcatc ttcaacaaga ggggcaatcc atgatctgcg    4740
atccagatgt gcttctggcc tcatactctg ccttcaggtt gatgttcact taattggtga    4800
```

-continued

```
cgaattcagc tgatttgctg cagtatgctt tgtgttggtt ctttccaggc ttgtgccagc    4860
catgagcgct ttgagagcat gttgtcacct ataaactcga gtaacggcca catattgttc    4920
actacttgaa tcacatacct aattttgata gaattgacat gtttaaagag ctgaggtagc    4980
tttaatgcct ctgaagtatt gtgacacagc ttctcacaga gtgagaatga aaagttggac    5040
tcccctaat gaagtaaaag tttcgtctct gaacggtgaa gagcatagat ccggcatcaa     5100
ctacctggct agactacgac gtcaattctg cggccttttg acctttatat atgtccatta    5160
atgcaataga ttcttttttt tttttttttt tttttttttt tttttttttt ttttgcccaa    5220
tttcgcagat caaagtggac gttatagcat cataactaag ctcagttgct gagggaagcc    5280
gtctactacc ttagcccatc catccagctc catccttga  tactttagac gtgaagcaat    5340
tcacactgta cgtctcgcag ctctccttcc cgctcttgct tccccactgg ggtccatggt    5400
gcgtgtatcg tccctcctt aattaaggcc atttaggccg ttgctggcgt ttttccatag     5460
gctccgcccc cctgacgagc atcacaaaaa tcgacgctca agtcagaggt ggcgaaaccc    5520
gacaggacta taaagatacc aggcgtttcc ccctggaagc tccctcgtgc gctctcctgt    5580
tccgaccctg ccgcttaccg gatacctgtc cgccttctc ccttcgggaa gcgtggcgct     5640
ttctcatagc tcacgctgta ggtatctcag ttcggtgtag gtcgttcgct ccaagctggg    5700
ctgtgtgcac gaacccccg ttcagcccga ccgctgcgcc ttatccggta actatcgtct     5760
tgagtccaac ccgtaagac acgacttatc gccactggca gcagccactg gtaacaggat     5820
tagcagagcg aggtatgtag gcggtgctac agagttcttg aagtggtggc ctaactacgg    5880
ctacactaga aggacagtat ttggtatctg cgctctgctg aagccagtta ccttcggaaa    5940
aagagttggt agctcttgat ccggcaaaca accaccgct  ggtagcggtg ttttttgt     6000
ttgcaagcag cagattacgc gcagaaaaaa aggatctcaa gaagatcctt tgatcttttc    6060
tacgggtct  gacgctcagt ggaacgaaaa ctcacgttaa ggcctgcagg ccgattttg     6120
gtcatgagat tatcaaaaag gatcttcacc tagatccttt taaattaaaa atgaagtttt    6180
aaatcaatct aaagtatata tgagtaaact tggtctgaca gttaccaatg cttaatcagt    6240
gaggcaccta tctcagcgat ctgtctattt cgttcatcca tagttgcctg actccccgtc    6300
gtgtagataa ctacgatacg ggagggctta ccatctggcc ccagtgctgc aatgataccg    6360
cgagacccac gctcaccggc tccagattta tcagcaataa accagccagc cggaagggcc    6420
gagcgcagaa gtggtcctgc aactttatcc gcctccatcc agtctattaa ttgttgccgg    6480
gaagctagag taagtagttc gccagttaat agtttgcgca acgttgttgc cattgctaca    6540
ggcatcgtgg tgtcacgctc gtcgtttggt atggcttcat tcagctccgg ttcccaacga    6600
tcaaggcgag ttacatgatc ccccatgttg tgcaaaaaag cggttagctc cttcggtcct    6660
ccgatcgttg tcagaagtaa gttggccgca gtgttatcac tcatggttat ggcagcactg    6720
cataattctc ttactgtcat gccatccgta agatgctttt ctgtgactgg tgagtactca    6780
accaagtcat tctgagaata gtgtatgcgg cgaccgagtt gctcttgccc ggcgtcaata    6840
cgggataata ccgcgccaca tagcagaact ttaaaagtgc tcatcattgg aaaacgttct    6900
tcggggcgaa aactctcaag gatcttaccg ctgttgagat ccagttcgat gtaacccact    6960
cgtgcaccca actgatcttc agcatctttt actttcacca gcgtttctgg gtgagcaaaa    7020
acaggaaggc aaaatgccgc aaaaaaggga ataaggcga  cacggaaatg ttgaatactc    7080
atactcttcc ttttcaata  ttattgaagc atttatcagg gttattgtct catgccatt     7140
taggcct                                                              7147
```

<210> SEQ ID NO 17
<211> LENGTH: 496
<212> TYPE: PRT
<213> ORGANISM: Aspergillus oryzae

<400> SEQUENCE: 17

```
Met Arg Ser Leu Leu Trp Ala Ser Leu Leu Ser Gly Val Leu Ala Gly
1               5                   10                  15

Arg Ala Leu Val Ser Pro Asp Glu Phe Pro Glu Asp Ile Gln Leu Glu
            20                  25                  30

Asp Leu Leu Glu Gly Ser Gln Gln Leu Glu Asp Phe Ala Tyr Ala Tyr
        35                  40                  45

Pro Glu Arg Asn Arg Val Phe Gly Gly Lys Ala His Asp Asp Thr Val
50                  55                  60

Asn Tyr Leu Tyr Glu Glu Leu Lys Lys Thr Gly Tyr Tyr Asp Val Tyr
65                  70                  75                  80

Lys Gln Pro Gln Val His Leu Trp Ser Asn Ala Asp Gln Thr Leu Lys
                85                  90                  95

Val Gly Asp Glu Glu Ile Glu Ala Lys Thr Met Thr Tyr Ser Pro Ser
            100                 105                 110

Val Glu Val Thr Ala Asp Val Ala Val Lys Asn Leu Gly Cys Ser
        115                 120                 125

Glu Ala Asp Tyr Pro Ser Asp Val Glu Gly Lys Val Ala Leu Ile Lys
    130                 135                 140

Arg Gly Glu Cys Pro Phe Gly Asp Lys Ser Val Leu Ala Ala Lys Ala
145                 150                 155                 160

Lys Ala Ala Ser Ile Val Tyr Asn Asn Val Ala Gly Ser Met Ala
                165                 170                 175

Gly Thr Leu Gly Ala Ala Gln Ser Asp Lys Gly Pro Tyr Ser Ala Ile
            180                 185                 190

Val Gly Ile Ser Leu Glu Asp Gly Gln Lys Leu Ile Lys Leu Ala Glu
        195                 200                 205

Ala Gly Ser Val Ser Val Asp Leu Trp Val Asp Ser Lys Gln Glu Asn
    210                 215                 220

Arg Thr Thr Tyr Asn Val Val Ala Gln Thr Lys Gly Gly Asp Pro Asn
225                 230                 235                 240

Asn Val Val Ala Leu Gly Gly His Thr Asp Ser Val Glu Ala Gly Pro
                245                 250                 255

Gly Ile Asn Asp Asp Gly Ser Gly Ile Ile Ser Asn Leu Val Ile Ala
            260                 265                 270

Lys Ala Leu Thr Gln Tyr Ser Val Lys Asn Ala Val Arg Phe Leu Phe
        275                 280                 285

Trp Thr Ala Glu Glu Phe Gly Leu Leu Gly Ser Asn Tyr Tyr Val Ser
    290                 295                 300

His Leu Asn Ala Thr Glu Leu Asn Lys Ile Arg Leu Tyr Leu Asn Phe
305                 310                 315                 320

Asp Met Ile Ala Ser Pro Asn Tyr Ala Leu Met Ile Tyr Asp Gly Asp
                325                 330                 335

Gly Ser Ala Phe Asn Gln Ser Gly Pro Ala Gly Ser Ala Gln Ile Glu
            340                 345                 350

Lys Leu Phe Glu Asp Tyr Tyr Asp Ser Ile Asp Leu Pro His Ile Pro
        355                 360                 365

Thr Gln Phe Asp Gly Arg Ser Asp Tyr Glu Ala Phe Ile Leu Asn Gly
```

```
                    370                 375                 380
Ile Pro Ser Gly Gly Leu Phe Thr Gly Ala Glu Gly Ile Met Ser Glu
385                 390                 395                 400

Glu Asn Ala Ser Arg Trp Gly Gly Gln Ala Gly Val Ala Tyr Asp Ala
                    405                 410                 415

Asn Tyr His Ala Ala Gly Asp Asn Met Thr Asn Leu Asn His Glu Ala
                420                 425                 430

Phe Leu Ile Asn Ser Lys Ala Thr Ala Phe Ala Val Ala Thr Tyr Ala
                435                 440                 445

Asn Asp Leu Ser Ser Ile Pro Lys Arg Asn Thr Thr Ser Ser Leu His
450                 455                 460

Arg Arg Ala Arg Thr Met Arg Pro Phe Gly Lys Arg Ala Pro Lys Thr
465                 470                 475                 480

His Ala His Val Ser Gly Ser Gly Cys Trp His Ser Gln Val Glu Ala
                485                 490                 495

<210> SEQ ID NO 18
<211> LENGTH: 483
<212> TYPE: PRT
<213> ORGANISM: Neosartorya fischeri

<400> SEQUENCE: 18

Asn Gly Pro Gly Trp Asp Trp Lys Pro Pro Val His Pro Lys Val Leu
1               5                   10                  15

Pro Gln Met Ile His Leu Trp Asp Leu Met His Gly Ala Gln Lys Leu
                20                  25                  30

Glu Asp Phe Ala Tyr Ala Tyr Pro Glu Arg Asn Arg Val Phe Gly Gly
            35                  40                  45

Pro Ala His Glu Asp Thr Val Asn Tyr Leu Tyr Arg Glu Leu Lys Lys
50                  55                  60

Thr Gly Tyr Tyr Asp Val Tyr Lys Gln Pro Gln Val His Gln Trp Thr
65                  70                  75                  80

Arg Ala Asp Gln Ala Leu Thr Val Asp Gly Lys Ser Tyr Val Ala Thr
                85                  90                  95

Thr Met Thr Tyr Ser Pro Ser Val Asn Val Thr Ala Pro Leu Ala Val
            100                 105                 110

Val Asn Asn Leu Gly Cys Val Glu Ser Asp Tyr Pro Ala Asp Leu Lys
        115                 120                 125

Gly Lys Ile Ala Leu Val Ser Arg Gly Glu Cys Pro Phe Ala Thr Lys
130                 135                 140

Ser Val Leu Ser Ala Lys Ala Gly Ala Ala Ala Ala Leu Val Tyr Asn
145                 150                 155                 160

Asn Ile Glu Gly Ser Met Ala Gly Thr Leu Gly Gly Pro Thr Ser Glu
                165                 170                 175

Leu Gly Pro Tyr Ala Pro Ile Ala Gly Ile Ser Leu Ala Asp Gly Gln
            180                 185                 190

Ala Leu Ile Gln Met Ile Gln Ala Gly Thr Val Thr Ala Asn Leu Trp
        195                 200                 205

Ile Asp Ser Lys Val Glu Asn Arg Thr Thr Tyr Asn Val Ile Ala Gln
    210                 215                 220

Thr Lys Gly Gly Asp Pro Asn Asn Val Val Ala Leu Gly Gly His Thr
225                 230                 235                 240

Asp Ser Val Glu Ala Gly Pro Gly Ile Asn Asp Asp Gly Ser Gly Ile
                245                 250                 255
```

```
Ile Ser Asn Leu Val Val Ala Lys Ala Leu Thr Arg Phe Ser Val Lys
            260                 265                 270

Asn Ala Val Arg Phe Cys Phe Trp Thr Ala Glu Glu Phe Gly Leu Leu
        275                 280                 285

Gly Ser Ser Tyr Tyr Val Asn Ser Leu Asn Ala Thr Glu Lys Ala Lys
    290                 295                 300

Ile Arg Leu Tyr Leu Asn Phe Asp Met Ile Ala Ser Pro Asn Tyr Ala
305                 310                 315                 320

Leu Met Ile Tyr Asp Gly Asp Gly Ser Ala Phe Asn Leu Thr Gly Pro
                325                 330                 335

Ala Gly Ser Ala Gln Ile Glu Arg Leu Phe Glu Asp Tyr Tyr Lys Ser
            340                 345                 350

Ile Arg Lys Pro Phe Val Pro Thr Glu Phe Asn Gly Arg Ser Asp Tyr
        355                 360                 365

Glu Ala Phe Ile Leu Asn Gly Ile Pro Ala Gly Ile Phe Thr Gly
    370                 375                 380

Ala Glu Ala Ile Lys Thr Glu Glu Gln Ala Lys Leu Phe Gly Gly Gln
385                 390                 395                 400

Ala Gly Val Ala Leu Asp Ala Asn Tyr His Ala Lys Gly Asp Asn Met
                405                 410                 415

Thr Asn Leu Asn Arg Glu Ala Phe Leu Ile Asn Ser Lys Ala Thr Ala
            420                 425                 430

Phe Ala Val Ala Thr Tyr Ala Asn Ser Leu Asp Ser Ile Pro Ser Arg
        435                 440                 445

Asn Met Ser Thr Val Val Lys Arg Ser Gln Leu Glu Gln Ala Lys Lys
    450                 455                 460

Ser Thr Pro His Thr His Thr Gly Gly Thr Gly Cys Tyr Lys Asp Arg
465                 470                 475                 480

Val Glu Gln

<210> SEQ ID NO 19
<211> LENGTH: 492
<212> TYPE: PRT
<213> ORGANISM: Myceliophthora thermophila

<400> SEQUENCE: 19

Gly Gly His Gly Gly Ser Ser Gly Leu Gly Cys Asp Ser Gln Arg Pro
1               5                   10                  15

Leu Val Ser Ser Glu Lys Leu Gln Ser Leu Ile Lys Lys Glu Asp Leu
            20                  25                  30

Leu Ala Gly Ser Gln Glu Leu Gln Asp Ile Ala Thr Ala His Gly Gly
        35                  40                  45

His Arg Ala Phe Gly Ser Gly His Asn Ala Thr Val Asp Phe Leu
    50                  55                  60

Tyr Tyr Thr Leu Lys Ala Leu Asp Tyr Asn Val Thr Lys Gln Pro
65                  70                  75                  80

Phe Lys Glu Ile Phe Ser Ser Gly Thr Gly Ser Leu Thr Val Asp Gly
                85                  90                  95

Glu Asp Ile Glu Ala Glu Thr Leu Thr Tyr Thr Pro Ser Gly Ser Ala
            100                 105                 110

Thr Asp Lys Pro Val Val Val Ala Asn Val Gly Cys Asp Ala Ala
        115                 120                 125

Asp Tyr Pro Ala Glu Val Ala Gly Asn Ile Ala Leu Ile Lys Arg Gly
    130                 135                 140
```

```
Thr Cys Thr Phe Ser Gln Lys Ser Val Asn Ala Lys Ala Ala Gly Ala
145                 150                 155                 160

Val Ala Ala Ile Ile Tyr Asn Asn Ala Glu Gly Lys Leu Ser Gly Thr
                165                 170                 175

Leu Gly Gln Pro Phe Leu Asp Tyr Ala Pro Val Leu Gly Ile Thr Leu
            180                 185                 190

Glu Ala Gly Glu Ala Leu Leu Ala Lys Leu Ala Gly Gly Pro Val Thr
        195                 200                 205

Ala Thr Leu Gln Ile Asp Ala Leu Val Glu Glu Arg Val Thr Tyr Asn
    210                 215                 220

Val Ile Ala Glu Thr Lys Glu Gly Asp His Ser Asn Val Leu Val Leu
225                 230                 235                 240

Gly Gly His Thr Asp Ser Val Pro Ala Gly Pro Gly Ile Asn Asp Asp
                245                 250                 255

Gly Ser Gly Thr Ile Gly Met Leu Thr Val Ala Lys Ala Leu Thr Lys
                260                 265                 270

Phe Arg Val Lys Asn Ala Val Arg Phe Ala Phe Trp Ser Ala Glu Glu
            275                 280                 285

Tyr Gly Leu Leu Gly Ser Tyr Ala Tyr Ile Lys Ser Ile Asn Ser Ser
        290                 295                 300

Ala Ala Glu Leu Ser Lys Ile Arg Ala Tyr Leu Asn Phe Asp Met Ile
305                 310                 315                 320

Ala Ser Pro Asn Tyr Ile Tyr Gly Ile Tyr Asp Gly Asp Gly Asn Ala
                325                 330                 335

Phe Asn Leu Thr Gly Pro Ala Gly Ser Asp Val Ile Glu Arg Asn Phe
                340                 345                 350

Glu Asn Phe Phe Lys Arg Lys His Thr Pro Ser Val Pro Thr Glu Phe
            355                 360                 365

Ser Gly Arg Ser Asp Tyr Ala Ala Phe Ile Glu Asn Gly Ile Pro Ser
        370                 375                 380

Gly Gly Leu Phe Thr Gly Ala Glu Val Leu Lys Thr Glu Arg Glu Ala
385                 390                 395                 400

Glu Leu Phe Gly Gly Arg Ala Gly Val Ala Tyr Asp Val Asn Tyr His
                405                 410                 415

Gln Ala Gly Asp Thr Val Asp Asn Leu Ala Leu Asp Ala Phe Leu Leu
                420                 425                 430

Asn Thr Lys Ala Ile Ala Asp Ser Val Ala Thr Tyr Ala Leu Ser Phe
            435                 440                 445

Asp Gly Leu Pro Arg Val Asp Gly Lys Lys Arg Arg Trp Asp Ala His
        450                 455                 460

Arg Ala Arg Met Leu Lys Arg Ser Ala Gly Ser His Gly His Ala His
465                 470                 475                 480

Leu His Ser Gly Pro Cys Gly Gly Gly Ala Ser Ile
                485                 490
```

<210> SEQ ID NO 20
<211> LENGTH: 474
<212> TYPE: PRT
<213> ORGANISM: Fusarium oxysporum

<400> SEQUENCE: 20

```
Thr Lys Lys Pro Leu Val Asn Glu Leu Lys Leu Gln Lys Asp Ile Asn
1               5                   10                  15

Ile Lys Asp Leu Met Ala Gly Ala Gln Lys Leu Gln Asp Ile Ala Glu
            20                  25                  30
```

```
Ala Asn Gly Asn Thr Arg Val Phe Gly Gly Gly His Asn Ala Thr
         35                  40                  45

Val Asp Tyr Leu Tyr Lys Thr Leu Lys Ala Thr Gly Tyr Tyr Asn Val
 50                      55                  60

Lys Lys Gln Pro Phe Thr Glu Leu Tyr Ser Ala Gly Thr Ala Ser Leu
 65                  70                  75                  80

Lys Val Asp Gly Asp Asp Ile Thr Ala Ala Ile Met Thr Tyr Thr Pro
                 85                  90                  95

Ala Gly Glu Ala Thr Gly Pro Leu Val Val Ala Glu Asn Leu Gly Cys
            100                 105                 110

Glu Ala Ser Asp Phe Pro Ala Glu Ser Glu Gly Lys Val Val Leu Val
            115                 120                 125

Leu Arg Gly Glu Cys Pro Phe Ser Gln Lys Ser Thr Asn Gly Lys Thr
130                 135                 140

Ala Gly Ala Ala Ala Val Ile Val Tyr Asn Asn Val Pro Gly Glu Leu
145                 150                 155                 160

Ala Gly Thr Leu Gly Glu Pro Phe Gly Glu Phe Ala Pro Ile Val Gly
                165                 170                 175

Ile Ser Gln Glu Asp Gly Gln Ala Ile Leu Ala Lys Thr Lys Ala Gly
                180                 185                 190

Glu Val Thr Val Asp Leu Lys Val Asp Ala Thr Val Glu Asn Arg Val
                195                 200                 205

Thr Phe Asn Val Ile Ala Glu Thr Lys Glu Gly Asp His Asp Asn Val
            210                 215                 220

Leu Val Val Gly Gly His Ser Asp Ser Val Ala Ala Gly Pro Gly Ile
225                 230                 235                 240

Asn Asp Asp Gly Ser Gly Ile Ile Gly Ile Leu Lys Val Ala Gln Ala
                245                 250                 255

Leu Thr Lys Tyr Arg Val Lys Asn Ala Val Arg Phe Gly Phe Trp Ser
                260                 265                 270

Ala Glu Glu Phe Gly Leu Leu Gly Ser Tyr Ala Tyr Met Lys Ser Ile
            275                 280                 285

Asn Gly Ser Asp Ala Glu Val Ala Lys Ile Arg Ala Tyr Leu Asn Phe
            290                 295                 300

Asp Met Ile Ala Ser Pro Asn Tyr Val Tyr Gly Ile Tyr Asp Gly Asp
305                 310                 315                 320

Gly Ser Ala Phe Asn Leu Thr Gly Pro Ala Gly Ser Asp Ala Ile Glu
                325                 330                 335

Lys Asp Phe Glu Arg Phe Lys Thr Lys Arg Leu Gly Tyr Val Pro
            340                 345                 350

Ser Glu Phe Ser Gly Arg Ser Asp Tyr Ala Ala Phe Ile Glu Asn Gly
            355                 360                 365

Ile Pro Ser Gly Gly Leu Phe Thr Gly Ala Glu Gln Leu Lys Thr Glu
370                 375                 380

Glu Glu Ala Lys Lys Phe Gly Gly Glu Ala Gly Val Ala Tyr Asp Ile
385                 390                 395                 400

Asn Tyr His Lys Ile Gly Asp Asp Ile Asn Asn Leu Asn Lys Glu Ala
                405                 410                 415

Phe Leu Val Asn Thr Gln Ala Ile Ala Asn Ser Val Ala Arg Tyr Ala
                420                 425                 430

Lys Thr Trp Lys Ser Leu Pro Lys Val Thr His Asn Thr Arg Arg Trp
                435                 440                 445
```

```
Asp Ala Glu Val Ala Ser Val Leu Lys Arg Ser Ser Gly His Ser His
            450             455                 460

Ala Gly Gly Pro Cys Gly Ser Val Ser Val
465                 470

<210> SEQ ID NO 21
<211> LENGTH: 488
<212> TYPE: PRT
<213> ORGANISM: Fusarium oxysporum

<400> SEQUENCE: 21

Leu Gln Ile Pro Leu Asn Leu Gln Val Pro Lys Leu Ser Trp Asn Leu
1               5                   10                  15

Phe Gly Asp Asp Leu Pro Leu Val Asp Thr Lys Glu Leu Gln Lys Ser
            20                  25                  30

Ile Lys Pro Glu Asn Leu Glu Ala Arg Ala Lys Asp Leu Tyr Glu Ile
        35                  40                  45

Ala Lys Asn Gly Glu Glu Glu Tyr Gly His Pro Thr Arg Val Ile Gly
    50                  55                  60

Ser Glu Gly His Leu Gly Thr Leu Ser Tyr Ile His Ala Glu Leu Ala
65                  70                  75                  80

Lys Leu Gly Gly Tyr Tyr Ser Val Ser Asn Gln Gln Phe Pro Ala Val
                85                  90                  95

Ser Gly Asn Val Phe Glu Ser Arg Leu Val Ile Gly Asp Ser Val Pro
            100                 105                 110

Lys Gln Ala Ser Pro Met Gly Leu Thr Pro Thr Lys Asn Lys Glu
        115                 120                 125

Pro Val His Gly Thr Leu Val Leu Val Asp Asn Glu Gly Cys Asp Ala
    130                 135                 140

Ser Asp Tyr Pro Glu Ala Val Lys Gly Asn Ile Ala Leu Ile Leu Arg
145                 150                 155                 160

Gly Thr Cys Pro Phe Gly Thr Lys Ser Gly Asn Ala Gly Lys Ala Gly
                165                 170                 175

Ala Val Ala Ala Val Val Tyr Asn Tyr Glu Lys Asp Glu Val His Gly
            180                 185                 190

Thr Leu Gly Thr Pro Ser Pro Asp His Val Ala Thr Phe Gly Leu Gly
        195                 200                 205

Gly Glu Glu Gly Lys Ala Val Ala Lys Lys Leu Lys Asp Gly Glu Lys
    210                 215                 220

Val Asp Ala Ile Ala Tyr Ile Asp Ala Glu Val Lys Thr Ile Ser Thr
225                 230                 235                 240

Thr Asn Ile Ile Ala Gln Thr Arg Gly Gly Asp Pro Asp Asn Cys Val
                245                 250                 255

Met Leu Gly Gly His Ser Asp Ser Val Ala Glu Gly Pro Gly Ile Asn
            260                 265                 270

Asp Asp Gly Ser Gly Ser Ile Ser Val Leu Glu Val Ala Val Gln Leu
        275                 280                 285

Thr Lys Tyr Arg Val Asn Asn Cys Val Arg Phe Ala Trp Trp Ala Ala
    290                 295                 300

Glu Glu Glu Gly Leu Leu Gly Ser Asp His Tyr Val Ser Val Leu Pro
305                 310                 315                 320

Glu Asp Glu Asn Arg Lys Ile Arg Leu Phe Met Asp Tyr Asp Met Met
                325                 330                 335

Ala Ser Pro Asn Phe Ala Tyr Gln Ile Tyr Asn Ala Thr Asn Ala Glu
            340                 345                 350
```

Asn Pro Lys Gly Ser Glu Glu Leu Arg Asp Leu Tyr Val Asn Trp Tyr
            355                 360                 365

Glu Glu Gln Gly Leu Asn Tyr Thr Phe Ile Pro Phe Asp Gly Arg Ser
    370                 375                 380

Asp Tyr Asp Gly Phe Ile Arg Gly Gly Ile Pro Ala Gly Gly Ile Ala
385                 390                 395                 400

Thr Gly Ala Glu Gly Val Lys Thr Glu Asp Glu Val Glu Met Phe Gly
                405                 410                 415

Gly Glu Ala Gly Val Trp Tyr Asp Lys Asn Tyr His Gln Ile Gly Asp
            420                 425                 430

Asp Leu Thr Asn Val Asn Tyr Thr Ala Trp Glu Val Asn Thr Lys Leu
                435                 440                 445

Ile Ala His Ser Val Ala Thr Tyr Ala Lys Ser Phe Lys Gly Phe Pro
            450                 455                 460

Glu Arg Glu Ile Glu Thr Ser Val Gln Thr Tyr Ser Asp Lys Thr Lys
465                 470                 475                 480

Tyr His Gly Ser Lys Leu Phe Ile
                485

<210> SEQ ID NO 22
<211> LENGTH: 486
<212> TYPE: PRT
<213> ORGANISM: Aspergillus clavatus

<400> SEQUENCE: 22

Asn Ala Pro Gly Gly Pro Gly Gly His Gly Arg Lys Leu Pro Val Asn
1               5                   10                  15

Pro Lys Thr Phe Pro Asn Glu Ile Arg Leu Lys Asp Leu Leu His Gly
            20                  25                  30

Ser Gln Lys Leu Glu Asp Phe Ala Tyr Ala Tyr Pro Glu Arg Asn Arg
        35                  40                  45

Val Phe Gly Gly Gln Ala His Leu Asp Thr Val Asn Tyr Leu Tyr Arg
    50                  55                  60

Glu Leu Lys Lys Thr Gly Tyr Tyr Asp Val Tyr Lys Gln Pro Gln Val
65                  70                  75                  80

His Gln Trp Thr Arg Ala Asp Gln Ser Leu Thr Leu Gly Gly Asp Ser
                85                  90                  95

Ile Gln Ala Ser Thr Met Thr Tyr Ser Pro Ser Val Asn Val Thr Ala
            100                 105                 110

Pro Leu Ser Leu Val Ser Lys Leu Gly Cys Ala Glu Gly Asp Tyr Ser
        115                 120                 125

Ala Asp Val Lys Gly Lys Ile Ala Leu Val Ser Arg Gly Glu Cys Ser
130                 135                 140

Phe Ala Gln Lys Ser Val Leu Ser Ala Lys Ala Gly Ala Val Ala Thr
145                 150                 155                 160

Ile Val Tyr Asn Asn Val Asp Gly Ser Leu Ala Gly Thr Leu Gly Gly
                165                 170                 175

Ala Thr Ser Glu Leu Gly Pro Tyr Ser Pro Ile Ile Gly Ile Thr Leu
            180                 185                 190

Ala Ala Gly Gln Asp Leu Val Ala Arg Leu Gln Ala Ala Pro Thr Glu
        195                 200                 205

Val Ser Leu Trp Ile Asp Ser Lys Val Glu Asn Arg Thr Thr Tyr Asn
    210                 215                 220

Val Ile Ala Gln Thr Lys Gly Gly Asp Pro Asn Asn Val Val Ala Leu

```
                225                 230                 235                 240
Gly Gly His Thr Asp Ser Val Glu Asn Gly Pro Gly Ile Asn Asp Asp
                245                 250                 255
Gly Ser Gly Val Ile Ser Asn Leu Val Val Ala Lys Ala Leu Thr Arg
                260                 265                 270
Tyr Ser Val Lys Asn Ala Val Arg Phe Cys Phe Trp Thr Ala Glu Glu
                275                 280                 285
Phe Gly Leu Leu Gly Ser Asn Tyr Tyr Val Asp Asn Leu Ser Pro Ala
                290                 295                 300
Glu Leu Ala Lys Ile Arg Leu Tyr Leu Asn Phe Asp Met Ile Ala Ser
305                 310                 315                 320
Pro Asn Tyr Ala Leu Met Ile Tyr Asp Gly Asp Ser Ala Phe Asn
                325                 330                 335
Leu Thr Gly Pro Pro Gly Ser Ala Gln Ile Glu Ser Leu Phe Glu Asn
                340                 345                 350
Tyr Tyr Lys Ser Ile Lys Gln Gly Phe Val Pro Thr Ala Phe Asp Gly
                355                 360                 365
Arg Ser Asp Tyr Glu Gly Phe Ile Leu Lys Gly Ile Pro Ala Gly Gly
                370                 375                 380
Val Phe Thr Gly Ala Glu Ser Leu Lys Thr Glu Glu Gln Ala Arg Leu
385                 390                 395                 400
Phe Gly Gly Gln Ala Gly Val Ala Leu Asp Ala Asn Tyr His Ala Lys
                405                 410                 415
Gly Asp Asn Met Thr Asn Leu Asn His Lys Ala Phe Leu Ile Asn Ser
                420                 425                 430
Arg Ala Thr Ala Phe Ala Val Ala Thr Tyr Ala Asn Asn Leu Ser Ser
                435                 440                 445
Ile Pro Pro Arg Asn Ala Thr Val Val Lys Arg Glu Ser Met Lys Trp
                450                 455                 460
Thr Lys Arg Glu Glu Pro His Thr His Gly Ala Asp Thr Gly Cys Phe
465                 470                 475                 480
Ala Ser Arg Val Lys Glu
                485

<210> SEQ ID NO 23
<211> LENGTH: 494
<212> TYPE: PRT
<213> ORGANISM: Chaetomium thermophilum var thermophilum DSM 1495

<400> SEQUENCE: 23

Gly Gly Pro His Gly Phe Gly Leu Pro Lys Ile Asp Leu Arg Pro Met
1               5                   10                  15
Val Ser Ser Asn Arg Leu Gln Ser Met Ile Thr Leu Lys Asp Leu Met
                20                  25                  30
Asp Gly Ala Lys Lys Leu Gln Asp Ile Ala Thr Lys Asn Gly Gly Asn
        35                  40                  45
Arg Ala Phe Gly Gly Ala Gly His Asn Ala Thr Val Asp Tyr Leu Tyr
    50                  55                  60
Lys Thr Leu Thr Ser Leu Gly Tyr Tyr Thr Val Lys Lys Gln Pro
65                  70                  75                  80
Phe Lys Glu Ile Phe Ser Ser Gly Ser Gly Ser Leu Ile Val Asp Gly
                85                  90                  95
Gln Gly Ile Asp Ala Gly Ile Met Thr Tyr Thr Pro Gly Gly Ser Ala
                100                 105                 110
```

```
Thr Ala Asn Leu Val Gln Val Ala Asn Leu Gly Cys Glu Asp Asp
            115                 120                 125
Tyr Pro Ala Glu Val Ala Gly Asn Ile Ala Leu Ile Ser Arg Gly Ser
        130                 135                 140
Cys Thr Phe Ser Ser Lys Ser Leu Lys Ala Lys Ala Ala Gly Ala Val
145                 150                 155                 160
Gly Ala Ile Val Tyr Asn Asn Val Pro Gly Glu Leu Ser Gly Thr Leu
                165                 170                 175
Gly Thr Pro Phe Leu Asp Tyr Ala Pro Ile Val Gly Ile Ser Gln Glu
            180                 185                 190
Asp Gly Gln Val Ile Leu Glu Lys Leu Ala Ala Gly Pro Val Thr Ala
        195                 200                 205
Thr Leu Asn Ile Asp Ala Ile Val Glu Glu Arg Thr Thr Tyr Asn Val
210                 215                 220
Ile Ala Glu Thr Lys Glu Gly Asp His Asn Asn Val Leu Ile Val Gly
225                 230                 235                 240
Gly His Ser Asp Ser Val Ala Ala Gly Pro Gly Ile Asn Asp Asp Gly
                245                 250                 255
Ser Gly Thr Ile Gly Ile Leu Thr Val Ala Lys Ala Leu Ala Lys Ala
            260                 265                 270
Asn Val Arg Ile Lys Asn Ala Val Arg Phe Ala Phe Trp Ser Ala Glu
        275                 280                 285
Glu Phe Gly Leu Leu Gly Ser Tyr Ala Tyr Met Lys Ser Leu Asn Glu
290                 295                 300
Ser Glu Ala Glu Val Ala Lys Ile Arg Ala Tyr Leu Asn Phe Asp Met
305                 310                 315                 320
Ile Ala Ser Pro Asn Tyr Ile Tyr Gly Ile Tyr Asp Gly Asp Gly Asn
                325                 330                 335
Ala Phe Asn Leu Thr Gly Pro Ala Gly Ser Asp Ile Ile Glu Lys Asp
            340                 345                 350
Phe Glu Asp Phe Lys Lys Lys Thr Pro Ser Val Pro Thr Glu
        355                 360                 365
Phe Ser Gly Arg Ser Asp Tyr Ala Ala Phe Ile Glu Asn Gly Ile Pro
370                 375                 380
Ser Gly Gly Leu Phe Thr Gly Ala Glu Val Leu Lys Thr Glu Glu Glu
385                 390                 395                 400
Ala Lys Leu Phe Gly Gly Lys Ala Gly Val Ala Tyr Asp Val Asn Tyr
                405                 410                 415
His Lys Ala Gly Asp Thr Val Asn Leu Ala Lys Ala Phe Leu
            420                 425                 430
Leu Asn Thr Lys Ala Ile Ala Asn Ser Val Ala Lys Tyr Ala Ala Ser
        435                 440                 445
Trp Ala Gly Phe Pro Lys Pro Ser Ala Val Arg Arg Tyr Asp Ala
450                 455                 460
Asp Met Ala Gln Leu Leu Lys Arg Ser Gly Val His Gly His Gly
465                 470                 475                 480
Pro His Thr His Ser Gly Pro Cys Gly Gly Asp Leu Leu
                485                 490

<210> SEQ ID NO 24
<211> LENGTH: 488
<212> TYPE: PRT
<213> ORGANISM: Aspergillus terreus

<400> SEQUENCE: 24
```

```
Glu Gly Leu Gly Asn His Gly Arg Lys Leu Asp Pro Asn Lys Phe Thr
  1               5                  10                  15

Lys Asp Ile Lys Leu Lys Asp Leu Leu Lys Gly Ser Gln Lys Leu Glu
             20                  25                  30

Asp Phe Ala Tyr Ala Tyr Pro Glu Arg Asn Arg Val Phe Gly Gly Lys
             35                  40                  45

Ala His Gln Asp Thr Val Asn Trp Ile Tyr Asn Glu Leu Lys Lys Thr
         50                  55                  60

Gly Tyr Tyr Asp Val Tyr Lys Gln Pro Gln Val His Leu Trp Ser Asn
 65                  70                  75                  80

Ala Glu Gln Ser Leu Thr Val Asp Gly Glu Ala Ile Asp Ala Thr Thr
                 85                  90                  95

Met Thr Tyr Ser Pro Ser Leu Lys Glu Thr Thr Ala Glu Val Val Val
                100                 105                 110

Val Pro Gly Leu Gly Cys Thr Ala Ala Asp Tyr Pro Ala Asp Val Ala
             115                 120                 125

Gly Lys Ile Ala Leu Ile Gln Arg Gly Ser Cys Thr Phe Gly Glu Lys
         130                 135                 140

Ser Val Tyr Ala Ala Ala Asn Ala Ala Ala Ala Ile Val Tyr Asn
145                 150                 155                 160

Asn Val Asp Gly Ser Leu Ser Gly Thr Leu Gly Ala Ala Thr Ser Glu
                 165                 170                 175

Leu Gly Pro Tyr Ala Pro Ile Val Gly Ile Ser Leu Ala Asp Gly Gln
             180                 185                 190

Asn Leu Val Ser Leu Ala Gln Ala Gly Pro Leu Thr Val Asp Leu Tyr
         195                 200                 205

Ile Asn Ser Gln Met Glu Asn Arg Thr Thr His Asn Val Ile Ala Lys
210                 215                 220

Ser Lys Gly Gly Asp Pro Asn Asn Val Ile Val Ile Gly Gly His Ser
225                 230                 235                 240

Asp Ala Val Asn Gln Gly Pro Gly Val Asn Asp Gly Ser Gly Ile
             245                 250                 255

Ile Ser Asn Leu Val Ile Ala Lys Ala Leu Thr Lys Tyr Ser Leu Lys
             260                 265                 270

Asn Ser Val Thr Trp Ala Phe Trp Thr Ala Glu Glu Phe Gly Leu Leu
         275                 280                 285

Gly Ser Glu Phe Tyr Val Asn Ser Leu Ser Ala Ala Glu Lys Asp Lys
290                 295                 300

Ile Lys Leu Tyr Leu Asn Phe Asp Met Ile Ala Ser Pro Asn Tyr Ala
305                 310                 315                 320

Leu Met Ile Tyr Asp Gly Asp Gly Ser Thr Phe Asn Met Thr Gly Pro
             325                 330                 335

Ala Gly Ser Ala Glu Ile Glu His Leu Phe Glu Asp Tyr Tyr Lys Ser
             340                 345                 350

Arg Gly Leu Ser Tyr Ile Pro Thr Ala Phe Asp Gly Arg Ser Asp Tyr
             355                 360                 365

Glu Ala Phe Ile Leu Asn Gly Ile Pro Ala Gly Gly Leu Phe Thr Gly
370                 375                 380

Ala Glu Gln Ile Lys Thr Glu Glu Gln Val Ala Met Phe Gly Gly Gln
385                 390                 395                 400

Ala Gly Val Ala Tyr Asp Pro Asn Tyr His Ala Gly Asp Asn Met
             405                 410                 415
```

Thr Asn Leu Ser Glu Ala Phe Leu Ile Asn Ser Lys Ala Thr Ala
            420                 425                 430

Phe Ala Val Ala Thr Tyr Ala Asn Ser Leu Glu Ser Ile Pro Pro Arg
        435                 440                 445

Asn Ala Thr Met Ser Ile Gln Thr Arg Ser Ala Ser Arg Arg Ala Ala
450                 455                 460

Ala His Arg Arg Ala Ala Lys Pro His Ser His Ser Gly Gly Thr Gly
465                 470                 475                 480

Cys Trp His Thr Arg Val Glu Leu
                485

<210> SEQ ID NO 25
<211> LENGTH: 486
<212> TYPE: PRT
<213> ORGANISM: Aspergillus nidulans FGSC A4

<400> SEQUENCE: 25

Gly Lys His Lys Pro Leu Val Thr Pro Glu Ala Leu Gln Asp Leu Ile
1               5                   10                  15

Thr Leu Asp Asp Leu Leu Ala Gly Ser Gln Gln Leu Gln Asp Phe Ala
            20                  25                  30

Tyr Ala Tyr Pro Glu Arg Asn Arg Val Phe Gly Gly Arg Ala His Asp
        35                  40                  45

Asp Thr Val Asn Trp Leu Tyr Arg Glu Leu Lys Arg Thr Gly Tyr Tyr
    50                  55                  60

His Val Tyr Lys Gln Pro Gln Val His Leu Tyr Ser Asn Ala Glu Glu
65                  70                  75                  80

Ser Leu Thr Val Asn Gly Glu Ala Ile Glu Ala Thr Thr Met Thr Tyr
                85                  90                  95

Ser Pro Ser Ala Asn Ala Ser Ala Glu Leu Ala Val Ile Ser Gly Leu
            100                 105                 110

Gly Cys Ser Pro Ala Asp Phe Ala Ser Asp Val Ala Gly Lys Val Val
        115                 120                 125

Leu Val Gln Arg Gly Asn Cys Thr Phe Gly Glu Lys Ser Val Tyr Ala
    130                 135                 140

Ala Ala Ala Asp Ala Ala Ala Thr Ile Val Tyr Asn Asn Val Glu Gly
145                 150                 155                 160

Ser Leu Ser Gly Thr Leu Gly Ala Ala Gln Ser Glu Gln Gly Pro Tyr
                165                 170                 175

Ser Gly Ile Val Gly Ile Ser Leu Ala Asp Gly Glu Ala Leu Leu Ala
            180                 185                 190

Leu Ala Glu Glu Gly Pro Val His Val Asp Leu Trp Ile Asp Ser Val
        195                 200                 205

Met Glu Asn Arg Thr Thr Tyr Asn Val Ile Ala Gln Thr Lys Gly Gly
    210                 215                 220

Asp Pro Asp Asn Val Val Thr Leu Gly Gly His Ser Asp Ser Val Glu
225                 230                 235                 240

Ala Gly Pro Gly Ile Asn Asp Asp Gly Ser Gly Ile Ile Ser Asn Leu
                245                 250                 255

Val Ile Ala Arg Ala Leu Thr Lys Phe Ser Thr Lys His Ala Val Arg
            260                 265                 270

Phe Phe Phe Trp Thr Ala Glu Glu Phe Gly Leu Leu Gly Ser Asp Tyr
        275                 280                 285

Tyr Val Ser Ser Leu Ser Pro Ala Glu Leu Ala Lys Ile Arg Leu Tyr
    290                 295                 300

-continued

Leu Asn Phe Asp Met Ile Ala Ser Pro Asn Tyr Gly Leu Leu Tyr
305                 310                 315                 320

Asp Gly Asp Gly Ser Ala Phe Asn Leu Thr Gly Pro Ala Gly Ser Asp
            325                 330                 335

Ala Ile Glu Lys Leu Phe Tyr Asp Tyr Phe Gln Ser Ile Gly Gln Ala
        340                 345                 350

Thr Val Glu Thr Glu Phe Asp Gly Arg Ser Asp Tyr Glu Ala Phe Ile
        355                 360                 365

Leu Asn Gly Ile Pro Ala Gly Val Phe Thr Gly Ala Glu Glu Ile
        370                 375                 380

Lys Ser Glu Glu Glu Val Ala Leu Trp Gly Gly Glu Ala Gly Val Ala
385                 390                 395                 400

Tyr Asp Ala Asn Tyr His Gln Val Gly Asp Thr Ile Asp Asn Leu Asn
            405                 410                 415

Thr Glu Ala Tyr Leu Leu Asn Ser Lys Ala Thr Ala Phe Ala Val Ala
        420                 425                 430

Thr Tyr Ala Asn Asp Leu Ser Thr Ile Pro Lys Arg Glu Met Thr Thr
        435                 440                 445

Ala Val Lys Arg Ala Asn Val Asn Gly His Met His Arg Arg Thr Met
    450                 455                 460

Pro Lys Lys Arg Gln Thr Ala His Arg His Ala Ala Lys Gly Cys Phe
465                 470                 475                 480

His Ser Arg Val Glu Gln
            485

<210> SEQ ID NO 26
<211> LENGTH: 13
<212> TYPE: PRT
<213> ORGANISM: Artificial Sequence
<220> FEATURE:
<223> OTHER INFORMATION: Synthetic peptide

<400> SEQUENCE: 26

Trp His Trp Leu Gln Leu Lys Pro Gly Gln Pro Met Tyr
1               5                   10

<210> SEQ ID NO 27
<211> LENGTH: 7
<212> TYPE: PRT
<213> ORGANISM: Artificial Sequence
<220> FEATURE:
<223> OTHER INFORMATION: Synthetic peptide

<400> SEQUENCE: 27

Lys Pro Gly Gln Pro Met Tyr
1               5

<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Gln Pro Met Tyr
1

<210> SEQ ID NO 29
<211> LENGTH: 6

-continued

```
<212> TYPE: PRT
<213> ORGANISM: Artificial Sequence
<220> FEATURE:
<223> OTHER INFORMATION: Synthetic peptide

<400> SEQUENCE: 29

Thr Pro Ala Ala Ala Arg
1               5

<210> SEQ ID NO 30
<211> LENGTH: 52
<212> TYPE: PRT
<213> ORGANISM: Artificial Sequence
<220> FEATURE:
<223> OTHER INFORMATION: Synthetic peptide

<400> SEQUENCE: 30

Thr Pro Asp Val Glu Ala Gln Gly Phe Pro Gly Phe Pro Asp Phe Pro
1               5                   10                  15

Lys Ile Pro Phe Pro Gly Asp Trp Tyr Asn Lys Phe Arg Gln Leu Thr
                20                  25                  30

Pro Glu Lys Leu Ile Trp His Ile Gly Ile Lys Asp Leu Met Ala Gly
        35                  40                  45

Ala Lys Lys Leu
    50

<210> SEQ ID NO 31
<211> LENGTH: 52
<212> TYPE: PRT
<213> ORGANISM: Ajellomyces capsulatus G186AR

<400> SEQUENCE: 31

Thr Pro Asp Val Glu Ala Gln Gly Phe Pro Gly Phe Pro Asp Phe Pro
1               5                   10                  15

Lys Ile Pro Phe Pro Gly Asp Trp Tyr Asn Lys Phe Arg Gln Leu Thr
                20                  25                  30

Pro Glu Lys Leu Ile Trp His Ile Gly Ile Lys Asp Leu Met Ala Gly
        35                  40                  45

Ala Lys Lys Leu
    50

<210> SEQ ID NO 32
<211> LENGTH: 52
<212> TYPE: PRT
<213> ORGANISM: Ajellomyces capsulatus H88

<400> SEQUENCE: 32

Thr Pro Asp Val Glu Ala Gln Gly Phe Pro Gly Phe Pro Asp Phe Pro
1               5                   10                  15

Lys Ile Pro Phe Pro Gly Asp Trp Tyr Asn Lys Phe Arg Gln Leu Thr
                20                  25                  30

Pro Glu Lys Leu Ile Trp His Ile Gly Ile Lys Asp Leu Met Ala Gly
        35                  40                  45

Ala Lys Lys Leu
    50

<210> SEQ ID NO 33
<211> LENGTH: 55
<212> TYPE: PRT
<213> ORGANISM: Ajellomyces dermatitidis ATCC 26199

<400> SEQUENCE: 33
```

Thr Pro Asp Val Glu Thr Gln Gly Phe Pro Gly Phe Pro Asp Phe Pro
1               5                   10                  15

Asp Phe Pro Lys Phe Pro Phe Pro Gly Asp Trp Tyr Asn Lys Phe Arg
                20                  25                  30

Gln Leu Thr Pro Glu Lys Leu Met Trp Phe Ile Arg Glu Arg Asp Leu
            35                  40                  45

Lys Ala Gly Ala Lys Lys Leu
        50              55

<210> SEQ ID NO 34
<211> LENGTH: 55
<212> TYPE: PRT
<213> ORGANISM: Ajellomyces dermatitidis ER-3

<400> SEQUENCE: 34

Thr Pro Asp Val Glu Thr Gln Gly Phe Pro Gly Phe Pro Asp Phe Pro
1               5                   10                  15

Asp Phe Pro Lys Phe Pro Phe Pro Gly Asp Trp Tyr Asn Lys Phe Arg
                20                  25                  30

Gln Leu Thr Pro Glu Lys Leu Met Trp Phe Ile Arg Glu Arg Asp Leu
            35                  40                  45

Lys Ala Gly Ala Lys Lys Leu
        50              55

<210> SEQ ID NO 35
<211> LENGTH: 55
<212> TYPE: PRT
<213> ORGANISM: Ajellomyces dermatitidis SLH14081

<400> SEQUENCE: 35

Thr Pro Asp Val Glu Thr Gln Gly Phe Pro Gly Phe Pro Asp Phe Pro
1               5                   10                  15

Asp Phe Pro Lys Phe Pro Phe Pro Gly Asp Trp Tyr Asn Lys Phe Arg
                20                  25                  30

Gln Leu Thr Pro Glu Lys Leu Met Trp Phe Ile Arg Glu Arg Asp Leu
            35                  40                  45

Lys Ala Gly Ala Lys Lys Leu
        50              55

<210> SEQ ID NO 36
<211> LENGTH: 55
<212> TYPE: PRT
<213> ORGANISM: Ajellomyces dermatitidis ATCC 18188

<400> SEQUENCE: 36

Thr Pro Asp Val Glu Thr Gln Gly Phe Pro Gly Phe Pro Asp Phe Pro
1               5                   10                  15

Asp Phe Pro Lys Phe Pro Phe Pro Gly Asp Trp Tyr Asn Lys Phe Arg
                20                  25                  30

Gln Leu Thr Pro Glu Lys Leu Met Trp Phe Ile Arg Glu Arg Asp Leu
            35                  40                  45

Lys Ala Gly Ala Lys Lys Leu
        50              55

<210> SEQ ID NO 37
<211> LENGTH: 47
<212> TYPE: PRT
<213> ORGANISM: Paracoccidioides brasiliensis Pb03

<400> SEQUENCE: 37

Val Pro Ala Val Lys Glu Val Arg Asp Gln Glu Ile Asp Gly Gly Arg
1               5                   10                  15

Gly Gly Pro Gly Gly Gly Asn Ala Lys Leu Ser Thr Lys Ala Leu Val
            20                  25                  30

Lys Gly Ile Glu Leu Glu Glu Leu Met Lys Gly Ala Arg Lys Leu
        35                  40                  45

<210> SEQ ID NO 38
<211> LENGTH: 47
<212> TYPE: PRT
<213> ORGANISM: Paracoccidioides sp. lutzii Pb01

<400> SEQUENCE: 38

Val Pro Ala Val Lys Lys Val Arg Asp Gln Glu Ile Ala Gly Gly Arg
1               5                   10                  15

Gly Gly Pro Gly Val Gly Asn Ala Lys Leu Ser Thr Lys Ala Leu Val
            20                  25                  30

Arg Gly Ile Glu Leu Glu Glu Leu Met Arg Gly Ala Arg Lys Leu
        35                  40                  45

<210> SEQ ID NO 39
<211> LENGTH: 32
<212> TYPE: PRT
<213> ORGANISM: Artificial Sequence
<220> FEATURE:
<223> OTHER INFORMATION: Synthetic peptide

<400> SEQUENCE: 39

Asn Gly Pro Gly Trp Asp Trp Lys Pro Pro Val His Pro Lys Val Leu
1               5                   10                  15

Pro Gln Met Ile His Leu Trp Asp Leu Met His Gly Ala Gln Lys Leu
            20                  25                  30

<210> SEQ ID NO 40
<211> LENGTH: 32
<212> TYPE: PRT
<213> ORGANISM: Neosartorya fischeri

<400> SEQUENCE: 40

Asn Gly Pro Gly Trp Asp Trp Lys Pro Pro Val His Pro Lys Val Leu
1               5                   10                  15

Pro Gln Met Ile His Leu Trp Asp Leu Met His Gly Ala Gln Lys Leu
            20                  25                  30

<210> SEQ ID NO 41
<211> LENGTH: 32
<212> TYPE: PRT
<213> ORGANISM: Aspergillus fumigatus Af293

<400> SEQUENCE: 41

Asn Gly Pro Gly Trp Asp Trp Lys Pro Arg Val His Pro Lys Val Leu
1               5                   10                  15

Pro Gln Met Ile His Leu Trp Asp Leu Leu Gln Gly Ala Gln Gln Leu
            20                  25                  30

<210> SEQ ID NO 42
<211> LENGTH: 32
<212> TYPE: PRT
<213> ORGANISM: Aspergillus fumigatus AAR96059

<400> SEQUENCE: 42

-continued

Asn Gly Pro Gly Trp Asp Trp Lys Pro Arg Val His Pro Lys Val Leu
1               5                   10                  15

Pro Gln Met Ile His Leu Trp Asp Leu Leu Gln Gly Ala Gln Gln Leu
            20                  25                  30

<210> SEQ ID NO 43
<211> LENGTH: 36
<212> TYPE: PRT
<213> ORGANISM: Artificial Sequence
<220> FEATURE:
<223> OTHER INFORMATION: Synthetic peptide

<400> SEQUENCE: 43

Asn Ala Pro Gly Gly Pro Gly Gly His Gly Arg Lys Leu Pro Val Asn
1               5                   10                  15

Pro Lys Thr Phe Pro Asn Glu Ile Arg Leu Lys Asp Leu Leu His Gly
            20                  25                  30

Ser Gln Lys Leu
        35

<210> SEQ ID NO 44
<211> LENGTH: 36
<212> TYPE: PRT
<213> ORGANISM: Aspergillus clavatus

<400> SEQUENCE: 44

Asn Ala Pro Gly Gly Pro Gly Gly His Gly Arg Lys Leu Pro Val Asn
1               5                   10                  15

Pro Lys Thr Phe Pro Asn Glu Ile Arg Leu Lys Asp Leu Leu His Gly
            20                  25                  30

Ser Gln Lys Leu
        35

<210> SEQ ID NO 45
<211> LENGTH: 26
<212> TYPE: PRT
<213> ORGANISM: Artificial Sequence
<220> FEATURE:
<223> OTHER INFORMATION: Synthetic peptide

<400> SEQUENCE: 45

Gly Arg Ala Leu Val Ser Pro Asp Glu Phe Pro Glu Asp Ile Gln Leu
1               5                   10                  15

Glu Asp Leu Leu Glu Gly Ser Gln Gln Leu
            20                  25

<210> SEQ ID NO 46
<211> LENGTH: 26
<212> TYPE: PRT
<213> ORGANISM: Aspergillus oryzae

<400> SEQUENCE: 46

Gly Arg Ala Leu Val Ser Pro Asp Glu Phe Pro Glu Asp Ile Gln Leu
1               5                   10                  15

Glu Asp Leu Leu Glu Gly Ser Gln Gln Leu
            20                  25

<210> SEQ ID NO 47
<211> LENGTH: 26
<212> TYPE: PRT
<213> ORGANISM: Artificial Sequence
<220> FEATURE:

-continued

<223> OTHER INFORMATION: Synthetic peptide

<400> SEQUENCE: 47

Gly Arg Ala Leu Val Ser Pro Asp Glu Phe Pro Glu Asp Ile Gln Leu
1               5                   10                  15
Glu Asp Leu Leu Glu Gly Ser Gln Gln Leu
            20                  25

<210> SEQ ID NO 48
<211> LENGTH: 30
<212> TYPE: PRT
<213> ORGANISM: Penicillium expansum KG056599

<400> SEQUENCE: 48

Glu Ala Ser Arg Lys Lys Pro Leu Val Ser Pro Asp Asp Phe Pro Ser
1               5                   10                  15
Thr Ile Arg Leu Lys Asp Leu Leu Lys Gly Thr Gln Gln Leu
            20                  25                  30

<210> SEQ ID NO 49
<211> LENGTH: 30
<212> TYPE: PRT
<213> ORGANISM: Penicillium expansum KG044619

<400> SEQUENCE: 49

Glu Ala Ser Arg Lys Lys Pro Leu Val Ser Pro Asp Asp Phe Pro Ser
1               5                   10                  15
Thr Ile Arg Leu Lys Asp Leu Leu Lys Gly Thr Gln Gln Leu
            20                  25                  30

<210> SEQ ID NO 50
<211> LENGTH: 28
<212> TYPE: PRT
<213> ORGANISM: Penicillium italicum

<400> SEQUENCE: 50

Ser Arg Lys Lys Pro Leu Val Ser Pro Asp Asp Phe Pro Pro Thr Ile
1               5                   10                  15
Arg Leu Lys Asp Leu Leu Lys Gly Thr Gln Lys Leu
            20                  25

<210> SEQ ID NO 51
<211> LENGTH: 28
<212> TYPE: PRT
<213> ORGANISM: Penicillium rubens

<400> SEQUENCE: 51

Gly Arg Lys Lys Pro Leu Val Ser Pro Asp Glu Phe Pro Ser Ala Ile
1               5                   10                  15
Arg Leu Lys Asp Leu Leu Lys Gly Thr Gln Gln Leu
            20                  25

<210> SEQ ID NO 52
<211> LENGTH: 28
<212> TYPE: PRT
<213> ORGANISM: Penicillium roqueforti

<400> SEQUENCE: 52

Gly Arg Lys Lys Pro Leu Val Ser Pro Asn Asp Phe Pro Ser Thr Ile
1               5                   10                  15
Arg Leu Lys Asp Leu Leu Lys Gly Thr Gln Gln Leu
            20                  25

-continued

<210> SEQ ID NO 53
<211> LENGTH: 28
<212> TYPE: PRT
<213> ORGANISM: Penicillium oxalicum

<400> SEQUENCE: 53

Gly Arg Lys Lys Pro Leu Val Ser Thr Asp Glu Leu Met Asp His Ile
1               5                   10                  15

Lys Leu Ser Asp Leu Leu Lys Gly Thr Gln Arg Leu
            20                  25

<210> SEQ ID NO 54
<211> LENGTH: 31
<212> TYPE: PRT
<213> ORGANISM: Artificial Sequence
<220> FEATURE:
<223> OTHER INFORMATION: Synthetic peptide

<400> SEQUENCE: 54

Glu Gly Leu Gly Asn His Gly Arg Lys Leu Asp Pro Asn Lys Phe Thr
1               5                   10                  15

Lys Asp Ile Lys Leu Lys Asp Leu Leu Lys Gly Ser Gln Lys Leu
            20                  25                  30

<210> SEQ ID NO 55
<211> LENGTH: 31
<212> TYPE: PRT
<213> ORGANISM: Aspergillus terreus

<400> SEQUENCE: 55

Glu Gly Leu Gly Asn His Gly Arg Lys Leu Asp Pro Asn Lys Phe Thr
1               5                   10                  15

Lys Asp Ile Lys Leu Lys Asp Leu Leu Lys Gly Ser Gln Lys Leu
            20                  25                  30

<210> SEQ ID NO 56
<211> LENGTH: 28
<212> TYPE: PRT
<213> ORGANISM: Artificial Sequence
<220> FEATURE:
<223> OTHER INFORMATION: Synthetic peptide

<400> SEQUENCE: 56

Gly Lys His Lys Pro Leu Val Thr Pro Glu Ala Leu Gln Asp Leu Ile
1               5                   10                  15

Thr Leu Asp Asp Leu Leu Ala Gly Ser Gln Gln Leu
            20                  25

<210> SEQ ID NO 57
<211> LENGTH: 28
<212> TYPE: PRT
<213> ORGANISM: Aspergillus nidutans

<400> SEQUENCE: 57

Gly Lys His Lys Pro Leu Val Thr Pro Glu Ala Leu Gln Asp Leu Ile
1               5                   10                  15

Thr Leu Asp Asp Leu Leu Ala Gly Ser Gln Gln Leu
            20                  25

<210> SEQ ID NO 58
<211> LENGTH: 33
<212> TYPE: PRT

<213> ORGANISM: Arthroderma otae

<400> SEQUENCE: 58

Glu Asp Ala Leu Asn Trp Pro Phe Lys Pro Leu Val Asn Ala Asp Asp
1               5                   10                  15

Leu Gln Asn Lys Ile Lys Leu Lys Asp Leu Met Ala Gly Val Gln Lys
            20                  25                  30

Leu

<210> SEQ ID NO 59
<211> LENGTH: 33
<212> TYPE: PRT
<213> ORGANISM: Trichophyton interdigitale

<400> SEQUENCE: 59

Gln Glu Pro Phe Gly Trp Pro Phe Lys Pro Met Val Thr Gln Asp Asp
1               5                   10                  15

Leu Gln Asn Lys Ile Lys Leu Lys Asp Ile Met Ala Gly Val Glu Lys
            20                  25                  30

Leu

<210> SEQ ID NO 60
<211> LENGTH: 33
<212> TYPE: PRT
<213> ORGANISM: Trichophyton equinum

<400> SEQUENCE: 60

Gln Glu Pro Phe Gly Trp Pro Phe Lys Pro Met Val Thr Gln Asp Asp
1               5                   10                  15

Leu Gln Asn Lys Ile Lys Leu Lys Asp Ile Met Ala Gly Val Glu Lys
            20                  25                  30

Leu

<210> SEQ ID NO 61
<211> LENGTH: 33
<212> TYPE: PRT
<213> ORGANISM: Trichophyton tonsurans

<400> SEQUENCE: 61

Gln Glu Pro Phe Gly Trp Pro Phe Lys Pro Met Val Thr Gln Asp Asp
1               5                   10                  15

Leu Gln Asn Lys Ile Lys Leu Lys Asp Ile Met Ala Gly Ile Glu Lys
            20                  25                  30

Leu

<210> SEQ ID NO 62
<211> LENGTH: 33
<212> TYPE: PRT
<213> ORGANISM: Trichophyton verrucosum

<400> SEQUENCE: 62

Gln Glu Pro Phe Gly Trp Pro Phe Lys Pro Met Val Thr Gln Asp Asp
1               5                   10                  15

Leu Gln Asn Lys Ile Lys Leu Lys Asp Ile Met Ala Gly Val Glu Lys
            20                  25                  30

Leu

<210> SEQ ID NO 63
<211> LENGTH: 33

```
<212> TYPE: PRT
<213> ORGANISM: Arthroderma benhamiae

<400> SEQUENCE: 63

Gln Glu Pro Phe Gly Trp Pro Phe Lys Pro Met Val Thr Gln Asp Asp
1               5                   10                  15

Leu Gln Asn Lys Ile Lys Leu Lys Asp Ile Met Ala Gly Val Glu Lys
            20                  25                  30

Leu

<210> SEQ ID NO 64
<211> LENGTH: 33
<212> TYPE: PRT
<213> ORGANISM: Trichophyton rubrum

<400> SEQUENCE: 64

Gln Glu Pro Phe Gly Trp Pro Phe Lys Pro Met Val Thr Gln Asp Asp
1               5                   10                  15

Leu Gln Asn Lys Ile Lys Leu Lys Asp Ile Met Ala Gly Val Glu Lys
            20                  25                  30

Leu

<210> SEQ ID NO 65
<211> LENGTH: 41
<212> TYPE: PRT
<213> ORGANISM: Uncinocarpus reesii

<400> SEQUENCE: 65

Ala Gly Leu Gln Asn Pro Gln Leu Gly Lys Arg Ile Pro Asp Ile Phe
1               5                   10                  15

Lys Pro Leu Val Ser His Asp Glu Leu Met Ala Arg Val Lys Leu Arg
            20                  25                  30

Asp Leu Glu Ala Gly Ile Asp Lys Leu
        35                  40

<210> SEQ ID NO 66
<211> LENGTH: 41
<212> TYPE: PRT
<213> ORGANISM: Coccidioides immitis

<400> SEQUENCE: 66

Ala Gly Leu Glu Lys Pro Glu Leu Gly Lys Arg Val Pro Tyr Ile Phe
1               5                   10                  15

Lys Asp Leu Val Ser His Asp Ala Leu Leu Ala Lys Ile Lys Leu Lys
            20                  25                  30

Asp Leu Glu Glu Gly Ile Gly Lys Leu
        35                  40

<210> SEQ ID NO 67
<211> LENGTH: 41
<212> TYPE: PRT
<213> ORGANISM: Coccidioides posadasii

<400> SEQUENCE: 67

Ala Gly Leu Glu Lys Pro Glu Leu Gly Lys Arg Val Pro Tyr Ile Phe
1               5                   10                  15

Lys Asp Leu Val Ser His Asp Ala Leu Leu Ala Lys Ile Lys Leu Lys
            20                  25                  30

Asp Leu Glu Asp Gly Ile Gly Lys Leu
        35                  40
```

-continued

```
<210> SEQ ID NO 68
<211> LENGTH: 39
<212> TYPE: PRT
<213> ORGANISM: Artificial Sequence
<220> FEATURE:
<223> OTHER INFORMATION: Synthetic peptide

<400> SEQUENCE: 68

Gly Gly His Gly Gly Ser Ser Gly Leu Gly Cys Asp Ser Gln Arg Pro
1               5                   10                  15

Leu Val Ser Ser Glu Lys Leu Gln Ser Leu Ile Lys Lys Glu Asp Leu
            20                  25                  30

Leu Ala Gly Ser Gln Glu Leu
        35

<210> SEQ ID NO 69
<211> LENGTH: 39
<212> TYPE: PRT
<213> ORGANISM: Myceliophthora thermophila

<400> SEQUENCE: 69

Gly Gly His Gly Gly Ser Ser Gly Leu Gly Cys Asp Ser Gln Arg Pro
1               5                   10                  15

Leu Val Ser Ser Glu Lys Leu Gln Ser Leu Ile Lys Lys Glu Asp Leu
            20                  25                  30

Leu Ala Gly Ser Gln Glu Leu
        35

<210> SEQ ID NO 70
<211> LENGTH: 38
<212> TYPE: PRT
<213> ORGANISM: Artificial Sequence
<220> FEATURE:
<223> OTHER INFORMATION: Synthetic peptide

<400> SEQUENCE: 70

Gly Gly Pro His Gly Phe Gly Leu Pro Lys Ile Asp Leu Arg Pro Met
1               5                   10                  15

Val Ser Ser Asn Arg Leu Gln Ser Met Ile Thr Leu Lys Asp Leu Met
            20                  25                  30

Asp Gly Ala Lys Lys Leu
        35

<210> SEQ ID NO 71
<211> LENGTH: 38
<212> TYPE: PRT
<213> ORGANISM: Chaetomium thermophilum var. thermophilum DSM 1495

<400> SEQUENCE: 71

Gly Gly Pro His Gly Phe Gly Leu Pro Lys Ile Asp Leu Arg Pro Met
1               5                   10                  15

Val Ser Ser Asn Arg Leu Gln Ser Met Ile Thr Leu Lys Asp Leu Met
            20                  25                  30

Asp Gly Ala Lys Lys Leu
        35

<210> SEQ ID NO 72
<211> LENGTH: 38
<212> TYPE: PRT
<213> ORGANISM: Chaetomium thermophilum
```

```
<400> SEQUENCE: 72

Gly Gly Pro His Gly Phe Gly Leu Pro Lys Ile Asp Leu Arg Pro Met
1               5                   10                  15

Val Ser Ser Asn Arg Leu Gln Ser Met Ile Thr Leu Lys Asp Leu Met
            20                  25                  30

Asp Gly Ala Lys Lys Leu
        35

<210> SEQ ID NO 73
<211> LENGTH: 38
<212> TYPE: PRT
<213> ORGANISM: Podospora anserina

<400> SEQUENCE: 73

Gly Asp Gly Lys Gly Lys Gly Lys Asp Lys Thr Pro Lys Lys Pro Leu
1               5                   10                  15

Val Ser Ser Ala Lys Leu Gln Ser Tyr Val Asn Lys Arg Asp Leu Leu
            20                  25                  30

Asn Asp Ala Asn Lys Leu
        35

<210> SEQ ID NO 74
<211> LENGTH: 27
<212> TYPE: PRT
<213> ORGANISM: Artificial Sequence
<220> FEATURE:
<223> OTHER INFORMATION: Synthetic peptide

<400> SEQUENCE: 74

Thr Lys Lys Pro Leu Val Asn Glu Leu Lys Leu Gln Lys Asp Ile Asn
1               5                   10                  15

Ile Lys Asp Leu Met Ala Gly Ala Gln Lys Leu
            20                  25

<210> SEQ ID NO 75
<211> LENGTH: 27
<212> TYPE: PRT
<213> ORGANISM: Fusarium oxysporum

<400> SEQUENCE: 75

Thr Lys Lys Pro Leu Val Asn Glu Leu Lys Leu Gln Lys Asp Ile Asn
1               5                   10                  15

Ile Lys Asp Leu Met Ala Gly Ala Gln Lys Leu
            20                  25

<210> SEQ ID NO 76
<211> LENGTH: 27
<212> TYPE: PRT
<213> ORGANISM: Fusarium fujikuroi

<400> SEQUENCE: 76

Thr Lys Lys Pro Leu Val Asn Glu Leu Lys Leu Gln Lys Asp Ile Asn
1               5                   10                  15

Ile Lys Asp Leu Met Ala Gly Ala Gln Lys Leu
            20                  25

<210> SEQ ID NO 77
<211> LENGTH: 27
<212> TYPE: PRT
<213> ORGANISM: Fusarium verticillioides

<400> SEQUENCE: 77
```

```
Thr Lys Lys Pro Leu Val Asn Glu Leu Lys Leu Gln Lys Asp Ile Asn
1               5                   10                  15

Ile Lys Gly Leu Met Glu Gly Ala Gln Lys Leu
            20                  25

<210> SEQ ID NO 78
<211> LENGTH: 28
<212> TYPE: PRT
<213> ORGANISM: Fusarium pseudograminearum

<400> SEQUENCE: 78

Thr Pro Lys Lys Pro Leu Val Asn Glu Leu Lys Leu Gln Lys Asp Ile
1               5                   10                  15

Thr Leu Lys Gly Leu Met Ala Gly Ala Gln Lys Leu
            20                  25

<210> SEQ ID NO 79
<211> LENGTH: 28
<212> TYPE: PRT
<213> ORGANISM: Fusarium graminearum

<400> SEQUENCE: 79

Thr Pro Lys Lys Pro Leu Val Asn Glu Leu Lys Leu Gln Lys Asp Ile
1               5                   10                  15

Thr Leu Lys Gly Leu Met Ala Gly Ala Gln Lys Leu
            20                  25

<210> SEQ ID NO 80
<211> LENGTH: 29
<212> TYPE: PRT
<213> ORGANISM: Nectria haematococca

<400> SEQUENCE: 80

Gly Ser Ser Lys Lys Pro Leu Val Asn Ser Leu Lys Leu Gln Lys Leu
1               5                   10                  15

Ile Asn Ile Asp Gly Leu Leu Ala Gly Ser Gln Lys Leu
            20                  25

<210> SEQ ID NO 81
<211> LENGTH: 39
<212> TYPE: PRT
<213> ORGANISM: Scedosporium apiospermum

<400> SEQUENCE: 81

Gly Gly Lys Gly Gly Lys Gly Gly His Gly Gly Gln Cys Ser Lys Pro
1               5                   10                  15

Leu Val Ser Ser Lys Lys Leu Gln Gln His Ile Lys Leu Lys Asp Leu
            20                  25                  30

Leu Ala Gly Ser Gln Lys Leu
        35

<210> SEQ ID NO 82
<211> LENGTH: 28
<212> TYPE: PRT
<213> ORGANISM: Verticillium dahliae

<400> SEQUENCE: 82

Ala Lys Cys Lys Pro Tyr Val Ser Ser Glu Ala Leu Gln Glu Leu Val
1               5                   10                  15

Lys Ile Glu Asp Leu Met Ala Gly Ser Gln Ala Leu
            20                  25
```

<210> SEQ ID NO 83
<211> LENGTH: 28
<212> TYPE: PRT
<213> ORGANISM: Verticillium alfalfae

<400> SEQUENCE: 83

Ala Lys Cys Lys Pro Tyr Val Ser Ser Glu Ala Leu Gln Glu Leu Val
1               5                   10                  15

Lys Ile Glu Asp Leu Met Ala Gly Ser Gln Ala Leu
            20                  25

<210> SEQ ID NO 84
<211> LENGTH: 34
<212> TYPE: PRT
<213> ORGANISM: Sordaria macrospora

<400> SEQUENCE: 84

Ser Thr Ser Gln Gly Gly Pro Thr Arg Lys Pro Tyr Val Cys Ser Asp
1               5                   10                  15

Ala Leu Gln His Leu Ile Thr Glu Lys Asp Ile Arg Ala Gly Ala Gln
            20                  25                  30

Thr Leu

<210> SEQ ID NO 85
<211> LENGTH: 34
<212> TYPE: PRT
<213> ORGANISM: Neurospora tetrasperma

<400> SEQUENCE: 85

Ala Thr Ile Gln Gly Gly Pro Thr Arg Lys Pro Tyr Val Cys Ser Asp
1               5                   10                  15

Ala Leu Gln Tyr Gln Ile Thr Glu Gln Asp Ile Arg Ala Gly Ala Gln
            20                  25                  30

Lys Leu

<210> SEQ ID NO 86
<211> LENGTH: 34
<212> TYPE: PRT
<213> ORGANISM: Neurospora crassa

<400> SEQUENCE: 86

Ala Thr Ile Gln Gly Gly Pro Thr Arg Lys Pro Tyr Val Cys Ser Asp
1               5                   10                  15

Ala Leu Gln Tyr Gln Ile Thr Glu Lys Asp Ile Arg Ala Gly Ala Gln
            20                  25                  30

Lys Leu

<210> SEQ ID NO 87
<211> LENGTH: 34
<212> TYPE: PRT
<213> ORGANISM: Acremonium chrysogenum

<400> SEQUENCE: 87

Lys Gly Pro Val Pro Phe Pro Gly Lys His Lys Tyr Val Thr Ser Glu
1               5                   10                  15

Ala Leu Gln Gln His Ile Thr Leu Asp Ser Leu Leu Ala Gly Ser Gln
            20                  25                  30

Lys Leu

<210> SEQ ID NO 88
<211> LENGTH: 28
<212> TYPE: PRT
<213> ORGANISM: Eutypa lata

<400> SEQUENCE: 88

Tyr Asn Thr Gln Pro Leu Val Thr Ser Glu Gln Leu Gln Glu Leu
1               5                   10                  15

Thr Ile Glu Asp Leu Leu Ala Gly Ser Gln Lys Leu
            20                  25

<210> SEQ ID NO 89
<211> LENGTH: 30
<212> TYPE: PRT
<213> ORGANISM: Pestatotiopsis fici

<400> SEQUENCE: 89

Ser Ser Glu Glu Gln Ser Pro Ala Val Thr Ser Glu Ala Ile Gln Glu
1               5                   10                  15

Leu Ile Leu Leu Glu Asp Leu Leu Ala Gly Ser Gln Lys Leu
            20                  25                  30

<210> SEQ ID NO 90
<211> LENGTH: 28
<212> TYPE: PRT
<213> ORGANISM: Stachybotrys chartarum IBT 40288

<400> SEQUENCE: 90

Gln Glu Cys Leu Glu His Val Thr Ser Glu Ala Leu Gln Glu Leu Ile
1               5                   10                  15

Thr Leu Glu Asp Leu Leu Ala Gly Ser Gln Lys Leu
            20                  25

<210> SEQ ID NO 91
<211> LENGTH: 28
<212> TYPE: PRT
<213> ORGANISM: Stachybotrys chartarum IBT 7711

<400> SEQUENCE: 91

Gln Glu Cys Leu Glu His Val Thr Ser Glu Ala Leu Gln Glu Leu Ile
1               5                   10                  15

Thr Leu Glu Asp Leu Leu Ala Gly Ser Gln Lys Leu
            20                  25

<210> SEQ ID NO 92
<211> LENGTH: 28
<212> TYPE: PRT
<213> ORGANISM: Stachybotrys chlorohalonata

<400> SEQUENCE: 92

Gln Glu Cys Leu Glu His Val Thr Ser Glu Ala Leu Gln Glu Leu Ile
1               5                   10                  15

Thr Leu Glu Asp Leu Leu Ala Gly Ser Gln Gln Leu
            20                  25

<210> SEQ ID NO 93
<211> LENGTH: 28
<212> TYPE: PRT
<213> ORGANISM: Colletotrichum gloeosporioides

<400> SEQUENCE: 93

Ala Lys Cys Lys Pro Tyr Val Asp Ser Glu Ser Leu Gln Glu Leu Ile

```
1               5                   10                  15
Thr Ile Glu Asp Leu Leu Ala Gly Ser Gln Lys Leu
            20                  25

<210> SEQ ID NO 94
<211> LENGTH: 32
<212> TYPE: PRT
<213> ORGANISM: Colletotrichum sublineola

<400> SEQUENCE: 94

Asn Lys Thr Tyr Val Glu Asn Lys Thr Tyr Val Glu Ser Asp Lys Leu
1               5                   10                  15

Gln Ala Leu Ile Thr Ile Asp Asp Leu Leu Ala Gly Ser Gln Lys Leu
            20                  25                  30

<210> SEQ ID NO 95
<211> LENGTH: 28
<212> TYPE: PRT
<213> ORGANISM: Colletotrichum graminicola

<400> SEQUENCE: 95

Phe Asp Val Lys Pro Tyr Val Glu Ser Asp Lys Leu Gln Ala Leu Ile
1               5                   10                  15

Asn Ile Asp Asp Leu Leu Ala Gly Ser Gln Lys Leu
            20                  25

<210> SEQ ID NO 96
<211> LENGTH: 32
<212> TYPE: PRT
<213> ORGANISM: Cyphellophora europaea

<400> SEQUENCE: 96

Gln Asp Trp Asp Asp Ser Asp Leu Pro Pro Val Ser Ser Glu Thr Leu
1               5                   10                  15

Val Asp Leu Val Thr Leu Glu Asp Leu Gln Ala Gly Ala Glu Lys Leu
            20                  25                  30

<210> SEQ ID NO 97
<211> LENGTH: 27
<212> TYPE: PRT
<213> ORGANISM: Exophiala aquamarina

<400> SEQUENCE: 97

Asn Asp Leu Pro Pro Val Thr Thr Glu Ala Leu Gln Ala Leu Ile Ala
1               5                   10                  15

Leu Asp Glu Leu Leu Ser Ala Ala Asn Gln Leu
            20                  25

<210> SEQ ID NO 98
<211> LENGTH: 29
<212> TYPE: PRT
<213> ORGANISM: Cladophialophora yegresii

<400> SEQUENCE: 98

Thr Glu Thr Glu Leu Pro Pro Val Thr Ser Glu Ala Leu Gln Ala Leu
1               5                   10                  15

Ile Ser Leu Asp Gly Leu Thr Ser Gly Ala Gln Gln Leu
            20                  25

<210> SEQ ID NO 99
<211> LENGTH: 29
<212> TYPE: PRT
```

<213> ORGANISM: Cladophialophora carrionii

<400> SEQUENCE: 99

```
Thr His Pro Thr Leu Pro Pro Val Thr Ser Glu Ala Leu Gln Ala Leu
1               5                   10                  15

Ile Ser Leu Asp Glu Leu Thr Ser Gly Ala Lys Gln Leu
            20                  25
```

<210> SEQ ID NO 100
<211> LENGTH: 44
<212> TYPE: PRT
<213> ORGANISM: Pyrenophora teres

<400> SEQUENCE: 100

```
Gln Tyr Asn Pro Lys Pro Glu Arg Ala Thr Val Lys Pro Arg Asn Thr
1               5                   10                  15

Ala Arg Glu Leu Gln Leu Val Ser Pro Asp Ala Leu Ile Lys Gln Ile
            20                  25                  30

Asn Leu Glu Asp Leu Leu Glu Gly Ser Gln Gln Leu
        35                  40
```

<210> SEQ ID NO 101
<211> LENGTH: 44
<212> TYPE: PRT
<213> ORGANISM: Pyrenophora triticirepentis

<400> SEQUENCE: 101

```
Gln Tyr Asp Ala Lys Pro Glu Arg Ala Thr Val Lys Pro Arg Asn Thr
1               5                   10                  15

Ala Arg Glu Leu Glu Leu Val Ser Pro Asp Ala Leu Ile Lys Gln Ile
            20                  25                  30

Asn Leu Glu Asp Leu Leu Glu Gly Ser Gln Gln Leu
        35                  40
```

<210> SEQ ID NO 102
<211> LENGTH: 47
<212> TYPE: PRT
<213> ORGANISM: Bipolaris zeicota

<400> SEQUENCE: 102

```
Gln Val Gly Pro Lys Pro Asn Pro Asn Thr Lys Pro Gly Lys Pro Gly
1               5                   10                  15

Lys His His Asp Lys Pro Lys Lys Leu Val Thr Pro Lys Asp Leu Ile
            20                  25                  30

Lys Asp Ile Lys Leu Glu Asp Leu Leu Lys Gly Ser Gln Lys Leu
        35                  40                  45
```

<210> SEQ ID NO 103
<211> LENGTH: 47
<212> TYPE: PRT
<213> ORGANISM: Bipolaris victoriae

<400> SEQUENCE: 103

```
Gln Val Gly Pro Lys Pro Asn Pro Asn Thr Lys Pro Gly Lys Pro Gly
1               5                   10                  15

Lys His His Asp Lys Pro Lys Lys Leu Val Thr Pro Lys Asp Leu Ile
            20                  25                  30

Lys Asp Ile Lys Leu Glu Asp Leu Leu Lys Gly Ser Gln Lys Leu
        35                  40                  45
```

-continued

<210> SEQ ID NO 104
<211> LENGTH: 48
<212> TYPE: PRT
<213> ORGANISM: Bipolaris oryzae

<400> SEQUENCE: 104

Gln Val Gly Pro Lys Pro Asn Pro Asn Thr Lys Pro Gly Lys Pro Pro
1               5                   10                  15

Gly Lys Pro His Asp Lys Pro Lys Lys Leu Val Thr Pro Lys Asp Leu
            20                  25                  30

Ile Lys Asp Ile Lys Leu Glu Asp Leu Leu Ala Gly Ser Gln Lys Leu
        35                  40                  45

<210> SEQ ID NO 105
<211> LENGTH: 47
<212> TYPE: PRT
<213> ORGANISM: Bipolaris maydis

<400> SEQUENCE: 105

Gln Val Gly Pro Lys Pro Asn Pro Asn Thr Lys Pro Gly Lys Pro Pro
1               5                   10                  15

Lys Pro Asp Asp Lys Pro Lys Lys Leu Val Thr Pro Lys Asp Leu Ile
            20                  25                  30

Lys Asp Ile Lys Leu Glu Asp Leu Leu Lys Gly Ser Gln Lys Leu
        35                  40                  45

<210> SEQ ID NO 106
<211> LENGTH: 47
<212> TYPE: PRT
<213> ORGANISM: Bipolaris sorokiniana

<400> SEQUENCE: 106

Gln Val Gly Pro Lys Pro Asn Pro Asn Thr Lys Pro Gly Lys Pro Gly
1               5                   10                  15

Lys Pro His Asp Lys Pro Lys Lys Leu Val Thr Pro Lys Asp Leu Ile
            20                  25                  30

Lys Asp Ile Lys Leu Glu Asp Leu Leu Lys Gly Ser Gln Lys Leu
        35                  40                  45

<210> SEQ ID NO 107
<211> LENGTH: 56
<212> TYPE: PRT
<213> ORGANISM: Setosphaeria turcica

<400> SEQUENCE: 107

Gln Tyr Asn Ala Met Pro Lys Pro Pro Gly Lys Pro Glu Thr Pro Pro
1               5                   10                  15

Lys Pro Ala Lys Pro Leu Gly Pro Gly Lys Pro Asp Gly Lys Pro Lys
            20                  25                  30

Lys Leu Val Thr Pro Asn Asp Leu Ile Lys Asp Ile Lys Leu Glu Asp
        35                  40                  45

Leu Leu Ala Gly Ser Gln Gln Leu
    50                  55

<210> SEQ ID NO 108
<211> LENGTH: 41
<212> TYPE: PRT
<213> ORGANISM: Phaeosphaeria nodorum

<400> SEQUENCE: 108

Gln Tyr Gly Val Ala Pro Asn Pro Pro Val Val Ser Pro Pro Ser Glu

```
                1               5                  10                  15
Lys Pro Leu Ile Ser Glu Ala Ala Leu Ile Lys Asp Val Lys Leu Glu
                    20                  25                  30

Asp Leu Leu Ala Gly Ser Gln Lys Leu
            35                  40
```

<210> SEQ ID NO 109
<211> LENGTH: 35
<212> TYPE: PRT
<213> ORGANISM: Leptosphaeria maculans

<400> SEQUENCE: 109

```
Gln Tyr Asp Ala Lys Pro Glu Pro Ser Asn Lys Lys Leu Val Ser Pro
1               5                   10                  15

Asn Glu Leu Ile Lys Lys Ile Lys Leu Glu Asp Leu Ile Ala Gly Ser
                20                  25                  30

Gln Lys Leu
        35
```

<210> SEQ ID NO 110
<211> LENGTH: 79
<212> TYPE: PRT
<213> ORGANISM: Neofusicoccum parvum

<400> SEQUENCE: 110

```
Ser Thr Pro Ala Gly His Val His Ala Val Arg Pro Ala Ser Leu Leu
1               5                   10                  15

Glu Arg Arg Gly Pro Gln Leu Phe Arg Arg Asp Trp Gln Pro Asp Val
                20                  25                  30

Glu Asn Trp Gly Pro Ala Pro Glu Thr Pro Asn Asp Ile Ala Val Ala
            35                  40                  45

Ala Ser Thr Asn Glu Thr Lys Pro Pro Val Ala Ser Asp Ala Leu Gln
        50                  55                  60

Asn Asp Ile Asp Ser Ala Ala Leu Leu Asp His Ala Glu Asn Leu
65                  70                  75
```

<210> SEQ ID NO 111
<211> LENGTH: 69
<212> TYPE: PRT
<213> ORGANISM: Macrophomina phaseolina

<400> SEQUENCE: 111

```
Val Arg Pro Ala Ser Arg Leu Gln Arg Arg Gly Pro Glu Leu Phe Pro
1               5                   10                  15

Arg Asp Trp Gln Pro Asp Val Gly Asn Trp Gly Pro Ala Pro Glu Thr
                20                  25                  30

Pro Asn Glu Ile Ser Val Gln Ala Arg Thr Glu Thr Lys Pro Leu Val
            35                  40                  45

Thr Ser Asp Ala Leu Gln Asn Asp Ile Ser Ser Glu Ala Leu Leu Asp
        50                  55                  60

His Ala Glu Asn Leu
65
```

<210> SEQ ID NO 112
<211> LENGTH: 68
<212> TYPE: PRT
<213> ORGANISM: Coniosporium apollinis

<400> SEQUENCE: 112

Ser Ser Pro Ser Pro Gln Gly Trp Arg Gly Glu Thr Lys Phe Pro
1               5                   10                  15

Lys Pro Trp Phe Pro Pro Lys Ser Trp Pro Gln Phe Pro Arg Leu Pro
            20                  25                  30

His Pro Phe His Pro Pro Arg Gly Pro Arg Glu Lys Pro Leu Val Lys
            35                  40                  45

Ser Glu Pro Leu Gln Ala Ser Ile Lys Glu Asp Ala Ile Arg Lys His
    50                  55                  60

Ala Glu Asn Leu
65

<210> SEQ ID NO 113
<211> LENGTH: 30
<212> TYPE: PRT
<213> ORGANISM: Pseudozyma flocculosa

<400> SEQUENCE: 113

Ala Pro Thr Lys Lys Gln Arg Leu Val Glu Pro Lys Arg Leu Arg Asn
1               5                   10                  15

Asp Leu Lys Val Lys Asp Leu Arg Arg Gly Ala Gln Lys Leu
            20                  25                  30

<210> SEQ ID NO 114
<211> LENGTH: 29
<212> TYPE: PRT
<213> ORGANISM: Pseudozyma hubeiensis

<400> SEQUENCE: 114

Arg Pro Gly Lys Leu Arg Pro Val Glu Ser Lys Arg Leu Arg Asn Asp
1               5                   10                  15

Ile Lys Arg Lys Asp Leu Leu Ser Gly Ala Arg Lys Leu
            20                  25

<210> SEQ ID NO 115
<211> LENGTH: 29
<212> TYPE: PRT
<213> ORGANISM: Pseudozyma brasiliensis

<400> SEQUENCE: 115

Arg Pro Gly Lys Leu Arg Pro Val Glu Ser Lys Arg Leu Arg Asp Asp
1               5                   10                  15

Ile Lys Arg His Asp Leu Leu Ser Gly Ala Arg Lys Leu
            20                  25

<210> SEQ ID NO 116
<211> LENGTH: 29
<212> TYPE: PRT
<213> ORGANISM: Sporisorium reilianum

<400> SEQUENCE: 116

Arg Pro Gly Lys Leu Arg Pro Val Glu Ser Lys Arg Leu Arg Asn Asp
1               5                   10                  15

Ile Lys Arg Lys Asp Leu Leu Ser Gly Ala Arg Lys Leu
            20                  25

<210> SEQ ID NO 117
<211> LENGTH: 29
<212> TYPE: PRT
<213> ORGANISM: Uslilago maydis

<400> SEQUENCE: 117

-continued

```
Arg Pro Pro Lys Leu Arg Pro Val Asp Ser Lys Arg Leu Arg Asn Asp
1               5                   10                  15

Ile Lys Arg Lys Asp Leu Leu Asp Gly Ala Arg Lys Leu
            20                  25

<210> SEQ ID NO 118
<211> LENGTH: 29
<212> TYPE: PRT
<213> ORGANISM: Pseudozyma antarctica

<400> SEQUENCE: 118

Ala Pro Gly Lys Lys Arg Pro Val Glu Ala Lys Arg Leu Arg Asn Asp
1               5                   10                  15

Val Lys Arg Lys Asp Leu Leu Asp Gly Ala Lys Arg Leu
            20                  25

<210> SEQ ID NO 119
<211> LENGTH: 70
<212> TYPE: PRT
<213> ORGANISM: Zymoseptoria tritici

<400> SEQUENCE: 119

Thr Asn Val Asp Gly Pro Ile Glu Ile Leu Glu Val Arg Gln Asp Ala
1               5                   10                  15

Arg Ile Ala Thr Pro Pro Ser Gly Pro Pro Lys Gly Lys Gly Pro Gly
            20                  25                  30

Lys Gly Lys Gly Pro Lys Gly Pro Pro Gly Tyr Pro Gly Gly Pro Pro
        35                  40                  45

Lys Gly Pro Pro Lys Arg Pro Val Asn Ser Lys Ala Leu Gln Leu Ala
    50                  55                  60

Ile Arg Glu Ser Glu Leu
65                  70

<210> SEQ ID NO 120
<211> LENGTH: 37
<212> TYPE: PRT
<213> ORGANISM: Sphaerulina musiva

<400> SEQUENCE: 120

His Glu Asn Gln Leu Asp Thr Arg Gln Tyr Gln Val Thr Pro Asn Val
1               5                   10                  15

Asp Ser Lys Lys Leu Gln Asp Ser Ile Thr Glu Ala Ala Leu Lys Gln
            20                  25                  30

Lys Ala Gln Glu Leu
        35

<210> SEQ ID NO 121
<211> LENGTH: 42
<212> TYPE: PRT
<213> ORGANISM: Neofusicoccum parvum

<400> SEQUENCE: 121

Ala Pro Asn Pro Tyr Val Trp Lys Pro Ala Pro Lys Pro Arg Asp Val
1               5                   10                  15

Trp Arg Pro Ala Val Ser Ser Glu Glu Leu Gln Ala Ser Ile Ser Gly
            20                  25                  30

Asp Ala Leu Tyr Glu His Glu Ala Gln Leu
        35                  40

<210> SEQ ID NO 122
```

```
<211> LENGTH: 42
<212> TYPE: PRT
<213> ORGANISM: Macrophomina phaseolina

<400> SEQUENCE: 122

Ala Pro Asn Pro Tyr Val Trp Lys Pro Ser Pro Lys Pro Arg Ala Ala
1               5                   10                  15

Trp Arg Pro Ala Val Thr Ser Glu Glu Leu Gln Ala Ala Ile Ser Gly
            20                  25                  30

Asp Ala Leu Tyr Glu His Glu Ala Gln Leu
        35                  40

<210> SEQ ID NO 123
<211> LENGTH: 41
<212> TYPE: PRT
<213> ORGANISM: Coniosporium apollinis

<400> SEQUENCE: 123

Ser Pro Lys Asn Pro Tyr Ile Trp Arg Pro Ala Arg Arg Gln Tyr Gly
1               5                   10                  15

Ala Gln Pro Val Asp Ser Glu Thr Leu Arg Ala Thr Ile Asp Ser Asp
            20                  25                  30

Ala Leu Leu Ala His Ser Arg Met Leu
        35                  40

<210> SEQ ID NO 124
<211> LENGTH: 32
<212> TYPE: PRT
<213> ORGANISM: Endocarpon pusillum

<400> SEQUENCE: 124

Gln Asp Ser Gly Thr Asp Ile Asp Gly Pro Phe Thr Arg Asp Glu Leu
1               5                   10                  15

Arg Ser Ser Ile Asn Leu Asp Asp Leu Leu Ala Asp Ala Gln Thr Leu
            20                  25                  30

<210> SEQ ID NO 125
<211> LENGTH: 41
<212> TYPE: PRT
<213> ORGANISM: Phaeosphaeria nodorum

<400> SEQUENCE: 125

Glu Leu Arg Gly Arg Gln Asp Gly His Asn Asp Lys Pro Cys Lys Asn
1               5                   10                  15

Arg Pro Met Val Gly Ser Arg Lys Leu Glu Ala Asp Ile Thr Ser Lys
            20                  25                  30

Lys Leu Leu Arg Gly Ala Gln Gln Leu
        35                  40

<210> SEQ ID NO 126
<211> LENGTH: 36
<212> TYPE: PRT
<213> ORGANISM: Glarea lozoyensis

<400> SEQUENCE: 126

Ala Pro Ser Thr Ser Val Val Glu Ser Arg Ala Leu Pro Leu Val Gln
1               5                   10                  15

Ser Asn Gln Leu Arg Arg Val Leu Leu Arg Ser Glu Leu Leu Lys Lys
            20                  25                  30

Gly Gln Ile Leu
        35
```

<210> SEQ ID NO 127
<211> LENGTH: 43
<212> TYPE: PRT
<213> ORGANISM: Glarea lozoyensis

<400> SEQUENCE: 127

Gly Pro Ala Pro Ala Pro Ile Ser Ser Pro Thr Glu Ala Leu Val Glu
1               5                   10                  15

Arg Asp Leu Pro Leu Val Gln Ser Asn Gln Leu Arg Arg Val Leu Leu
            20                  25                  30

Arg Ser Glu Leu Leu Ala Lys Ala Arg Ile Leu
        35                  40

<210> SEQ ID NO 128
<211> LENGTH: 44
<212> TYPE: PRT
<213> ORGANISM: Coprinopsis cinerea

<400> SEQUENCE: 128

Gln Glu Ala Ser Thr Thr Gly Ile Gly Gly Leu Ile Trp Asp Ala Leu
1               5                   10                  15

Thr Pro Leu Lys Pro Leu Val Gln Thr Asp Leu Leu Gln Leu Leu Ile
            20                  25                  30

Ser Asp Arg Ala Leu Phe Asn His Ala Lys Gln Phe
        35                  40

<210> SEQ ID NO 129
<211> LENGTH: 35
<212> TYPE: PRT
<213> ORGANISM: Tuber metanosporum

<400> SEQUENCE: 129

Thr Pro Leu Ala Pro Ala Pro Thr His Asn Val Ser Leu Val Glu Ser
1               5                   10                  15

Lys Lys Leu Arg Arg Val Leu Asn Lys Lys Ala Leu Tyr Glu His Ala
            20                  25                  30

Lys Glu Phe
        35

<210> SEQ ID NO 130
<211> LENGTH: 34
<212> TYPE: PRT
<213> ORGANISM: Eutypa lata

<400> SEQUENCE: 130

Glu Pro Ile Arg Arg Ser Ser Cys Gly Leu Pro Leu Val Gln Asp Glu
1               5                   10                  15

Ala Leu Val Asp Ala Val Val Ile Asp Asp Leu Leu Gln Cys Ala Gln
            20                  25                  30

Asp Leu

<210> SEQ ID NO 131
<211> LENGTH: 45
<212> TYPE: PRT
<213> ORGANISM: Artificial Sequence
<220> FEATURE:
<223> OTHER INFORMATION: Synthetic peptide

<400> SEQUENCE: 131

Leu Gln Ile Pro Leu Asn Leu Gln Val Pro Lys Leu Ser Trp Asn Leu

```
                1               5              10              15

Phe Gly Asp Asp Leu Pro Leu Val Asp Thr Lys Glu Leu Gln Lys Ser
                    20                  25                  30

Ile Lys Pro Glu Asn Leu Glu Ala Arg Ala Lys Asp Leu
            35                  40                  45

<210> SEQ ID NO 132
<211> LENGTH: 45
<212> TYPE: PRT
<213> ORGANISM: Fusarium oxysporum

<400> SEQUENCE: 132

Leu Gln Ile Pro Leu Asn Leu Gln Val Pro Lys Leu Ser Trp Asn Leu
1               5                   10                  15

Phe Gly Asp Asp Leu Pro Leu Val Asp Thr Lys Glu Leu Gln Lys Ser
                    20                  25                  30

Ile Lys Pro Glu Asn Leu Glu Ala Arg Ala Lys Asp Leu
            35                  40                  45

<210> SEQ ID NO 133
<211> LENGTH: 6
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa may be any amino acid other than cysteine

<400> SEQUENCE: 133

Xaa Pro Ala Ala Ala Arg
1               5

<210> SEQ ID NO 134
<211> LENGTH: 83
<212> TYPE: DNA
<213> ORGANISM: Artificial Sequence
<220> FEATURE:
<223> OTHER INFORMATION: Synthetic sequence

<400> SEQUENCE: 134
acaagtttgt acaaaaaagc aggcttcacc atgcagacct cggtgctttt tctcgtttcc    60
ttcctcgccg ccaggtaagt tgg                                           83
```

AMINOPEPTIDASES FOR PROTEIN HYDROLYZATES

CROSS-REFERENCE TO RELATED APPLICATIONS

This application claims priority under 35 USC 071 as a national phase of International Patent Application No. PCT/US2016/039494 (filed Jun. 27, 2016; and published on Dec. 29, 2016 as Publication No. WO2016210395A1), which claims priority to and the benefit of U.S. provisional patent application No. 62/185,503, filed Jun. 26, 2015; and 62/235,937, filed Oct. 1, 2015; each provisional application titled "NOVEL AMINOPEPTIDASES FOR PROTEIN HYDROLYSATES'.

INCORPORATION BY REFERENCE OF THE SEQUENCE LISTING

The sequence listing provided in the file named "20160610_NB40989-PCT sequence listing prj_ST25.txt" with a size of 192,505 bytes which was created on Jun. 10, 2016 and which is filed herewith, is incorporated by reference herein in its entirety.

BACKGROUND

Various food and feed products contain protein hydrolysates. This hydrolysis was conventionally accomplished using chemical hydrolysis. However, such chemical hydrolysis led to severe degradation of the amino acids obtained during the hydrolysis, and also to hazardous byproducts formed in the course of the chemical reaction. Increasing concern over the use of protein hydrolysates obtained by chemical hydrolysis has led to the development of enzymatic hydrolysis processes.

Enzymatic hydrolysis processes of proteinaceous materials aim at obtaining a high degree of hydrolysis. Polypeptides having aminopeptidase activity catalyze the removal of one or more amino acid residues from the N-terminus of peptides, polypeptides, and proteins. The production of protein hydrolysates with desirable properties and high degrees of hydrolysis generally requires the use of a mixture of peptidase activities. It would be desirable to provide a single component peptidase enzyme which has activity useful for improving the properties and degree of hydrolysis of protein hydrolysates used in food and or feed products either alone or in combination with other enzymes.

The present disclosure provides novel polypeptides having improved aminopeptidase activity as well as methods for obtaining protein hydrolysates with desirable qualities and high degrees of hydrolysis.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which.

DETAILED DESCRIPTION OF THE INVENTION

The present disclosure provides polypeptides having aminopeptidase activity. The present invention also relates to nucleic acid sequences encoding the polypeptides and to nucleic acid constructs, vectors, and host cells comprising the nucleic acid sequences as well as methods for producing the polypeptides. The present disclosure also relates to methods for obtaining hydrolysates from proteinaceous substrates which comprise subjecting the proteinaceous material to a polypeptide with aminopeptidase activity alone or in combination with a protease, e.g. an endopeptidase. The present disclosure also relates to methods for obtaining from a proteinaceous substrate a hydrolysate enriched in free glutamic acid and/or peptide bound glutamic acid residues, which methods comprise subjecting the substrate to a polypeptide having aminopeptidase activity. The present disclosure further relates to flavor improving compositions comprising a polypeptide with aminopeptidase activity. The compositions may further comprise additional enzymatic activities.

In another aspect, the methods described herein may be used in food related applications to improve flavor, such as baking. Alternatively, flavor improvement in foods may be achieved by the addition of hydrolysates obtained by the methods of the invention. In some embodiments, the hydrolysate produced using the aminopeptidases described herein may also have reduced bitterness when compared to an untreated hydrolysate.

In some embodiments, the invention provides new fungal aminopeptidases (PepNs), their high yield production in a production host (e.g. *Trichoderma reesei*), and their use for the generation of protein hydrolysates, e.g., for debittering and for glutamate production. As demonstrated in Example 9, aminopeptidases type 2 according to the invention showed improved glutamate release compared with aminopeptidases type 1. Initial results suggest that these PepNs are tolerant to Proline in P1' which is surprising compared to other known aminopeptidases. Thus, the proline tolerant aminopeptidases taught for use in the present invention are capable of acting on a wide range of peptide and/or protein substrates and due to having such a broad substrate-specificity are not readily inhibited from cleaving substrates enriched in certain amino acids (e.g. proline and/or lysine and/or arginine and/or glycine).

Figure 9:
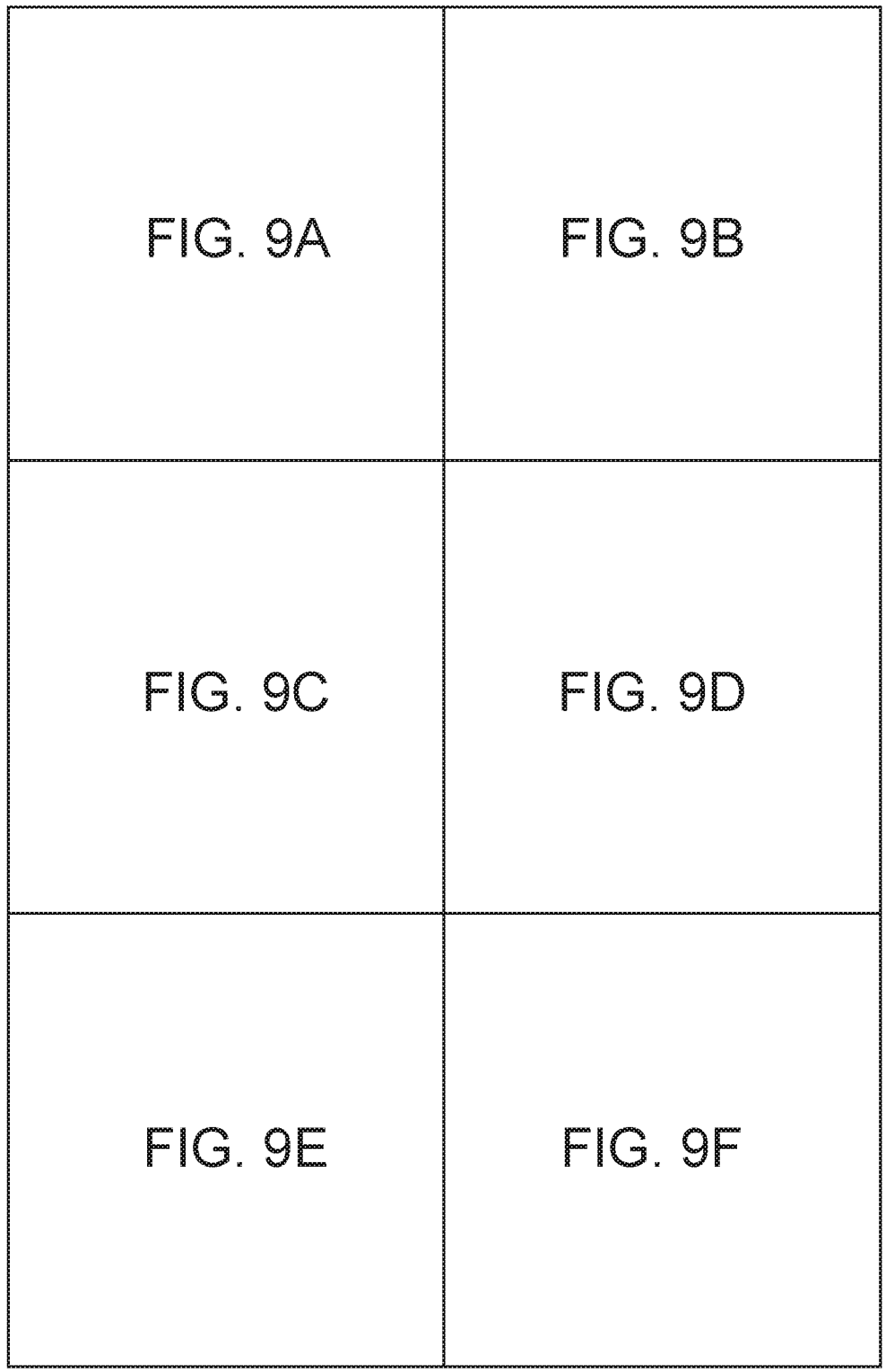
FIG. 9 shows the spatial arrangement of six panels FIG. 9A-9F which detail a sequence alignment of several PepN 2 enzymes.
Figure 9B:
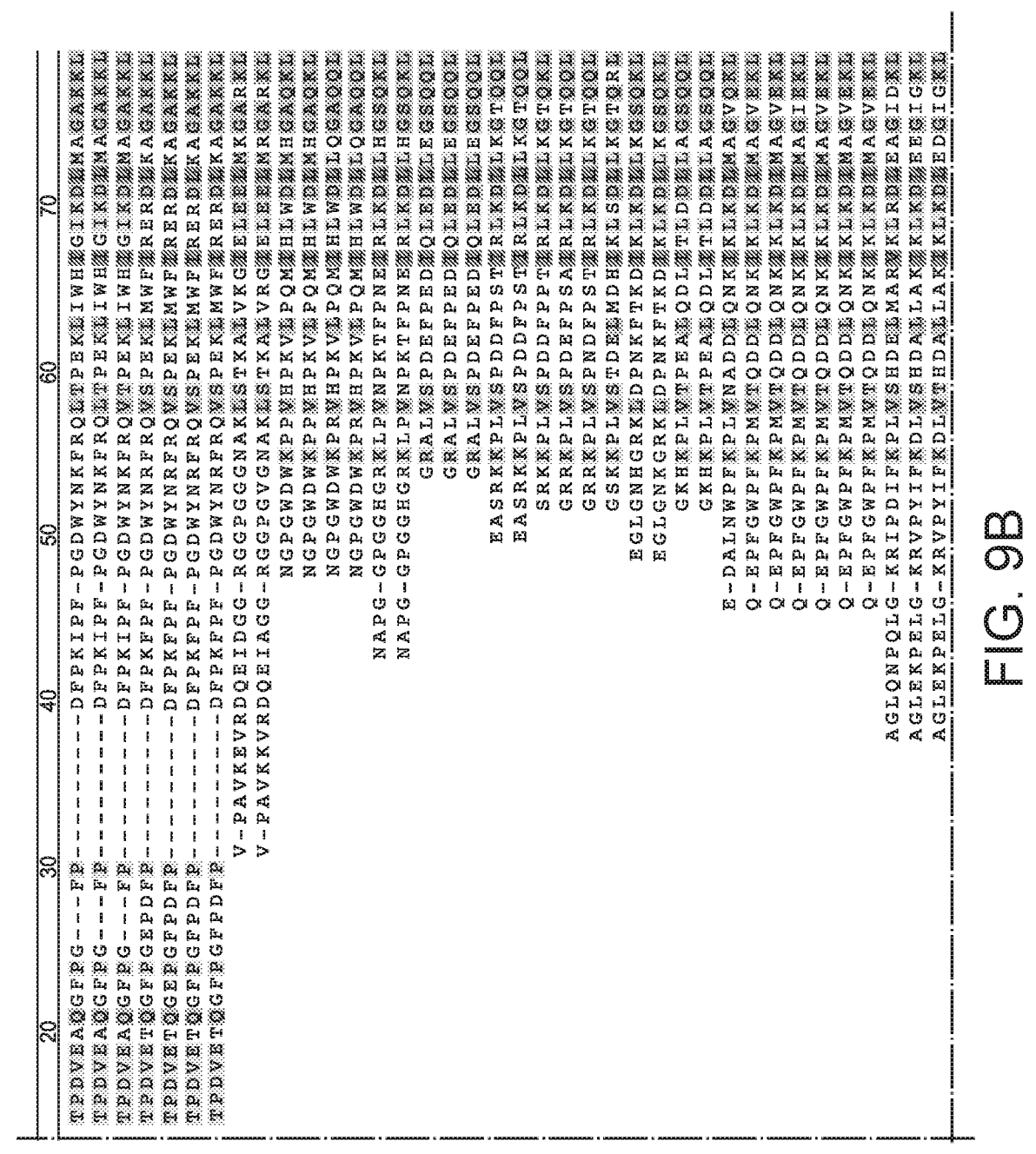
Figure 9F:
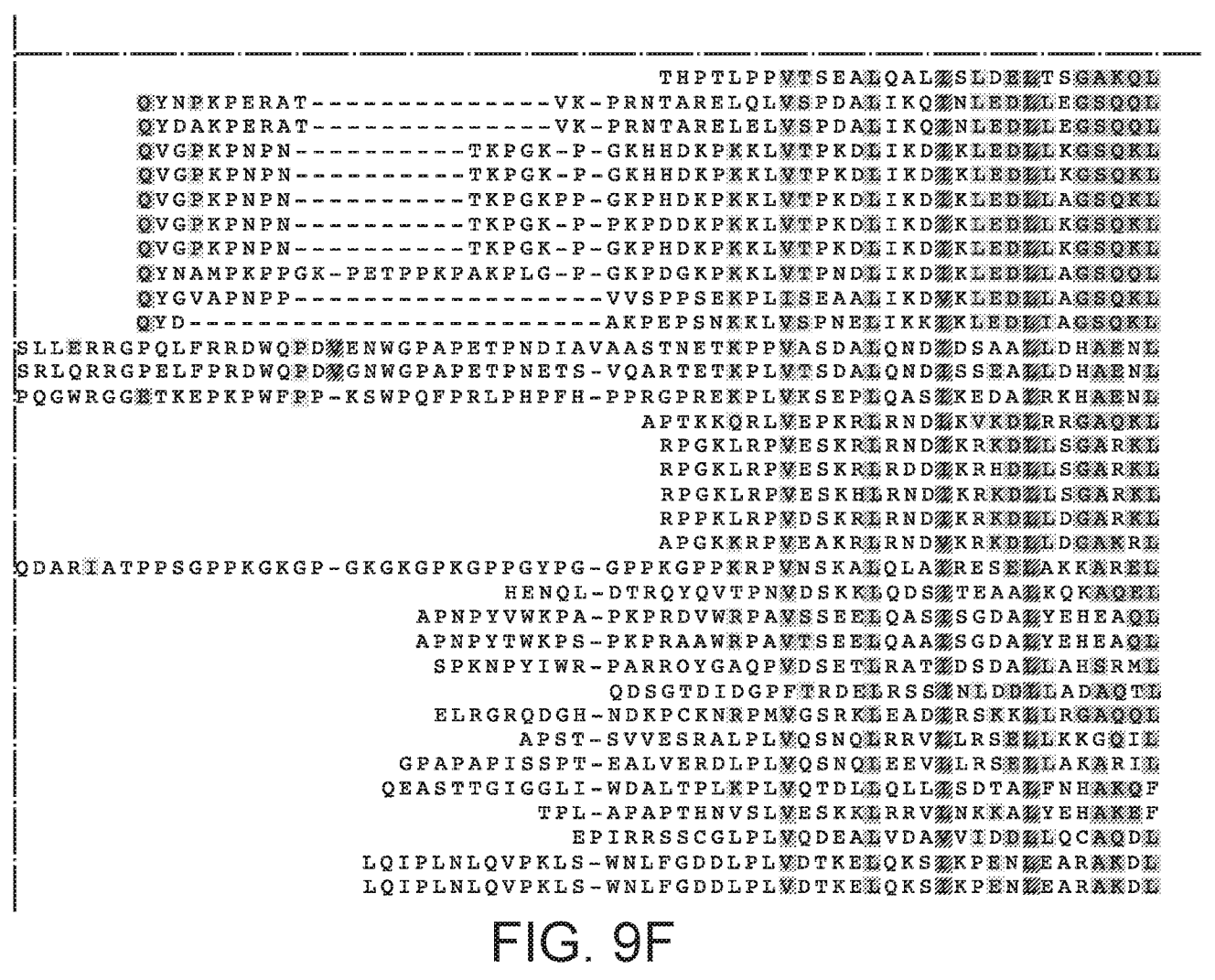

The present inventors surprisingly found that aminopeptidases type 2 have better performance that aminopeptidases type 1. Furthermore, the present inventors surprisingly found a group of fungal aminopeptidases type 2 with improved performance. This group of fungal aminopeptidases type 2 has a longer N-terminal in their mature amino acid sequences. FIG. 9 shows the amino acid sequence alignment of several aminopeptidases type 2.

The term "aminopeptidase activity" is defined herein as a peptidase activity which catalyzes the removal of amino acids from the N-terminal end of peptides, oligopeptides or proteins. Defined in a general manner, the aminopeptidase activity is capable of cleaving the amino acid X from the N-terminus of a peptide, polypeptide, or protein, wherein X may represent any amino acid residue selected from the group consisting of Ala, Arg, Asn, Asp, Cys, Gln, Glu, Gly, His, Ile, Leu, Lys, Met, Phe, Pro, Ser, Thr, Trp, Tyr, and Val, but at least Leu, Glu, Gly, Ala, and/or Pro. It will be understood that the polypeptides having aminopeptidase activity of the present invention may be unspecific as to the amino acid to be cleaved of the N-terminus of the peptide, polypeptide substrate.

In some embodiments, the present invention relates to an isolated polypeptide having aminopeptidase activity which has a predicted mature sequence with more than 13 residues on the N-terminal side of the conserved residue I/V in position 67 as shown in the sequence alignment of FIG. 9, or a fragment thereof, wherein the fragment has aminopeptidase activity.

In some embodiments, the present invention relates to isolated polypeptides having an amino acid sequence which has a degree of identity to the mature amino acid sequence of SEQ ID NO: 1 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 1. In some embodiments, the polypeptides of the present invention comprise the amino acid sequence of SEQ ID NO: 1, the mature amino sequence or an allelic variant; and a fragment thereof, wherein the fragment has aminopeptidase activity. In some embodiments, the polypeptides of the present invention comprise the amino acid sequence of SEQ ID NO: 1. In another embodiment, the polypeptide of the present invention has the amino acid sequence of SEQ ID NO: 1 or a fragment thereof, wherein the fragment has aminopeptidase activity. A fragment of SEQ ID NO: 1 is a polypeptide having one or more amino acids deleted from the amino and/or carboxy terminus of this amino acid sequence. In some embodiments the fragment comprises the sequence of SEQ ID NO:18. In some embodiments, the polypeptide has the amino acid sequence of SEQ ID NO: 1.

In some embodiments, the present invention relates to isolated polypeptides having an amino acid sequence which has a degree of identity to the mature amino acid sequence of SEQ ID NO: 2 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 2. In some embodiments, the polypeptides of the present invention comprise the amino acid sequence of SEQ ID NO: 2, the mature amino sequence or an allelic variant; and a fragment thereof, wherein the fragment has aminopeptidase activity. In some embodiments, the polypeptides of the present invention comprise the amino acid sequence of SEQ ID NO: 2. In another embodiment, the polypeptide of the present invention has the amino acid sequence of SEQ ID NO: 2 or a fragment thereof, wherein the fragment has aminopeptidase activity. A fragment of SEQ ID NO: 2 is a polypeptide having one or more amino acids deleted from the amino and/or carboxy terminus of this amino acid sequence. In some embodiments the fragment comprises the sequence of SEQ ID NO:19. In some embodiments, the polypeptide has the amino acid sequence of SEQ ID NO: 2.

In some embodiments, the present invention relates to isolated polypeptides having an amino acid sequence which has a degree of identity to the mature amino acid sequence of SEQ ID NO: 3 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 3. In some embodiments, the polypeptides of the present invention comprise the amino acid sequence of SEQ ID NO: 3, the mature amino sequence or an allelic variant; and a fragment thereof, wherein the fragment has aminopeptidase activity. In some embodiments, the polypeptides of the present invention comprise the amino acid sequence of SEQ ID NO: 3. In another embodiment, the polypeptide of the present invention has the amino acid sequence of SEQ ID NO: 3 or a fragment thereof, wherein the fragment has aminopeptidase activity. A fragment of SEQ ID NO: 3 is a polypeptide having one or more amino acids deleted from the amino and/or carboxy terminus of this amino acid sequence. In some embodiments the fragment comprises the sequence of SEQ ID NO:20. In some embodiments, the polypeptide has the amino acid sequence of SEQ ID NO: 3.

In some embodiments, the present invention relates to isolated polypeptides having an amino acid sequence which has a degree of identity to the mature amino acid sequence of SEQ ID NO: 4 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 4. In some embodiments, the polypeptides of the present invention comprise the amino acid sequence of SEQ ID NO: 4, the mature amino sequence or an allelic variant; and a fragment thereof, wherein the fragment has aminopeptidase activity. In some embodiments, the polypeptides of the present invention comprise the amino acid sequence of SEQ ID NO: 4. In another embodiment, the polypeptide of the present invention has the amino acid sequence of SEQ ID NO: 4 or a fragment thereof, wherein the fragment has aminopeptidase activity. A fragment of SEQ ID NO: 4 is a polypeptide having one or more amino acids deleted from the amino and/or carboxy terminus of this amino acid sequence. In some embodiments the fragment comprises the sequence of SEQ ID NO:21. In some embodiments, the polypeptide has the amino acid sequence of SEQ ID NO: 4.

In some embodiments, the present invention relates to isolated polypeptides having an amino acid sequence which has a degree of identity to the mature amino acid sequence of SEQ ID NO: 5 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 5. In some embodiments, the polypeptides of the present invention comprise the amino acid sequence of SEQ ID NO: 5, the mature amino sequence or an allelic variant; and a fragment thereof, wherein the fragment has aminopeptidase activity. In some embodiments, the polypeptides of the present invention comprise the amino acid sequence of SEQ ID NO: 5. In another embodiment, the polypeptide of the present invention has the amino acid sequence of SEQ ID NO: 5 or a fragment thereof, wherein the fragment has aminopeptidase activity. A fragment of SEQ ID NO: 5 is a polypeptide having one or more amino acids deleted from the amino and/or carboxy terminus of this amino acid sequence. In some embodiments the fragment comprises the sequence of SEQ ID NO:22. In some embodiments, the polypeptide has the amino acid sequence of SEQ ID NO: 5.

In some embodiments, the present invention relates to isolated polypeptides having an amino acid sequence which has a degree of identity to the mature amino acid sequence of SEQ ID NO: 6 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 6. In some embodiments, the polypeptides of the present invention comprise the amino acid sequence of SEQ ID NO: 6, the mature amino sequence or an allelic variant; and a fragment thereof, wherein the fragment has aminopeptidase activity. In some embodiments, the polypeptides of the present invention comprise the amino acid sequence of SEQ ID NO: 6. In another embodiment, the polypeptide of the present invention has the amino acid sequence of SEQ ID NO: 6 or a fragment thereof, wherein the fragment has aminopeptidase activity. A fragment of SEQ ID NO: 6 is a polypeptide having one or more amino acids deleted from the amino and/or carboxy terminus of this amino acid sequence. In some embodiments the fragment comprises the sequence of SEQ ID NO:23. In some embodiments, the polypeptide has the amino acid sequence of SEQ ID NO: 6.

In some embodiments, the present invention relates to isolated polypeptides having an amino acid sequence which has a degree of identity to the mature amino acid sequence of SEQ ID NO: 7 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 7. In some embodiments, the polypeptides of the present invention comprise the amino acid sequence of SEQ ID NO: 7, the mature amino sequence or an allelic variant; and a fragment thereof, wherein the fragment has aminopeptidase activity. In some embodiments, the polypeptides of the present invention comprise the amino acid sequence of SEQ ID NO: 7. In another embodiment, the polypeptide of the present invention has the amino acid sequence of SEQ ID NO: 7 or a fragment thereof, wherein the fragment has aminopeptidase activity. A fragment of SEQ ID NO: 7 is a polypeptide having one or more amino acids deleted from the amino and/or carboxy terminus of this amino acid sequence. In some embodiments the fragment comprises the sequence of SEQ ID NO:24. In some embodiments, the polypeptide has the amino acid sequence of SEQ ID NO: 7.

In some embodiments, the present invention relates to isolated polypeptides having an amino acid sequence which has a degree of identity to the mature amino acid sequence of SEQ ID NO: 8 of at least about 50%, preferably at least about 60%, preferably at least about 70%, more preferably at least about 80%, even more preferably at least about 90%, most preferably at least about 95%, and even most preferably at least about 97%, which have aminopeptidase activity (hereinafter "homologous polypeptides"). In some embodiments, the homologous polypeptides have an amino acid sequence which differs by five amino acids, preferably by four amino acids, more preferably by three amino acids, even more preferably by two amino acids, and most preferably by one amino acid from the amino acid sequence of SEQ ID NO: 8. In some embodiments, the polypeptides of the present invention comprise the amino acid sequence of SEQ ID NO: 8, the mature amino sequence or an allelic variant; and a fragment thereof, wherein the fragment has aminopeptidase activity. In some embodiments, the polypeptides of the present invention comprise the amino acid sequence of SEQ ID NO: 8. In another embodiment, the polypeptide of the present invention has the amino acid sequence of SEQ ID NO: 8 or a fragment thereof, wherein the fragment has aminopeptidase activity. A fragment of SEQ ID NO: 8 is a polypeptide having one or more amino acids deleted from the amino and/or carboxy terminus of this amino acid sequence. In some embodiments the fragment comprises the sequence of SEQ ID NO:25. In some embodiments, the polypeptide has the amino acid sequence of SEQ ID NO: 8.

Preferably, a fragment contains at least 330 amino acid residues, more preferably at least 380 amino acid residues, and most preferably at least 430 amino acid residues.

An allelic variant denotes any of two or more alternative forms of a gene occupying the same chromosomal locus. Allelic variation arises naturally through mutation, and may result in phenotypic polymorphism within populations.

The "parent enzyme" as used herein is an aminopeptidase enzyme which has all of the amino acid residues of the polypeptide as shown in SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8. In this respect, and for example, the parent will have all of the modifications (which may be zero, one or more than one depending on the variant) of the variant polypeptide.

In some embodiments, the present invention relates to isolated polypeptides having aminopeptidase activity which are encoded by nucleic acid sequences which hybridize under low stringency conditions, more preferably medium stringency conditions, and most preferably high stringency conditions, with an oligonucleotide probe which hybridizes under the same conditions with the polypeptide encoding part of nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16 or its complementary strand (J. Sambrook, E. F. Fritsch, and T. Maniatis, 1989, Molecular Cloning, A Laboratory Manual, 2d edition, Cold Spring Harbor, N.Y.); or allelic variants and fragments of the polypeptides, wherein the fragments have aminopeptidase activity.

Hybridization indicates that the nucleic acid sequence hybridizes to the oligonucleotide probe corresponding to the polypeptide encoding part of the nucleic acid sequence shown in SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16, under low to high stringency conditions (i.e., prehybridization and hybridization at 42° C. in 5×SSPE, 0.3% SDS, 200 Pg/ml sheared and denatured salmon sperm DNA, and either 25, 35 or 50% formamide for low, medium and high stringencies, respectively), following standard Southern blotting procedures.

The amino acid sequence of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8, or a partial sequence thereof may be used to design an oligonucleotide probe, or a nucleic acid sequence encoding a polypeptide of the present invention, such as the polypeptide encoding part of nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16, or a subsequence thereof, may be used to identify and clone DNA encoding polypeptides having aminopeptidase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 40 nucleotides in length. Longer probes can also be used. Both DNA and RNA probes can be used. The probes are typically labeled for detecting the corresponding gene (for example, with 32P, 3H, 35S, biotin, or avidin).

Thus, a genomic, cDNA or combinatorial chemical library prepared from such other organisms may be screened for DNA which hybridizes with the probes described above and which encodes a polypeptide having aminopeptidase activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with the polypeptide encoding part of nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16, the carrier material is used in a Southern blot in which the carrier material is finally washed three times for 30 minutes each using 2×SSC, 0.2% SDS preferably at least 50° C., more preferably at least 55° C., more preferably at least 60° C., more preferably at least 65° C., even more preferably at least 70° C., and most preferably at least 75° C. Molecules to which the oligonucleotide probe hybridizes under these conditions are detected using X-ray film.

The terms "modifying" and "modification" as used herein refers to a substitution when compared with the wild-type aminopeptidase polypeptide sequence of the closest identity. The comparison is made by aligning both the variant aminopeptidase polypeptide and the wild-type aminopeptidase with the reference sequence shown as SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8.

Likewise, "equivalent modification" as used herein refers to carrying out the same modification (usually a substitution) to an amino acid which is at an equivalent position in another aminopeptidase.

In one aspect, the aminopeptidase sequence according to the present invention is in an isolated form. The term "isolated" means that the aminopeptidase sequence is at least substantially free from at least one other component with which the aminopeptidase sequence is naturally associated in nature and as found in nature. The aminopeptidase sequence of the present invention may be provided in a form that is substantially free of one or more contaminants with which the substance might otherwise be associated. Thus, for example it may be substantially free of one or more potentially contaminating polypeptides and/or nucleic acid molecules.

In one aspect, the aminopeptidase sequence according to the present invention is in a purified form. The term "purified" means that a given component is present at a high level. The component is desirably the predominant component present in a composition. Preferably, the aminopeptidase is present at a level of at least about 90%, or at least about 95% or at least about 98%, said level being determined on a dry weight/dry weight basis with respect to the total composition under consideration.

As used herein, the singular "a," "an" and "the" includes the plural unless the context clearly indicates otherwise. Unless otherwise indicated, nucleic acid sequences are written left to right in 5' to 3' orientation; and amino acid sequences are written left to right in amino to carboxy orientation. It is to be understood that this disclosure is not limited to the particular methodology, protocols, and reagents described herein, absent an indication to the contrary.

Terms and abbreviations not defined should be accorded their ordinary meaning as used in the art. Unless defined otherwise herein, all technical and scientific terms used herein have the same meaning as commonly understood by one of ordinary skill in the art. Unless otherwise indicated, the practice of the present disclosure involves conventional techniques commonly used in molecular biology, protein engineering, and microbiology. Although any methods and materials similar or equivalent to those described herein find use in the practice of the present disclosure, some suitable methods and materials are described herein. The terms defined immediately below are more fully described by reference to the Specification as a whole.

Nucleotide Sequence

The scope of the present invention encompasses nucleotide sequences encoding aminopeptidases having the specific properties as defined herein.

In some embodiments, the nucleic acid sequence encodes a polypeptide obtained from *Aspergillus*, e.g., *Aspergillus clavatus*. In some embodiments, the nucleic acid sequence encodes a polypeptide obtained from *Neosartorya*, e.g. *Neosartorya fischeri*.

In some embodiments, the present invention relates to a nucleic acid encoding a polypeptide having aminopeptidase activity which has a predicted mature sequence with more than 13 residues on the N-terminal side of the conserved residue I/V in position 67 as shown in the sequence alignment of FIG. 9, or a fragment thereof, wherein the fragment has aminopeptidase activity.

In some embodiments, the polynucleotide of the present invention is a polynucleotide having a specified degree of nucleic acid homology to the exemplified polynucleotide. In some embodiments, the polynucleotide comprises a nucleic acid sequence having at least 50, 60, 65, 70, 75, 80, 85, 90, 91, 92, 93, 94, 95, 96, 97, 98, 99 or 100% identity to the polypeptide encoding part of nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16. In some embodiments, the polynucleotide comprises a nucleic acid sequence selected from the group consisting of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16. In other embodiments, the polynucleotide of the present invention may also have a complementary nucleic acid sequence to a nucleic acid sequence selected from the group consisting of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16. In some embodiments, the polynucleotide comprises a nucleic acid sequence encoding a recombinant polypeptide or an active fragment thereof, comprising an amino acid sequence having at least 70, 75, 80, 85, 90, 95, 96, 97, 98, 99, or 100% identity to the amino acid sequence selected from the group consisting of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8. In some embodiments, the polynucleotide comprises a nucleic acid sequence encoding a recombinant polypeptide or an active fragment thereof, comprising an amino acid sequence selected from the group consisting of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8. Homology can be determined by amino acid sequence alignment, e.g., using a program such as BLAST, ALIGN, or CLUSTAL, as described herein.

The present invention also encompasses nucleic acid sequences which encode a polypeptide having the amino acid sequence of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8, which differ from SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8 by virtue of the degeneracy of the genetic code. The present invention also relates to subsequences of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16 which encode fragments of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8 which have aminopeptidase activity. A subsequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16 is a nucleic acid sequence encompassed by SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16 except that one or more nucleotides from the 5' end and/or 3' end have been deleted. Preferably, a subsequence contains at least 990 nucleotides, more preferably at least 1140 nucleotides, and most preferably at least 1290 nucleotides.

The term "nucleotide sequence" as used herein refers to an oligonucleotide sequence or polynucleotide sequence, and variant, homologues, fragments and derivatives thereof (such as portions thereof). The nucleotide sequence may be of genomic or synthetic or recombinant origin, which may be double-stranded or single-stranded whether representing the sense or antisense strand.

The term "nucleotide sequence" in relation to the present invention includes genomic DNA, cDNA, synthetic DNA, and RNA. Preferably it means DNA, more preferably cDNA sequence coding for the present invention.

In a preferred embodiment, the nucleotide sequence when relating to and when encompassed by the per se scope of the present invention does not include the native nucleotide sequence according to the present invention when in its natural environment and when it is linked to its naturally associated sequence(s) that is/are also in its/their natural environment. For ease of reference, we shall call this preferred embodiment the "non-native nucleotide sequence". In this regard, the term "native nucleotide sequence" means an entire nucleotide sequence that is in its native environment and when operatively linked to an entire promoter with which it is naturally associated, which promoter is also in its native environment. However, the amino acid sequence encompassed by scope the present invention can be isolated and/or purified post expression of a nucleotide sequence in its native organism. Preferably, however, the amino acid sequence encompassed by scope of the present invention may be expressed by a nucleotide sequence in its native organism but wherein the nucleotide sequence is not under the control of the promoter with which it is naturally associated within that organism.

Typically, the nucleotide sequence encompassed by the scope of the present invention is prepared using recombinant DNA techniques (i.e. recombinant DNA). However, in an alternative embodiment of the invention, the nucleotide sequence could be synthesized, in whole or in part, using chemical methods well known in the art (see Caruthers M H et al., (1980) *Nuc Acids Res Symp Ser* 215-23 and Horn T et al., (1980) *Nuc Acids Res Symp Ser* 225-232).

The present invention also relates to nucleic acid sequences which have a degree of homology to the nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16 of at least about 50%, preferably about 60%, preferably about 70%, preferably about 80%, more preferably about 90%, even more preferably about 95%, and most preferably about 97% homology, which encode an active polypeptide. For purposes of the present invention, the degree of homology between two nucleic acid sequences is determined by the CLUSTAL method (Higgins, 1989, supra) with an identity table, a gap penalty of 10, and a gap length penalty of 10.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source. For example, it may be of interest to synthesize variants of the polypeptide where the variants differ in specific activity, thermostability, pH optimum, or the like using, e.g., site-directed mutagenesis. The analogous sequence may be constructed on the basis of the nucleic acid sequence presented as the polypeptide encoding part of nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16, e.g., a subsequence thereof, and/or by introduction of nucleotide substitutions which do not give rise to another amino acid sequence of the polypeptide encoded by the nucleic acid sequence, but which corresponds to the codon usage of the host organism intended for production of the enzyme, or by introduction of nucleotide substitutions which may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine scanning mutagenesis (see, e.g., Cunningham and Wells, 1989, Science 244: 1081-1085). In the latter technique, mutations are introduced at every positively charged residue in the molecule, and the resultant mutant molecules are tested for aminopeptidase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labelling (see, e.g., de Vos et al., 1992, *Science* 255: 306-312; Smith et al., 1992, *Journal of Molecular Biology* 224: 899-904; Wlodaver et al., 1992, *FEBS Letters* 309: 59-64).

Compositions

In one aspect, the present invention also relates to compositions comprising aminopeptidases and amino acid sequences and/or nucleotide sequences as described herein.

In some embodiments, the present invention provides compositions comprising a polypeptide having aminopeptidase activity which has a predicted mature sequence with more than 13 residues on the N-terminal side of the conserved residue I/V in position 67 as shown in the sequence alignment of FIG. 9, or a fragment thereof, wherein the fragment has aminopeptidase activity. In some embodiments, the compositions comprise polypeptides having at least about 50%, preferably at least about 60%, preferably at least about 70%, more preferably at least about 80%, even more preferably at least about 90%, most preferably at least about 95%, and even most preferably at least about 97% homology to a polypeptide having aminopeptidase activity which has a predicted mature sequence with more than 13 residues on the N-terminal side of the conserved residue IN in position 67 as shown in the sequence alignment of FIG. 9.

In some embodiments, the present invention provides a general composition comprising at least one aminopeptidase having an amino acid sequence which has a degree of identity to the amino acid sequence of SEQ ID NO: 1 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 1. In some embodiments, the compositions comprise the amino acid sequence of SEQ ID NO: 1 or an allelic variant; and a fragment thereof, wherein the fragment has aminopeptidase activity. In some embodiments, the compositions comprise the amino acid sequence of SEQ ID NO: 1. In another embodiment, the compositions comprise an aminopeptidase having the amino acid sequence of SEQ ID NO: 1 or a fragment thereof, wherein the fragment has aminopeptidase activity. In some embodiments, the compositions comprise a polypeptide having the amino acid sequence of SEQ ID NO: 1

In some embodiments, the present invention provides a general composition comprising at least one aminopeptidase having an amino acid sequence which has a degree of identity to the amino acid sequence of SEQ ID NO: 2 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 2. In some embodiments, the compositions comprise the amino acid sequence of SEQ ID NO: 2 or an allelic variant; and a fragment thereof, wherein the fragment has aminopeptidase activity. In some embodiments, the compositions comprise the amino acid sequence of SEQ ID NO: 2. In another embodiment, the compositions comprise an aminopeptidase having the amino acid sequence of SEQ ID NO: 2 or a fragment thereof, wherein the fragment has aminopeptidase activity. In some embodiments, the compositions comprise a polypeptide having the amino acid sequence of SEQ ID NO: 2.

In some embodiments, the present invention provides a general composition comprising at least one aminopeptidase having an amino acid sequence which has a degree of identity to the amino acid sequence of SEQ ID NO: 3 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 3. In some embodiments, the compositions comprise the amino acid sequence of SEQ ID NO: 3 or an allelic variant; and a fragment thereof, wherein the fragment has aminopeptidase activity. In some embodiments, the compositions comprise the amino acid sequence of SEQ ID NO: 3. In another embodiment, the compositions comprise an aminopeptidase having the amino acid sequence of SEQ ID NO: 3 or a fragment thereof, wherein the fragment has aminopeptidase activity. In some embodiments, the compositions comprise a polypeptide having the amino acid sequence of SEQ ID NO: 3.

In some embodiments, the present invention provides a general composition comprising at least one aminopeptidase having an amino acid sequence which has a degree of identity to the amino acid sequence of SEQ ID NO: 4 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 4. In some embodiments, the compositions comprise the amino acid sequence of SEQ ID NO: 4 or an allelic variant; and a fragment thereof, wherein the fragment has aminopeptidase activity. In some embodiments, the compositions comprise the amino acid sequence of SEQ ID NO: 4. In another embodiment, the compositions comprise an aminopeptidase having the amino acid sequence of SEQ ID NO: 4 or a fragment thereof, wherein the fragment has aminopeptidase activity. In some embodiments, the compositions comprise a polypeptide having the amino acid sequence of SEQ ID NO: 4.

In some embodiments, the present invention provides a general composition comprising at least one aminopeptidase having an amino acid sequence which has a degree of identity to the amino acid sequence of SEQ ID NO: 5 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 5. In some embodiments, the compositions comprise the amino acid sequence of SEQ ID NO: 5 or an allelic variant; and a fragment thereof, wherein the fragment has aminopeptidase activity. In some embodiments, the compositions comprise the amino acid sequence of SEQ ID NO: 5. In another embodiment, the compositions comprise an aminopeptidase having the amino acid sequence of SEQ ID NO: 5 or a fragment thereof, wherein the fragment has aminopeptidase activity. In some embodiments, the compositions comprise a polypeptide having the amino acid sequence of SEQ ID NO: 5.

In some embodiments, the present invention provides a general composition comprising at least one aminopeptidase having an amino acid sequence which has a degree of identity to the amino acid sequence of SEQ ID NO: 6 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 6. In some embodiments, the compositions comprise the amino acid sequence of SEQ ID NO: 6 or an allelic variant; and a fragment thereof, wherein the fragment has aminopeptidase activity. In some embodiments, the compositions comprise the amino acid sequence of SEQ ID NO: 6. In another embodiment, the compositions comprise an aminopeptidase having the amino acid sequence of SEQ ID NO: 6 or a fragment thereof, wherein the fragment has aminopeptidase activity. In some embodiments, the compositions comprise a polypeptide having the amino acid sequence of SEQ ID NO: 6.

In some embodiments, the present invention provides a general composition comprising at least one aminopeptidase having an amino acid sequence which has a degree of identity to the amino acid sequence of SEQ ID NO: 7 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 7. In some embodiments, the compositions comprise the amino acid sequence of SEQ ID NO: 7 or an allelic variant; and a fragment thereof, wherein the fragment has aminopeptidase activity. In some embodiments, the compositions comprise the amino acid sequence of SEQ ID NO: 7. In another embodiment, the compositions comprise an aminopeptidase having the amino acid sequence of SEQ ID NO: 7 or a fragment thereof, wherein the fragment has aminopeptidase activity. In some embodiments, the compositions comprise a polypeptide having the amino acid sequence of SEQ ID NO: 7.

In some embodiments, the present invention provides a general composition comprising at least one aminopeptidase having an amino acid sequence which has a degree of identity to the amino acid sequence of SEQ ID NO: 8 of at least about 50%, preferably at least about 60%, preferably at least about 70%, more preferably at least about 80%, even more preferably at least about 90%, most preferably at least about 95%, and even most preferably at least about 97%. In some embodiments, the compositions comprise homologous polypeptides having an amino acid sequence which differs by five amino acids, preferably by four amino acids, more preferably by three amino acids, even more preferably by two amino acids, and most preferably by one amino acid from the amino acid sequence of SEQ ID NO: 8. In some embodiments, the compositions comprise the amino acid sequence of SEQ ID NO: 8 or an allelic variant; and a fragment thereof, wherein the fragment has aminopeptidase activity. In some embodiments, the compositions comprise the amino acid sequence of SEQ ID NO: 8. In another embodiment, the compositions comprise an aminopeptidase having the amino acid sequence of SEQ ID NO: 8 or a fragment thereof, wherein the fragment has aminopeptidase activity. In some embodiments, the compositions comprise a polypeptide having the amino acid sequence of SEQ ID NO: 8.

In some embodiments, the compositions comprise a polynucleotide having a specified degree of nucleic acid homology to the exemplified polynucleotide. In some embodiments, the compositions comprise a polynucleotide comprising a nucleic acid sequence having at least 50, 60, 65, 70, 75, 80, 85, 90, 91, 92, 93, 94, 95, 96, 97, 98, 99 or 100% identity to the nucleic acid sequence of the polypeptide encoding part of nucleic acid sequence of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16. In some embodiments, the polynucleotide comprises a nucleic acid sequence selected from the group consisting of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16 In other embodiments, the compositions comprise a polynucleotide with a complementary nucleic acid sequence to a nucleic acid sequence selected from the group consisting of SEQ ID NO: 9, or SEQ ID NO: 10, or SEQ ID NO: 11, or SEQ ID NO: 12, or SEQ ID NO: 13, SEQ ID NO: 14, or SEQ ID NO: 15, or SEQ ID NO: 16. In some embodiments, the compositions comprise a polynucleotide comprising a nucleic acid sequence encoding a recombinant polypeptide or an active fragment thereof, comprising an amino acid sequence having at least 70, 75, 80, 85, 90, 95, 96, 97, 98, 99, or 100% identity to the amino acid sequence selected from the group consisting of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8. In some embodiments, the compositions comprise a polynucleotide comprising a nucleic acid sequence encoding a recombinant polypeptide or an active fragment thereof, comprising an amino acid sequence selected from the group consisting of SEQ ID NO: 1, or SEQ ID NO: 2, or SEQ ID NO: 3, or SEQ ID NO: 4, or SEQ ID NO: 5, SEQ ID NO: 6, or SEQ ID NO: 7, or SEQ ID NO: 8.

In some embodiments, the composition may comprise multiple enzymatic activities, such as an aminopeptidase, an amylase, a carbohydrase, a carboxypeptidase, a catalase, a cellulase, a chitinase, a cutinase, a cyclodextrin glycosyltransferase, a deoxyribonuclease, an esterase, an alpha-galactosidase, a beta-galactosidase, a glucoamylase, an alpha-glucosidase, a beta-glucosidase, a haloperoxidase, an invertase, a laccase, a lipase, a mannosidase, an oxidase, a pectinolytic enzyme, a peptidoglutaminase, a peroxidase, a phytase, a polyphenoloxidase, a proteolytic enzyme, a ribonuclease, a transglutaminase, or a xylanase. The additional enzyme(s) may be producible by means of a microorganism belonging to the genus *Aspergillus*, preferably *Aspergillus aculeatus*, *Aspergillus awamori*, *Aspergillus niger*, or *Aspergillus oryzae*, or *Trichoderma*, *Humicola*, preferably *Humicola insolens*, or *Fusarium*, preferably *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarchroum*, *Fusarium sporotrichioides*, *Fusarium sulphureum*, *Fusarium torulosum*, *Fusarium trichothecioides*, or *Fusarium venenaium*.

In some embodiments, the invention relates to compositions comprising a polypeptide with aminopeptidase activity and a suitable carrier. Any suitable carrier known in the art may be used including those described herein. In another embodiment, the compositions further comprise an endopeptidase. In some embodiments, the compositions further comprise one or more unspecific-acting endo- and/or exo-peptidase enzymes. In some embodiments, the compositions further comprise one or more specific-acting endo- and/or exo-peptidase enzymes.

In some embodiments, the specific acting proteolytic enzyme is an endopeptidase such as a glutamylendopeptidase (EC 3.4.21.19); a lysyl endopeptidase (EC 3.4.21.50); a leucyl endopeptidase (EC 3.4.21.57); a glycyl endopeptidase (EC 3.4.22.25); a prolyl endopeptidase (EC 3.4.21.26); trypsin (EC 3.4.21.4) or a trypsin-like (lysine/arginine specific) endopeptidase; or a peptidyl-Asp metalloendopeptidase (EC 3.4.24.33).

In some embodiments, the exopeptidase enzyme is selected from the group consisting of tripeptidyl aminopeptidase, dipeptidyl aminopeptidase, carboxypeptidase and other aminopeptidases.

In some embodiments, the one or more endo- and/or exo-peptidase enzymes are selected from the group consisting of acid fungal endopeptidase, metallo neutral endopeptidase, alkaline serine endopeptidase, subtilisin, bromelain, thermostable bacterial neutral endopeptidase, alkaline serine endopeptidase.

In some embodiments, the endo- and/or exo-peptidase enzymes for use in the present invention may be one or more of the proteases in one or more of the commercial products below:

| Commercial product | Company | Protease type | Protease source |
|---|---|---|---|
| ALPHALASE ® AFP | Genencor/DuPont | Acid fungal endopeptidase | *Trichoderma reesei* |
| FOODPRO ® PAL | Genencor/DuPont | Acid fungal endopeptidase | *Aspergillus niger* |
| FOODPRO ® PNL | Genencor/DuPont | Metallo neutral endopeptidase | *Bacillus amyloliquefaciens* |
| FOODPRO ® Alkaline Protease | Genencor/DuPont | Alkaline Serine Endopeptidase | *Bacillus licheniformis* |
| FOODPRO ® PBR | Genencor/DuPont | Bromelain | *Ananas comosus* |
| FOODPRO ® PHT | Genencor/DuPont | Thermostable bacterial neutral endopeptidase | *Geobacillus* sp. |
| FOODPRO ® 30L | Genencor/DuPont | Alkaline Serine Endopeptidase | |
| FOODPRO ® 51FP | Genencor/DuPont | Endo-/Exopeptidase | |

| Commercial product | Company | Protease type | Protease source |
|---|---|---|---|
| FOODPRO ® PXT | Genencor/DuPont | subtilisin | *B. lentus* |
| ESPERASE ® 8.0L | Novozymes | protease | *Bacillus* sp. |
| EVERLASE ® 16.0 | | subtilisin | *Bacillus* sp. |
| ALCALASE ® 2.4 | Novozymes | subtilisin | *Bacillus* sp. |
| NEUTRASE ® 0.8L | Novozymes | protease | *B. amyloliquefaciens* |
| Allzyme FD | Alltech | Serine protease* | *Aspergillus niger* |
| Arazyme One-Q | Insect Biotech Co. | metalloprotease | *Serratia proteamacula* ns HY-3 |
| SAVINASE ® | Novozymes | subtilisin | *Bacillus* sp. |
| RONOZYME ® ProAct | DSM/Novozymes | Alkaline serine protease | *Nocardiopsis prasina* gene expressed in *Bacillus licheniformis* |
| VALKERASE ®/CIBENZA ® IND900 | Novus | Keratinase | *Bacillus licheniformis* |

Additionally, or in the alternative endo- and/or exopeptidase enzymes may be comprised in one or more of the following commercially available products: KANNASE™, NOVOCARNE™ Tender and Novozym 37020, NOVO-PRO™ D (all available from Novozymes); BioSorb-ACDP (Noor Creations, India); ANGEL® Acid Protease (Angel Yeast Co, Ltd., China) or COROLASE® LAP (from AB Enzymes).

In some embodiments, the invention also provides a feed and/or food additive composition comprising at least one of the aminopeptidases described herein.

In another embodiment there is provided a composition and/or food additive and/or feed additive composition comprising a hydrolysate of the invention. Suitably, such a food and/or feed additive composition may further comprise an aminopeptidase (optionally in combination with an endo-protease).

Materials may be added to an enzyme-containing liquid to improve the properties of the liquid composition. Non-limiting examples of such additives include: salts (e.g., alkali salts, earth metal salts, additional chloride salts, sulfate salts, nitrate salts, carbonate salts, where exemplary counter ions are calcium, potassium, and sodium), inorganic minerals or clays (e.g., zeolites, kaolin, bentonite, talc's and/or silicates), carbohydrates (e.g., sucrose and/or starch), coloring pigments (e.g., titanium dioxide), biocides (e.g., RODALON®, PROXEL®), dispersants, anti-foaming agents, reducing agents, acid agents, alkaline agents, enzyme stabilizers (e.g. polyol such as glycerol, propylene glycol, sorbitol, inorganic salts, sugars, sugar or a sugar alcohol, lactic acid, boric acid, or a boric acid derivative and combinations thereof), enzyme inhibitors, preservative (e.g. methyl paraben, propyl paraben, benzoate, sorbate or other food approved preservatives) and combinations thereof. Excipients which may be used in the preparation/composition include maltose, sucrose, glucose including glucose syrup or dried glucose syrup, pre-cooked starch, gelatinised starch, L-lactic, ascorbyl palmitate, tocopherols, lecithins, citric acid, citrates, phosphoric, phosphates, sodium alginate, carrageenan, locust bean gum, guar gum, xanthan gum, pectins, sodium carboxymethylcellulose, mono- and diglycerides, citric acid esters of mono- and diglycerides, sucrose esters, carbon dioxide, argon, helium, nitrogen, nitrous oxide, oxygen, hydrogen, and starch sodium octenylsuccinate. As demonstrated in Example 7 herein, an aminopeptidase according to the present invention may retain its enzymatic activity in a composition comprising sodium chloride.

Forms

The product and/or the composition of the present invention may be used in any suitable form—whether when alone or when present in a composition. Likewise, aminopeptidase of the present invention when combined with, e.g. exo- and/or endo-proteases may be used in any suitable form for use in the food industry as a food processing aid or foodstuff additive (i.e. ingredients—such as food ingredients, functional food ingredients or pharmaceutical ingredients).

Suitable examples of forms include one or more of: tablets, pills, capsules, ovules, solutions or suspensions, which may contain flavouring or colouring agents, for immediate-, delayed-, modified-, sustained-, pulsed- or controlled-release applications.

By way of example, if the product and/or the composition are used in a tablet form—such as for use as a functional ingredient—the tablets may also contain one or more of: excipients such as microcrystalline cellulose, lactose, sodium citrate, calcium carbonate, dibasic calcium phosphate and glycine; disintegrants such as starch (preferably corn, potato or tapioca starch), sodium starch glycollate, croscarmellose sodium and certain complex silicates; granulation binders such as polyvinylpyrrolidone, hydroxypropylmethylcellulose (HPMC), hydroxypropylcellulose (HPC), sucrose, gelatin and acacia; lubricating agents such as magnesium stearate, stearic acid, glyceryl behenate and talc may be included.

Examples of nutritionally acceptable carriers for use in preparing the forms include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Preferred excipients for the forms include lactose, starch, a cellulose, milk sugar or high molecular weight polyethylene glycols.

For aqueous suspensions and/or elixirs, aminopeptidase and/or the composition of the present invention may be combined with various sweetening or flavouring agents, colouring matter or dyes, with emulsifying and/or suspending agents and with diluents such as water, ethanol, propylene glycol and glycerine, and combinations thereof.

The forms may also include gelatin capsules; fibre capsules, fibre tablets etc.

Methods

In some embodiments, the polypeptides of the present invention may be used in the production of protein hydrolysates, e.g., for enhancing the degree of hydrolysis, general debittering of protein hydrolysates and enhancing flavor development, production of glutamate and/or other uses like FAN generation during malting or brewing.

The present invention further relates to methods for using a polypeptide of the present invention in combination with a protease (e.g., an endopeptidase) to produce a high degree of hydrolysis of a protein-rich material. The method comprises treating of a proteinaceous substrate with the polypeptide and an endopeptidase. The substrate may be treated with the enzymes concurrently or consecutively.

A polypeptide of the present invention is added to the proteinaceous substrate in an effective amount conventionally employed in protein hydrolysis processes. In some embodiments, a polypeptide of the present invention is added to the proteinaceous substrate in the range of from about 0.1 to about 100,000 aminopeptidase units per 100 g of protein, or in the range of from about 1 to about 10,000 aminopeptidase units per 100 g of protein. As defined herein, one aminopeptidase unit (APU) is the amount of enzyme needed to release 1 micromole of p-nitroanilide per minute from Ala-p-nitroanilide (Sigma Chemical Co., St. Louis Mo.) under the specified conditions. In the aminopeptidase assay the hydrolysis of the peptide substrate H-Ala-nitroanilide is measured by the release of p-nitroanilid (pNA). The absorbance of pNA is determined at a wavelength of 405 nm using an ELISA reader. The reaction is run with 180 µl 20 mM CPB buffer, 15 µl diluted enzyme and 20 µl substrate at 30° C. The CPB-Buffer is made up of 20 mM Citric acid, 20 mM Phosphate, 20 mM Boric acid and adjusted to pH 9.0. The substrate is 20 mg H-Ala-pNA from BACHEM (L-1070) in 1 ml DMSO (Dimethyl Sulphoxide from SIGMA (catalog # D2650).

The endopeptidase may be obtained from a strain of *Bacillus*, preferably *Bacillus licheniformis* or *Bacillus subtilis*, a strain of *Staphylococcus*, preferably *Staphylococcus aureus*, a strain of *Streptomyces*, preferably *Streptomyces thermovularis* or *Streptomyces griseus*, a strain of *Actinomyces* species, a strain of *Aspergillus*, preferably *Aspergillus aculeatus*, *Aspergillus awamori*, *Aspergillus foetidus*, *Aspergillus nidulans*, *Aspergillus niger*, or *Aspergillus oryzae*, or a strain of *Trichoderma*, preferably *Trichoderma reesei*, or *Fusarium*, preferably *Fusarium venenatum*. In some embodiments, the endopeptidase is selected from the group consisting of ALPHALASE® AFP, FOODPRO® PAL, FOODPRO® PNL, FOODPRO® Alkaline Protease, FOODPRO® PXT, FOODPRO® PBR, FOODPRO® PHT, FOODPRO® 30L, and FOODPRO® 51FP.

The endopeptidase is added to the proteinaceous substrate in an effective amount conventionally employed in protein hydrolysis processes, preferably in the range of from about 0.05 to about 15 AU/100 g of protein, and more preferably from about 0.1 to about 8 AU/100 g of protein. One AU (Anson Unit) is defined as the amount of enzyme which under standard conditions (i.e., 25° C., pH 7.5 and 10 min. reaction time) digests hemoglobin at an initial rate such that there is liberated per minute an amount of TCA soluble product which gives the same color with phenol reagent as one milliequivalent of tyrosine. In some embodiments, the endopeptidase may be dosed in an amount of about 10 to about 3000 mg of enzyme per kg of protein substrate, e.g. 0.01 to 3 g of enzyme per metric ton (MT) of protein substrate.

The enzymatic treatment, i.e., the incubation of the substrate with the enzyme preparations, may take place at any convenient temperature at which the enzyme preparation does not become inactivated, preferably in the range of from about 20° C. to about 70° C. In accordance with established practice, the enzyme preparations may be suitably inactivated by increasing the temperature of the incubation mixture to a temperature where the enzymes become inactivated, e.g., to above about 70° C., or similarly by decreasing the pH of the incubation mixture to a point where the enzymes become inactivated, e.g., below about 4.0.

Furthermore, the methods of the present invention result in enhancement of the degree of hydrolysis of a proteinaceous substrate. As used herein, the degree of hydrolysis (DH) is the percentage of the total number of amino bonds in a protein that has been hydrolyzed by a proteolytic enzyme. In one aspect, an enzyme according to the present invention may facilitate an increase or enhancement of at least about 5, 7, 10, 12, 15, 17, 20, 22, 25, 27, 30, 35, 40, 45 or 50% of the DH of a proteinaceous substrate. In one example the increase may be relative to a type 1 aminopeptidase, although any suitable comparison may be made. In a preferred embodiment, the protein hydrolysates have an increased content of Leu, Gly, Glu, Ser, Asp, Asn, Pro, Cys, Ala, and/or Gln, e.g., at least 1.1 times greater.

In some embodiments, the protein hydrolysates have an increased content of Glu. In some embodiments, the protein hydrolysates have an increased content of Leu. In some embodiments, the protein hydrolysates have an increased content of Gly. In some embodiments, the protein hydrolysates have an increased content of Ser. In some embodiments, the protein hydrolysates have an increased content of Asp. In some embodiments, the protein hydrolysates have an increased content of Asn. In some embodiments, the protein hydrolysates have an increased content of Pro. In some embodiments, the protein hydrolysates have an increased content of Cys. In some embodiments, the protein hydrolysates have an increased content of Ala. In another more preferred embodiment, the protein hydrolysates have an increased content of Gln.

Aminopeptidase enzymes according to the present invention may exhibit decreased inhibition from the product of the enzymatic reaction. As demonstrated in Example 8 herein, two PepN 2 enzymes according to the present invention exhibited less inhibition by product than the enzyme leucine aminopeptidase 2 from *Aspergillus oryzae* RIB40 (NCBI Reference Sequence: XP_001819545.1), which is set out below as SEQ ID NO:17:

```
  1 mrsllwasll sgvlagralv spdefpediq ledllegsqq ledfayaype rnrvfggkah
 61 ddtvnylyee lkktgyydvy kqpqvhlwsn adqtlkvgde eieaktmtys psvevtadva
121 vvknlgcsea dypsdvegkv alikrgecpf gdksvlaaka kaaasivynn vagsmagtlg
181 aaqsdkgpys aivgisledg qkliklaeag svsvdlwvds kqenrttynv vaqtkggdpn
```

```
-continued
241 nvvalgghtd sveagpgind dgsgiisnlv iakaltqysv knavrflfwt aeefgllgsn 301 yyvshlnate lnkirlylnf dmiaspnyal miydgdgsaf nqsgpagsaq ieklfedyyd 361 sidlphiptq fdgrsdyeaf ilngipsggl ftgaegimse enasrwggqa gvaydanyha 421 agdnmtnlnh eaflinskat afavatyand lssipkrntt sslhrrartm rpfgkrapkt 481 hahvsgsgcw hsqvea
```

As such, in one embodiment the invention provides an isolated polypeptide that has aminopeptidase activity that has decreased product inhibition compared to the aminopeptidase of SEQ ID NO:17 (which is also referred to as TRI063 herein—see e.g. the Examples). In particular, an isolated polypeptide according to the present invention that has aminopeptidase activity may have a product inhibition constant (Ki) value of greater than 2, 3, 4 or 5 mM. In a preferred embodiment the isolated polypeptide that has aminopeptidase activity is an aminopeptidase type 2 enzyme. In a further preferred embodiment the aminopeptidase type 2 enzyme is as set out in any of SEQ ID NOs:1-8 as defined herein, particularly SEQ ID NO:1 or 5.

Aminopeptidase enzymes according to the present invention may be capable of hydrolyzing a polypeptide with a proline residue in position 2, as numbered from the N-terminus. In particular, aminopeptidase enzymes according to the present invention may be capable of hydrolyzing a polypeptide with a proline residue in position 2, as numbered from the N-terminus, to over half the starting concentration within 2 hours of incubation. The degree of hydrolysis can be measured by any suitable protocol known in the art, for example, the method presented in Example 10. As demonstrated in Example 10, two PepN 2 enzymes according to the present invention (TRI032 and TRI035) are able to hydrolyze the peptide TPAAAR (SEQ 11) NO:29) over time to less than half the concentration within 2 hr incubation, whereas TR1063 (A. oryzae) and COROLASE® LAP show no hydrolysis of TPAAAR within 12 h.

The present invention also relates to methods for obtaining a protein hydrolysate enriched in free glutamic acid and/or peptide bound glutamic acid residues, which method comprises: subjecting the substrate to the action of a polypeptide having aminopeptidase activity. The present invention also relates to methods for obtaining a protein hydrolysate enriched in free glutamine or glutamic acid and/or oligopeptide bound glutamine or glutamic acid residues, which method comprises: subjecting the substrate to the action of a polypeptide having aminopeptidase activity.

The present invention also relates to methods for debittering a protein hydrolysate, which method comprises: subjecting the substrate to the action of a polypeptide having aminopeptidase activity.

In some embodiments, the methods further comprise subjecting the substrate to a deamidation process. The deamidation process may be performed simultaneously, prior or subsequently to the subjecting the substrate to the action of a polypeptide having aminopeptidase activity.

In some embodiments, the methods of the present invention produce protein hydrolysates with enhanced flavor because glutamic acid (Glu), whether free or oligopeptide bound, plays an important role in the flavor and palatability of protein hydrolysates. In some embodiments, the method also produces protein hydrolysates having improved functionality, in particular, improved solubility, improved emulsifying properties, increased degree of hydrolysis, and improved foaming properties.

The conversion of amides (glutamine or asparagine) into charged acids (glutamic acid or aspartic acid) via the liberation of ammonia is known as deamidation. Deamidation may take place as a non-enzymatic or as an enzymatic deamidation process.

In some embodiments, the deamidation is carried out as an enzymatic deamidation process, e.g., by subjecting the substrate to a glutaminase, transglutaminase and/or peptidoglutaminase.

In some embodiments the glutaminase is GLUTAMINASE SD-C100S™ (Amano, Japan).

In some embodiments, the glutaminase may be dosed in an amount of about 1 mg to 20 mg per g of substrate protein. In some embodiments, the glutaminase may be dosed in an amount of about 5 mg to 15 mg per g of substrate protein. In some embodiments, the glutaminase may be dosed in an amount of about 10 mg per g of substrate protein.

The present invention also relates to methods for the production of glutamate, which method comprises: subjecting a protein substrate to the action of a polypeptide having aminopeptidase activity.

The transglutaminase may be of any convenient source including mammals, see e.g., JP 1050382 and JP 5023182, including activated Factor XIII, see e.g., WO 93/15234; those derived from fish, see e.g., EP 555,649; and those obtained from microorganisms, see e.g., EP 379,606, WO 96/06931 and WO 96/22366. In some embodiments, the transglutaminase is obtained from an Oomycete, including a strain of *Phytophthora*, preferably *Phytophthora cactorum*, or a strain of *Pythium*, preferably *Pythium irregulare, Pythium* sp., *Pythium intermedium, Pythium ltimum,* or *Pythium periilum* (or *Pythium periplocum*). In some embodiments, the transglutaminase is of bacterial origin and is obtained from a strain of *Bacillus*, preferably *Bacillus subtilis*, a strain of *Streptoverticillium*, preferably *Streptoverticillium mobaraensis, Streptoverticillium griseocarneum*, or *Streptoverticillium cinnamoneum*, and a strain of *Streptomyces*, preferably *Streptomyces lydicus*.

The peptidoglutaminase may be a peptidoglutaminase I (peptidyl-glutaminase; EC 3.5.1.43), or a peptidoglutaminase II (protein-glutamine glutaminase; EC 3.5.1.44), or any mixture thereof. The peptidoglutaminase may be obtained from a strain of *Aspergillus*, preferably *Aspergillus japonicus*, a strain of *Bacillus*, preferably *Bacillus circulans*, a strain of *Cryptococcus*, preferably *Cryptococcus albidus*, or a strain of *Debaryomyces*, preferably *Debaryomyces kloecheri*.

The transglutaminase is added to the proteinaceous substrate in an effective amount conventionally employed in deamidation processes, preferably in the range of from about 0.01 to about 5% (w/w), and more preferably in the range of from about 0.1 to about 1% (w/w) of enzyme preparation relating to the amount of substrate.

The peptidoglutaminase is added to the proteinaceous substrate in an effective amount conventionally employed in deamidation processes, preferably in the range of from about 0.01 to about 100,000 PGase Units per 100 g of substrate, and more preferably in the range of from about 0.1 to about 10,000 PGase Units per 100 g of substrate.

The peptidoglutaminase activity may be determined according to the procedure of Cedrangoro et al. (1965, *Enzymologia* Vol. 29 page 143). According to this procedure, 0.5 ml of an enzyme sample, adjusted to pH 6.5 with 1 N NaOH, is charged into a small vessel. Then 1 ml of a borate pH 10.8 buffer solution is added to the vessel. The discharged ammonia is absorbed by 5 N sulphuric acid, and by use of Nessler's reagent the mixture is allowed to form color which is measured at 420 nm. One PGase unit is the amount of enzyme capable of producing 1 micromole of ammonia per minute under these conditions.

The present invention also relates to methods for the production of free amino nitrogen (FAN) during malting and/or brewing, which method comprises: subjecting a substrate during a malting and/or brewing process to the action of a polypeptide having aminopeptidase activity.

In some embodiments of the methods of the present invention, a protein substrate is subjected to a polypeptide of the present invention. A polypeptide of the present invention is added to the proteinaceous substrate in an effective amount conventionally employed in protein hydrolysis processes, preferably in the range of from about 0.001 to about 0.5 AU/100 g of substrate, more preferably in the range of from about 0.01 to about 0.1 AU/100 g of substrate.

In another embodiment, the methods of the present invention for producing a hydrolysate enriched in free glutamic acid and/or peptide bound glutamic acid residues further comprise: subjecting the substrate to one or more unspecific acting endo- and/or exo-peptidase enzymes. This step may take place simultaneously, or may follow the step of subjecting a protein substrate with a polypeptide of the present invention.

In a preferred embodiment, the unspecific acting endo- and/or exo-peptidase enzyme is obtained from a strain of *Aspergillus*, or a strain of *Bacillus*.

The unspecific acting endo- and/or exo-peptidase enzyme is added to the substrate in an effective amount conventionally employed in protein hydrolysis processes, preferably in the range of from about.

In some embodiments, the endo- and/or exo-peptidase may be dosed in an amount of about 50 to about 3000 mg of enzyme per kg of protein substrate, e.g. 0.05 to 3 g of enzyme per metric ton (MT) of protein substrate.

Suitably, the endo- and/or exo-peptidase may be dosed in an amount of less than about 4.0 g of enzyme per MT of protein substrate.

In another embodiment, the endo- and/or exo-peptidase may be dosed at between about 0.5 g and about 5.0 g of enzyme per MT of protein substrate. Suitably the endo- and/or exo-peptidase may be dosed at between about 0.5 g and about 3.0 g of enzyme per MT of protein substrate. More suitably, the endoprotease may be dosed at about 1.0 g to about 2.0 g of enzyme per MT of protein substrate.

In some embodiments, a polypeptide of the present invention may be dosed in an amount of between about 0.5 mg to about 2 g of enzyme per kg of protein substrate and/or food and/or feed additive composition. Suitably a polypeptide of the present invention may be dosed in an amount of between about 1 mg to about 2 g of enzyme per kg of protein substrate and/or food and/or feed additive composition. More suitably in an amount of between about 5 mg to about 1.5 g of enzyme per kg of protein substrate and/or food and/or feed additive composition.

In the preparation of a hydrolysate a polypeptide of the present invention may be dosed in an amount of between about 0.5 mg to about 2 g of enzyme per kg of protein substrate. Suitably a polypeptide of the present invention may be dosed in an amount of between about 1 mg to about 2 g of enzyme per kg of protein substrate. More suitably in an amount of between about 5 mg to about 1.5 g of enzyme per kg of protein substrate.

In one embodiment, a polypeptide of the present invention may be dosed in an amount of between about 5 mg to about 500 mg of enzyme per kg of protein substrate. Suitably a polypeptide of the present invention may be dosed in an amount of between about 50 mg to about 500 mg of enzyme per kg of protein substrate. Suitably a polypeptide of the present invention may be dosed in an amount of between about 100 mg to about 450 mg of enzyme per kg of protein substrate.

Each enzymatic treatment may take place at any temperature at which the enzyme preparation does not become inactivated, preferably in the range of from about 20° C. to about 70° C. The enzyme preparation may then be inactivated by increasing the temperature, e.g., to above about 70° C., or by decreasing the pH, e.g., below about 4.0.

The proteinaceous substrate used in the methods of the present invention may consist of intact proteins, prehydrolyzed proteins (i.e., peptides), or a mixture thereof. The proteinaceous substrate may be of vegetable or animal origin. In some embodiments, the proteinaceous substrate is of vegetable origin, e.g., soy protein, grain protein, e.g., wheat gluten, corn gluten, barley, rye, oat, rice, zein, lupine, cotton seed protein, rape seed protein, peanut, alfalfa protein, pea protein, fabaceous bean protein, sesame seed protein, or sunflower. A proteinaceous substrate of animal origin may be whey protein, casein, meat proteins, fish protein, red blood cells, egg white, gelatin, lactoalbumin, hair proteins or feather proteins.

The present invention also relates to protein hydrolysates produced by these methods.

Preparation of the Nucleotide Sequence

A nucleotide sequence encoding either a protein which has the specific properties as defined herein or a protein which is suitable for modification may be identified and/or isolated and/or purified from any cell or organism producing said protein. Various methods are well known within the art for the identification and/or isolation and/or purification of nucleotide sequences. By way of example, PCR amplification techniques to prepare more of a sequence may be used once a suitable sequence has been identified and/or isolated and/or purified.

By way of further example, a genomic DNA and/or cDNA library may be constructed using chromosomal DNA or messenger RNA from the organism producing the enzyme. If the amino acid sequence of the enzyme is known, labelled oligonucleotide probes may be synthesized and used to identify enzyme-encoding clones from the genomic library prepared from the organism. Alternatively, a labelled oligonucleotide probe containing sequences homologous to another known enzyme gene could be used to identify enzyme-encoding clones. In the latter case, hybridization and washing conditions of lower stringency are used.

Alternatively, enzyme-encoding clones could be identified by inserting fragments of genomic DNA into an expression vector, such as a plasmid, transforming enzyme-negative bacteria with the resulting genomic DNA library, and then plating the transformed bacteria onto agar plates containing a substrate for enzyme (i.e., maltose), thereby allowing clones expressing the enzyme to be identified.

In a yet further alternative, the nucleotide sequence encoding the enzyme may be prepared synthetically by established standard methods, e.g. the phosphoramidite method described by Beucage S. L. et al., (1981) *Tetrahedron Letters* 22, p 1859-1869, or the method described by Matthes et al., (1984) *EMBO J.* 3, p 801-805. In the phosphoramidite method, oligonucleotides are synthesized, e.g. in an automatic DNA synthesizer, purified, annealed, ligated and cloned in appropriate vectors.

The nucleotide sequence may be of mixed genomic and synthetic origin, mixed synthetic and cDNA origin, or mixed genomic and cDNA origin, prepared by ligating fragments of synthetic, genomic or cDNA origin (as appropriate) in accordance with standard techniques. Each ligated fragment corresponds to various parts of the entire nucleotide sequence. The DNA sequence may also be prepared by polymerase chain reaction (PCR) using specific primers, for instance as described in U.S. Pat. No. 4,683,202 or in Saiki R K et al., (*Science* (1988) 239, pp 487-491).

Amino Acid Sequences

The scope of the present invention also encompasses amino acid sequences of enzymes having the specific properties as defined herein.

As used herein, the term "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

The amino acid sequence may be prepared/isolated from a suitable source, or it may be made synthetically or it may be prepared by use of recombinant DNA techniques.

The protein encompassed in the present invention may be used in conjunction with other proteins, particularly proline endoprotease, tripeptidyl exopeptidases, and other forms of endo or exoproteases. Thus the present invention also covers a combination of proteins wherein the combination comprises the aminopeptidase of the present invention and another enzyme, which may be another aminopeptidase according to the present invention. This aspect is discussed in a later section.

Preferably the amino acid sequence when relating to and when encompassed by the per se scope of the present invention is not a native enzyme. In this regard, the term "native enzyme" means an entire enzyme that is in its native environment and when it has been expressed by its native nucleotide sequence.

Sequence Identity or Sequence Homology

The present invention also encompasses the use of sequences having a degree of sequence identity or sequence homology with amino acid sequence(s) of a polypeptide having the specific properties defined herein or of any nucleotide sequence encoding such a polypeptide (hereinafter referred to as a "homologous sequence(s)"). Here, the term "homologue" means an entity having a certain homology with the subject amino acid sequences and the subject nucleotide sequences. Here, the term "homology" can be equated with "identity".

The homologous amino acid sequence and/or nucleotide sequence should provide and/or encode a polypeptide which retains the functional activity and/or enhances the activity of the aminopeptidase.

In the present context, a homologous sequence is taken to include an amino acid sequence which may be at least 75, 85 or 90% identical, preferably at least 95 or 98% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 80, 85 or 90% identical, preferably at least 95 or 98% identical to a nucleotide sequence encoding a polypeptide of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate percentage homology between two or more sequences.

Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in percentage homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. However, it is preferred to use the default values when using such software for sequence comparisons.

Calculation of maximum percentage homology therefore firstly requires the production of an optimal alignment, taking into consideration gap penalties. A suitable computer program for carrying out such an alignment is the Vector NTI (Invitrogen Corp.). Examples of software that can perform sequence comparisons include, but are not limited to, the BLAST package (see Ausubel et al. 1999, *Short Protocols in Molecular Biology*, 4th Ed—Chapter 18), BLAST 2 (see *FEMS Microbial Lett* 1999 174(2): 247-50; *FEMS Microbial Lett* 1999 177(1): 187-8 and tatiana@ncbi.nlm.nih.gov), FASTA (Altschul et al, 1990 *J. Mol. Biol.* 403-410) and AlignX for example. At least BLAST, BLAST 2 and FASTA are available for offline and online searching (see Ausubel et al. 1999, supra, pages 7-58 to 7-60).

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. Vector NTI programs generally use either the public default values or a custom symbol comparison table if supplied (see user manual for further details). For some applications, it is preferred to use the default values for the Vector NTI package.

Alternatively, percentage homologies may be calculated using the multiple alignment feature in Vector NTI (Invitrogen Corp.), based on an algorithm, analogous to CLUSTAL (Higgins D G & Sharp P M (1988), *Gene* 73(1), 237-244).

Once the software has produced an optimal alignment, it is possible to calculate percentage homology, preferably percentage sequence identity. The software typically does this as part of the sequence comparison and generates a numerical result.

Should Gap Penalties be used when determining sequence identity, then preferably the following parameters are used for pairwise alignment:

| FOR BLAST | | | |
| --- | --- | --- | --- |
| GAP OPEN | | 0 | |
| GAP EXTENSION | | 0 | |
| FOR CLUSTAL | DNA | PROTEIN | |
| WORD SIZE | 2 | 1 | K triple |
| GAP PENALTY | 15 | 10 | |
| GAP EXTENSION | 6.66 | 0.1 | |

In one embodiment, CLUSTAL may be used with the gap penalty and gap extension set as defined above.

Suitably, the degree of identity with regard to a nucleotide sequence is determined over at least 20 contiguous nucleotides, preferably over at least 30 contiguous nucleotides, preferably over at least 40 contiguous nucleotides, preferably over at least 50 contiguous nucleotides, preferably over at least 60 contiguous nucleotides, preferably over at least 100 contiguous nucleotides.

Suitably, the degree of identity with regard to a nucleotide sequence may be determined over the whole sequence.

Variants/Homologues/Derivatives

The present invention also encompasses the use of variants, homologues and derivatives of any amino acid sequence of a protein or of any nucleotide sequence encoding such a protein Here, the term "homologue" means an entity having a certain homology with the subject amino acid sequences and the subject nucleotide sequences. Here, the term "homology" can be equated with "identity".

In the present context, a homologous sequence is taken to include an amino acid sequence which may be at least 75, 80, 85 or 90% identical, preferably at least 95, 96, 97, 98 or 99% identical to the subject sequence. Typically, the homologues will comprise the same active sites etc. as the subject amino acid sequence. Although homology can also be considered in terms of similarity (i.e. amino acid residues having similar chemical properties/functions), in the context of the present invention it is preferred to express homology in terms of sequence identity.

In the present context, a homologous sequence is taken to include a nucleotide sequence which may be at least 75, 80, 85 or 90% identical, preferably at least 95, 96, 97, 98 or 99% identical to a nucleotide sequence encoding an enzyme of the present invention (the subject sequence). Typically, the homologues will comprise the same sequences that code for the active sites etc. as the subject sequence. Although homology can also be considered in terms of similarity (i.e. amino acid residues having similar chemical properties/functions), in the context of the present invention it is preferred to express homology in terms of sequence identity.

Homology comparisons can be conducted by eye, or more usually, with the aid of readily available sequence comparison programs. These commercially available computer programs can calculate percentage homology between two or more sequences. Percentage homology may be calculated over contiguous sequences, i.e. one sequence is aligned with the other sequence and each amino acid in one sequence is directly compared with the corresponding amino acid in the other sequence, one residue at a time. This is called an "ungapped" alignment. Typically, such ungapped alignments are performed only over a relatively short number of residues.

Although this is a very simple and consistent method, it fails to take into consideration that, for example, in an otherwise identical pair of sequences, one insertion or deletion will cause the following amino acid residues to be put out of alignment, thus potentially resulting in a large reduction in percentage homology when a global alignment is performed. Consequently, most sequence comparison methods are designed to produce optimal alignments that take into consideration possible insertions and deletions without penalizing unduly the overall homology score. This is achieved by inserting "gaps" in the sequence alignment to try to maximize local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimized alignments with fewer gaps. Most alignment programs allow the gap penalties to be modified. However, it is preferred to use the default values when using such software for sequence comparisons. For example, when using the GCG Wisconsin Bestfit package the default gap penalty for amino acid sequences is −12 for a gap and −4 for each extension.

Calculation of maximum percentage homology therefore firstly requires the production of an optimal alignment, taking into consideration gap penalties. A suitable computer program for carrying out such an alignment is the GCG Wisconsin Bestfit package (Devereux et al 1984 Nuc. Acids Research 12 p 387). Examples of other software than can perform sequence comparisons include, but are not limited to, the BLAST package (see Ausubel et al., 1999, supra), FASTA (Altschul et al., 1990 *J. Mol. Biol.* 403-410) and the GENEWORKS suite of comparison tools. Both BLAST and FASTA are available for offline and online searching (see Ausubel et al., 1999, supra). However, for some applications, it is preferred to use the GCG Bestfit program. A new tool, called BLAST 2 Sequences is also available for comparing protein and nucleotide sequence.

Although the final percentage homology can be measured in terms of identity, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). For some applications, it is preferred to use the public default values for the GCG package, or in the case of other software, the default matrix, such as BLOSUM62.

Alternatively, percentage homologies may be calculated using the multiple alignment feature in DNASIS™ (Hitachi Software), based on an algorithm, analogous to CLUSTAL (Higgins D G & Sharp P M (1988), supra).

Once the software has produced an optimal alignment, it is possible to calculate percentage homology, preferably percentage sequence identity. The software typically does this as part of the sequence comparison and generates a numerical result.

The sequences may also have deletions, insertions or substitutions of amino acid residues which produce a silent change and result in a functionally equivalent substance. Deliberate amino acid substitutions may be made on the basis of similarity in polarity, charge, solubility, hydrophobicity, hydrophilicity, and/or the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Conservative substitutions may be made, for example according to the Table below. Amino acids in the same block in the second column and preferably in the same line in the third column may be substituted for each other:

| ALIPHATIC | Non-polar | G A P |
| | | I L V |
| | Polar - uncharged | C S T M |
| | | N Q |
| | Polar - charged | D E |
| | | K R |
| AROMATIC | | H F W Y |

The present invention also encompasses homologous substitution (substitution and replacement are both used herein to mean the interchange of an existing amino acid residue, with an alternative residue) that may occur i.e. like-for-like substitution such as basic for basic, acidic for acidic, polar for polar etc. Non-homologous substitution may also occur i.e. from one class of residue to another or alternatively involving the inclusion of unnatural amino acids such as ornithine (hereinafter referred to as Z), diaminobutyric acid ornithine (hereinafter referred to as B), norleucine ornithine (hereinafter referred to as O), pyriylalanine, thienylalanine, naphthylalanine and phenylglycine.

Replacements may also be made by unnatural amino acids include; alpha* and alpha-disubstituted* amino acids, N-alkyl amino acids*, lactic acid*, halide derivatives of natural amino acids such as trifluorotyrosine*, p-Cl-phenylalanine*, p-Br-phenylalanine*, p-I-phenylalanine*, L-allyl-glycine*, β-alanine*, L-α-amino butyric acid*, L-γ-amino butyric acid*, L-α-amino isobutyric acid*, L-ε-amino caproic acid#, 7-amino heptanoic acid*, L-methionine sulfone#*, L-norleucine*, L-norvaline*, p-nitro-L-phenylalanine*, L-hydroxyproline#, L-thioproline*, methyl derivatives of phenylalanine (Phe) such as 4-methyl-Phe*, pentamethyl-Phe*, L-Phe (4-amino)#, L-Tyr (methyl)*, L-Phe (4-isopropyl)*, L-Tic (1,2,3,4-tetrahydroisoquinoline-3-carboxyl acid)*, L-diaminopropionic acid # and L-Phe (4-benzyl)*. The notation * has been utilized for the purpose of the discussion above (relating to homologous or non-homologous substitution), to indicate the hydrophobic nature of the derivative whereas # has been utilized to indicate the hydrophilic nature of the derivative, #* indicates amphipathic characteristics.

Variant amino acid sequences may include suitable spacer groups that may be inserted between any two amino acid residues of the sequence including alkyl groups such as methyl, ethyl or propyl groups in addition to amino acid spacers such as glycine or β-alanine residues. A further form of variation, involves the presence of one or more amino acid residues in peptoid form, will be well understood by those skilled in the art. For the avoidance of doubt, "the peptoid form" is used to refer to variant amino acid residues wherein the α-carbon substituent group is on the residue's nitrogen atom rather than the α-carbon. Processes for preparing peptides in the peptoid form are known in the art, for example Simon R J et al., *PNAS* (1992) 89 (20), 9367-9371 and Horwell D C, *Trends Biotechnol.* (1995) 13 (4), 132-134.

The nucleotide sequences for use in the present invention may include within them synthetic or modified nucleotides. A number of different types of modification to oligonucleotides are known in the art. These include methylphosphonate and phosphorothioate backbones and/or the addition of acridine or polylysine chains at the 3' and/or 5' ends of the molecule. For the purposes of the present invention, it is to be understood that the nucleotide sequences described herein may be modified by any method available in the art. Such modifications may be carried out in order to enhance the in vivo activity or life span of nucleotide sequences of the present invention.

The present invention also encompasses the use of nucleotide sequences that are complementary to the sequences presented herein, or any derivative, fragment or derivative thereof. If the sequence is complementary to a fragment thereof then that sequence can be used as a probe to identify similar coding sequences in other organisms etc.

Polynucleotides which are not 100% homologous to the sequences of the present invention but fall within the scope of the invention can be obtained in a number of ways. Other variants of the sequences described herein may be obtained for example by probing DNA libraries made from a range of individuals, for example individuals from different populations. In addition, other homologues may be obtained and such homologues and fragments thereof in general will be capable of selectively hybridizing to the sequences shown in the sequence listing herein. Such sequences may be obtained by probing cDNA libraries made from or genomic DNA libraries from other animal species, and probing such libraries with probes comprising all or part of any one of the sequences in the attached sequence listings under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example, the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site directed mutagenesis of characterized sequences. This may be useful where for example silent codon sequence changes are required to optimize codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides (nucleotide sequences) of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as DNA polynucleotides and probes according to the invention may be produced recombinantly, synthetically, or by any means available to those of skill in the art. They may also be cloned by standard techniques.

In general, primers will be produced by synthetic means, involving a stepwise manufacture of the desired nucleic acid sequence one nucleotide at a time. Techniques for accomplishing these using automated techniques are readily available in the art.

Longer polynucleotides will generally be produced using recombinant means, for example using a PCR (polymerase chain reaction) cloning techniques. The primers may be designed to contain suitable restriction enzyme recognition sites so that the amplified DNA can be cloned into a suitable cloning vector.

Hybridization

The present invention also encompasses sequences that are complementary to the nucleic acid sequences of the present invention or sequences that are capable of hybridizing either to the sequences of the present invention or to sequences that are complementary thereto.

The term "hybridization" as used herein shall include "the process by which a strand of nucleic acid joins with a complementary strand through base pairing" as well as the process of amplification as carried out in polymerase chain reaction (PCR) technologies.

The present invention also encompasses the use of nucleotide sequences that are capable of hybridizing to the sequences that are complementary to the sequences presented herein, or any derivative, fragment or derivative thereof.

The term "variant" also encompasses sequences that are complementary to sequences that are capable of hybridizing to the nucleotide sequences presented herein.

Preferably, the term "variant" encompasses sequences that are complementary to sequences that are capable of hybridizing under stringent conditions (e.g. 50° C. and 0.2×SSC {1×SSC=0.15 M NaCl, 0.015 M Na$_3$citrate pH 7.0}) to the nucleotide sequences presented herein.

More preferably, the term "variant" encompasses sequences that are complementary to sequences that are capable of hybridizing under high stringent conditions (e.g. 65° C. and 0.1×SSC {1×SSC=0.15 M NaCl, 0.015 M Na$_3$citrate pH 7.0}) to the nucleotide sequences presented herein.

The present invention also relates to nucleotide sequences that can hybridize to the nucleotide sequences of the present invention (including complementary sequences of those presented herein).

The present invention also relates to nucleotide sequences that are complementary to sequences that can hybridize to the nucleotide sequences of the present invention (including complementary sequences of those presented herein).

Also included within the scope of the present invention are polynucleotide sequences that are capable of hybridizing to the nucleotide sequences presented herein under conditions of intermediate to maximal stringency.

In a preferred aspect, the present invention covers nucleotide sequences that can hybridize to the nucleotide sequence of the present invention, or the complement thereof, under stringent conditions (e.g. 50° C. and 0.2×SSC).

In a more preferred aspect, the present invention covers nucleotide sequences that can hybridize to the nucleotide sequence of the present invention, or the complement thereof, under high stringent conditions (e.g. 65° C. and 0.1×SSC).

Molecular Evolution

As a non-limiting example, it is possible to produce numerous site directed or random mutations into a nucleotide sequence, either in vivo or in vitro, and to subsequently screen for improved functionality of the encoded polypeptide by various means.

In addition, mutations or natural variants of a polynucleotide sequence can be recombined with either the wildtype or other mutations or natural variants to produce new variants. Such new variants can also be screened for improved functionality of the encoded polypeptide. The production of new preferred variants can be achieved by various methods well established in the art, for example the Error Threshold Mutagenesis (WO 92/18645), oligonucleotide mediated random mutagenesis (U.S. Pat. No. 5,723,323), DNA shuffling (U.S. Pat. No. 5,605,793), exo-mediated gene assembly WO00/58517. The application of these and similar random directed molecular evolution methods allows the identification and selection of variants of the enzymes of the present invention which have preferred characteristics without any prior knowledge of protein structure or function, and allows the production of non-predictable but beneficial mutations or variants. There are numerous examples of the application of molecular evolution in the art for the optimization or alteration of enzyme activity, such examples include, but are not limited to one or more of the following:

optimized expression and/or activity in a host cell or in vitro, increased enzymatic activity, altered substrate and/or product specificity, increased or decreased enzymatic or structural stability, altered enzymatic activity/specificity in preferred environmental conditions, e.g. temperature, pH, substrate Site-Directed Mutagenesis Once a protein-encoding nucleotide sequence has been isolated, or a putative protein-encoding nucleotide sequence has been identified, it may be desirable to mutate the sequence in order to prepare a protein of the present invention.

Mutations may be introduced using synthetic oligonucleotides. These oligonucleotides contain nucleotide sequences flanking the desired mutation sites.

A suitable method is disclosed in Morinaga et al., (*Biotechnology* (1984) 2, p 646-649). Another method of introducing mutations into enzyme-encoding nucleotide sequences is described in Nelson and Long (*Analytical Biochemistry* (1989), 180, p 147-151).

Recombinant

In one aspect the sequence for use in the present invention is a recombinant sequence—i.e. a sequence that has been prepared using recombinant DNA techniques.

These recombinant DNA techniques are within the capabilities of a person of ordinary skill in the art. Such techniques are explained in the literature, for example, J. Sambrook, E. F. Fritsch, and T. Maniatis, 1989, *Molecular Cloning: A Laboratory Manual*, Second Edition, Books 1-3, Cold Spring Harbor Laboratory Press.

Synthetic

In one aspect the sequence for use in the present invention is a synthetic sequence—i.e. a sequence that has been prepared by in vitro chemical or enzymatic synthesis. It includes, but is not limited to, sequences made with optimal codon usage for host organisms—such as the methylotrophic yeasts *Pichia* and *Hansenula*.

Expression

Expression of Enzymes

The nucleotide sequence for use in the present invention may be incorporated into a recombinant replicable vector. The vector may be used to replicate and express the nucleotide sequence, in protein/enzyme form, in and/or from a compatible host cell.

Expression may be controlled using control sequences e.g. regulatory sequences.

The protein produced by a host recombinant cell by expression of the nucleotide sequence may be secreted or may be contained intracellularly depending on the sequence and/or the vector used. The coding sequences may be designed with signal sequences which direct secretion of the substance coding sequences through a particular prokaryotic or eukaryotic cell membrane.

Expression Vector

The term "expression vector" means a construct capable of in vivo or in vitro expression.

Preferably, the expression vector is incorporated into the genome of a suitable host organism. The term "incorporated" preferably covers stable incorporation into the genome.

The nucleotide sequence of the present invention may be present in a vector in which the nucleotide sequence is operably linked to regulatory sequences capable of providing for the expression of the nucleotide sequence by a suitable host organism.

The vectors for use in the present invention may be transformed into a suitable host cell as described below to provide for expression of a polypeptide of the present invention.

The choice of vector e.g. a plasmid, cosmid, or phage vector will often depend on the host cell into which it is to be introduced.

The vectors for use in the present invention may contain one or more selectable marker genes—such as a gene, which confers antibiotic resistance e.g. ampicillin, kanamycin, chloramphenicol or tetracyclin resistance. Alternatively, the selection may be accomplished by co-transformation (as described in WO91/17243).

Vectors may be used in vitro, for example for the production of RNA or used to transfect, transform, transduce or infect a host cell.

Thus, in a further embodiment, the invention provides a method of making nucleotide sequences of the present invention by introducing a nucleotide sequence of the present invention into a replicable vector, introducing the vector into a compatible host cell, and growing the host cell under conditions which bring about replication of the vector.

The vector may further comprise a nucleotide sequence enabling the vector to replicate in the host cell in question. Examples of such sequences are the origins of replication of plasmids pUC19, pACYC177, pUB110, pE194, pAMB1 and pIJ702.

Regulatory Sequences

In some applications, the nucleotide sequence for use in the present invention is operably linked to a regulatory sequence which is capable of providing for the expression of the nucleotide sequence, such as by the chosen host cell. By way of example, the present invention covers a vector comprising the nucleotide sequence of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the nucleotide sequence encoding the enzyme of the present invention may also be achieved by the selection of heterologous regulatory regions, e.g. promoter, secretion leader and terminator regions.

Preferably, the nucleotide sequence according to the present invention is operably linked to at least a promoter.

Other promoters may even be used to direct expression of the polypeptide of the present invention.

Examples of suitable promoters for directing the transcription of the nucleotide sequence in a bacterial, fungal or yeast host are well known in the art.

The promoter can additionally include features to ensure or to increase expression in a suitable host. For example, the features can be conserved regions such as a Pribnow Box or a TATA box.

Constructs

The term "construct"—which is synonymous with terms such as "conjugate", "cassette" and "hybrid"—includes a nucleotide sequence for use according to the present invention directly or indirectly attached to a promoter.

An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In some cases, the terms do not cover the natural combination of the nucleotide sequence coding for the protein ordinarily associated with the wild type gene promoter and when they are both in their natural environment.

The construct may even contain or express a marker, which allows for the selection of the genetic construct.

For some applications, preferably the construct of the present invention comprises at least the nucleotide sequence of the present invention operably linked to a promoter.

Host Cells

The term "host cell"—in relation to the present invention includes any cell that comprises either the nucleotide sequence or an expression vector as described above and which is used in the recombinant production of a protein having the specific properties as defined herein.

Thus, a further embodiment of the present invention provides host cells transformed or transfected with a nucleotide sequence that expresses the protein of the present invention. The cells will be chosen to be compatible with the said vector and may for example be prokaryotic (for example bacterial), fungal, yeast or plant cells.

Examples of suitable bacterial host organisms are gram positive or gram negative bacterial species.

Depending on the nature of the nucleotide sequence encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly secreted from the yeast cell, or in some cases are not processed properly (e.g. hyperglycosylation in yeast). In these instances, a different fungal host organism should be selected.

The use of suitable host cells—such as yeast, fungal and plant host cells—may provide for post-translational modifications (e.g. myristoylation, glycosylation, truncation, lipidation and tyrosine, serine or threonine phosphorylation) as may be needed to confer optimal biological activity on recombinant expression products of the present invention.

The host cell may be an aminopeptidase deficient or aminopeptidase minus strain. The present invention also relates to methods for producing a mutant cell of a parent cell, which comprises disrupting or deleting a nucleic acid sequence encoding the polypeptide or a control sequence thereof, which results in the mutant cell producing less of the polypeptide than the parent cell.

The construction of strains which have reduced aminopeptidase activity may be conveniently accomplished by modification or inactivation of a nucleic acid sequence necessary for expression of the polypeptide having aminopeptidase activity in the cell.

Organism

The term "organism" in relation to the present invention includes any organism that could comprise the nucleotide sequence coding for the polypeptide according to the present invention and/or products obtained therefrom, and/or wherein a promoter can allow expression of the nucleotide sequence according to the present invention when present in the organism.

Suitable organisms may include a prokaryote, fungus, yeast or a plant.

The term "transgenic organism" in relation to the present invention includes any organism that comprises the nucleotide sequence coding for the polypeptide according to the present invention and/or the products obtained therefrom, and/or wherein a promoter can allow expression of the nucleotide sequence according to the present invention within the organism. Preferably the nucleotide sequence is incorporated in the genome of the organism.

The term "transgenic organism" does not cover native nucleotide coding sequences in their natural environment when they are under the control of their native promoter which is also in its natural environment.

Therefore, the transgenic organism of the present invention includes an organism comprising any one of, or combinations of, the nucleotide sequence coding for the polypeptide according to the present invention, constructs according to the present invention, vectors according to the present invention, plasmids according to the present invention, cells according to the present invention, tissues according to the present invention, or the products thereof.

For example, the transgenic organism may also comprise the nucleotide sequence coding for the polypeptide of the present invention under the control of a heterologous promoter.

Transformation of Host Cells/Organisms

As indicated earlier, the host organism can be a prokaryotic or a eukaryotic organism. Examples of suitable prokaryotic hosts include *E. coli* and *Bacillus subtilis*.

Teachings on the transformation of prokaryotic hosts are well documented in the art, for example see Sambrook et al (supra). If a prokaryotic host is used, then the nucleotide sequence may need to be suitably modified before transformation—such as by removal of introns.

Filamentous fungi cells may be transformed using various methods known in the art—such as a process involving protoplast formation and transformation of the protoplasts followed by regeneration of the cell wall in a manner known. The use of *Aspergillus* as a host microorganism is described in EP 0 238 023.

Another host organism can be a plant. A review of the general techniques used for transforming plants may be found in articles by Potrykus (*Annu Rev Plant Physiol Plant Mol Biol*, 1991, 42:205-225) and Christou (*Agro-Food-Industry Hi-Tech* March/April 1994 17-27). Further teachings on plant transformation may be found in EP-A-0449375.

General teachings on the transformation of fungi, yeasts and plants are presented in following sections.

Transformed Fungus

A host organism may be a fungus—such as a mold. Examples of suitable such hosts include any member belonging to the genera *Thermomyces, Acremonium, Aspergillus, Penicillium, Mucor, Neurospora, Trichoderma* and the like.

In one embodiment, the host organism may be a filamentous fungus.

Transforming filamentous fungi is discussed in U.S. Pat. No. 5,741,665 which states that standard techniques for transformation of filamentous fungi and culturing the fungi are well known in the art. An extensive review of techniques as applied to *N. crassa* is found, for example in Davis and de Serres, *Methods Enzymol* (1971) 17A: 79-143.

Further teachings which may also be utilized in transforming filamentous fungi are reviewed in U.S. Pat. No. 5,674,707.

In addition, gene expression in filamentous fungi is taught in Punt et al. (2002) *Trends Biotechnol* 2002 May; 20(5): 200-6, Archer & Peberdy, *Crit Rev Biotechnol* (1997) 17(4): 273-306.

The present invention encompasses the production of transgenic filamentous fungi according to the present invention prepared by use of these standard techniques.

In one aspect, the host organism can be of the genus *Aspergillus*, such as *Aspergillus niger*.

A transgenic *Aspergillus* according to the present invention can also be prepared by following, for example, the teachings of Turner, G. 1994 (Vectors for genetic manipulation. In: Martinelli S. D., Kinghorn J. R. (Editors) *Aspergillus: 50 years on. Progress in industrial microbiology* vol 29. Elsevier Amsterdam 1994. pp. 641-666).

In one aspect, the host organism can be of the genus *Trichoderma*, such as *Trichoderma Reesei*.

Transformed Yeast

In another embodiment, the transgenic organism can be a yeast.

A review of the principles of heterologous gene expression in yeast are provided in, for example, *Methods Mol Biol* (1995), 49:341-54, and *Curr Opin Biotechnol* (1997) October; 8(5):554-60

In this regard, yeast—such as the species *Saccharomyces cerevisae* or *Pichia pastoris* (see *FEMS Microbiol Rev* (2000 24(1):45-66), may be used as a vehicle for heterologous gene expression.

A review of the principles of heterologous gene expression in *Saccharomyces cerevisiae* and secretion of gene products is given by E Hinchcliffe E Kenny (1993, "Yeast as a vehicle for the expression of heterologous genes", *Yeasts*, Vol 5, Anthony H Rose and J Stuart Harrison, eds, 2nd edition, Academic Press Ltd.).

For the transformation of yeast, several transformation protocols have been developed. For example, a transgenic *Saccharomyces* according to the present invention can be prepared by following the teachings of Hinnen et al., (1978, *PNAS USA* 75, 1929); Beggs, J D (1978, *Nature*, 275, 104); and Ito, H et al (1983, *J Bacteriology* 153, 163-168).

The transformed yeast cells may be selected using various selective markers—such as auxotrophic markers dominant antibiotic resistance markers.

Culturing and Production

Host cells transformed with the nucleotide sequence of the present invention may be cultured under conditions conducive to the production of the encoded polypeptide and which facilitate recovery of the polypeptide from the cells and/or culture medium.

The medium used to cultivate the cells may be any conventional medium suitable for growing the host cell in questions and obtaining expression of the polypeptide.

The protein produced by a recombinant cell may be displayed on the surface of the cell.

The protein may be secreted from the host cells and may conveniently be recovered from the culture medium using well-known procedures.

Secretion

Often, it is desirable for the protein to be secreted from the expression host into the culture medium from where the protein may be more easily recovered. According to the present invention, the secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces*, *Kluyveromyces* and *Hansenula*) or the α-amylase gene (*Bacillus*).

By way of example, the secretion of heterologous proteins in *E. coli* is reviewed in *Methods Enzymol* (1990) 182:132-43.

Detection

A variety of protocols for detecting and measuring the expression of the amino acid sequence are known in the art. Examples include enzyme-linked immunosorbent assay (ELISA), radioimmunoassay (MA) and fluorescent activated cell sorting (FACS).

A wide variety of labels and conjugation techniques are known by those skilled in the art and can be used in various nucleic and amino acid assays.

A number of companies such as Pharmacia Biotech (Piscataway, N.J.), Promega (Madison, Wis.), and US Biochemical Corp (Cleveland, Ohio) supply commercial kits and protocols for these procedures.

Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241.

Also, recombinant immunoglobulins may be produced as shown in U.S. Pat. No. 4,816,567.

Fusion Proteins

The amino acid sequence for use according to the present invention may be produced as a fusion protein, for example to aid in extraction and purification. Examples of fusion protein partners include Glutathione-S-transferase (GST), 6×His, GAL4 (DNA binding and/or transcriptional activation domains) and (β-galactosidase). It may also be convenient to include a proteolytic cleavage site between the fusion protein partner and the protein sequence of interest to allow removal of fusion protein sequences.

Preferably, the fusion protein will not hinder the activity of the protein sequence.

Gene fusion expression systems in *E. coli* have been reviewed in *Curr Opin Biotechnol* (1995) 6(5):501-6.

In another embodiment of the invention, the amino acid sequence may be ligated to a heterologous sequence to encode a fusion protein. For example, for screening of peptide libraries for agents capable of affecting the substance activity, it may be useful to encode a chimeric substance expressing a heterologous epitope that is recognized by a commercially available antibody.

Additional Proteins of Interest (POIs)

The sequences for use according to the present invention may also be used in conjunction with one or more additional proteins of interest (POIs) or nucleotide sequences of interest (NOIs).

Non-limiting examples of POIs include: proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, hemicellulases, hexose oxidases, hydrolases, invertases, isomerases, tripeptidyl exopeptidases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proline endoproteases, rhamno-galacturonases, ribonucleases, thaumatin, transferases, exoproteases, transport proteins, transglutaminases, aminopeptidases, hexose oxidase (D-hexose: $O_2$-oxidoreductase, EC 1.1.3.5) or combinations thereof. The NOI may even be an antisense sequence for any of those sequences.

The POI may even be a fusion protein, for example to aid in extraction and purification.

The POI may even be fused to a secretion sequence.

Other sequences can also facilitate secretion or increase the yield of secreted POI. Such sequences could code for chaperone proteins as for example the product of *Aspergillus niger* cyp B gene described in UK patent application 9821198.0.

The NOI may be engineered in order to alter their activity for a number of reasons, including but not limited to, alterations which modify the processing and/or expression of the expression product thereof. By way of further example, the NOI may also be modified to optimize expression in a particular host cell. Other sequence changes may be desired in order to introduce restriction enzyme recognition sites.

The NOI may include within it synthetic or modified nucleotides—such as methylphosphonate and phosphorothioate backbones.

The NOI may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

General Recombinant DNA Methodology Techniques

The present invention employs, unless otherwise indicated, conventional techniques of chemistry, molecular biology, microbiology, recombinant DNA and immunology, which are within the capabilities of a person of ordinary skill in the art. Such techniques are explained in the literature. See, for example, J. Sambrook, E. F. Fritsch, and T. Maniatis, 1989, *Molecular Cloning: A Laboratory Manual*, Second Edition, Books 1-3, Cold Spring Harbor Laboratory Press; Ausubel, F. M. et al. (1995 and periodic supplements; *Current Protocols in Molecular Biology*, ch. 9, 13, and 16, John Wiley & Sons, New York, N.Y.); B. Roe, J. Crabtree, and A. Kahn, 1996, *DNA Isolation and Sequencing: Essential Techniques*, John Wiley & Sons; M. J. Gait (Editor), 1984, *Oligonucleotide Synthesis: A Practical Approach*, Irl Press; and, D. M. J. Lilley and J. E. Dahlberg, 1992, *Methods of Enzymology: DNA Structure Part A: Synthesis and Physical Analysis of DNA* in *Methods in Enzymology*, Academic Press. Each of these general texts is herein incorporated by reference.

EXAMPLES

The present disclosure is described in further detail in the following examples, which are not in any way intended to limit the scope of the disclosure as claimed. The attached figures are meant to be considered as integral parts of the specification and description of the disclosure. The following examples are offered to illustrate, but not to limit the claimed disclosure.

Example 1—Cloning and Transformation of TRI031, TRI032, TRI033, TRI034, TRI035, TRI036, TRI037, TRI038

Synthetic genes (TRI031, TRI032, TRI033, TRI034, TRI035, TRI036, TRI037, TRI038) encoding fungal aminopeptidases type-2 (pepN_2, belonging to Merops family M28.008; merops.sanger.ac.uk/) were ordered from Geneart (Life Technologies) as codon-optimized genes for expression in *Trichoderma reesei*. TRI031 corresponds to NCBI accession number: XP_001258675 from *Neosartorya fischeri* NRRL 181; TRI032 corresponds to NCBI accession number: XP_003667354 from *Myceliophthora thermophila* ATCC® 42464; TRI033 corresponds to NCBI accession number: EGU74500 from *Fusarium oxysporum* Fo5176; TRI034 corresponds to NCBI accession number: ENH69875 from *Fusarium oxysporum* f. sp. *cubense* race 1; TRI035 corresponds to NCBI accession number: XP_001273779 from *Aspergillus clavatus* NRRL 1; TRI036 corresponds to NCBI accession number: EGS23402 *Chaetomium thermophilum* var. *thermophilum* DSM 1495; TRI037 corresponds to NCBI accession number: XP_001217759 from *Aspergillus terreus* NIH2624; and TRI038 corresponds to NCBI accession number: XP_681714 from *Aspergillus nidulans* FGSC A4.

Figure 1:
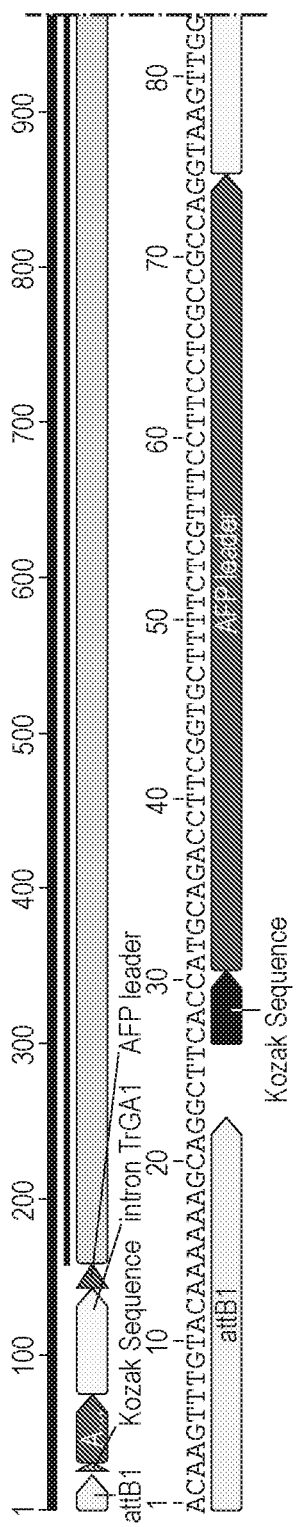
FIG. 1 shows on the top an example of the overall design of the synthetic genes encoding the pepN_2's enzymes, and at the bottom a close-up of the leader sequence that was used instead of the endogenous secretion signal sequences.
Figure 1:
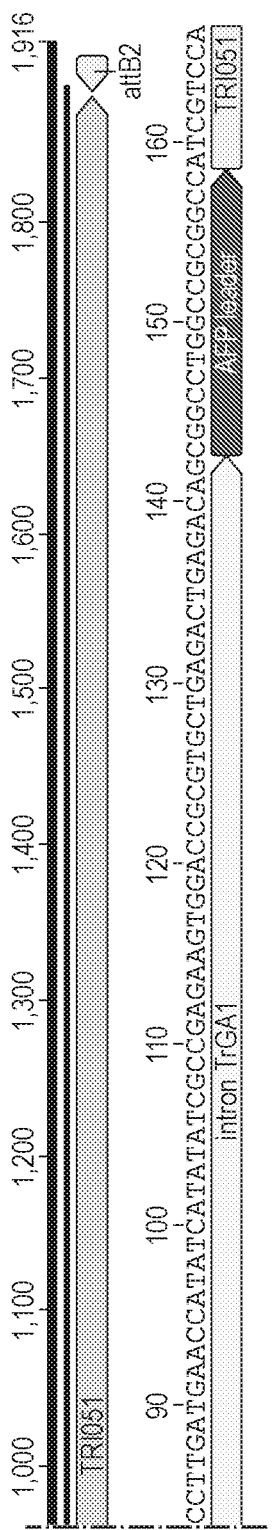

The genes were ordered with Gateway-specific recombination sites (attB1 and attB2) (Life Technologies) flanking the coding region and delivered as plasmid stocks in the pDonr221 Gateway vector (Life Technologies). The TRI031, TRI032, TRI033, TRI034, TRI035, TRI036, TRI037, TRI038 amino acid sequences have predicted secretion signal sequences (SignalP 4.0: discriminating signal peptides from transmembrane regions. Thomas Nordahl Petersen, Soren Brunak, Gunnar von Heijne & Henrik Nielsen. Nature Methods, 8:785-786, 2011) and these endogenous signal sequences were replaced by a leader sequence containing a Kozak sequence, the secretion signal sequence from the *Trichoderma reesei* acidic fungal protease (AFP) and an intron from a *Trichoderma reesei* glucoamylase gene (TrGA1) (see FIG. 1).

The synthetic genes in the pDonr221 vector was recombined into the destination vector pTrex8gM using LR CLONASE™ enzyme mix (Life Technologies) resulting in the expression vectors pTrex8gM_TRI031 (SEQ ID NO: 9), pTrex8gM_TRI032 (SEQ ID NO: 10), pTrex8gM_TRI033 (SEQ ID NO: 11), pTrex8gM_TRI034 (SEQ ID NO: 12), pTrex8gM_TRI035 (SEQ ID NO: 13), pTrex8gM_TRI036 (SEQ ID NO: 14), pTrex8gM_TRI037 (SEQ ID NO: 15), and pTrex8gM_TRI038 (SEQ ID NO: 16).

1.5-17 µg of the expression vectors were transformed individually into a *Trichoderma reesei* strain Cellulight™ using PEG mediated protoplast transformation essentially as described in (U.S. Pat. No. 8,592,194 B2). PEG-Protoplast method with slight modifications was used for transformation, as indicated. For protoplasts preparation, spores were grown for approximately 18 hours at 26° C. in *Trichoderma* germination medium with 10 mM uridine to complement the pyr auxotrophy. (*Trichoderma* germination medium: 40 ml 50% glucose, 2 g/L peptone, 15 g/L KH$_2$PO$_4$, 5 g/L (NH$_4$)$_2$SO$_4$, 2.4 ml 1M MgSO$_4$, 4.1 ml 1M CaCl$_2$, 1 ml of 400× *T reesei* Trace elements solution {200 g/L FeSO$_4$×7H$_2$O, 16 g/L ZnSO$_4$×7H$_2$O, 1.4 g/L MnSO$_4$×H$_2$O, 3.2 g/L CuSO$_4$×5H$_2$O, 0.8 g/L H$_3$BO$_3$, 175 g/L citric acid}) at shaking speed of 200 rpm. Germinating spores were harvested by centrifugation, washed and treated with 45 mg/ml of lysing enzyme solution (*Trichoderma harzianum*, Sigma cat # L1412) to lyse the fungal cell walls. Further preparation of protoplasts was performed by a standard method, as described by Penttilä et al. (*Gene* 61(1987) 155-164).

In general, transformation mixtures containing 1.5-17 µg of DNA and ~5×10$^7$ protoplasts in a total volume of 200 µL were treated with 2 mL of 25% PEG solution, diluted with 2 volumes of 1.2M sorbitol/10 mM Tris, pH7.5/10 mM CaCl$_2$ solution, mixed with 3% selective top agarose, 1 M sorbitol, 10 mM NH$_4$Cl, 1× MM solution (2× MM solution:

30 g/L KH$_2$PO$_4$, 20 mL 1M acetamide, 20 ml 1M CsCl, 6 ml 20% MgSO$_4$×7H$_2$O, 6 ml 20% CaCl$_2$×2H$_2$O, 2 mL *T. reesei* Trace elements solution (400×), 80 mL 50% glucose, make up to 1 liter, pH 4.5) and poured on to MM plates with 10 mM NH$_4$Cl (MM plates 2% agar, 1× MM solution). Transformants were selected for prototrophic growth on MM plates (lacking uridine). Plates were incubated for 5-7 days at 28° C. until sporulation occurred. Stable looking transformants were transferred to new MM plates with 10 mM NH$_4$Cl for better sporulation. When sporulated, spores were harvested using a solution of 0.85% NaCl, 0.015% TWEEN® 80 Spore suspensions were used to inoculate liquid cultures either in a 24-well MTP format (for screening) or shake flasks (for validation studies). Preculture in 3 mL YEG medium (5 g/L yeast extract, 22 g/L glucose, H$_2$O) Main culture in the following production medium (Production medium: 35 g/L 61% glucose/sophorose mix, 9 g/L casmino acids, 5 g/L (NH$_4$)$_2$SO$_4$, 4.5 g/L KH$_2$PO$_4$, 1 g/L CaCl$_2$×2H$_2$O, 1 g/L MgSO$_4$×7H$_2$O, 33 g/L PIPPS buffer, pH 5.5, 2.5 mL/L of 400× *T. reesei* trace elements (175 g/L citric acid, 200 g/L FeSO$_4$×7H$_2$O, 16 g/L ZnSO$_4$×7H$_2$O, 3.2 g/L CuSO$_4$×5H$_2$O, 1.4 g/L MnSO$_4$×H$_2$O, 0.8 g/L boric acid) pH 5.5. 3 mL of production medium was added to produce variants in 24-well MTPs. For shake flasks, volumes were scaled up.

Cultures were grown for 7 days at 28° C. and 80% humidity with shaking at 180 rpm. Culture supernatants were harvested by vacuum filtration and used to assay their performance as well as expression level.

The amino acid and nucleotide sequences for the pepN_2 enzymes are depicted below:

SEQ ID NO: 1=Amino acid sequence of TRI031. Underlined is the secretion signal encoded by the leader sequence described in FIG. 1:

```
                                         (Seq ID no 1)
MQTFGAFLVSFLAASGLAAANGPGWDWKPPVHPKVLPQMIHLWDLMHGAQ

KLEDFAYAYPERNRVFGGPAHEDTVNYLYRELKKTGYYDVYKQPQVHQWT

RADQALTVDGKSYVATTMTYSPSVNVTAPLAVVNNLGCVESDYPADLKGK

IALVSRGECPFATKSVLSAKAGAAAALVYNNIEGSMAGTLGGPTSELGPY

APIAGISLADGQALIQMIQAGTVTANLWIDSKVENRTTYNVIAQTKGGDP

NNVVALGGHTDSVEAGPGINDDGSGIISNLVVAKALTRFSVKNAVRFCFW

TAEEFGLLGSSYYVNSLNATEKAKIRLYLNFDMIASPNYALMIYDGDGSA

FNLTGPAGSAQIERLFEDYYKSIRKPFVPTEFNGRSDYEAFILNGIPAGG

IFTGAEAIKTEEQAKLFGGQAGVALDANYHAKGDNMTNLNREAFLINSKA

TAFAVATYANSLDSIPSRNMSTVVKRSQLEQAKKSTPHTHTGGTGCYKDR

VEQ
```

The sequence absent the underlined leader sequence is denoted SEQ ID NO: 18.

SEQ ID NO: 2=Amino acid sequence of TRI032. Underlined is the secretion signal encoded by the leader sequence described in FIG. 1.

```
                                         (Seq ID no 2)
MQTFGAFLVSFLAASGLAAAGGHGGSSGLGCDSQRPLVSSEKLQSLIKKE

DLLAGSQELQDIATAHGGHRAFGSSGHNATVDFLYYTLKALDYYNVTKQP

FKEIFSSGTGSLTVDGEDIEAETLTYTPSGSATDKPVVVANVGCDAADY
```

```
                                         -continued
PAEVAGNIALIKRGTCTFSQKSVNAKAAGAVAAIIYNNAEGKLSGTLGQP

FLDYAPVLGITLEAGEALLAKLAGGPVTATLQIDALVEERVTYNVIAETK

EGDHSNVLVLGGHTDSVPAGPGINDDGSGTIGMLTVAKALTKFRVKNAVR

FAFWSAEEYGLLGSYAYIKSINSSAAELSKIRAYLNFDMIASPNYIYGIY

DGDGNAFNLTGPAGSDVIERNFENFFKRKHTPSVPTEFSGRSDYAAFIEN

GIPSGGLFTGAEVLKTEREAELFGGRAGVAYDVNYHQAGDTVDNLALDAF

LLNTKAIADSVATYALSFDGLPRVDGKKRRWDAHRARMLKRSAGSHGHAH

LHSGPCGGGASI
```

The sequence absent the underlined leader sequence is denoted SEQ ID NO: 19.

SEQ ID NO: 3=Amino acid sequence of TRI033. Underlined is the secretion signal encoded by the leader sequence described in FIG. 1.

```
                                         (Seq ID no 3)
MQTFGAFLVSFLAASGLAAATKKPLVNELKLQKDINIKDLMAGAQKLQDI

AEANGNTRVFGGAGHNATVDYLYKTLKATGYYNVKKQPFTELYSAGTASL

KVDGDDITAAIMTYTPAGEATGPLVVAENLGCEASDFPAESEGKVVLVLR

GECPFSQKSTNGKTAGAAAVIVYNNVPGELAGTLGEPFGEFAPIVGISQE

DGQAILAKTKAGEVTVDLKVDATVENRVTFNVIAETKEGDHDNVLVVGGH

SDSVAAGPGINDDGSGIIGILKVAQALTKYRVKNAVRFGFWSAEEFGLLG

SYAYMKSINGSDAEVAKIRAYLNFDMIASPNYVYGIYDGDGSAFNLTGPA

GSDAIEKDFERFFKTKRLGYVPSEFSGRSDYAAFIENGIPSGGLFTGAEQ

LKTEEEAKKFGGEAGVAYDINYHKIGDDINNLNKEAFLVNTQAIANSVAR

YAKTWKSLPKVTHNTRRWDAEVASVLKRSSGHSHAGGPCGSVSV
```

The sequence absent the underlined leader sequence is denoted SEQ ID NO: 20.

SEQ ID NO: 4=Amino acid sequence of TRI034. Underlined is the secretion signal encoded by the leader sequence described in FIG. 1.

```
                                         (Seq ID no 4)
MQTFGAFLVSFLAASGLAAALQIPLNLQVPKLSWNLFGDDLPLVDTKELQ

KSIKPENLEARAKDLYEIAKNGEEEYGHPTRVIGSEGHLGTLSYIHAELA

KLGGYYSVSNQQFPAVSGNVFESRLVIGDSVPKQASPMGLTPPTKNKEPV

HGTLVLVDNEGCDASDYPEAVKGNIALILRGTCPFGTKSGNAGKAGAVAA

VVYNYEKDEVHGTLGTPSPDHVATFGLGGEEGKAVAKKLKDGEKVDAIAY

IDAEVKTISTTNIIAQTRGGDPDNCVMLGGHSDSVAEGPGINDDGSGSIS

VLEVAVQLTKYRVNNCVRFAWWAAEEEGLLGSDHYVSVLPEDENRKIRLF

MDYDMMASPNFAYQIYNATNAENPKGSEELRDLYVNWYEEQGLNYTFIPF

DGRSDYDGFIRGGIPAGGIATGAEGVKTEDEVEMFGGEAGVWYDKNYHQI

GDDLTNVNYTAWEVNTKLIAHSVATYAKSFKGFPEREIETSVQTYSDKTK

YHGSKLFI
```

The sequence absent the underlined leader sequence is denoted SEQ ID NO: 21.

SEQ ID NO: 5=Amino acid sequence of TRI035. Underlined is the secretion signal encoded by the leader sequence described in FIG. 1.

(Seq ID no 5)
<u>MQTFGAFLVSFLAASGLAAA</u>NAPGGPGGHGRKLPVNPKTFPNEIRLKDLL

HGSQKLEDFAYAYPERNRVFGGQAHLDTVNYLYRELKKTGYYDVYKQPQV

HQWTRADQSLTLGGDSIQASTMTYSPSVNVTAPLSLVSKLGCAEGDYSAD

VKGKIALVSRGECSFAQKSVLSAKAGAVATIVYNNVDGSLAGTLGGATSE

LGPYSPIIGITLAAGQDLVARLQAAPTEVSLWIDSKVENRTTYNVIAQTK

GGDPNNVVALGGHTDSVENGPGINDDGSGVISNLVVAKALTRYSVKNAVR

FCFWTAEEFGLLGSNYYVDNLSPAELAKIRLYLNFDMIASPNYALMIYDG

DGSAFNLTGPPGSAQIESLFENYYKSIKQGFVPTAFDGRSDYEGFILKGI

PAGGVFTGAESLKTEEQARLFGGQAGVALDANYHAKGDNMTNLNHKAFLI

NSRATAFAVATYANNLSSIPPRNATVVKRESMKWTKREEPHTHGADTGCF

ASRVKE

The sequence absent the underlined leader sequence is denoted SEQ ID NO: 22.

SEQ ID NO: 6=Amino acid sequence of TRI036. Underlined is the secretion signal encoded by the leader sequence described in FIG. 1.

(Seq ID no 6)
<u>MQTFGAFLVSFLAASGLAAA</u>GGPHGFGLPKIDLRPMVSSNRLQSMITLKD

LMDGAKKLQDIATKNGGNRAFGGAGHNATVDYLYKTLTSLGGYYTVKKQP

FKEIFSSGSGSLIVDGQGIDAGIMTYTPGGSATANLVQVANLGCEDEDYP

AEVAGNIALISRGSCTFSSKSLKAKAAGAVGAIVYNNVPGELSGTLGTPF

LDYAPIVGISQEDGQVILEKLAAGPVTATLNIDAIVEERTTYNVIAETKE

GDHNNVLIVGGHSDSVAAGPGINDDGSGTIGILTVAKALAKANVRIKNAV

RFAFWSAEEFGLLGSYAYMKSLNESEAEVAKIRAYLNFDMIASPNYIYGI

YDGDGNAFNLTGPAGSDIIEKDFEDFFKKKKTPSVPTEFSGRSDYAAFIE

NGIPSGGLFTGAEVLKTEEEAKLFGGKAGVAYDVNYHKAGDTVDNLAKDA

FLLNTKAIANSVAKYAASWAGFPKPSAVRRRYDADMAQLLKRSGGVHGHG

PHTHSGPCGGGDLL

The sequence absent the underlined leader sequence is denoted SEQ ID NO: 23.

SEQ ID NO: 7=Amino acid sequence of TRI037. Underlined is the secretion signal encoded by the leader sequence described in FIG. 1.

(Seq ID no 7)
<u>MQTFGAFLVSFLAASGLAAA</u>EGLGNHGRKLDPNKFTKDIKLKDLLKGSQK

LEDFAYAYPERNRVFGGKAHQDTVNWIYNELKKTGYYDVYKQPQVHLWSN

AEQSLTVDGEAIDATTMTYSPSLKETTAEVVVVPGLGCTAADYPADVAGK

IALIQRGSCTFGEKSVYAAAANAAAAIVYNNVDGSLSGTLGAATSELGPY

APIVGISLADGQNLVSLAQAGPLTVDLYINSQMENRTTHNVIAKSKGGDP

NNVIVIGGHSDAVNQGPGVNDDGSGIISNLVIAKALTKYSLKNSVTWAFW

TAEEFGLLGSEFYVNSLSAAEKDKIKLYLNFDMIASPNYALMIYDGDGST

FNMTGPAGSAEIEHLFEDYYKSRGLSYIPTAFDGRSDYEAFILNGIPAGG

LFTGAEQIKTEEQVAMFGGQAGVAYDPNYHAAGDNMTNLSEEAFLINSKA

TAFAVATYANSLESIPPRNATMSIQTRSASRRAAAHRRAAKPHSHSGGTG

CWHTRVEL

The sequence absent the underlined leader sequence is denoted SEQ ID NO: 24.

SEQ ID NO: 8=Amino acid sequence of TRI038. Underlined is the secretion signal encoded by the leader sequence described in FIG. 1.

(Seq ID no 8)
<u>MQTFGAFLVSFLAASGLAAA</u>GKHKPLVTPEALQDLITLDDLLAGSQQLQD

FAYAYPERNRVFGGRAHDDTVNWLYRELKRTGYYHVYKQPQVHLYSNAEE

SLTVNGEAIEATTMTYSPSANASAELAVISGLGCSPADFASDVAGKVVLV

QRGNCTFGEKSVYAAAADAAATIVYNNVEGSLSGTLGAAQSEQGPYSGIV

GISLADGEALLALAEEGPVHVDLWIDSVMENRTTYNVIAQTKGGDPDNVV

TLGGHSDSVEAGPGINDDGSGIISNLVIARALTKFSTKHAVRFFFWTAEE

FGLLGSDYYVSSLSPAELAKIRLYLNFDMIASPNYGLLLYDGDGSAFNLT

GPAGSDAIEKLFYDYFQSIGQATVETEFDGRSDYEAFILNGIPAGGVFTG

AEEIKSEEEVALWGGEAGVAYDANYHQVGDTIDNLNTEAYLLNSKATAFA

VATYANDLSTIPKREMTTAVKRANVNGHMHRRTMPKKRQTAHRHAAKGCF

HSRVEQ

The sequence absent the underlined leader sequence is denoted SEQ ID NO: 25.

SEQ ID NO: 9=Nucleotide sequence of the pTrex8gM_TRI031 expression construct.

(Seq ID no 9)
CTAGAGTTGTGAAGTCGGTAATCCCGCTGTATAGTAATACGAGTCGCATC

TAAATACTCCGAAGCTGCTGCGAACCCGGAGAATCGAGATGTGCTGGAAA

GCTTCTAGCGAGCGGCTAAATTAGCATGAAAGGCTATGAGAAATTCTGGA

GACGGCTTGTTGAATCATGGCGTTCCATTCTTCGACAAGCAAAGCGTTCC

GTCGCAGTAGCAGGCACTCATTCCCGAAAAAACTCGGAGATTCCTAAGTA

GCGATGGAACCGGAATAATATAATAGGCAATACATTGAGTTGCCTCGACG

GTTGCAATGCAGGGGTACTGAGCTTGGACATAACTGTTCCGTACCCCACC

TCTTCTCAACCTTTGGCGTTTCCCTGATTCAGCGTACCCGTACAAGTCGT

AATCACTATTAACCCAGACTGACCGGACGTGTTTTGCCCTTCATTTGGAG

AAATAATGTCATTGCGATGTGTAATTTGCCTGCTTGACCGACTGGGGCTG

TTCGAAGCCCGAATGTAGGATTGTTATCCGAACTCTGCTCGTAGAGGCAT

GTTGTGAATCTGTGTCGGGCAGGACACGCCTCGAAGGTTCACGGCAAGGG

AAACCACCGATAGCAGTGTCTAGTAGCAACCTGTAAAGCCGCAATGCAGC

ATCACTGGAAAATACAAACCAATGGCTAAAGTACATAAGTTAATGCCTA

AAGAAGTCATATACCAGCGGCTAATAATTGTACAATCAAGTGGCTAAACG

TACCGTAATTTGCCAACGGCTTGTGGGGTTGCAGAAGCAACGGCAAAGCC

-continued

CCACTTCCCCACGTTTGTTTCTTCACTCAGTCCAATCTCAGCTGGTGATC

CCCCAATTGGGTCGCTTGTTTGTTCCGGTGAAGTGAAAGAAGACAGAGGT

AAGAATGTCTGACTCGGAGCGTTTTGCATACAACCAAGGGCAGTGATGGA

AGACAGTGAAATGTTGACATTCAAGGAGTATTTAGCCAGGGATGCTTGAG

TGTATCGTGTAAGGAGGTTTGTCTGCCGATACGACGAATACTGTATAGTC

ACTTCTGATGAAGTGGTCCATATTGAAATGTAAGTCGGCACTGAACAGGC

AAAAGATTGAGTTGAAACTGCCTAAGATCTCGGGCCCTCGGGCCTTCGGC

CTTTGGGTGTACATGTTTGTGCTCCGGGCAAATGCAAAGTGTGGTAGGAT

CGAACACACTGCTGCCTTTACCAAGCAGCTGAGGGTATGTGATAGGCAAA

TGTTCAGGGGCCACTGCATGGTTTCGAATAGAAAGAGAAGCTTAGCCAAG

AACAATAGCCGATAAAGATAGCCTCATTAAACGGAATGAGCTAGTAGGCA

AAGTCAGCGAATGTGTATATATAAAGGTTCGAGGTCCGTGCCTCCCTCAT

GCTCTCCCCATCTACTCATCAACTCAGATCCTCCAGGAGACTTGTACACC

ATCTTTTGAGGCACAGAAACCCAATAGTCAACCATCACAAGTTTGTACAA

AAAAGCAGGCTTCACCATGCAGACCTTCGGTGCTTTTCTCGTTTCCTTCC

TCGCCGCCAGGTAAGTTGGCCTTGATGAACCATATCATATATCGCCGAGA

AGTGGACCGCGTGCTGAGACTGAGACAGCGGCCTGGCCGCGGCCAACGGA

CCTGGATGGGATTGGAAGCCCCCCGTCCACCCCAAGGTCCTCCCCCAGAT

GATCCACCTCTGGGACCTCATGCACGGCGCCCAGAAGCTCGAAGATTTCG

CCTACGCCTACCCCGAGCGCAACCGCGTCTTTGGCGGCCCTGCCCACGAG

GACACCGTCAACTACCTCTACCGCGAGCTGAAGAAGACCGGCTACTACGA

CGTCTACAAGCAGCCCCAGGTCCACCAGTGGACCCGAGCCGATCAGGCCC

TCACCGTCGACGGCAAGAGCTACGTCGCCACCACCATGACCTACAGCCCC

AGCGTCAACGTCACCGCCCCTCTCGCCGTCGTCAACAACCTCGGCTGCGT

CGAGAGCGACTACCCCGCCGACCTCAAGGGCAAGATCGCCCTCGTTTCTC

GCGGCGAGTGCCCCTTCGCCACCAAGTCTGTCCTCAGCGCCAAGGCTGGC

GCCGCTGCCGCTCTCGTCTACAACAACATCGAGGGCAGCATGGCCGGCAC

CCTCGGCGGACCTACTTCTGAGCTGGGCCCCTACGCCCCCATTGCCGGCA

TTTCTCTCGCCGACGGCCAGGCCCTCATCCAGATGATTCAGGCCGGCACC

GTCACCGCCAACCTCTGGATCGACAGCAAGGTCGAGAACCGCACCACCTA

CAACGTCATTGCCCAGACCAAGGGCGGCGACCCCAACAACGTCGTCGCTC

TCGGCGGCCACACCGACTCTGTTGAGGCTGGCCCTGGCATCAACGACGAC

GGCAGCGGCATCATCAGCAACCTCGTCGTCGCCAAGGCCCTCACCCGCTT

CAGCGTCAAGAACGCCGTCCGCTTCTGCTTCTGGACCGCCGAAGAGTTCG

GCCTCCTCGGCAGCAGCTACTACGTCAACAGCCTCAACGCCACCGAGAAG

GCCAAGATCCGCCTCTACCTCAACTTCGACATGATCGCCAGCCCCAACTA

CGCCCTCATGATCTACGACGGCGACGCAGCGCCTTCAACCTCACTGGCC

CTGCTGGCAGCGCCCAGATCGAGCGCCTCTTCGAGGACTACTACAAGAGC

ATCCGCAAGCCCTTCGTCCCCACCGAGTTCAACGGCCGCAGCGACTACGA

GGCCTTCATCCTCAACGGCATCCCCGCTGGCGGCATCTTCACTGGCGCCG

-continued

AGGCCATCAAGACCGAGGAACAGGCCAAGCTGTTCGGCGGCCAGGCTGGC

GTCGCCCTCGATGCCAACTACCACGCCAAGGGCGACAACATGACCAACCT

CAACCGCGAGGCCTTCCTCATCAACAGCAAGGCCACCGCCTTCGCCGTCG

CCACCTACGCCAACTCCCTCGACAGCATCCCCAGCCGCAACATGAGCACC

GTCGTCAAGCGCAGCCAGCTTGAGCAGGCCAAGAAGTCCACCCCCCACAC

CCACACTGGCGGCACCGGCTGCTACAAGGACCGCGTCGAACAGTAAGACC

CAGCTTTCTTGTACAAAGTGGTGATCGCGCCAGCTCCGTGCGAAAGCCTG

ACGCACCGGTAGATTCTTGGTGAGCCCGTATCATGACGGCGGCGGGAGCT

ACATGGCCCCGGGTGATTTATTTTTTTTGTATCTACTTCTGACCCTTTTC

AAATATACGGTCAACTCATCTTTCACTGGAGATGCGGCCTGCTTGGTATT

GCGATGTTGTCAGCTTGGCAAATTGTGGCTTTCGAAAACACAAAACGATT

CCTTAGTAGCCATGCATTTTAAGATAACGGAATAGAAGAAAGAGGAAATT

AAAAAAAAAAAAAAAACAAACATCCCGTTCATAACCCGTAGAATCGCCGC

TCTTCGGCTAGCTAGTTACGCTTGTTTATTTACGACAAGATCTAGAAGAT

TCGAGATAGAATAATAATAATAACAACAATTTGCCTCTTCTTTCCACCTT

TTCAGTCTTACTCTCCCTTCTGACATTGAACGCCTCAATCAGTCAGTCGC

CTTGTACTTGGCACGGTAATCCTCCGTGTTCTTGATATCCTCAGGGGTAG

CAAAGCCCTTCATGCCATCGATAATGTCATCCAGAGTGAGGATGGCAAAG

ATGGGGATGCCGTACTCCTTCCTCAGCTCGCCAATGGCACTCGGTCCAGG

CTTGGAGTCGTCGCCATCCGCAGCGGGGAGCTTCTCCATGCGGTCCAGGG

CCACGACGATGCCGGCGACGATGCCGCCCTCCTTGGTGATCTTCTCAATG

GCGTCCCTCTTGGCGGTGCCGGCGGTGATGACGTCGTCGACAATCAGGAC

CCTCTTGCCCTTGAGCGAAGCGCCGACGATGTTGCCGCCCTCGCCGTGGT

CCTTGGCCTCCTTGCGGTCAAACGAGTAGGAGACGCGGTCCAGGTTCTGG

GGCGCCAGCTCGCCGAGCTTGATGGTGATGGCGGAGCACAGCGGGATGCC

CTTGTAGGCCGGGCCGAAGACGATGTCGAACTCTAGGCCGGCCTTCTCCT

GGGCCTCGATGATGGTCTTTGCAAAGGCGGAGGCGATGGCGCCGGCGAGG

CGCGCCGTGTGGAATTCGCCCGCGTTGAAGAAGTAGGGGGATATCCGCTT

GGACTTGAGCTCGAAGCTGCCAAACTTGAGGACGCCGCCGTCGATGGCGG

ATTTGAGGAAGTCCTGCTTGTAGGCAGGCAGCTGGGAGGTGGTAGCCATT

CTGTTGGATTTGGATAGTGTCCTTATTCTCTGATTTGAACAGTAGATCAG

GACGAGTGAGAGGGATGCAGAGGTTGGATTGGAGTGGTTGAGCTATAAAA

TTTAGAGGCGCGCCGTATCGAGTTTTCACATGGAAGTCAAAGCGTACAGT

GCGAGCTTGTACGTTGGTCTTAGTATCCCACAAGCTTCTGTCTAGGTATG

ATGATGGCTATAAGTCACCCAAGGCAGAACTCATCTTGAAGATTGTCTAG

AGTGATTTTACCGCTGATGAAATGACTGGACTCCCTCCTCCTGCTCTTAT

ACGAAAAATTGCCTGACTCTGCAAAGGTTGTTTGTCTTGGAAGATGATGT

GCCCCCCCATCGCTCTTATCTCATACCCCGCCATCTTTCTAGATTCTCAT

CTTCAACAAGAGGGGCAATCCATGATCTGCGATCCAGATGTGCTTCTGGC

CTCATACTCTGCCTTCAGGTTGATGTTCACTTAATTGGTGACGAATTCAG

CTGATTTGCTGCAGTATGCTTTGTGTTGGTTCTTTCCAGGCTTGTGCCAG

```
CCATGAGCGCTTTGAGAGCATGTTGTCACCTATAAACTCGAGTAACGGCC
ACATATTGTTCACTACTTGAATCACATACCTAATTTTGATAGAATTGACA
TGTTTAAAGAGCTGAGGTAGCTTTAATGCCTCTGAAGTATTGTGACACAG
CTTCTCACAGAGTGAGAATGAAAAGTTGGACTCCCCCTAATGAAGTAAAA
GTTTCGTCTCTGAACGGTGAAGAGCATAGATCCGGCATCAACTACCTGGC
TAGACTACGACGTCAATTCTGCGGCCTTTTGACCTTTATATATGTCCATT
AATGCAATAGATTCTTTTTTTTTTTTTTTTTTTTTTTTTTTTTTTTTTT
TTTTTGCCCAATTTCGCAGATCAAAGTGGACGTTATAGCATCATAACTAA
GCTCAGTTGCTGAGGGAAGCCGTCTACTACCTTAGCCCATCCATCCAGCT
CCATACCTTGATACTTTAGACGTGAAGCAATTCACACTGTACGTCTCGCA
GCTCTCCTTCCCGCTCTTGCTTCCCCACTGGGGTCCATGGTGCGTGTATC
GTCCCCTCCTTAATTAAGGCCATTTAGGCCGTTGCTGGCGTTTTTCCATA
GGCTCCGCCCCCTGACGAGCATCACAAAAATCGACGCTCAAGTCAGAGG
TGGCGAAACCCGACAGGACTATAAAGATACCAGGCGTTTCCCCCTGGAAG
CTCCCTCGTGCGCTCTCCTGTTCCGACCCTGCCGCTTACCGGATACCGT
CCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCA
CGAACCCCCGTTCAGCCCGACCGCTGCGCCTTATCCGGTAACTATCGTC
TTGAGTCCAACCCGGTAAGACACGACTTATCGCCACTGGCAGCAGCCACT
GGTAACAGGATTAGCAGAGCGAGGTATGTAGGCGGTGCTACAGAGTTCTT
GAAGTGGTGGCCTAACTACGGCTACACTAGAAGGACAGTATTTGGTATCT
GCGCTCTGCTGAAGCCAGTTACCTTCGGAAAAGAGTTGGTAGCTCTTGA
TCCGGCAAACAAACCACCGCTGGTAGCGGTGGTTTTTTTGTTTGCAAGCA
GCAGATTACGCGCAGAAAAAAAGGATCTCAAGAAGATCCTTTGATCTTTT
CTACGGGGTCTGACGCTCAGTGGAACGAAAACTCACGTTAAGGCCTGCAG
GGCCGATTTTGGTCATGAGATTATCAAAAAGGATCTTCACCTAGATCCTT
TTAAATTAAAAATGAAGTTTTAAATCAATCTAAAGTATATATGAGTAAAC
TTGGTCTGACAGTTACCAATGCTTAATCAGTGAGGCACCTATCTCAGCGA
TCTGTCTATTTCGTTCATCCATAGTTGCCTGACTCCCCGTCGTGTAGATA
ACTACGATACGGGAGGGCTTACCATCTGGCCCCAGTGCTGCAATGATACC
GCGAGACCCACGCTCACCGGCTCCAGATTTATCAGCAATAAACCAGCCAG
CCGGAAGGGCCGAGCGCAGAAGTGGTCCTGCAACTTTATCCGCCTCCATC
CAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCT
CGTCGTTTGGTATGGCTTCATTCAGCTCCGGTTCCCAACGATCAAGGCGA
GTTACATGATCCCCCATGTTGTGCAAAAAAGCGGTTAGCTCCTTCGGTCC
TCCGATCGTTGTCAGAAGTAAGTTGGCCGCAGTGTTATCACTCATGGTTA
TGGCAGCACTGCATAATTCTCTTACTGTCATGCCATCCGTAAGATGCTTT
TCTGTGACTGGTGAGTACTCAACCAAGTCATTCTGAGAATAGTGTATGCG
GCGACCGAGTTGCTCTTGCCCGGCGTCAATACGGGATAATACCGCGCCAC
ATAGCAGAACTTTAAAAGTGCTCATCATTGGAAAACGTTCTTCGGGGCGA
AAACTCTCAAGGATCTTACCGCTGTTGAGATCCAGTTCGATGTAACCCAC
TCGTGCACCCAACTGATCTTCAGCATCTTTTACTTTCACCAGCGTTTCTG
GGTGAGCAAAAACAGGAAGGCAAAATGCCGCAAAAAAGGGAATAAGGGCG
ACACGGAAATGTTGAATACTCATACTCTTCCTTTTTCAATATTATTGAAG
CATTTATCAGGGTTATTGTCTCATGCCATTTAGGCCT
```

SEQ ID NO: 10=Nucleotide sequence of the pTrex8gM_TR1032 expression construct.

(Seq ID no 10)
```
CTAGAGTTGTGAAGTCGGTAATCCCGCTGTATAGTAATACGAGTCGCATC
TAAATACTCCGAAGCTGCTGCGAACCCGGAGAATCGAGATGTGCTGGAAA
GCTTCTAGCGAGCGGCTAAATTAGCATGAAAGGCTATGAGAAATTCTGGA
GACGGCTTGTTGAATCATGGCGTTCCATTCTTCGACAAGCAAAGCGTTCC
GTCGCAGTAGCAGGCACTCATTCCCGAAAAAACTCGGAGATTCCTAAGTA
GCGATGGAACCGGAATAATATAATAGGCAATACATTGAGTTGCCTCGACG
GTTGCAATGCAGGGGTACTGAGCTTGGACATAACTGTTCCGTACCCCACC
TCTTCTCAACCTTTGGCGTTTCCCTGATTCAGCGTACCCGTACAAGTCGT
AATCACTATTAACCCAGACTGACCGGACGTGTTTTGCCCTTCATTTGGAG
AAATAATGTCATTGCGATGTGTAATTTGCCTGCTTGACCGACTGGGGCTG
TTCGAAGCCCGAATGTAGGATTGTTATCCGAACTCTGCTCGTAGAGGCAT
GTTGTGAATCTGTGTCGGGCAGGACACGCCTCGAAGGTTCACGGCAAGGG
AAACCACCGATAGCAGTGTCTAGTAGCAACCTGTAAAGCCGCAATGCAGC
ATCACTGGAAAATACAAACCAATGGCTAAAAGTACATAAGTTAATGCCTA
AAGAAGTCATATACCAGCGGCTAATAATTGTACAATCAAGTGGCTAAACG
TACCGTAATTTGCCAACGGCTTGTGGGGTTGCAGAAGCAACGGCAAAGCC
CCACTTCCCCACGTTTGTTTCTTCACTCAGTCCAATCTCAGCTGGTGATC
CCCCAATTGGGTCGCTTGTTTGTTCCGGTGAAGTGAAAGAAGACAGAGGT
AAGAATGTCTGACTCGGAGCGTTTTGCATACAACCAAGGGCAGTGATGGA
AGACAGTGAAATGTTGACATTCAAGGAGTATTTAGCCAGGGATGCTTGAG
TGTATCGTGTAAGGAGGTTTGTCTGCCGATACGACGAATACTGTATAGTC
ACTTCTGATGAAGTGGTCCATATTGAAATGTAAGTCGGCACTGAACAGGC
AAAAGATTGAGTTGAAACTGCCTAAGATCTCGGGCCCTCGGGCCTTCGGC
CTTTGGGTGTACATGTTTGTGCTCCGGGCAAATGCAAAGTGTGGTAGGAT
CGAACACACTGCTGCCTTTACCAAGCAGCTGAGGGTATGTGATAGGCAAA
TGTTCAGGGGCCACTGCATGGTTTCGAATAGAAAGAGAAGCTTAGCCAAG
AACAATAGCCGATAAAGATAGCCTCATTAAACGGAATGAGCTAGTAGGCA
AAGTCAGCGAATGTGTATATATAAAGGTTCGAGGTCCGTGCCTCCCTCAT
GCTCTCCCCATCTACTCATCAACTCAGATCCTCCAGGAGACTTGTACACC
ATCTTTTGAGGCACAGAAACCCAATAGTCAACCATCACAAGTTTGTACAA
AAAAGCAGGCTTCACCATGCAGACCTTCGGTGCTTTTCTCGTTTCCTTCC
TCGCCGCCAGGTAAGTTGGCCTTGATGAACCATATCATATATCGCCGAGA
```

AGTGGACCGCGTGCTGAGACTGAGACAGCGGCCTGGCCGCGGCCGGTGGA
CATGGTGGATCTTCAGGCCTCGGCTGCGACAGCCAGCGCCCTCTTGTCAG
CAGCGAGAAGCTCCAGAGCCTGATCAAGAAGGAAGATCTCCTCGCCGGCA
GCCAAGAGCTTCAGGACATTGCCACTGCCCACGGCGGCCACCGAGCCTTT
GGAAGCTCTGGCCACAACGCCACCGTCGACTTTCTCTACTACACCCTCAA
GGCCCTCGACTACTACAACGTCACCAAGCAGCCCTTCAAGGAAATCTTCA
GCAGCGGCACCGGCAGCCTCACCGTGGACGGCGAGGACATCGAGGCCGAG
ACTCTCACCTACACCCCAGCGGCAGCGCCACCGACAAGCCTGTCGTCGT
CGTCGCCAACGTCGGCTGCGACGCCGCCGATTACCCTGCTGAGGTCGCCG
GCAACATTGCCCTCATCAAGCGCGGCACGTGCACCTTCAGCCAGAAGTCC
GTCAACGCCAAGGCCGCTGGCGCCGTCGCCGCCATCATCTACAACAACGC
CGAGGGCAAGCTCAGCGGAACCCTCGGCCAGCCCTTCCTCGACTACGCTC
CCGTCCTCGGCATCACCCTTGAGGCCGGCGAGGCCCTCCTCGCCAAGCTC
GCTGGTGGCCCTGTCACCGCCACCCTCCAGATTGACGCCCTCGTCGAGGA
ACGCGTCACCTACAACGTCATTGCCGAGACTAAGGAAGGCGACCACAGCA
ACGTCCTCGTCCTCGGCGGCCACACCGATAGCGTCCCTGCTGGCCCTGGC
ATCAACGACGACGGCAGCGGCACCATCGGCATGCTCACTGTCGCCAAGGC
CCTCACCAAGTTCCGCGTCAAGAACGCCGTCCGCTTCGCCTTCTGGTCCG
CCGAGGAATACGGCCTCCTCGGCAGCTACGCCTACATCAAGAGCATCAAC
AGCTCTGCCGCCGAGCTGAGCAAGATCCGCGCCTACCTCAACTTCGACAT
GATCGCCAGCCCCAACTACATCTACGGCATCTACGACGGCGACGGCAACG
CCTTCAACCTCACTGGCCCTGCCGGCAGCGACGTCATCGAGCGCAACTTC
GAGAACTTCTTCAAGCGCAAGCACACCCCCTCCGTCCCCACCGAGTTTAG
CGGCCGATCTGACTACGCCGCCTTCATCGAGAACGGCATCCCCAGCGGCG
GACTCTTCACTGGCGCCGAGGTCCTCAAGACCGAGCGCGAGGCTGAGCTG
TTTGGCGGCCGAGCTGGCGTCGCCTACGACGTCAACTACCACCAGGCCGG
CGACACCGTCGACAACCTCGCCCTCGACGCCTTCCTGCTCAACACCAAGG
CCATTGCCGACAGCGTCGCCACCTACGCCCTCAGCTTTGACGGCCTCCCT
CGCGTCGACGGCAAGAAGCGACGTTGGGACGCTCACCGAGCCCGCATGCT
CAAGCGATCTGCTGGCTCTCACGGCCACGCCCACCTTCACTCTGGCCCTT
GTGGCGGCGGAGCCAGCATCTAAGACCCAGCTTTCTTGTACAAAGTGGTG
ATCGCGCCAGCTCCGTGCGAAAGCCTGACGCACCGGTAGATTCTTGGTGA
GCCCGTATCATGACGGCGGCGGGAGCTACATGGCCCCGGGTGATTTATTT
TTTTTGTATCTACTTCTGACCCTTTTCAAATATACGGTCAACTCATCTTT
CACTGGAGATGCGGCCTGCTTGGTATTGCGATGTTGTCAGCTTGGCAAAT
TGTGGCTTTCGAAAACACAAAACGATTCCTTAGTAGCCATGCATTTTAAG
ATAACGGAATAGAAGAAAGAGGGAAATTAAAAAAAAAAAAAAAACAAACAT
CCCGTTCATAACCCGTAGAATCGCCGCTCTTCGGCTAGCTAGTTACGCTT
GTTTATTTACGACAAGATCTAGAAGATTCGAGATAGAATAATAATAATAA
CAACAATTTGCCTCTTCTTTCCACCTTTTCAGTCTTACTCTCCCTTCTGA

CATTGAACGCCTCAATCAGTCAGTCGCCTTGTACTTGGCACGGTAATCCT
CCGTGTTCTTGATATCCTCAGGGGTAGCAAAGCCCTTCATGCCATCGATA
ATGTCATCCAGAGTGAGGATGGCAAAGATGGGGATGCCGTACTCCTTCCT
CAGCTCGCCAATGGCACTCGGTCCAGGCTTGGAGTCGTCGCCATCCGCAG
CGGGGAGCTTCTCCATGCGGTCCAGGGCCACGACGATGCCGGCGACGATG
CCGCCCTCCTTGGTGATCTTCTCAATGGCGTCCCTCTTGGCGGTGCCGGC
GGTGATGACGTCGTCGACAATCAGGACCCTCTTGCCCTTGAGCGAAGCGC
CGACGATGTTGCCGCCCTCGCCGTGGTCCTTGGCCTCCTTGCGGTCAAAC
GAGTAGGAGACGCGGTCCAGGTTCTGGGGCGCCAGCTCGCCGAGCTTGAT
GGTGATGGCGGAGCACAGCGGGATGCCCTTGTAGGCCGGGCCGAAGACGA
TGTCGAACTCTAGGCCGGCCTTCTCCTGGGCCTCGATGATGGTCTTTGCA
AAGGCGGAGGCGATGGCGCCGGCGAGGCGCGCCGTGTGGAATTCGCCCGC
GTTGAAGAAGTAGGGGGATATCCGCTTGGACTTGAGCTCGAAGCTGCCAA
ACTTGAGGACGCCGCCGTCGATGGCGGATTTGAGGAAGTCCTGCTTGTAG
GCAGGCAGCTGGGAGGTGGTAGCCATTCTGTTGGATTTGGATAGTGTCCT
TATTCTCTGATTTGAACAGTAGATCAGGACGAGTGAGAGGGATGCAGAGG
TTGGATTGGAGTGGTTGAGCTATAAAATTTAGAGGCGCGCCGTATCGAGT
TTTCACATGGAAGTCAAAGCGTACAGTGCGAGCTTGTACGTTGGTCTTAG
TATCCCACAAGCTTCTGTCTAGGTATGATGATGGCTATAAGTCACCCAAG
GCAGAACTCATCTTGAAGATTGTCTAGAGTGATTTTACCGCTGATGAAAT
GACTGGACTCCCTCCTCCTGCTCTTATACGAAAAATTGCCTGACTCTGCA
AAGGTTGTTTGTCTTGGAAGATGATGTGCCCCCCCATCGCTCTTATCTCA
TACCCCGCCATCTTTCTAGATTCTCATCTTCAACAAGAGGGCAATCCAT
GATCTGCGATCCAGATGTGCTTCTGGCCTCATACTCTGCCTTCAGGTTGA
TGTTCACTTAATTGGTGACGAATTCAGCTGATTTGCTGCAGTATGCTTTG
TGTTGGTTCTTTCCAGGCTTGTGCCAGCCATGAGCGCTTTGAGAGCATGT
TGTCACCTATAAACTCGAGTAACGGCCACATATTGTTCACTACTTGAATC
ACATACCTAATTTTGATAGAATTGACATGTTTAAAGAGCTGAGGTAGCTT
TAATGCCTCTGAAGTATTGTGACACAGCTTCTCACAGAGTGAGAATGAAA
AGTTGGACTCCCCCTAATGAAGTAAAAGTTTCGTCTCTGAACGGTGAAGA
GCATAGATCCGGCATCAACTACCTGGCTAGACTACGACGTCAATTCTGCG
GCCTTTTGACCTTTATATATGTCCATTAATGCAATAGATTCTTTTTTTTT
TTTTTTTTTTTTTTTTTTTTTTTTTTTGCCCAATTTCGCAGATCA
AAGTGGACGTTATAGCATCATAACTAAGCTCAGTTGCTGAGGGAAGCCGT
CTACTACCTTAGCCCATCCATCCAGCTCCATACCTTGATACTTTAGACGT
GAAGCAATTCACACTGTACGTCTCGCAGCTCTCCTTCCCGCTCTTGCTTC
CCCACTGGGGTCCATGGTGCGTGTATCGTCCCCTCCTTAATTAAGGCCAT
TTAGGCCGTTGCTGGCGTTTTTCCATAGGCTCCGCCCCCTGACGAGCAT
CACAAAAATCGACGCTCAAGTCAGAGGTGGCGAAACCCGACAGGACTATA
AAGATACCAGGCGTTTCCCCCTGGAAGCTCCCTCGTGCGCTCTCCTGTTC
CGACCCTGCCGCTTACCGGATACCTGTCCGCCTTTCTCCCTTCGGGAAGC

GTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACAC

GACTTATCGCCACTGGCAGCAGCCACTGGTAACAGGATTAGCAGAGCGAG

GTATGTAGGCGGTGCTACAGAGTTCTTGAAGTGGTGGCCTAACTACGGCT

ACACTAGAAGGACAGTATTTGGTATCTGCGCTCTGCTGAAGCCAGTTACC

TTCGGAAAAAGAGTTGGTAGCTCTTGATCCGGCAAACAAACCACCGCTGG

TAGCGGTGGTTTTTTTGTTTGCAAGCAGCAGATTACGCGCAGAAAAAAAG

GATCTCAAGAAGATCCTTTGATCTTTTCTACGGGGTCTGACGCTCAGTGG

AACGAAAACTCACGTTAAGGCCTGCAGGGCCGATTTTGGTCATGAGATTA

TCAAAAAGGATCTTCACCTAGATCCTTTTAAATTAAAAATGAAGTTTTAA

ATCAATCTAAAGTATATATGAGTAAACTTGGTCTGACAGTTACCAATGCT

TAATCAGTGAGGCACCTATCTCAGCGATCTGTCTATTTCGTTCATCCATA

GTTGCCTGACTCCCCGTCGTGTAGATAACTACGATACGGGAGGGCTTACC

ATCTGGCCCCAGTGCTGCAATGATACCGCGAGACCCACGCTCACCGGCTC

CAGATTTATCAGCAATAAACCAGCCAGCCGGAAGGGCCGAGCGCAGAAGT

GGTCCTGCAACTTTATCCGCCTCCATCCAGTCTATTAATTGTTGCCGGGA

AGCTAGAGTAAGTAGTTCGCCAGTTAATAGTTTGCGCAACGTTGTTGCCA

TTGCTACAGGCATCGTGGTGTCACGCTCGTCGTTTGGTATGGCTTCATTC

AGCTCCGGTTCCCAACGATCAAGGCGAGTTACATGATCCCCCATGTTGTG

CAAAAAAGCGGTTAGCTCCTTCGGTCCTCCGATCGTTGTCAGAAGTAAGT

TGGCCGCAGTGTTATCACTCATGGTTATGGCAGCACTGCATAATTCTCTT

ACTGTCATGCCATCCGTAAGATGCTTTTCTGTGACTGGTGAGTACTCAAC

CAAGTCATTCTGAGAATAGTGTATGCGGCGACCGAGTTGCTCTTGCCCGG

CGTCAATACGGGATAATACCGCGCCACATAGCAGAACTTTAAAAGTGCTC

ATCATTGGAAAACGTTCTTCGGGGCGAAAACTCTCAAGGATCTTACCGCT

GTTGAGATCCAGTTCGATGTAACCCACTCGTGCACCCAACTGATCTTCAG

CATCTTTTACTTTCACCAGCGTTTCTGGGTGAGCAAAAACAGGAAGGCAA

AATGCCGCAAAAAAGGGAATAAGGGCGACACGGAAATGTTGAATACTCAT

ACTCTTCCTTTTTCAATATTATTGAAGCATTTATCAGGGTTATTGTCTCA

TGGCCATTTAGGCCT

SEQ ID NO: 11=Nucleotide sequence of the pTrex8gM_TR1033 expression construct.

(Seq ID no 11)
CTAGAGTTGTGAAGTCGGTAATCCCGCTGTATAGTAATACGAGTCGCATC

TAAATACTCCGAAGCTGCTGCGAACCCGGAGAATCGAGATGTGCTGGAAA

GCTTCTAGCGAGCGGCTAAATTAGCATGAAAGGCTATGAGAAATTCTGGA

GACGGCTTGTTGAATCATGGCGTTCCATTCTTCGACAAGCAAAGCGTTCC

GTCGCAGTAGCAGGCACTCATTCCCGAAAAAACTCGGAGATTCCTAAGTA

GCGATGGAACCGGAATAATATAATAGGCAATACATTGAGTTGCCTCGACG

GTTGCAATGCAGGGGTACTGAGCTTGGACATAACTGTTCCGTACCCCACC

TCTTCTCAACCTTTGGCGTTTCCCTGATTCAGCGTACCCGTACAAGTCGT

AATCACTATTAACCCAGACTGACCGGACGTGTTTTGCCCTTCATTTGGAG

AAATAATGTCATTGCGATGTGTAATTTGCCTGCTTGACCGACTGGGGCTG

TTCGAAGCCCGAATGTAGGATTGTTATCCGAACTCTGCTCGTAGAGGCAT

GTTGTGAATCTGTGTCGGGCAGGACACGCCTCGAAGGTTCACGGCAAGGG

AAACCACCGATAGCAGTGTCTAGTAGCAACCTGTAAAGCCGCAATGCAGC

ATCACTGGAAAATACAAACCAATGGCTAAAAGTACATAAGTTAATGCCTA

AAGAAGTCATATACCAGCGGCTAATAATTGTACAATCAAGTGGCTAAACG

TACCGTAATTTGCCAACGGCTTGTGGGGTTGCAGAAGCAACGGCAAAGCC

CCACTTCCCCACGTTTGTTTCTTCACTCAGTCCAATCTCAGCTGGTGATC

CCCCAATTGGGTCGCTTGTTTGTTCCGGTGAAGTGAAAGAAGACAGAGGT

AAGAATGTCTGACTCGGAGCGTTTTGCATACAACCAAGGGCAGTGATGGA

AGACAGTGAAATGTTGACATTCAAGGAGTATTTAGCCAGGGATGCTTGAG

TGTATCGTAAGGAGGTTTGTCTGCCGATACGACGAATACTGTATAGTC

ACTTCTGATGAAGTGGTCCATATTGAAATGTAAGTCGGCACTGAACAGGC

AAAAGATTGAGTTGAAACTGCCTAAGATCTCGGGCCCTCGGGCCTTCGGC

CTTTGGGTGTACATGTTTGTGCTCCGGGCAAATGCAAAGTGTGGTAGGAT

CGAACACACTGCTGCCTTTACCAAGCAGCTGAGGGTATGTGATAGGCAAA

TGTTCAGGGGCCACTGCATGGTTTCGAATAGAAAGAGAAGCTTAGCCAAG

AACAATAGCCGATAAAGATAGCCTCATTAAACGGAATGAGCTAGTAGGCA

AAGTCAGCGAATGTGTATATATAAAGGTTCGAGGTCCGTGCCTCCCTCAT

GCTCTCCCCATCTACTCATCAACTCAGATCCTCCAGGAGACTTGTACACC

ATCTTTTGAGGCACAGAAACCCAATAGTCAACCATCACAAGTTTGTACAA

AAAAGCAGGCTTCACCATGCAGACCTTCGGTGCTTTTCTCGTTTCCTTCC

TCGCCGCCAGGTAAGTTGGCCTTGATGAACCATATCATATATCGCCGAGA

AGTGGACCGCGTGCTGAGACTGAGACAGCGGCCTGGCCGCGGCCACCAAG

AAGCCCCTCGTCAACGAGCTGAAGCTCCAGAAGGACATCAACATCAAGGA

CCTCATGGCTGGCGCCCAGAAGCTCCAGGACATTGCCGAGGCCAACGGCA

ACACCCGCGTCTTTGGCGGCGCTGGCCACAACGCCACCGTCGACTACCTC

TACAAGACCCTCAAGGCCACCGGCTACTACAACGTCAAGAAGCAGCCCTT

CACCGAGCTGTACAGCGCCGGCACCGCCAGCCTCAAGGTCGACGGCGACG

ACATCACCGCCGCCATCATGACCTACACCCCTGCCGGCGAGGCCACCGGC

CCTCTTGTCGTCGCTGAGAACCTTGGCTGCGAGGCCAGCGACTTCCCCGC

TGAGTCTGAGGGCAAGGTCGTCCTCGTCCTCCGCGGCGAGTGCCCCTTCA

GCCAGAAGTCCACCAACGGCAAGACTGCCGGCGCTGCCGCCGTCATCGTC

TACAACAACGTCCCCGGCGAGCTGGCCGGCACTCTCGGCGAACCCTTTGG

CGAGTTCGCCCCCATCGTCGGCATCAGCCAAGAGGACGGCCAGGCCATCC

TCGCCAAGACCAAGGCCGGCGAGGTCACGGTCGACCTGAAGGTCGACGCC

ACGGTCGAGAACCGCGTCACCTTCAACGTCATTGCCGAGACTAAGGAAGG

CGACCACGACAACGTCCTCGTCGTCGGCGGCCACTCTGATAGCGTCGCTG

```
CCGGCCCTGGCATCAACGACGACGGCAGCGGCATCATCGGCATCCTCAAG
GTCGCCCAGGCCCTCACCAAGTACCGCGTCAAGAACGCCGTCCGCTTCGG
CTTCTGGTCCGCCGAAGAGTTCGGCCTCCTCGGCAGCTACGCCTACATGA
AGTCGATCAACGGCTCCGACGCCGAGGTCGCCAAGATCCGCGCCTACCTC
AACTTCGACATGATCGCCAGCCCCAACTACGTCTACGGCATCTACGACGG
CGACGGCAGCGCCTTCAACCTCACTGGCCCTGCCGGCTCGGACGCCATCG
AGAAGGACTTCGAGCGCTTCTTCAAGACCAAGCGCCTCGGCTACGTCCCC
AGCGAGTTTAGCGGCCGCTCTGACTACGCCGCCTTCATCGAGAACGGCAT
CCCCAGCGGCGGACTCTTCACTGGCGCCGAGCAGCTCAAGACCGAGGAAG
AGGCCAAGAAGTTCGGCGGCGAGGCCGGCGTCGCCTACGACATCAACTAC
CACAAGATCGGCGACGATATCAACAACCTCAACAAGGAAGCCTTCCTCGT
CAACACCCAGGCCATTGCCAACAGCGTCGCCCGCTACGCCAAGACCTGGA
AGTCCCTGCCCAAGGTCACCCACAACACCCGCCGATGGGACGCCGAGGTT
GCCTCCGTCCTCAAGCGAAGCAGCGGCCACTCTCACGCTGGCGGCCCTTG
TGGCTCTGTCAGCGTCTAAGACCCAGCTTTCTTGTACAAAGTGGTGATCG
CGCCAGCTCCGTGCGAAAGCCTGACGCACCGGTAGATTCTTGGTGAGCCC
GTATCATGACGGCGGCGGGAGCTACATGGCCCCGGGTGATTTATTTTTTT
TGTATCTACTTCTGACCCTTTTCAAATATACGGTCAACTCATCTTTCACT
GGAGATGCGGCCTGCTTGGTATTGCGATGTTGTCAGCTTGGCAAATTGTG
GCTTTCGAAAACACAAAACGATTCCTTAGTAGCCATGCATTTTAAGATAA
CGGAATAGAAGAAAGAGGGAAATTAAAAAAAAAAAAAAAACAAACATCCCG
TTCATAACCCGTAGAATCGCCGCTCTTCGGCTAGCTAGTTACGCTTGTTT
ATTTACGACAAGATCTAGAAGATTCGAGATAGAATAATAATAATAACAAC
AATTTGCCTCTTCTTTCCACCTTTTCAGTCTTACTCTCCCTTCTGACATT
GAACGCCTCAATCAGTCAGTCGCCTTGTACTTGGCACGGTAATCCTCCGT
GTTCTTGATATCCTCAGGGGTAGCAAAGCCCTTCATGCCATCGATAATGT
CATCCAGAGTGAGGATGGCAAAGATGGGGATGCCGTACTCCTTCCTCAGC
TCGCCAATGGCACTCGGTCCAGGCTTGGAGTCGTCGCCATCCGCAGCGGG
GAGCTTCTCCATGCGGTCCAGGGCCACGACGATGCCGGCGACGATGCCGC
CCTCCTTGGTGATCTTCTCAATGGCGTCCCTCTTGGCGGTGCCGGCGGTG
ATGACGTCGTCGACAATCAGGACCCTCTTGCCCTTGAGCGAAGCGCCGAC
GATGTTGCCGCCCTCGCCGTGGTCCTTGGCCTCCTTGCGGTCAAACGAGT
AGGAGACGCGGTCCAGGTTCTGGGCGCCAGCTCGCCGAGCTTGATGGTG
ATGGCGGAGCACAGCGGGATGCCCTTGTAGGCCGGGCCGAAGACGATGTC
GAACTCTAGGCCGGCCTTCTCCTGGGCCTCGATGATGGTCTTTGCAAAGG
CGGAGGCGATGGCGCCGGCGAGGCGCGCCGTGTGGAATTCGCCCGCGTTG
AAGAAGTAGGGGATATCCGCTTGGACTTGAGCTCGAAGCTGCCAAACTT
GAGGACGCCGCCGTCGATGGCGGATTTGAGGAAGTCCTGCTTGTAGGCAG
GCAGCTGGGAGGTGGTAGCCATTCTGTTGGATTTGGATAGTGTCCTTATT
CTCTGATTTGAACAGTAGATCAGGACGAGTGAGAGGGATGCAGAGGTTGG
ATTGGAGTGGTTGAGCTATAAAATTTAGAGGCGCGCCGTATCGAGTTTTC
ACATGGAAGTCAAAGCGTACAGTGCGAGCTTGTACGTTGGTCTTAGTATC
CCACAAGCTTCTGTCTAGGTATGATGATGGCTATAAGTCACCCAAGGCAG
AACTCATCTTGAAGATTGTCTAGAGTGATTTTACCGCTGATGAAATGACT
GGACTCCCTCCTCCTGCTCTTATACGAAAAATTGCCTGACTCTGCAAAGG
TTGTTTGTCTTGGAAGATGATGTGCCCCCCCATCGCTCTTATCTCATACC
CCGCCATCTTTCTAGATTCTCATCTTCAACAAGAGGGGCAATCCATGATC
TGCGATCCAGATGTGCTTCTGGCCTCATACTCTGCCTTCAGGTTGATGTT
CACTTAATTGGTGACGAATTCAGCTGATTTGCTGCAGTATGCTTTGTGTT
GGTTCTTTCCAGGCTTGTGCCAGCCATGAGCGCTTTGAGAGCATGTTGTC
ACCTATAAACTCGAGTAACGGCCACATATTGTTCACTACTTGAATCACAT
ACCTAATTTTGATAGAATTGACATGTTTAAAGAGCTGAGGTAGCTTTAAT
GCCTCTGAAGTATTGTGACACAGCTTCTCACAGAGTGAGAATGAAAAGTT
GGACTCCCCCTAATGAAGTAAAAGTTTCGTCTCTGAACGGTGAAGAGCAT
AGATCCGGCATCAACTACCTGGCTAGACTACGACGTCAATTCTGCGGCCT
TTTGACCTTTATATATGTCCATTAATGCAATAGATTCTTTTTTTTTTTT
TTTTTTTTTTTTTTTTTTTTTTTGCCCAATTTCGCAGATCAAAGT
GGACGTTATAGCATCATAACTAAGCTCAGTTGCTGAGGGAAGCCGTCTAC
TACCTTAGCCCATCCATCCAGCTCCATACCTTGATACTTTAGACGTGAAG
CAATTCACACTGTACGTCTCGCAGCTCTCCTTCCCGCTCTTGCTTCCCCA
CTGGGGTCCATGGTGCGTGTATCGTCCCCTCCTTAATTAAGGCCATTTAG
GCCGTTGCTGGCGTTTTTCCATAGGCTCCGCCCCCCTGACGAGCATCACA
AAAATCGACGCTCAAGTCAGAGGTGGCGAAACCCGACAGGACTATAAAGA
TACCAGGCGTTTCCCCCTGGAAGCTCCCTCGTGCGCTCTCCTGTTCCGAC
CCTGCCGCTTACCGGATACCTGTCCGCCTTTCTCCCTTCGGGAAGCGTGG
CGCTTTCTCATAGCTCACGCTGTAGGTATCTCAGTTCGGTGTAGGTCGTT
CGCTCCAAGCTGGGCTGTGTGCACGAACCCCCCGTTCAGCCCGACCGCTG
CGCCTTATCCGGTAACTATCGTCTTGAGTCCAACCCGGTAAGACACGACT
TATCGCCACTGGCAGCAGCCACTGGTAACAGGATTAGCAGAGCGAGGTAT
GTAGGCGGTGCTACAGAGTTCTTGAAGTGGTGGCCTAACTACGGCTACAC
TAGAAGGACAGTATTTGGTATCTGCGCTCTGCTGAAGCCAGTTACCTTCG
GAAAAAGAGTTGGTAGCTCTTGATCCGGCAAACAAACCACCGCTGGTAGC
GGTGGTTTTTTGTTTGCAAGCAGCAGATTACGCGCAGAAAAAAAGGATC
TCAAGAAGATCCTTTGATCTTTTCTACGGGGTCTGACGCTCAGTGGAACG
AAAACTCACGTTAAGGCCTGCAGGGCCGATTTTGGTCATGAGATTATCAA
AAAGGATCTTCACCTAGATCCTTTTAAATTAAAAATGAAGTTTTAAATCA
ATCTAAAGTATATATGAGTAAACTTGGTCTGACAGTTACCAATGCTTAAT
CAGTGAGGCACCTATCTCAGCGATCTGTCTATTTCGTTCATCCATAGTTG
CCTGACTCCCCGTCGTGTAGATAACTACGATACGGGAGGGCTTACCATCT
GGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTC
```

-continued

CTGCAACTTTATCCGCCTCCATCCAGTCTATTAATTGTTGCCGGGAAGCT

AGAGTAAGTAGTTCGCCAGTTAATAGTTTGCGCAACGTTGTTGCCATTGC

TACAGGCATCGTGGTGTCACGCTCGTCGTTTGGTATGGCTTCATTCAGCT

CCGGTTCCCAACGATCAAGGCGAGTTACATGATCCCCCATGTTGTGCAAA

AAAGCGGTTAGCTCCTTCGGTCCTCCGATCGTTGTCAGAAGTAAGTTGGC

CGCAGTGTTATCACTCATGGTTATGGCAGCACTGCATAATTCTCTTACTG

TCATGCCATCCGTAAGATGCTTTTCTGTGACTGGTGAGTACTCAACCAAG

TCATTCTGAGAATAGTGTATGCGGCGACCGAGTTGCTCTTGCCCGGCGTC

AATACGGGATAATACCGCGCCACATAGCAGAACTTTAAAAGTGCTCATCA

TTGGAAAACGTTCTTCGGGGCGAAAACTCTCAAGGATCTTACCGCTGTTG

AGATCCAGTTCGATGTAACCCACTCGTGCACCCAACTGATCTTCAGCATC

TTTTACTTTCACCAGCGTTTCTGGGTGAGCAAAAACAGGAAGGCAAAATG

CCGCAAAAAAGGGAATAAGGGCGACACGGAAATGTTGAATACTCATACTC

TTCCTTTTTCAATATTATTGAAGCATTTATCAGGGTTATTGTCTCATGGC

CATTTAGGCCT

SEQ ID NO: 12=Nucleotide sequence of the pTrex8gM_TR1034 expression construct.

(Seq ID no 12)
CTAGAGTTGTGAAGTCGGTAATCCCGCTGTATAGTAATACGAGTCGCATC

TAAATACTCCGAAGCTGCTGCGAACCCGGAGAATCGAGATGTGCTGGAAA

GCTTCTAGCGAGCGGCTAAATTAGCATGAAAGGCTATGAGAAATTCTGGA

GACGGCTTGTTGAATCATGGCGTTCCATTCTTCGACAAGCAAAGCGTTCC

GTCGCAGTAGCAGGCACTCATTCCCGAAAAAACTCGGAGATTCCTAAGTA

GCGATGGAACCGGAATAATATAATAGGCAATACATTGAGTTGCCTCGACG

GTTGCAATGCAGGGGTACTGAGCTTGGACATAACTGTTCCGTACCCCACC

TCTTCTCAACCTTTGGCGTTTCCCTGATTCAGCGTACCCGTACAAGTCGT

AATCACTATTAACCCAGACTGACCGGACGTGTTTTGCCCTTCATTTGGAG

AAATAATGTCATTGCGATGTGTAATTTGCCTGCTTGACCGACTGGGGCTG

TTCGAAGCCCGAATGTAGGATTGTTATCCGAACTCTGCTCGTAGAGGCAT

GTTGTGAATCTGTGTCGGGCAGGACACGCCTCGAAGGTTCACGGCAAGGG

AAACCACCGATAGCAGTGTCTAGTAGCAACCTGTAAAGCCGCAATGCAGC

ATCACTGGAAAATACAAACCAATGGCTAAAAGTACATAAGTTAATGCCTA

AAGAAGTCATATACCAGCGGCTAATAATTGTACAATCAAGTGGCTAAACG

TACCGTAATTTGCCAACGGCTTGTGGGGTTGCAGAAGCAACGGCAAAGCC

CCACTTCCCCACGTTTGTTTCTTCACTCAGTCCAATCTCAGCTGGTGATC

CCCCAATTGGGTCGCTTGTTTGTTCCGGTGAAGTGAAAGAAGACAGAGGT

AAGAATGTCTGACTCGGAGCGTTTTGCATACAACCAAGGGCAGTGATGGA

AGACAGTGAAATGTTGACATTCAAGGAGTATTTAGCCAGGGATGCTTGAG

TGTATCGTGTAAGGAGGTTTGTCTGCCGATACGACGAATACTGTATAGTC

ACTTCTGATGAAGTGGTCCATATTGAAATGTAAGTCGGCACTGAACAGGC

AAAAGATTGAGTTGAAACTGCCTAAGATCTCGGGCCCTCGGGCCTTCGGC

CTTTGGGTGTACATGTTTGTGCTCCGGGCAAATGCAAAGTGTGGTAGGAT

CGAACACACTGCTGCCTTTACCAAGCAGCTGAGGGTATGTGATAGGCAAA

TGTTCAGGGGCCACTGCATGGTTTCGAATAGAAAGAGAAGCTTAGCCAAG

AACAATAGCCGATAAAGATAGCCTCATTAAACGGAATGAGCTAGTAGGCA

AAGTCAGCGAATGTGTATATATAAAGGTTCGAGGTCCGTGCCTCCCTCAT

GCTCTCCCCATCTACTCATCAACTCAGATCCTCCAGGAGACTTGTACACC

ATCTTTTGAGGCACAGAAACCCAATAGTCAACCATCACAAGTTTGTACAA

AAAAGCAGGCTTCACCATGCAGACCTTCGGTGCTTTTCTCGTTTCCTTCC

TCGCCGCCAGGTAAGTTGGCCTTGATGAACCATATCATATATCGCCGAGA

AGTGGACCGCGTGCTGAGACTGAGACAGCGGCCTGGCCGCGGCCCTCCAG

ATTCCTCTCAACCTCCAGGTCCCCAAGCTCAGCTGGAACCTCTTCGGCGA

CGACCTCCCCCTGGTCGACACCAAGGAACTCCAGAAGTCCATCAAGCCCG

AGAACCTTGAGGCCCGAGCCAAGGACCTCTACGAGATCGCCAAGAACGGC

GAGGAAGAGTACGGCCACCCCACCCGCGTCATTGGCTCTGAGGGCCACCT

CGGCACCCTCAGCTACATCCACGCCGAGCTGGCTAAGCTCGGCGGCTACT

ACAGCGTCAGCAACCAGCAGTTCCCCGCCGTCAGCGGCAACGTCTTTGAG

AGCCGCCTCGTCATCGGCGACAGCGTCCCTAAGCAGGCCAGCCCTATGGG

CCTCACCCCCCCCACCAAGAACAAGGAACCCGTCCACGGCACCCTCGTCC

TCGTCGACAACGAGGGCTGCGACGCCAGCGACTACCCCGAGGCTGTCAAG

GGCAACATTGCCCTCATCCTCCGCGGCACGTGCCCCTTCGGCACCAAGTC

TGGCAACGCCGGCAAGGCTGGCGCCGTCGCTGCTGTCGTCTACAACTACG

AGAAGGACGAGGTCCACGGCACGCTGGGCACCCCTAGCCCTGATCACGTC

GCCACCTTTGGCCTCGGCGGCGAAGAGGGCAAGGCCGTCGCCAAGAAGCT

CAAGGACGGCGAGAAGGTCGACGCCATTGCCTACATTGACGCCGAGGTCA

AGACCATCAGCACCACCAACATCATTGCCCAGACCCGAGGCGGCGACCCC

GACAACTGCGTTATGCTTGGCGGCCACAGCGACAGCGTCGCTGAGGGCCC

TGGCATCAACGACGATGGCAGCGGCAGCATCAGCGTCCTTGAGGTCGCCG

TCCAGCTCACCAAGTACCGCGTCAACAACTGCGTCCGCTTCGCCTGGTGG

GCCGCTGAGGAAGAGGGCCTCCTTGGCAGCGACCACTACGTCAGCGTCCT

CCCCGAGGACGAGAACCGCAAGATCCGCCTCTTCATGGACTACGACATGA

TGGCCAGCCCCAACTTCGCCTACCAGATCTACAACGCCACCAACGCCGAG

AACCCCAAGGGCAGCGAGGAACTCCGCGACCTCTACGTCAACTGGTACGA

GGAACAGGGCCTCAACTACACCTTCATTCCCTTCGACGGCCGCAGCGACT

ACGACGGCTTTATCCGAGGCGGCATCCCCGCTGGCGGCATTGCTACTGGC

GCTGAGGGCGTCAAGACCGAGGACGAGGTCGAGATGTTCGGCGGCGAGGC

CGGCGTCTGGTACGACAAGAACTACCACCAGATTGGCGACGACCTGACCA

ACGTCAACTACACCGCCTGGGAGGTCAACACCAAGCTGATCGCCCACAGC

GTCGCCACCTACGCCAAGAGCTTCAAGGGCTTCCCCGAGCGCGAGATCGA

GACTAGCGTCCAGACCTACAGCGACAAGACCAAGTACCACGGCAGCAAGC

TGTTCATCTAAGACCCAGCTTTCTTGTACAAAGTGGTGATCGCGCCAGCT

```
CCGTGCGAAAGCCTGACGCACCGGTAGATTCTTGGTGAGCCCGTATCATG
ACGGCGGCGGGAGCTACATGGCCCCGGGTGATTTATTTTTTTGTATCTA
CTTCTGACCCTTTTCAAATATACGGTCAACTCATCTTTCACTGGAGATGC
GGCCTGCTTGGTATTGCGATGTTGTCAGCTTGGCAAATTGTGGCTTTCGA
AAACACAAAACGATTCCTTAGTAGCCATGCATTTTAAGATAACGGAATAG
AAGAAAGAGGAAATTAAAAAAAAAAAAAAAACAAACATCCCGTTCATAAC
CCGTAGAATCGCCGCTCTTCGGCTAGCTAGTTACGCTTGTTTATTTACGA
CAAGATCTAGAAGATTCGAGATAGAATAATAATAATAACAACAATTTGCC
TCTTCTTTCCACCTTTTCAGTCTTACTCTCCCTTCTGACATTGAACGCCT
CAATCAGTCAGTCGCCTTGTACTTGGCACGGTAATCCTCCGTGTTCTTGA
TATCCTCAGGGGTAGCAAAGCCCTTCATGCCATCGATAATGTCATCCAGA
GTGAGGATGGCAAAGATGGGGATGCCGTACTCCTTCCTCAGCTCGCCAAT
GGCACTCGGTCCAGGCTTGGAGTCGTCGCCATCCGCAGCGGGGAGCTTCT
CCATGCGGTCCAGGGCCACGACGATGCCGGCGACGATGCCGCCCTCCTTG
GTGATCTTCTCAATGGCGTCCCTCTTGGCGGTGCCGGCGGTGATGACGTC
GTCGACAATCAGGACCCTCTTGCCCTTGAGCGAAGCGCCGACGATGTTGC
CGCCCTCGCCGTGGTCCTTGGCCTCCTTGCGGTCAAACGAGTAGGAGACG
CGGTCCAGGTTCTGGGGCGCCAGCTCGCCGAGCTTGATGGTGATGGCGGA
GCACAGCGGGATGCCCTTGTAGGCCGGGCCGAAGACGATGTCGAACTCTA
GGCCGGCCTTCTCCTGGGCCTCGATGATGGTCTTTGCAAAGGCGGAGGCG
ATGGCGCCGGCGAGGCGCGCCGTGTGGAATTCGCCCGCGTTGAAGAAGTA
GGGGGATATCCGCTTGGACTTGAGCTCGAAGCTGCCAAACTTGAGGACGC
CGCCGTCGATGGCGGATTTGAGGAAGTCCTGCTTGTAGGCAGGCAGCTGG
GAGGTGGTAGCCATTCTGTTGGATTTGGATAGTGTCCTTATTCTCTGATT
TGAACAGTAGATCAGGACGAGTGAGAGGGATGCAGAGGTTGGATTGGAGT
GGTTGAGCTATAAAATTTAGAGGCGCGCCGTATCGAGTTTTCACATGGAA
GTCAAAGCGTACAGTGCGAGCTTGTACGTTGGTCTTAGTATCCCACAAGC
TTCTGTCTAGGTATGATGATGGCTATAAGTCACCCAAGGCAGAACTCATC
TTGAAGATTGTCTAGAGTGATTTTACCGCTGATGAAATGACTGGACTCCC
TCCTCCTGCTCTTATACGAAAAATTGCCTGACTCTGCAAAGGTTGTTTGT
CTTGGAAGATGATGTGCCCCCCCATCGCTCTTATCTCATACCCCGCCATC
TTTCTAGATTCTCATCTTCAACAAGAGGGGCAATCCATGATCTGCGATCC
AGATGTGCTTCTGGCCTCATACTCTGCCTTCAGGTTGATGTTCACTTAAT
TGGTGACGAATTCAGCTGATTTGCTGCAGTATGCTTTGTGTTGGTTCTTT
CCAGGCTTGTGCCAGCCATGAGCGCTTTGAGAGCATGTTGTCACCTATAA
ACTCGAGTAACGGCCACATATTGTTCACTACTTGAATCACATACCTAATT
TTGATAGAATTGACATGTTTAAAGAGCTGAGGTAGCTTTAATGCCTCTGA
AGTATTGTGACACAGCTTCTCACAGAGTGAGAATGAAAAGTTGGACTCCC
CCTAATGAAGTAAAAGTTTCGTCTCTGAACGGTGAAGAGCATAGATCCGG
CATCAACTACCTGGCTAGACTACGACGTCAATTCTGCGGCCTTTTGACCT
TTATATATGTCCATTAATGCAATAGATTCTTTTTTTTTTTTTTTTTTTT
TTTTTTTTTTTTTTTTTTGCCCAATTTCGCAGATCAAAGTGGACGTTA
TAGCATCATAACTAAGCTCAGTTGCTGAGGGAAGCCGTCTACTACCTTAG
CCCATCCATCCAGCTCCATACCTTGATACTTTAGACGTGAAGCAATTCAC
ACTGTACGTCTCGCAGCTCTCCTTCCCGCTCTTGCTTCCCCACTGGGGTC
CATGGTGCGTGTATCGTCCCCTCCTTAATTAAGGCCATTTAGGCCGTTGC
TGGCGTTTTTCCATAGGCTCCGCCCCCTGACGAGCATCACAAAAATCGA
CGCTCAAGTCAGAGGTGGCGAAACCCGACAGGACTATAAAGATACCAGGC
GTTTCCCCCTGGAAGCTCCCTCGTGCGCTCTCCTGTTCCGACCCTGCCGC
TTACCGGATACCTGTCCGCCTTTCTCCCTTCGGGAAGCGTGGCGCTTTCT
CATAGCTCACGCTGTAGGTATCTCAGTTCGGTGTAGGTCGTTCGCTCCAA
GCTGGGCTGTGTGCACGAACCCCCCGTTCAGCCCGACCGCTGCGCCTTAT
CCGGTAACTATCGTCTTGAGTCCAACCCGGTAAGACACGACTTATCGCCA
CTGGCAGCAGCCACTGGTAACAGGATTAGCAGAGCGAGGTATGTAGGCGG
TGCTACAGAGTTCTTGAAGTGGTGGCCTAACTACGGCTACACTAGAAGGA
CAGTATTTGGTATCTGCGCTCTGCTGAAGCCAGTTACCTTCGGAAAAAGA
GTTGGTAGCTCTTGATCCGGCAAACAAACCACCGCTGGTAGCGGTGGTTT
TTTTGTTTGCAAGCAGCAGATTACGCGCAGAAAAAAAGGATCTCAAGAAG
ATCCTTTGATCTTTTCTACGGGGTCTGACGCTCAGTGGAACGAAAACTCA
CGTTAAGGCCTGCAGGGCCGATTTTGGTCATGAGATTATCAAAAAGGATC
TTCACCTAGATCCTTTTAAATTAAAAATGAAGTTTTAAATCAATCTAAAG
TATATATGAGTAAACTTGGTCTGACAGTTACCAATGCTTAATCAGTGAGG
CACCTATCTCAGCGATCTGTCTATTTCGTTCATCCATAGTTGCCTGACTC
CCCGTCGTGTAGATAACTACGATACGGGAGGGCTTACCATCTGGCCCCAG
TGCTGCAATGATACCGCGAGACCCACGCTCACCGGCTCCAGATTTATCAG
CAATAAACCAGCCAGCCGGAAGGGCCGAGCGCAGAAGTGGTCCTGCAACT
TTATCCGCCTCCATCCAGTCTATTAATTGTTGCCGGGAAGCTAGAGTAAG
TAGTTCGCCAGTTAATAGTTTGCGCAACGTTGTTGCCATTGCTACAGGCA
TCGTGGTGTCACGCTCGTCGTTTGGTATGGCTTCATTCAGCTCCGGTTCC
CAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGT
TATCACTCATGGTTATGGCAGCACTGCATAATTCTCTTACTGTCATGCCA
TCCGTAAGATGCTTTTCTGTGACTGGTGAGTACTCAACCAAGTCATTCTG
AGAATAGTGTATGCGGCGACCGAGTTGCTCTTGCCCGGCGTCAATACGGG
ATAATACCGCGCCACATAGCAGAACTTTAAAAGTGCTCATCATTGGAAAA
CGTTCTTCGGGGCGAAAACTCTCAAGGATCTTACCGCTGTTGAGATCCAG
TTCGATGTAACCCACTCGTGCACCCAACTGATCTTCAGCATCTTTTACTT
TCACCAGCGTTTCTGGGTGAGCAAAAACAGGAAGGCAAAATGCCGCAAAA
AAGGGAATAAGGGCGACACGGAAATGTTGAATACTCATACTCTTCCTTTT
TCAATATTATTGAAGCATTTATCAGGGTTATTGTCTCATGGCCATTTAGG
CCT
```

SEQ ID NO: 13=Nucleotide sequence of the pTrex8gM_TRI035 expression construct.

(Seq ID no 13)
CTAGAGTTGTGAAGTCGGTAATCCCGCTGTATAGTAATACGAGTCGCATC
TAAATACTCCGAAGCTGCTGCGAACCCGGAGAATCGAGATGTGCTGGAAA
GCTTCTAGCGAGCGGCTAAATTAGCATGAAAGGCTATGAGAAATTCTGGA
GACGGCTTGTTGAATCATGGCGTTCCATTCTTCGACAAGCAAAGCGTTCC
GTCGCAGTAGCAGGCACTCATTCCCGAAAAAACTCGGAGATTCCTAAGTA
GCGATGGAACCGGAATAATATAATAGGCAATACATTGAGTTGCCTCGACG
GTTGCAATGCAGGGGTACTGAGCTTGGACATAACTGTTCCGTACCCCACC
TCTTCTCAACCTTTGGCGTTTCCCTGATTCAGCGTACCCGTACAAGTCGT
AATCACTATTAACCCAGACTGACCGGACGTGTTTTGCCCTTCATTTGGAG
AAATAATGTCATTGCGATGTGTAATTTGCCTGCTTGACCGACTGGGGCTG
TTCGAAGCCCGAATGTAGGATTGTTATCCGAACTCTGCTCGTAGAGGCAT
GTTGTGAATCTGTGTCGGGCAGGACACGCCTCGAAGGTTCACGGCAAGGG
AAACCACCGATAGCAGTGTCTAGTAGCAACCTGTAAAGCCGCAATGCAGC
ATCACTGGAAAATACAAACCAATGGCTAAAAGTACATAAGTTAATGCCTA
AAGAAGTCATATACCAGCGGCTAATAATTGTACAATCAAGTGGCTAAACG
TACCGTAATTTGCCAACGGCTTGTGGGGTTGCAGAAGCAACGGCAAAGCC
CCACTTCCCCACGTTTGTTTCTTCACTCAGTCCAATCTCAGCTGGTGATC
CCCCAATTGGGTCGCTTGTTTGTTCCGGTGAAGTGAAAGAAGACAGAGGT
AAGAATGTCTGACTCGGAGCGTTTTGCATACAACCAAGGGCAGTGATGGA
AGACAGTGAAATGTTGACATTCAAGGAGTATTTAGCCAGGGATGCTTGAG
TGTATCGTGTAAGGAGGTTTGTCTGCCGATACGACGAATACTGTATAGTC
ACTTCTGATGAAGTGGTCCATATTGAAATGTAAGTCGGCACTGAACAGGC
AAAAGATTGAGTTGAAACTGCCTAAGATCTCGGGCCCTCGGGCCTTCGGC
CTTTGGGTGTACATGTTTGTGCTCCGGGCAAATGCAAAGTGTGGTAGGAT
CGAACACACTGCTGCCTTTACCAAGCAGCTGAGGGTATGTGATAGGCAAA
TGTTCAGGGGCCACTGCATGGTTTCGAATAGAAAGAGAAGCTTAGCCAAG
AACAATAGCCGATAAAGATAGCCTCATTAAACGGAATGAGCTAGTAGGCA
AAGTCAGCGAATGTGTATATATAAAGGTTCGAGGTCCGTGCCTCCCTCAT
GCTCTCCCCATCTACTCATCAACTCAGATCCTCCAGGAGACTTGTACACC
ATCTTTTGAGGCACAGAAACCCAATAGTCAACCATCACAAGTTTGTACAA
AAAAGCAGGCTTCACCATGCAGACCTTCGGTGCTTTTCTCGTTTCCTTCC
TCGCCGCCAGGTAAGTTGGCCTTGATGAACCATATCATATATCGCCGAGA
AGTGGACCGCGTGCTGAGACTGAGACAGCGGCCTGGCCGCGCCAACGCT
CCTGGTGGACCTGGTGGTCACGGCCGCAAGCTCCCCGTCAACCCCAAGAC
CTTCCCCAACGAGATCCGCCTCAAGGACCTCCTCCACGGCAGCCAGAAGC
TCGAAGATTTCGCCTACGCCTACCCCGAGCGCAACCGCGTCTTTGGCGGC
CAGGCCCACCTCGACACCGTCAACTACCTCTACCGCGAGCTGAAGAAGAC
CGGCTACTACGACGTCTACAAGCAGCCCCAGGTGCACCAGTGGACCCGAG

CCGACCAGTCTCTCACTCTCGGCGGCGACAGCATCCAGGCCAGCACCATG
ACCTACAGCCCCAGCGTCAACGTCACCGCCCCTCTCAGCCTCGTCAGCAA
GCTCGGCTGCGCCGAGGGCGACTACAGCGCCGATGTCAAGGGCAAGATCG
CCCTCGTCAGCCGAGGCGAGTGCAGCTTCGCCCAGAAGTCCGTCCTCAGC
GCCAAGGCTGGCGCCGTCGCCACCATCGTCTACAACAACGTCGACGGCAG
CCTCGCCGGCACCCTTGGCGGAGCTACTTCTGAGCTGGGCCCCTACTCCC
CCATCATCGGCATCACTCTCGCCGCTGGCCAGGACCTCGTCGCCCGACTT
CAGGCCGCTCCTACCGAGGTCAGCCTCTGGATCGACAGCAAGGTCGAGAA
CCGCACCACCTACAACGTCATTGCCCAGACCAAGGGCGGCGACCCCAACA
ACGTCGTCGCTCTCGGCGGCCACACCGACAGCGTTGAGAACGGCCCTGGC
ATCAACGACGACGGCTCCGGCGTCATCAGCAACCTCGTCGTCGCCAAGGC
CCTCACCCGCTACAGCGTCAAGAACGCCGTCCGCTTCTGCTTCTGGACCG
CCGAAGAGTTCGGCCTCCTCGGCAGCAACTACTACGTCGACAACCTCAGC
CCTGCCGAGCTGGCCAAGATCCGCCTCTACCTCAACTTCGACATGATCGC
CAGCCCCAACTACGCCCTCATGATCTACGACGGCGACGGCAGCGCCTTCA
ACCTCACTGGACCCCCTGGCAGCGCCCAGATCGAGAGCCTCTTCGAGAAC
TACTACAAGAGCATCAAGCAGGGCTTCGTCCCCACCGCCTTCGACGGCCG
ATCTGACTACGAGGGCTTCATCCTCAAGGGCATCCCCGCTGGCGGCGTCT
TTACTGGCGCCGAGAGCCTCAAGACCGAGGAACAGGCCCGCCTGTTCGGC
GGCCAGGCTGGCGTTGCTCTCGACGCCAACTACCACGCCAAGGGCGACAA
CATGACCAACCTCAACCACAAGGCCTTTCTCATCAACAGCCGCGCCACGG
CCTTCGCCGTCGCTACCTACGCCAACAACCTCAGCAGCATCCCCCCTCGC
AACGCCACCGTCGTCAAGCGCGAGAGCATGAAGTGGACCAAGCGCGAGGA
ACCCCACACCCACGGCGCCGACACTGGCTGCTTTGCCAGCCGCGTCAAGG
AGTAAGACCCAGCTTTCTTGTACAAAGTGGTGATCGCGCCAGCTCCGTGC
GAAAGCCTGACGCACCGGTAGATTCTTGGTGAGCCCGTATCATGACGGCG
GCGGGAGCTACATGGCCCCGGGTGATTTATTTTTTTGTATCTACTTCTG
ACCCTTTTCAAATATACGGTCAACTCATCTTTCACTGGAGATGCGGCCTG
CTTGGTATTGCGATGTGTCAGCTTGGCAAATTGTGGCTTTCGAAAACAC
AAAACGATTCCTTAGTAGCCATGCATTTTAAGATAACGGAATAGAAGAAA
GAGGAAATTAAAAAAAAAAAAAAAACAAACATCCCGTTCATAACCCGTAG
AATCGCCGCTCTTCGGCTAGCTAGTTACGCTTGTTTATTTACGACAAGAT
CTAGAAGATTCGAGATAGAATAATAATAATAACAACAATTTGCCTCTTCT
TTCCACCTTTTCAGTCTTACTCTCCCTTCTGACATTGAACGCCTCAATCA
GTCAGTCGCCTTGTACTTGGCACGGTAATCCTCCGTGTTCTTGATATCCT
CAGGGGTAGCAAAGCCCTTCATGCCATCGATAATGTCATCCAGAGTGAGG
ATGGCAAAGATGGGGATGCCGTACTCCTTCCTCAGCTCGCCAATGGCACT
CGGTCCAGGCTTGGAGTCGTCGCCATCCGCAGCGGGGAGCTTCTCCATGC
GGTCCAGGGCCACGACGATGCCGGCGACGATGCCGCCCTCCTTGGTGATC
TTCTCAATGGCGTCCCTCTTGGCGGTGCCGGCGGTGATGACGTCGTCGAC
AATCAGGACCCTCTTGCCCTTGAGCGAAGCGCCGACGATGTTGCCGCCCT

-continued

```
CGCCGTGGTCCTTGGCCTCCTTGCGGTCAAACGAGTAGGAGACGCGGTCC
AGGTTCTGGGGCGCCAGCTCGCCGAGCTTGATGGTGATGGCGGAGCACAG
CGGGATGCCCTTGTAGGCCGGGCCGAAGACGATGTCGAACTCTAGGCCGG
CCTTCTCCTGGGCCTCGATGATGGTCTTTGCAAAGGCGGAGGCGATGGCG
CCGGCGAGGCGCGCCGTGTGGAATTCGCCCGCGTTGAAGAAGTAGGGGGA
TATCCGCTTGGACTTGAGCTCGAAGCTGCCAAACTTGAGGACGCCGCCGT
CGATGGCGGATTTGAGGAAGTCCTGCTTGTAGGCAGGCAGCTGGGAGGTG
GTAGCCATTCTGTTGGATTTGGATAGTGTCCTTATTCTCTGATTTGAACA
GTAGATCAGGACGAGTGAGAGGGATGCAGAGGTTGGATTGGAGTGGTTGA
GCTATAAAATTTAGAGGCGCGCCGTATCGAGTTTTCACATGGAAGTCAAA
GCGTACAGTGCGAGCTTGTACGTTGGTCTTAGTATCCCACAAGCTTCTGT
CTAGGTATGATGATGGCTATAAGTCACCCAAGGCAGAACTCATCTTGAAG
ATTGTCTAGAGTGATTTTACCGCTGATGAAATGACTGGACTCCCTCCTCC
TGCTCTTATACGAAAAATTGCCTGACTCTGCAAAGGTTGTTTGTCTTGGA
AGATGATGTGCCCCCCCATCGCTCTTATCTCATACCCCGCCATCTTTCTA
GATTCTCATCTTCAACAAGAGGGGCAATCCATGATCTGCGATCCAGATGT
GCTTCTGGCCTCATACTCTGCCTTCAGGTTGATGTTCACTTAATTGGTGA
CGAATTCAGCTGATTTGCTGCAGTATGCTTTGTGTTGGTCTTTCCAGGC
TTGTGCCAGCCATGAGCGCTTTGAGAGCATGTTGTCACCTATAAACTCGA
GTAACGGCCACATATTGTTCACTACTTGAATCACATACCTAATTTTGATA
GAATTGACATGTTTAAAGAGCTGAGGTAGCTTTAATGCCTCTGAAGTATT
GTGACACAGCTTCTCACAGAGTGAGAATGAAAAGTTGGACTCCCCCTAAT
GAAGTAAAAGTTTCGTCTCTGAACGGTGAAGAGCATAGATCCGGCATCAA
CTACCTGGCTAGACTACGACGTCAATTCTGCGGCCTTTTGACCTTTATAT
ATGTCCATTAATGCAATAGATTCTTTTTTTTTTTTTTTTTTTTTTTTT
TTTTTTTTTTTTGCCCAATTTCGCAGATCAAAGTGGACGTTATAGCAT
CATAACTAAGCTCAGTTGCTGAGGGAAGCCGTCTACTACCTTAGCCCATC
CATCCAGCTCCATACCTTGATACTTTAGACGTGAAGCAATTCACACTGTA
CGTCTCGCAGCTCTCCTTCCCGCTCTTGCTTCCCCACTGGGGTCCATGGT
GCGTGTATCGTCCCTCCTTAATTAAGGCCATTTAGGCCGTTGCTGGCGT
TTTTCCATAGGCTCCGCCCCCCTGACGAGCATCACAAAAATCGACGCTCA
AGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTA
ACTATCGTCTTGAGTCCAACCCGGTAAGACACGACTTATCGCCACTGGCA
GCAGCCACTGGTAACAGGATTAGCAGAGCGAGGTATGTAGGCGGTGCTAC
AGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGT
```

-continued
```
AGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTT
TGATCTTTTCTACGGGGTCTGACGCTCAGTGGAACGAAAACTCACGTTAA
GGGCTGCAGGGCCGATTTTGGTCATGAGATTATCAAAAAGGATCTTCACC
TAGATCCTTTTAAATTAAAAATGAAGTTTTAAATCAATCTAAAGTATATA
TGAGTAAACTTGGTCTGACAGTTACCAATGCTTAATCAGTGAGGCACCTA
TCTCAGCGATCTGTCTATTTCGTTCATCCATAGTTGCCTGACTCCCCGTC
GTGTAGATAACTACGATACGGGAGGGCTTACCATCTGGCCCCAGTGCTGC
AATGATACCGCGAGACCCACGCTCACCGGCTCCAGATTTATCAGCAATAA
ACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGA
TCAAGGCGAGTTACATGATCCCCCATGTTGTGCAAAAAAGCGGTTAGCTC
CTTCGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTTCTGTGACTGGTGAGTACTCAACCAAGTCATTCTGAGAATA
GTGTATGCGGCGACCGAGTTGCTCTTGCCCGGCGTCAATACGGGATAATA
CCGCGCCACATAGCAGAACTTTAAAAGTGCTCATCATTGGAAAACGTTCT
TCGGGGCGAAAACTCTCAAGGATCTTACCGCTGTTGAGATCCAGTTCGAT
GTAACCCACTCGTGCACCCAACTGATCTTCAGCATCTTTTACTTTCACCA
GCGTTTCTGGGTGAGCAAAAACAGGAAGGCAAAATGCCGCAAAAAAGGGA
ATAAGGGCGACACGGAAATGTTGAATACTCATACTCTTCCTTTTTCAATA
TTATTGAAGCATTTATCAGGGTTATTGTCTCATGGCCATTTAGGCCT
```

SEQ ID NO: 14=Nucleotide sequence of the pTrex8gM_TRI036 expression construct.

(Seq ID no 14)
```
CTAGAGTTGTGAAGTCGGTAATCCCGCTGTATAGTAATACGAGTCGCATC
TAAATACTCCGAAGCTGCTGCGAACCCGGAGAATCGAGATGTGCTGGAAA
GCTTCTAGCGAGCGGCTAAATTAGCATGAAAGGCTATGAGAAATTCTGGA
GACGGCTTGTTGAATCATGGCGTTCCATTCTTCGACAAGCAAAGCGTTCC
GTCGCAGTAGCAGGCACTCATTCCCGAAAAAACTCGGAGATTCCTAAGTA
GCGATGGAACCGGAATAATATAATAGGCAATACATTGAGTTGCCTCGACG
GTTGCAATGCAGGGGTACTGAGCTTGGACATAACTGTTCCGTACCCCACC
TCTTCTCAACCTTTGGCGTTTCCCTGATTCAGCGTACCCGTACAAGTCGT
AATCACTATTAACCCAGACTGACCGGACGTGTTTTGCCCTTCATTTGGAG
AAATAATGTCATTGCGATGTGTAATTTGCCTGCTTGACCGACTGGGGCTG
TTCGAAGCCCGAATGTAGGATTGTTATCCGAACTCTGCTCGTAGAGGCAT
GTTGTGAATCTGTGTCGGGCAGGACACGCCTCGAAGGTTCACGGCAAGGG
AAACCACCGATAGCAGTGTCTAGTAGCAACCTGTAAAGCCGCAATGCAGC
ATCACTGGAAAATACAAACCAATGGCTAAAAGTACATAAGTTAATGCCTA
```

```
AAGAAGTCATATACCAGCGGCTAATAATTGTACAATCAAGTGGCTAAACG
TACCGTAATTTGCCAACGGCTTGTGGGGTTGCAGAAGCAACGGCAAAGCC
CCACTTCCCCACGTTTGTTTCTTCACTCAGTCCAATCTCAGCTGGTGATC
CCCCAATTGGGTCGCTTGTTTGTTCCGGTGAAGTGAAAGAAGACAGAGGT
AAGAATGTCTGACTCGGAGCGTTTTGCATACAACCAAGGGCAGTGATGGA
AGACAGTGAAATGTTGACATTCAAGGAGTATTTAGCCAGGGATGCTTGAG
TGTATCGTGTAAGGAGGTTTGTCTGCCGATACGACGAATACTGTATAGTC
ACTTCTGATGAAGTGGTCCATATTGAAATGTAAGTCGGCACTGAACAGGC
AAAAGATTGAGTTGAAACTGCCTAAGATCTCGGGCCCTCGGGCCTTCGGC
CTTTGGGTGTACATGTTTGTGCTCCGGGCAAATGCAAAGTGTGGTAGGAT
CGAACACACTGCTGCCTTTACCAAGCAGCTGAGGGTATGTGATAGGCAAA
TGTTCAGGGGCCACTGCATGGTTTCGAATAGAAAGAGAAGCTTAGCCAAG
AACAATAGCCGATAAAGATAGCCTCATTAAACGGAATGAGCTAGTAGGCA
AAGTCAGCGAATGTGTATATATAAAGGTTCGAGGTCCGTGCCTCCCTCAT
GCTCTCCCCATCTACTCATCAACTCAGATCCTCCAGGAGACTTGTACACC
ATCTTTTGAGGCACAGAAACCCAATAGTCAACCATCACAAGTTTGTACAA
AAAAGCAGGCTTCACCATGCAGACCTTCGGTGCTTTTCTCGTTTCCTTCC
TCGCCGCCAGGTAAGTTGGCCTTGATGAACCATATCATATATCGCCGAGA
AGTGGACCGCGTGCTGAGACTGAGACAGCGGCCTGGCCGCGGCCGGTGGC
CCTCATGGATTTGGCCTCCCCAAGATCGACCTCCGCCCTATGGTCAGCAG
CAACCGCCTCCAGAGCATGATCACCCTCAAGGACCTCATGGACGGCGCCA
AGAAGCTCCAGGACATTGCCACCAAGAACGGCGGCAACCGCGCCTTTGGC
GGCGCTGGCCACAACGCCACTGTCGACTACCTCTACAAGACCCTCACCAG
CCTCGGCGGCTACTACACCGTCAAGAAGCAGCCCTTCAAGGAAATCTTCA
GCAGCGGCAGCGGCAGCCTCATCGTCGACGGCCAGGGCATCGACGCCGGC
ATCATGACCTATACCCCTGGCGGCAGCGCCACCGCCAACCTCGTCCAGGT
TGCTAACCTCGGCTGCGAGGACGAGGACTACCCTGCCGAGGTCGCCGGCA
ACATTGCCCTCATTAGCCGCGGCAGCTGCACCTTCAGCAGCAAGAGCCTC
AAGGCCAAGGCCGCTGGCGCCGTCGGCGCTATCGTCTACAACAACGTCCC
CGGCGAGCTGAGCGGAACCCTCGGCACCCCCTTTCTCGACTACGCCCCCA
TCGTCGGCATCAGCCAAGAGGACGGCCAGGTCATCCTTGAGAAGCTCGCC
GCTGGCCCCGTCACCGCCACCCTCAACATCGACGCCATCGTCGAGGAACG
CACCACCTACAACGTCATTGCCGAGACTAAGGAAGGCGACCACAACAACG
TGCTCATTGTCGGCGGCCACAGCGACAGCGTTGCTGCCGGCCCTGGCATC
AACGACGACGGCTCTGGCACCATCGGCATCCTCACCGTCGCCAAGGCCCT
CGCCAAGGCCAACGTCCGCATCAAGAACGCCGTCCGCTTCGCCTTCTGGT
CCGCCGAAGAGTTCGGCCTCCTCGGCAGCTACGCCTACATGAAGTCCCTC
AACGAGAGCGAGGCCGAGGTGGCCAAGATCCGCGCCTACCTCAACTTCGA
CATGATCGCCAGCCCCAACTACATCTACGGCATCTACGACGGCGACGGCA
ACGCCTTCAACCTCACTGGCCCTGCCGGCAGCGACATCATCGAGAAGGAC
TTCGAGGACTTCTTCAAGAAGAAGAAGACCCCCAGCGTCCCCACCGAGTT
CAGCGGCCGATCTGACTACGCCGCCTTCATCGAGAACGGCATCCCCAGCG
GCGGACTCTTCACTGGCGCCGAGGTCCTCAAGACCGAGGAAGAGGCCAAG
CTGTTCGGCGGCAAGGCCGGCGTCGCCTACGACGTCAACTACCACAAGGC
CGGCGACACCGTCGACAACCTCGCCAAGGACGCCTTCCTGCTCAACACCA
AGGCCATTGCCAACAGCGTCGCCAAGTACGCCGCCAGCTGGGCCGGCTTT
CCTAAGCCTTCTGCCGTCCGCCGACGCTACGACGCCGATATGGCCCAGCT
CCTCAAGCGCTCTGGCGGCGTTCATGGCCACGGCCCTCACACTCATAGCG
GCCCTTGTGGCGGCGGTGACCTCCTCTAAGACCCAGCTTTCTTGTACAAA
GTGGTGATCGCGCCAGCTCCGTGCGAAAGCCTGACGCACCGGTAGATTCT
TGGTGAGCCCGTATCATGACGGCGGCGGGAGCTACATGGCCCCGGGTGAT
TTATTTTTTTGTATCTACTTCTGACCCTTTTCAAATATACGGTCAACTC
ATCTTTCACTGGAGATGCGGCCTGCTTGGTATTGCGATGTTGTCAGCTTG
GCAAATTGTGGCTTTCGAAAACACAAAACGATTCCTTAGTAGCCATGCAT
TTTAAGATAACGGAATAGAAGAAAGAGGAAATTAAAAAAAAAAAAAAAAC
AAACATCCCGTTCATAACCCGTAGAATCGCCGCTCTTCGGCTAGCTAGTT
ACGCTTGTTTATTTACGACAAGATCTAGAAGATTCGAGATAGAATAATAA
TAATAACAACAATTTGCCTCTTCTTTCCACCTTTTCAGTCTTACTCTCCC
TTCTGACATTGAACGCCTCAATCAGTCAGTCGCCTTGTACTTGGCACGGT
AATCCTCCGTGTTCTTGATATCCTCAGGGGTAGCAAAGCCCTTCATGCCA
TCGATAATGTCATCCAGAGTGAGGATGGCAAAGATGGGGATGCCGTACTC
CTTCCTCAGCTCGCCAATGGCACTCGGTCCAGGCTTGGAGTCGTCGCCAT
CCGCAGCGGGGAGCTTCTCCATGCGGTCCAGGGCACGACGATGCCGGCG
ACGATGCCGCCCTCCTTGGTGATCTTCTCAATGGCGTCCCTCTTGGCGGT
GCCGGCGGTGATGACGTCGTCGACAATCAGGACCCTCTTGCCCTTGAGCG
AAGCGCCGACGATGTTGCCGCCCTCGCCGTGGTCCTTGGCCTCCTTGCGG
TCAAACGAGTAGGAGACGCGGTCCAGGTTCTGGGGCGCCAGCTCGCCGAG
CTTGATGGTGATGGCGGAGCACAGCGGGATGCCCTTGTAGGCCGGGCCGA
AGACGATGTCGAACTCTAGGCCGGCCTTCTCCTGGGCCTCGATGATGGTC
TTTGCAAAGGCGGAGGCGATGGCGCCGGCGAGGCGCGCCGTGTGGAATTC
GCCCGCGTTGAAGAAGTAGGGGGATATCCGCTTGGACTTGAGCTCGAAGC
TGCCAAACTTGAGGACGCCGCCGTCGATGGCGGATTTGAGGAAGTCCTGC
TTGTAGGCAGGCAGCTGGGAGGTGGTAGCCATTCTGTTGGATTTGGATAG
TGTCCTTATTCTCTGATTTGAACAGTAGATCAGGACGAGTGAGAGGGATG
CAGAGGTTGGATTGGAGTGGTTGAGCTATAAAATTTAGAGGCGCGCCGTA
TCGAGTTTTCACATGGAAGTCAAAGCGTACAGTGCGAGCTTGTACGTTGG
TCTTAGTATCCCACAAGCTTCTGTCTAGGTATGATGATGGCTATAAGTCA
CCCAAGGCAGAACTCATCTTGAAGATTGTCTAGAGTGATTTTACCGCTGA
TGAAATGACTGGACTCCCTCCTCCTGCTCTTATACGAAAAATTGCCTGAC
TCTGCAAAGGTTGTTTGTCTTGGAAGATGATGTGCCCCCCCATCGCTCTT
ATCTCATACCCCGCCATCTTTCTAGATTCTCATCTTCAACAAGAGGGGCA
```

```
ATCCATGATCTGCGATCCAGATGTGCTTCTGGCCTCATACTCTGCCTTCA
GGTTGATGTTCACTTAATTGGTGACGAATTCAGCTGATTTGCTGCAGTAT
GCTTTGTGTTGGTTCTTTCCAGGCTTGTGCCAGCCATGAGCGCTTTGAGA
GCATGTTGTCACCTATAAACTCGAGTAACGGCCACATATTGTTCACTACT
TGAATCACATACCTAATTTTGATAGAATTGACATGTTTAAAGAGCTGAGG
TAGCTTTAATGCCTCTGAAGTATTGTGACACAGCTTCTCACAGAGTGAGA
ATGAAAAGTTGGACTCCCCCTAATGAAGTAAAAGTTTCGTCTCTGAACGG
TGAAGAGCATAGATCCGGCATCAACTACCTGGCTAGACTACGACGTCAAT
TCTGCGGCCTTTTGACCTTTATATATGTCCATTAATGCAATAGATTCTTT
TTTTTTTTTTTTTTTTTTTTTTTTTTTTTTTTTTTGCCCAATTTCGC
AGATCAAAGTGGACGTTATAGCATCATAACTAAGCTCAGTTGCTGAGGGA
AGCCGTCTACTACCTTAGCCCATCCATCCAGCTCCATACCTTGATACTTT
AGACGTGAAGCAATTCACACTGTACGTCTCGCAGCTCTCCTTCCCGCTCT
TGCTTCCCCACTGGGGTCCATGGTGCGTGTATCGTCCCCTCCTTAATTAA
GGCCATTTAGGCCGTTGCTGGCGTTTTTCCATAGGCTCCGCCCCCTGAC
GAGCATCACAAAAATCGACGCTCAAGTCAGAGGTGGCGAAACCCGACAGG
ACTATAAAGATACCAGGCGTTTCCCCCTGGAAGCTCCCTCGTGCGCTCTC
CTGTTCCGACCCTGCCGCTTACCGGATACCTGTCCGCCTTTCTCCCTTCG
GGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGC
CCGACCGCTGCGCCTTATCCGGTAACTATCGTCTTGAGTCCAACCCGGTA
AGACACGACTTATCGCCACTGGCAGCAGCCACTGGTAACAGGATTAGCAG
AGCGAGGTATGTAGGCGGTGCTACAGAGTTCTTGAAGTGGTGGCCTAACT
ACGGCTACACTAGAAGGACAGTATTTGGTATCTGCGCTCTGCTGAAGCCA
GTTACCTTCGGAAAAAGAGTTGGTAGCTCTTGATCCGGCAAACAAACCAC
CGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCT
CAGTGGAACGAAAACTCACGTTAAGGCCTGCAGGGCCGATTTTGGTCATG
AGATTATCAAAAGGATCTTCACCTAGATCCTTTTAAATTAAAAATGAAG
TTTTAAATCAATCTAAAGTATATATGAGTAAACTTGGTCTGACAGTTACC
AATGCTTAATCAGTGAGGCACCTATCTCAGCGATCTGTCTATTTCGTTCA
TCCATAGTTGCCTGACTCCCCGTCGTGTAGATAACTACGATACGGGAGGG
CTTACCATCTGGCCCCAGTGCTGCAATGATACCGCGAGACCCACGCTCAC
CGGCTCCAGATTTATCAGCAATAAACCAGCCAGCCGGAAGGGCCGAGCGC
AGAAGTGGTCCTGCAACTTTATCCGCCTCCATCCAGTCTATTAATTGTTG
CCGGGAAGCTAGAGTAAGTAGTTCGCCAGTTAATAGTTTGCGCAACGTTG
TTGCCATTGCTACAGGCATCGTGGTGTCACGCTCGTCGTTTGGTATGGCT
TCATTCAGCTCCGGTTCCCAACGATCAAGGCGAGTTACATGATCCCCCAT
GTTGTGCAAAAAAGCGGTTAGCTCCTTCGGTCCTCCGATCGTTGTCAGAA
GTAAGTTGGCCGCAGTGTTATCACTCATGGTTATGGCAGCACTGCATAAT

TCTCTTACTGTCATGCCATCCGTAAGATGCTTTTCTGTGACTGGTGAGTA
CTCAACCAAGTCATTCTGAGAATAGTGTATGCGGCGACCGAGTTGCTCTT
GCCCGGCGTCAATACGGGATAATACCGCGCCACATAGCAGAACTTTAAAA
GTGCTCATCATTGGAAAACGTTCTTCGGGGCGAAAACTCTCAAGGATCTT
ACCGCTGTTGAGATCCAGTTCGATGTAACCCACTCGTGCACCCAACTGAT
CTTCAGCATCTTTTACTTTCACCAGCGTTTCTGGGTGAGCAAAAACAGGA
AGGCAAAATGCCGCAAAAAAGGGAATAAGGGCGACACGGAAATGTTGAAT
ACTCATACTCTTCCTTTTTCAATATTATTGAAGCATTTATCAGGGTTATT
GTCTCATGGCCATTTAGGCCT
```

SEQ ID NO: 15=Nucleotide sequence of the pTrex8gM_TR1037 expression construct.

(Seq ID no 15)
```
CTAGAGTTGTGAAGTCGGTAATCCCGCTGTATAGTAATACGAGTCGCATC
TAAATACTCCGAAGCTGCTGCGAACCCGGAGAATCGAGATGTGCTGGAAA
GCTTCTAGCGAGCGGCTAAATTAGCATGAAAGGCTATGAGAAATTCTGGA
GACGGCTTGTTGAATCATGGCGTTCCATTCTTCGACAAGCAAAGCGTTCC
GTCGCAGTAGCAGGCACTCATTCCCGAAAAAACTCGGAGATTCCTAAGTA
GCGATGGAACCGGAATAATATAATAGGCAATACATTGAGTTGCCTCGACG
GTTGCAATGCAGGGGTACTGAGCTTGGACATAACTGTTCCGTACCCCACC
TCTTCTCAACCTTTGGCGTTTCCCTGATTCAGCGTACCCGTACAAGTCGT
AATCACTATTAACCCAGACTGACCGGACGTGTTTTGCCCTTCATTTGGAG
AAATAATGTCATTGCGATGTGTAATTTGCCTGCTTGACCGACTGGGGCTG
TTCGAAGCCCGAATGTAGGATTGTTATCCGAACTCTGCTCGTAGAGGCAT
GTTGTGAATCTGTGTCGGGCAGGACACGCCTCGAAGGTTCACGGCAAGGG
AAACCACCGATAGCAGTGTCTAGTAGCAACCTGTAAAGCCGCAATGCAGC
ATCACTGGAAAATACAAACCAATGGCTAAAAGTACATAAGTTAATGCCTA
AAGAAGTCATATACCAGCGGCTAATAATTGTACAATCAAGTGGCTAAACG
TACCGTAATTTGCCAACGGCTTGTGGGGTTGCAGAAGCAACGGCAAAGCC
CCACTTCCCCACGTTTGTTTCTTCACTCAGTCCAATCTCAGCTGGTGATC
CCCCAATTGGGTCGCTTGTTTGTTCCGGTGAAGTGAAAGAAGACAGAGGT
AAGAATGTCTGACTCGGAGCGTTTTGCATACAACCAAGGGCAGTGATGGA
AGACAGTGAAATGTTGACATTCAAGGAGTATTTAGCCAGGGATGCTTGAG
TGTATCGTGTAAGGAGGTTTGTCTGCCGATACGACGAATACTGTATAGTC
ACTTCTGATGAAGTGGTCCATATTGAAATGTAAGTCGGCACTGAACAGGC
AAAAGATTGAGTTGAAACTGCCTAAGATCTCGGGCCCTCGGGCCTTCGGC
CTTTGGGTGTACATGTTTGTGCTCCGGGCAAATGCAAAGTGTGGTAGGAT
CGAACACACTGCTGCCTTTACCAAGCAGCTGAGGGTATGTGATAGGCAAA
TGTTCAGGGGCACTGCATGTTTCGAATAGAAAGAAGCTTAGCCAAG
AACAATAGCCGATAAAGATAGCCTCATTAAACGGAATGAGCTAGTAGGCA
AAGTCAGCGAATGTGTATATATAAAGGTTCGAGGTCCGTGCCTCCCTCAT
GCTCTCCCCATCTACTCATCAACTCAGATCCTCCAGGAGACTTGTACACC
```

ATCTTTTGAGGCACAGAAACCCAATAGTCAACCATCACAAGTTTGTACAA
AAAAGCAGGCTTCACCATGCAGACCTTCGGTGCTTTTCTCGTTTCCTTCC
TCGCCGCCAGGTAAGTTGGCCTTGATGAACCATATCATATATCGCCGAGA
AGTGGACCGCGTGCTGAGACTGAGACAGCGGCCTGGCCGCGGCCGAGGGA
CTTGGAAACCACGGCCGAAAGCTCGACCCCAACAAGTTCACCAAGGATAT
CAAGCTCAAGGACCTCCTCAAGGGCAGCCAGAAGCTCGAAGATTTCGCCT
ACGCCTACCCCGAGCGCAACCGCGTCTTTGGCGGCAAGGCCCACCAGGAC
ACCGTCAACTGGATCTACAACGAGCTGAAGAAGACCGGCTACTACGACGT
CTACAAGCAGCCCCAGGTCCACCTCTGGTCCAACGCCGAGCAGAGCCTCA
CCGTCGATGGCGAGGCCATCGACGCCACCACCATGACCTACAGCCCCAGC
CTCAAGGAAACCACCGCCGAGGTCGTCGTCGTCCCTGGCCTTGGCTGCAC
TGCCGCCGACTACCCTGCTGACGTCGCCGGCAAGATCGCCCTCATTCAGC
GCGGCAGCTGCACCTTCGGCGAGAAGTCCGTCTACGCCGCTGCCGCCAAC
GCCGCTGCTGCCATCGTCTACAACAACGTCGACGGCAGCCTCAGCGGCAC
CCTCGGCGCTGCTACTTCTGAGCTGGGCCCCTACGCCCCCATCGTCGGCA
TTTCTCGCCGACGGCCAGAACCTCGTCAGCCTCGCTCAGGCTGGCCCCC
CTGACCGTCGACCTCTACATCAACAGCCAGATGGAAAACCGCACCACCCA
CAACGTCATTGCCAAGAGCAAGGGCGGCGACCCTAACAACGTCATCGTCA
TCGGCGGCCACAGCGACGCCGTCAACCAGGGACCTGGCGTCAACGATGAC
GGCAGCGGCATCATCAGCAACCTCGTGATCGCCAAGGCCCTCACCAAGTA
CAGCCTCAAGAACAGCGTCACCTGGGCCTTTTGGACCGCCGAAGAGTTCG
GCCTCCTCGGCAGCGAGTTCTACGTCAACAGCCTCTCTGCCGCCGAGAAG
GACAAGATCAAGCTCTACCTCAACTTCGACATGATCGCCAGCCCCAACTA
CGCCCTCATGATCTACGACGGCGACGGCAGCACCTTCAACATGACCGGCC
CTGCCGGCTCCGCCGAGATCGAGCACCTCTTCGAGGACTACTACAAGTCT
CGCGGCCTCAGCTACATCCCCACCGCCTTTGACGGCCGCAGCGACTACGA
GGCCTTCATCCTCAACGGCATCCCCGCTGGCGGCCTCTTCACTGGCGCCG
AGCAGATCAAGACCGAGGAACAGGTCGCCATGTTCGGCGGCCAGGCTGGC
GTCGCCTACGACCCCAACTATACGCCGCTGGCGACAACATGACCAACCT
CAGCGAGGAAGCCTTCCTCATCAACAGCAAGGCCACCGCCTTCGCCGTCG
CCACCTACGCCAACAGCCTTGAGAGCATCCCCCTCGCAACGCCACCATG
AGCATCCAGACCCGCTCTGCCTCTCGCCGAGCCGCTGCTCATCGACGAGC
CGCCAAGCCTCACTCTCACTCTGGCGGCACTGGCTGCTGGCACACCCGAG
TCGAGCTGTAAGACCCAGCTTTCTTGTACAAAGTGGTGATCGCGCCAGCT
CCGTGCGAAAGCCTGACGCACCGGTAGATTCTTGGTGAGCCCGTATCATG
ACGGCGGCGGGAGCTACATGGCCCCGGGTGATTTATTTTTTTGTATCTA
CTTCTGACCCTTTTCAAATATACGGTCAACTCATCTTTCACTGGAGATGC
GGCCTGCTTGGTATTGCGATGTTGTCAGCTTGGCAAATTGTGGCTTTCGA
AAACACAAAACGATTCCTTAGTAGCCATGCATTTTAAGATAACGGAATAG
AAGAAAGAGGAAATTAAAAAAAAAAAAAAAAAACAAACATCCCGTTCATAAC

CCGTAGAATCGCCGCTCTTCGGCTAGCTAGTTACGCTTGTTTATTTACGA
CAAGATCTAGAAGATTCGAGATAGAATAATAATAATAACAACAATTTGCC
TCTTCTTTCCACCTTTTCAGTCTTACTCTCCCTTCTGACATTGAACGCCT
CAATCAGTCAGTCGCCTTGTACTTGGCACGGTAATCCTCCGTGTTCTTGA
TATCCTCAGGGGTAGCAAAGCCCTTCATGCCATCGATAATGTCATCCAGA
GTGAGGATGGCAAAGATGGGGATGCCGTACTCCTTCCTCAGCTCGCCAAT
GGCACTCGGTCCAGGCTTGGAGTCGTCGCCATCCGCAGCGGGGAGCTTCT
CCATGCGGTCCAGGGCCACGACGATGCCGGCGACGATGCCGCCCTCCTTG
GTGATCTTCTCAATGGCGTCCCTCTTGGCGGTGCCGGCGGTGATGACGTC
GTCGACAATCAGGACCCTCTTGCCCTTGAGCGAAGCGCCGACGATGTTGC
CGCCCTCGCCGTGGTCCTTGGCCTCCTTGCGGTCAAACGAGTAGGAGACG
CGGTCCAGGTTCTGGGGCGCCAGCTCGCCGAGCTTGATGGTGATGGCGGA
GCACAGCGGGATGCCCTTGTAGGCCGGGCCAAGACGATGTCGAACTCTA
GGCCGGCCTTCTCCTGGGCCTCGATGATGGTCTTTGCAAAGGCGGAGGCG
ATGGCGCCGGCGAGGCGCGCCGTGTGGAATTCGCCCGCGTTGAAGAAGTA
GGGGGATATCCGCTTGGACTTGAGCTCGAAGCTGCCAAACTTGAGGACGC
CGCCGTCGATGGCGGATTTGAGGAAGTCCTGCTTGTAGGCAGGCAGCTGG
GAGGTGGTAGCCATTCTGTTGGATTTGGATAGTGTCCTTATTCTCTGATT
TGAACAGTAGATCAGGACGAGTGAGAGGGATGCAGAGGTTGGATTGGAGT
GGTTGAGCTATAAAATTTAGAGGCGCGCCGTATCGAGTTTTCACATGGAA
GTCAAAGCGTACAGTGCGAGCTTGTACGTTGGTCTTAGTATCCCACAAGC
TTCTGTCTAGGTATGATGATGGCTATAAGTCACCCAAGGCAGAACTCATC
TTGAAGATTGTCTAGAGTGATTTTACCGCTGATGAAATGACTGGACTCCC
TCCTCCTGCTCTTATACGAAAAATTGCCTGACTCTGCAAAGGTTGTTTGT
CTTGGAAGATGATGTGCCCCCCCATCGCTCTTATCTCATACCCCGCCATC
TTTCTAGATTCTCATCTTCAACAAGAGGGGCAATCCATGATCTGCGATCC
AGATGTGCTTCTGGCCTCATACTCTGCCTTCAGGTTGATGTTCACTTAAT
TGGTGACGAATTCAGCTGATTTGCTGCAGTATGCTTTGTGTTGGTTCTTT
CCAGGCTTGTGCCAGCCATGAGCGCTTTGAGAGCATGTTGTCACCTATAA
ACTCGAGTAACGGCCACATATTGTTCACTACTTGAATCACATACCTAATT
TTGATAGAATTGACATGTTTAAAGAGCTGAGGTAGCTTTAATGCCTCTGA
AGTATTGTGACACAGCTTCTCACAGAGTGAGAATGAAAAGTTGGACTCCC
CCTAATGAAGTAAAAGTTTCGTCTCTGAACGGTGAAGAGCATAGATCCGG
CATCAACTACCTGGCTAGACTACGACGTCAATTCTGCGGCCTTTTGACCT
TTATATATGTCCATTAATGCAATAGATTCTTTTTTTTTTTTTTTTTTTT
TTTTTTTTTTTTTTTTTTGCCCAATTTCGCAGATCAAAGTGGACGTTA
TAGCATCATAACTAAGCTCAGTTGCTGAGGGAAGCCGTCTACTACCTTAG
CCCATCCATCCAGCTCCATACCTTGATACTTTAGACGTGAAGCAATTCAC
ACTGTACGTCTCGCAGCTCTCCTTCCCGCTCTTGCTTCCCCACTGGGGTC
CATGGTGCGTGTATCGTCCCCTCCTTAATTAAGGCCATTTAGGCCGTTGC
TGGCGTTTTTCCATAGGCTCCGCCCCCCTGACGAGCATCACAAAAATCGA

-continued

CGCTCAAGTCAGAGGTGGCGAAACCCGACAGGACTATAAAGATACCAGGC

GTTTCCCCCTGGAAGCTCCCTCGTGCGCTCTCCTGTTCCGACCCTGCCGC

TTACCGGATACCTGTCCGCCTTTCTCCCTTCGGGAAGCGTGGCGCTTTCT

CATAGCTCACGCTGTAGGTATCTCAGTTCGGTGTAGGTCGTTCGCTCCAA

GCTGGGCTGTGTGCACGAACCCCCCGTTCAGCCCGACCGCTGCGCCTTAT

CCGGTAACTATCGTCTTGAGTCCAACCCGGTAAGACACGACTTATCGCCA

CTGGCAGCAGCCACTGGTAACAGGATTAGCAGAGCGAGGTATGTAGGCGG

TGCTACAGAGTTCTTGAAGTGGTGGCCTAACTACGGCTACACTAGAAGGA

CAGTATTTGGTATCTGCGCTCTGCTGAAGCCAGTTACCTTCGGAAAAGA

GTTGGTAGCTCTTGATCCGGCAAACAAACCACCGCTGGTAGCGGTGGTTT

TTTTGTTTGCAAGCAGCAGATTACGCGCAGAAAAAAAGGATCTCAAGAAG

ATCCTTTGATCTTTTCTACGGGGTCTGACGCTCAGTGGAACGAAAACTCA

CGTTAAGGCCTGCAGGGCCGATTTTGGTCATGAGATTATCAAAAAGGATC

TTCACCTAGATCCTTTTAAATTAAAAATGAAGTTTTAAATCAATCTAAAG

TATATATGAGTAAACTTGGTCTGACAGTTACCAATGCTTAATCAGTGAGG

CACCTATCTCAGCGATCTGTCTATTTCGTTCATCCATAGTTGCCTGACTC

CCCGTCGTGTAGATAACTACGATACGGGAGGGCTTACCATCTGGCCCCAG

TGCTGCAATGATACCGCGAGACCCACGCTCACCGGCTCCAGATTTATCAG

CAATAAACCAGCCAGCCGGAAGGGCCGAGCGCAGAAGTGGTCCTGCAACT

TTATCCGCCTCCATCCAGTCTATTAATTGTTGCCGGGAAGCTAGAGTAAG

TAGTTCGCCAGTTAATAGTTTGCGCAACGTTGTTGCCATTGCTACAGGCA

TCGTGGTGTCACGCTCGTCGTTTGGTATGGCTTCATTCAGCTCCGGTTCC

CAACGATCAAGGCGAGTTACATGATCCCCCATGTTGTGCAAAAAAGCGGT

TAGCTCCTTCGGTCCTCCGATCGTTGTCAGAAGTAAGTTGGCCGCAGTGT

TATCACTCATGGTTATGGCAGCACTGCATAATTCTCTTACTGTCATGCCA

TCCGTAAGATGCTTTTCTGTGACTGGTGAGTACTCAACCAAGTCATTCTG

AGAATAGTGTATGCGGCGACCGAGTTGCTCTTGCCCGGCGTCAATACGGG

ATAATACCGCGCCACATAGCAGAACTTTAAAAGTGCTCATCATTGGAAAA

CGTTCTTCGGGGCGAAAACTCTCAAGGATCTTACCGCTGTTGAGATCCAG

TTCGATGTAACCCACTCGTGCACCCAACTGATCTTCAGCATCTTTTACTT

TCACCAGCGTTTCTGGGTGAGCAAAAACAGGAAGGCAAAATGCCGCAAAA

AAGGGAATAAGGGCGACACGGAAATGTTGAATACTCATACTCTTCCTTTT

TCAATATTATTGAAGCATTTATCAGGGTTATTGTCTCATGGCCATTTAGG

CCT

SEQ ID NO: 16=Nucleotide sequence of the pTrex8gM_TRI038 expression construct.

(Seq ID no 16)
CTAGAGTTGTGAAGTCGGTAATCCCGCTGTATAGTAATACGAGTCGCATC

TAAATACTCCGAAGCTGCTGCGAACCCGGAGAATCGAGATGTGCTGGAAA

GCTTCTAGCGAGCGGCTAAATTAGCATGAAAGGCTATGAGAAATTCTGGA

GACGGCTTGTTGAATCATGGCGTTCCATTCTTCGACAAGCAAAGCGTTCC

GTCGCAGTAGCAGGCACTCATTCCCGAAAAAACTCGGAGATTCCTAAGTA

GCGATGGAACCGGAATAATATAATAGGCAATACATTGAGTTGCCTCGACG

GTTGCAATGCAGGGGTACTGAGCTTGGACATAACTGTTCCGTACCCCACC

TCTTCTCAACCTTTGGCGTTTCCCTGATTCAGCGTACCCGTACAAGTCGT

AATCACTATTAACCCAGACTGACCGGACGTGTTTTGCCCTTCATTTGGAG

AAATAATGTCATTGCGATGTGTAATTTGCCTGCTTGACCGACTGGGGCTG

TTCGAAGCCCGAATGTAGGATTGTTATCCGAACTCTGCTCGTAGAGGCAT

GTTGTGAATCTGTGTCGGGCAGGACACGCCTCGAAGGTTCACGGCAAGGG

AAACCACCGATAGCAGTGTCTAGTAGCAACCTGTAAAGCCGCAATGCAGC

ATCACTGGAAAATACAAACCAATGGCTAAAAGTACATAAGTTAATGCCTA

AAGAAGTCATATACCAGCGGCTAATAATTGTACAATCAAGTGGCTAAACG

TACCGTAATTTGCCAACGGCTTGTGGGGTTGCAGAAGCAACGGCAAAGCC

CCACTTCCCCACGTTTGTTTCTTCACTCAGTCCAATCTCAGCTGGTGATC

CCCCAATTGGGTCGCTTGTTTGTTCCGGTGAAGTGAAAGAAGACAGAGGT

AAGAATGTCTGACTCGGAGCGTTTTGCATACAACCAAGGGCAGTGATGGA

AGACAGTGAAATGTTGACATTCAAGGAGTATTTAGCCAGGGATGCTTGAG

TGTATCGTGTAAGGAGGTTTGTCTGCCGATACGACGAATACTGTATAGTC

ACTTCTGATGAAGTGGTCCATATTGAAATGTAAGTCGGCACTGAACAGGC

AAAAGATTGAGTTGAAACTGCCTAAGATCTCGGGCCCTCGGGCCTTCGGC

CTTTGGGTGTACATGTTTGTGCTCCGGGCAAATGCAAAGTGTGGTAGGAT

CGAACACACTGCTGCCTTTACCAAGCAGCTGAGGGTATGTGATAGGCAAA

TGTTCAGGGGCCACTGCATGGTTTCGAATAGAAAGAGAAGCTTAGCCAAG

AACAATAGCCGATAAAGATAGCCTCATTAAACGGAATGAGCTAGTAGGCA

AAGTCAGCGAATGTGTATATATAAAGGTTCGAGGTCCGTGCCTCCCTCAT

GCTCTCCCCATCTACTCATCAACTCAGATCCTCCAGGAGACTTGTACACC

ATCTTTTGAGGCACAGAAACCCAATAGTCAACCATCACAAGTTTGTACAA

AAAAGCAGGCTTCACCATGCAGACCTTCGGTGCTTTTCTCGTTTCCTTCC

TCGCCGCCAGGTAAGTTGGCCTTGATGAACCATATCATATATCGCCGAGA

AGTGGACCGCGTGCTGAGACTGAGACAGCGGCCTGGCCGCGGCCGGCAAG

CACAAGCCTCTTGTCACCCCTGAGGCCCTCCAGGACCTGATTACCCTCGA

CGACCTCCTCGCCGGCAGCCAGCAGCTCCAGGACTTCGCCTACGCCTACC

CCGAGCGCAACCGCGTCTTTGCGGCCGAGCCCACGACGACACCGTCAAC

TGGCTCTACCGCGAGCTGAAGCGCACCGGCTACTACCACGTCTACAAGCA

GCCCCAGGTCCACCTCTACGACAACGCCGAGGAAAGCCTCACCGTCAACG

GCGAGGCCATCGAGGCCACCACCATGACCTACAGCCCCAGCGCCAACGCC

TCTGCCGAGCTGGCTGTCATCAGCGGCCTTGGCTGCTCTCCCGCCGACTT

CGCCTCTGACGTCGCCGGCAAGGTCGTCCTCGTCCAGCGAGGCAACTGCA

CCTTCGGCGAGAAGTCCGTCTACGCCGCTGCCGCCGATGCCGCCGCTACG

ATCGTCTACAACAACGTCGAGGGCAGCCTCAGCGGCACCCTCGGCGCTGC

TCAGTCTGAGCAAGGCCCCTACAGCGGCATCGTCGGCATCAGCCTCGCTG

```
ACGGCGAGGCCCTCCTCGCCCTTGCTGAGGAAGGCCCTGTCCACGTCGAC
CTCTGGATCGACAGCGTCATGGAAAACCGCACCACCTACAACGTCATTGC
CCAGACCAAGGGCGGCGACCCCGACAACGTCGTCACTCTTGGCGGCCACA
GCGACAGCGTCGAGGCTGGCCCTGGCATCAACGACGACGGCAGCGGCATC
ATCAGCAACCTCGTCATTGCCCGAGCCCTCACCAAGTTCAGCACCAAGCA
CGCCGTCCGCTTTTTCTTCTGGACCGCCGAAGAGTTCGGCCTCCTCGGCA
GCGACTACTACGTCAGCAGCCTCAGCCCCGCTGAGCTGGCCAAGATCCGC
CTCTACCTCAACTTCGACATGATCGCCAGCCCCAACTACGGCCTCCTCCT
CTACGATGGCGACGGCAGCGCCTTCAACCTCACTGGCCCTGCTGGCAGCG
ACGCCATCGAGAAGCTGTTCTACGACTACTTCCAGAGCATCGGCCAGGCC
ACCGTCGAGACTGAGTTCGACGGCCGCAGCGACTACGAGGCCTTCATCCT
CAACGGCATCCCCGCTGGCGGCGTCTTTACTGGCGCCGAGGAAATCAAGA
GCGAGGAAGAGGTCGCCCTCTGGGGCGGAGAGGCTGGCGTCGCCTACGAC
GCCAACTACCACCAGGTCGGCGACACCATCGACAACCTCAACACCGAGGC
CTACCTGCTCAACAGCAAGGCCACCGCCTTCGCCGTCGCCACCTACGCCA
ACGACCTCAGCACCATCCCCAAGCGCGAGATGACCACCGCCGTCAAGCGA
GCCAACGTCAACGGCCACATGCACCGCCGCACCATGCCCAAGAAGCGCCA
GACTGCCCACCGCCACGCTGCCAAGGGCTGCTTTCACAGCCGCGTCGAGC
AGTAAGACCCAGCTTTCTTGTACAAAGTGGTGATCGCGCCAGCTCCGTGC
GAAAGCCTGACGCACCGGTAGATTCTTGGTGAGCCCGTATCATGACGGCG
GCGGGAGCTACATGGCCCCGGGTGATTTATTTTTTTGTATCTACTTCTG
ACCCTTTTCAAATATACGGTCAACTCATCTTTCACTGGAGATGCGGCCTG
CTTGGTATTGCGATGTTGTCAGCTTGGCAAATTGTGGCTTTCGAAAACAC
AAAACGATTCCTTAGTAGCCATGCATTTTAAGATAACGGAATAGAAGAAA
GAGGAAATTAAAAAAAAAAAAAAAAACAAACATCCCGTTCATAACCCGTAG
AATCGCCGCTCTTCGGCTAGCTAGTTACGCTTGTTTATTTACGACAAGAT
CTAGAAGATTCGAGATAGAATAATAATAATAACAACAATTTGCCTCTTCT
TTCCACCTTTTCAGTCTTACTCTCCCTTCTGACATTGAACGCCTCAATCA
GTCAGTCGCCTTGTACTTGGCACGGTAATCCTCCGTGTTCTTGATATCCT
CAGGGGTAGCAAAGCCCTTCATGCCATCGATAATGTCATCCAGAGTGAGG
ATGGCAAAGATGGGGATGCCGTACTCCTTCCTCAGCTCGCCAATGGCACT
CGGTCCAGGCTTGGAGTCGTCGCCATCCGCAGCGGGGAGCTTCTCCATGC
GGTCCAGGGCCACGACGATGCCGGCGACGATGCCGCCCTCCTTGGTGATC
TTCTCAATGGCGTCCCTCTTGGCGGTGCCGGCGGTGATGACGTCGTCGAC
AATCAGGACCCTCTTGCCCTTGAGCGAAGCGCCGACGATGTTGCCGCCCT
CGCCGTGGTCCTTGGCCTCCTTGCGGTCAAACGAGTAGGAGACGCGGTCC
AGGTTCTGGGGCGCCAGCTCGCCGAGCTTGATGGTGATGGCGGAGCACAG
CGGGATGCCCTTGTAGGCCGGGCCGAAGACGATGTCGAACTCTAGGCCGG
CCTTCTCCTGGGCCTCGATGATGGTCTTTGCAAAGGCGGAGGCGATGGCG
CCGGCGAGGCGCGCCGTGTGGAATTCGCCCGCGTTGAAGAAGTAGGGGA
TATCCGCTTGGACTTGAGCTCGAAGCTGCCAAACTTGAGGACGCCGCCGT
CGATGGCGGATTTGAGGAAGTCCTGCTTGTAGGCAGGCAGCTGGGAGGTG
GTAGCCATTCTGTTGGATTTGGATAGTGTCCTTATTCTCTGATTTGAACA
GTAGATCAGGACGAGTGAGAGGGATGCAGAGGTTGGATTGGAGTGGTTGA
GCTATAAAATTTAGAGGCGCGCCGTATCGAGTTTTCACATGGAAGTCAAA
GCGTACAGTGCGAGCTTGTACGTTGGTCTTAGTATCCCACAAGCTTCTGT
CTAGGTATGATGATGGCTATAAGTCACCCAAGGCAGAACTCATCTTGAAG
ATTGTCTAGAGTGATTTTACCGCTGATGAAATGACTGGACTCCCTCCTCC
TGCTCTTATACGAAAAATTGCCTGACTCTGCAAAGGTTGTTTGTCTTGGA
AGATGATGTGCCCCCCATCGCTCTTATCTCATACCCCGCCATCTTTCTA
GATTCTCATCTTCAACAAGAGGGGCAATCCATGATCTGCGATCCAGATGT
GCTTCTGGCCTCATACTCTGCCTTCAGGTTGATGTTCACTTAATTGGTGA
CGAATTCAGCTGATTTGCTGCAGTATGCTTTGTGTTGGTTCTTTCCAGGC
TTGTGCCAGCCATGAGCGCTTTGAGAGCATGTTGTCACCTATAAACTCGA
GTAACGGCCACATATTGTTCACTACTTGAATCACATACCTAATTTTGATA
GAATTGACATGTTTAAAGAGCTGAGGTAGCTTTAATGCCTCTGAAGTATT
GTGACACGCTTCTCACAGAGTGAGAATGAAAAGTTGGACTCCCCCTAAT
GAAGTAAAAGTTTCGTCTCTGAACGGTGAAGAGCATAGATCCGGCATCAA
CTACCTGGCTAGACTACGACGTCAATTCTGCGGCCTTTTGACCTTTATAT
ATGTCCATTAATGCAATAGATTCTTTTTTTTTTTTTTTTTTTTTTTT
TTTTTTTTTTTTTGCCCAATTTCGCAGATCAAAGTGGACGTTATAGCAT
CATAACTAAGCTCAGTTGCTGAGGGAAGCCGTCTACTACCTTAGCCCATC
CATCCAGCTCCATACCTTGATACTTTAGACGTGAAGCAATTCACACTGTA
CGTCTCGCAGCTCTCCTTCCCGCTCTTGCTTCCCCACTGGGGTCCATGGT
GCGTGTATCGTCCCCTCCTTAATTAAGGCCCATTTAGGCCGTTGCTGGCGT
TTTTTCCATAGGCTCCGCCCCCCTGACGAGCATCACAAAAATCGACGCTCA
AGTCAGAGGTGGCGAAACCCGACAGGACTATAAAGATACCAGGCGTTTCC
CCCTGGAAGCTCCCTCGTGCGCTCTCCTGTTCCGACCCTGCCGCTTACCG
GATACCTGTCCGCCTTTCTCCCTTCGGGAAGCGTGGCGCTTTCTCATAGC
TCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTA
ACTATCGTCTTGAGTCCAACCCGGTAAGACACGACTTATCGCCACTGGCA
GCAGCCACTGGTAACAGGATTAGCAGAGCGAGGTATGTAGGCGGTGCTAC
AGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTT
TGATCTTTTCTACGGGGTCTGACGCTCAGTGGAACGAAAACTCACGTTAA
GGCCTGCAGGGCCGATTTTGGTCATGAGATTATCAAAAAGGATCTTCACC
TAGATCCTTTTAAATTAAAAATGAAGTTTTAAATCAATCTAAAGTATATA
TGAGTAAACTTGGTCTGACAGTTACCAATGCTTAATCAGTGAGGCACCTA
```

-continued

```
TCTCAGCGATCTGTCTATTTCGTTCATCCATAGTTGCCTGACTCCCCGTC
GTGTAGATAACTACGATACGGGAGGGCTTACCATCTGGCCCCAGTGCTGC
AATGATACCGCGAGACCCACGCTCACCGGCTCCAGATTTATCAGCAATAA
ACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTC
GCCAGTTAATAGTTTGCGCAACGTTGTTGCCATTGCTACAGGCATCGTGG
TGTCACGCTCGTCGTTTGGTATGGCTTCATTCAGCTCCGGTTCCCAACGA
TCAAGGCGAGTTACATGATCCCCATGTTGTGCAAAAAAGCGGTTAGCTC
CTTCGGTCCTCCGATCGTTGTCAGAAGTAAGTTGGCCGCAGTGTTATCAC
TCATGGTTATGGCAGCACTGCATAATTCTCTTACTGTCATGCCATCCGTA
AGATGCTTTCTGTGACTGGTGAGTACTCAACCAAGTCATTCTGAGAATA
GTGTATGCGGCGACCGAGTTGCTCTTGCCCGGCGTCAATACGGGATAATA
CCGCGCCACATAGCAGAACTTTAAAAGTGCTCATCATTGGAAAACGTTCT
TCGGGGCGAAAACTCTCAAGGATCTTACCGCTGTTGAGATCCAGTTCGAT
GTAACCCACTCGTGCACCCAACTGATCTTCAGCATCTTTTACTTTCACCA
GCGTTTCTGGGTGAGCAAAAACAGGAAGGCAAAATGCCGCAAAAAAGGGA
ATAAGGGCGACACGGAAATGTTGAATACTCATACTCTTCCTTTTTCAATA
TTATTGAAGCATTTATCAGGGTTATTGTCTCATGGCCATTTAGGCCT
```

Figure 2:
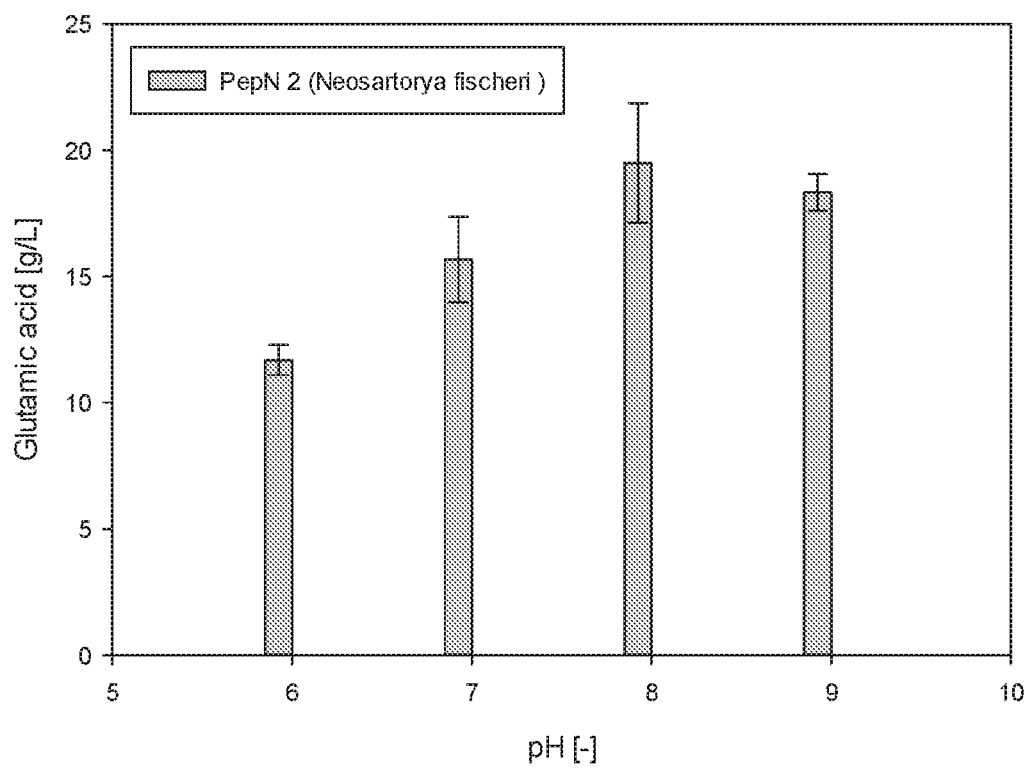
FIG. 2 shows pH dependent glutamic acid liberation of the PepN 2 from *Neosartorya fischeri* in gluten hydrolyses (no pH-control during hydrolyses).

Example 2—Operational pH- and Temperature Optimum of the PepN 2 from *Neosartorya fischeri* (TRI031) in Gluten Hydrolyses The liberation of glutamic acid is an important quality parameter in vegetable protein hydrolyses such as soy or gluten hydrolyses. The liberated glutamic acid can be perceived as the so-called "umami-flavor". In order to determine the effect of the initially applied pH in gluten hydrolyses in terms of glutamic acid and glutamine liberation, the initial pH of a gluten hydrolyses was adjusted just after the liquefaction of the gluten after 15-30 min with 1 M HCl. Gluten was treated with Glutaminase (Amano, Japan). In addition, gluten was treated with FoodPro Alkaline Protease, FoodPro PNL as well as PepN 2 (*Neosartorya fischeri*). After 20 hr, the hydrolysis was terminated employing ultrafiltration (10 kDa cut-off, Sartorius Stedium Biotech, Göttingen, Germany). The permeate was applied for the enzymatic glutamic acid analyses (enzymatic L-glutamic acid analysis kit, Roche, Mannheim, Germany). As shown in FIG. 2, the PepN 2 performed more efficient within the pH range of 7.0-9.0 compared to pH 6.0.

Figure 3:
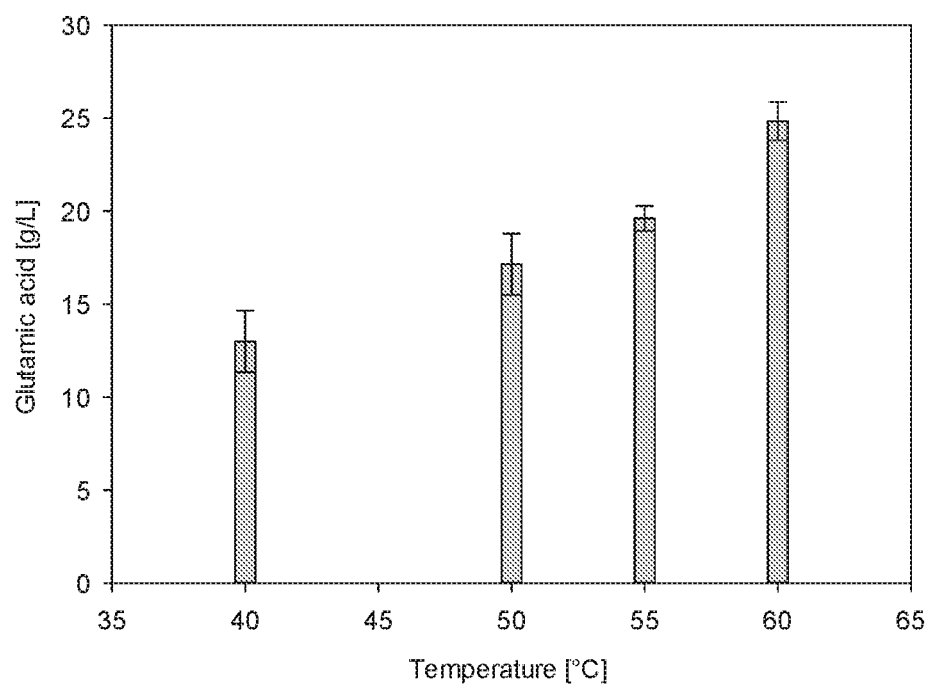
FIG. 3 shows Temperature dependent glutamic acid liberation of the PepN 2 from *Neosartorya fischeri* in gluten hydrolyses (no pH-control during hydrolyses).

In order to determine the effect of the applied temperature during the gluten hydrolyses in terms of glutamic acid and glutamine liberation, the initial pH was adjusted with 1 M HCl to pH 7.0 just after the liquefaction of the gluten suspension after 15-30 min. A temperature range from 40-60° C. was applied as shown in FIG. 3. Gluten was combined with Glutaminase (Amano, Japan). In addition, gluten was combined FOODPRO® Alkaline Protease, FOODPRO® PNL as well as PepN 2 (*Neosartorya fischeri*). After 20 h of hydrolysis, the hydrolysis was terminated employing ultrafiltration (10 kDa cut-off, Sartorius Stedium, Göttingen, Germany). The permeate was applied for the enzymatic glutamic acid analyses (enzymatic L-glutamic acid analysis kit, Roche, Mannheim, Germany). The PepN 2 from *Neosartorya fischeri* performed most efficient at 60° C.

Example 3—Comparison of the PepN 2 from *Neosartorya fischeri* (TRI031) and *Aspergillus clavatus* (TRI035) in Terms of Degree of Hydrolyses The degree of hydrolyses (DH) describes the relative amount of cleaved peptides bounds compared to an acid hydrolyses of the same amount of protein conducted e.g. in 6 M HCL at ~120° C. for ~24 h. The higher the DH can therefore be applied to assess the efficiency of amino acid liberation of a general PepN such as a PepN 1 or a PepN 2 type. The cell free culture broth was concentrated (10 kDa cut-off, Sartorius, Göttingen, Germany) and desalted applying a disposal desalting column (PD10, GE, Munchen, Germany) as described by the manufacturer. As substrates were pre-hydrolysed 10% (w/w) Na-caseinate (DMK, Germany), whey protein isolate (WPI; Arla, Viby, Denmark), soy protein isolate (SPI; SUPRO® 760, DuPont, Brabrand, Denmark) and gluten suspensions were applied. The pre-hydrolysis was conducted with 1% (w/w$_{protein}$) of FOODPRO® Alkaline Protease, 1% (w/w$_{protein}$) FOODPRO® PNL for the Na-Caseinate, the WPI as well as the SPI suspension. All pre-hydrolyses were conducted at 55° C. for 18 h followed by an inactivation step at 95° C. for 20 min. Each applied PepN 2 has been inactivated at 95 C for 15 min as a control of the elimination of any carryover of amino acids from the culture broth to the final hydrolyses as well as for the sufficient inactivation of the applied endopeptidases. The hydrolyses were conducted in a 96-well micro titer plate format and consisted of 150 µL of the pre-hydrolyzed protein suspension combined with 50 µL of a PepN 2 stock solution as indicated in Table 1 below. The hydrolyses were conducted at 50° C. for 20 hr, subsequently, the hydrolysis were stopped by the addition of 20 µL 2 M TCA (Trichloroacetic acid, Sigma-Aldrich, Schnelldorf, Germany). The efficiency of the amino acid liberation of the PepN 2 types from *Neosartorya fischeri* and *Aspergillus clavatus* can be seen in Table 1 (B) and (A). In particular, for the substrates, Na-caseinate, WPI, and SPI, significantly higher DHs were achieved upon the application of the PepN 2 types from *N. fischeri* and *A. clavatus*. In addition, the achieved DH at a PepN 2 stock solution concentration could be significantly increased. For the gluten hydrolyses, an increased DH was noticed in the protein range from 0.02-0.3 mg/mL PepN 2.

TABLE 1

Comparison of the degree of hydrolyses of the PepN 2 types from N. fischeri and A. clavatus.

| Substrate | water | inactivated enzyme at the highest conc. | 0.02 | 0.03 | 0.04 | 0.05 | 0.1 | 0.15 | 0.2 | 0.25 | 0.3 | 0.35 |
|---|---|---|---|---|---|---|---|---|---|---|---|---|
| | | | \multicolumn{10}{c}{Degree of hydrolysis [%]} | | | | | | | | | |
| \multicolumn{13}{c}{A PepN 2 from Neosartorya fischeri (mg/mL)} | | | | | | | | | | | | | |
| Casein | 7 | 8 | 14 | 15 | 16 | 20 | 19 | 21 | 23 | 22 | 24 | 24 |
| WPI | 7 | 8 | 17 | 19 | 19 | 21 | 23 | 28 | 24 | 26 | 27 | 29 |
| SPI | 5 | 6 | 11 | 13 | 14 | 15 | 17 | 18 | 19 | 19 | 19 | 22 |
| Gluten | 3 | 4 | 10 | 13 | 15 | 14 | 17 | 18 | 19 | 19 | 21 | 20 |
| \multicolumn{13}{c}{B PepN 2 from Aspergillus clavatus (mg/mL)} | | | | | | | | | | | | | |
| Casein | 8 | 8 | 16 | 19 | 19 | 20 | 21 | 23 | 24 | 24 | 24 | 27 |
| WPI | 7 | 8 | 19 | 20 | 21 | 22 | 23 | 27 | 25 | 28 | 29 | 29 |
| SPI | 6 | 6 | 11 | 12 | 13 | 14 | 16 | 15 | 17 | 21 | 21 | 21 |
| Gluten | 3 | 4 | 12 | 14 | 15 | 15 | 17 | 18 | 17 | 19 | 19 | 22 |

Example 4—Gluten Hydrolyses Applying Two Endopeptidases in Combination with the PepN 2 Candidates TRI032, TRI033, TRI034, TRI035, TRI037 and TRI038

Figure 4:
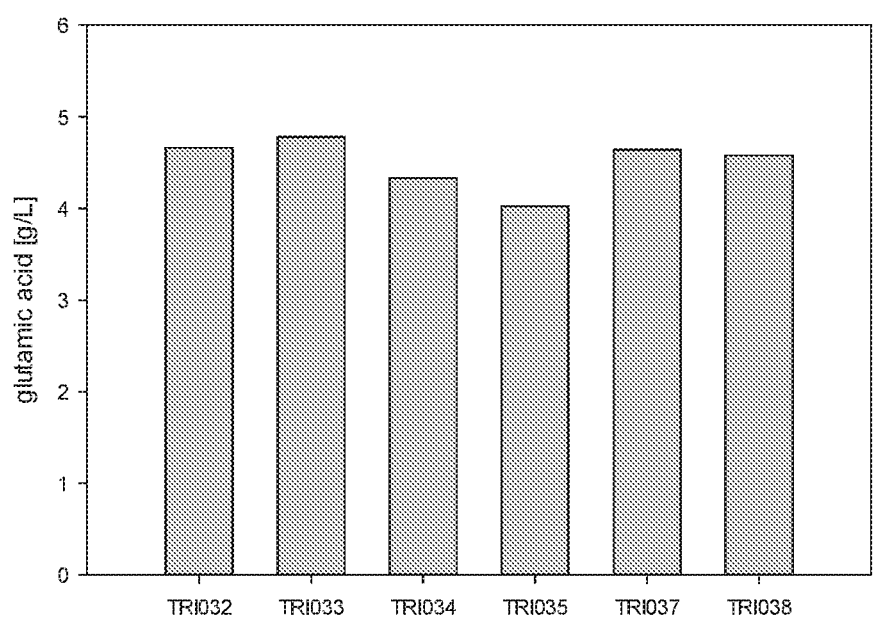
FIG. 4 shows glutamic acid liberation of different PepN 2.

A pre-hydrolysed gluten suspension was prepared by addition of FOODPRO® Alkaline Protease (FPAP) and FOODPRO® PNL (FPPNL). The hydrolysis was conducted at 55° C. After ~18 hr, the hydrolysis was terminated by heating to 90° C. for 10 min. After cooling to 50° C., glutaminase was applied to the gluten. Subsequently, 150 µL of the pre-hydrolyzed gluten was transferred to each well of a 96-well microtiter plate. The glutamic acid liberation was conducted applying 50 µL (protein concentration: 0.5 mg/mL) of TRI032, TRI033, TRI034, TRI035, TRI037, and TRI038. The hydrolysis was performed for 18 hr and terminated by addition of 20 µL 2 M TCA. The terminated hydrolyses were filtered (0.22 mm) and further analyzed with the enzymatic glutamic acid analyses kit (Roche, Mannheim, Germany). The liberated glutamic acid concentrations are shown in FIG. 4.

Example 5—Hydrolysis of Proline Containing Peptide

The peptide WHWLQLKPGQPMY (SEQ ID NO:26) was hydrolysed with TRI03 and TRI035. The peptide (1 mg/mL) was incubated with 1 ug/mL of the aminopeptidase in 20 mM CPB-Buffer (20 mM Citric acid, 20 mM Phosphate. 20 mM Boric acid) at 55° C. Aliquots (50 µL) were stopped with 50 rel 5% TFA at the indicated time points and subjected to LC-MS analysis.

Figure 5:
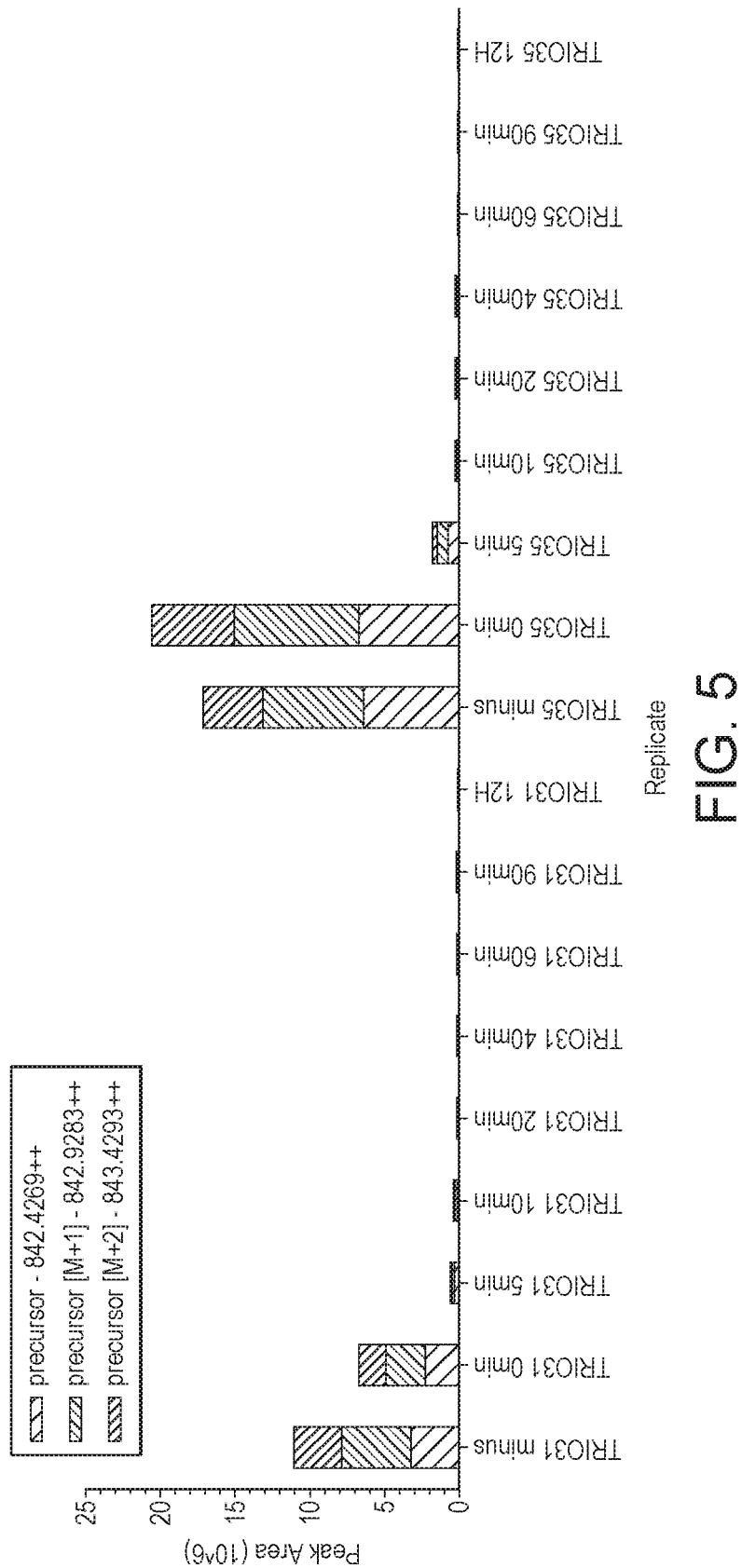
FIG. 5 shows hydrolysis of WHWLQLKPGQPMY (SEQ ID NO: 26)
Figure 6:
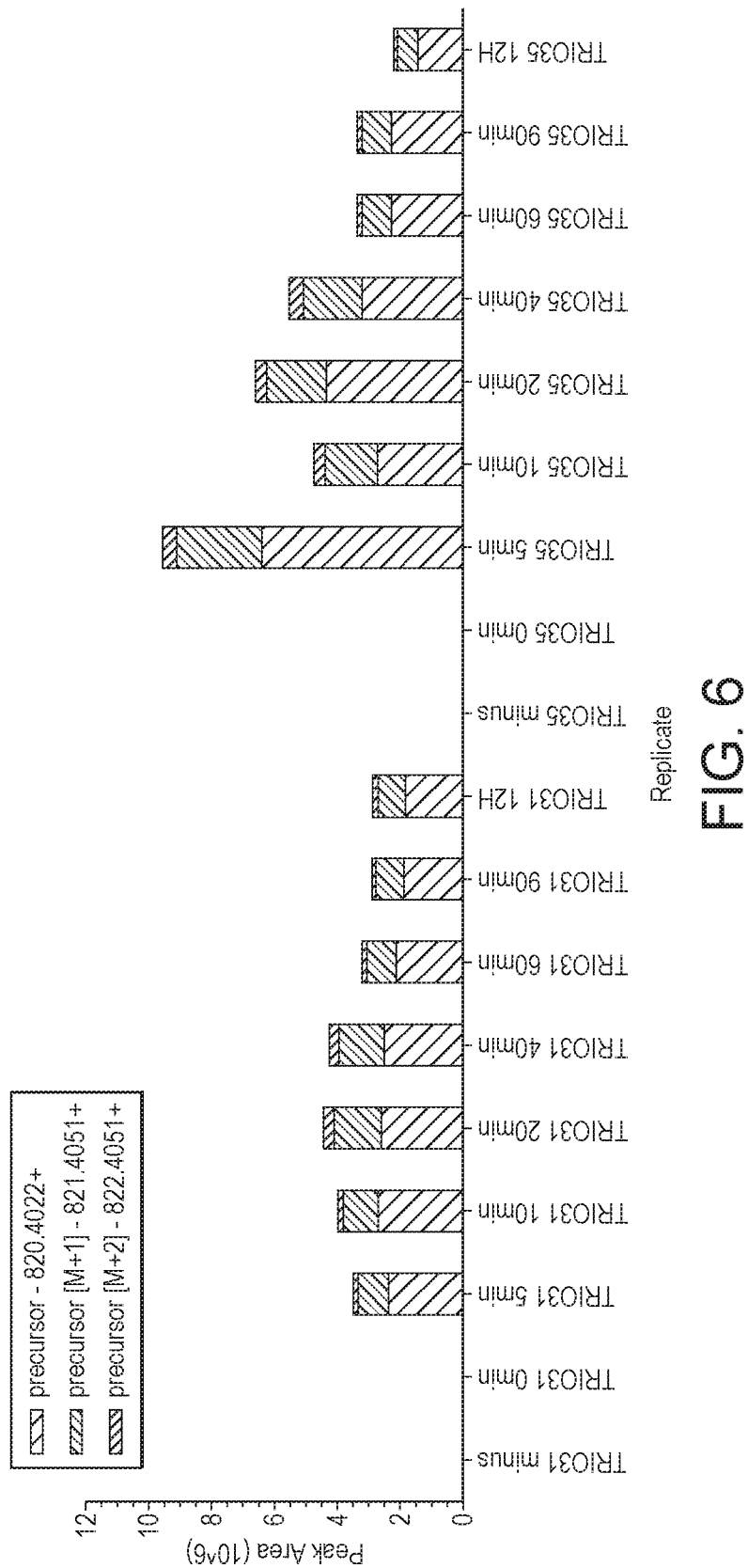
FIG. 6 shows hydrolysis of KPGQPMY. (SEQ ID NO: 27)
Figure 7:
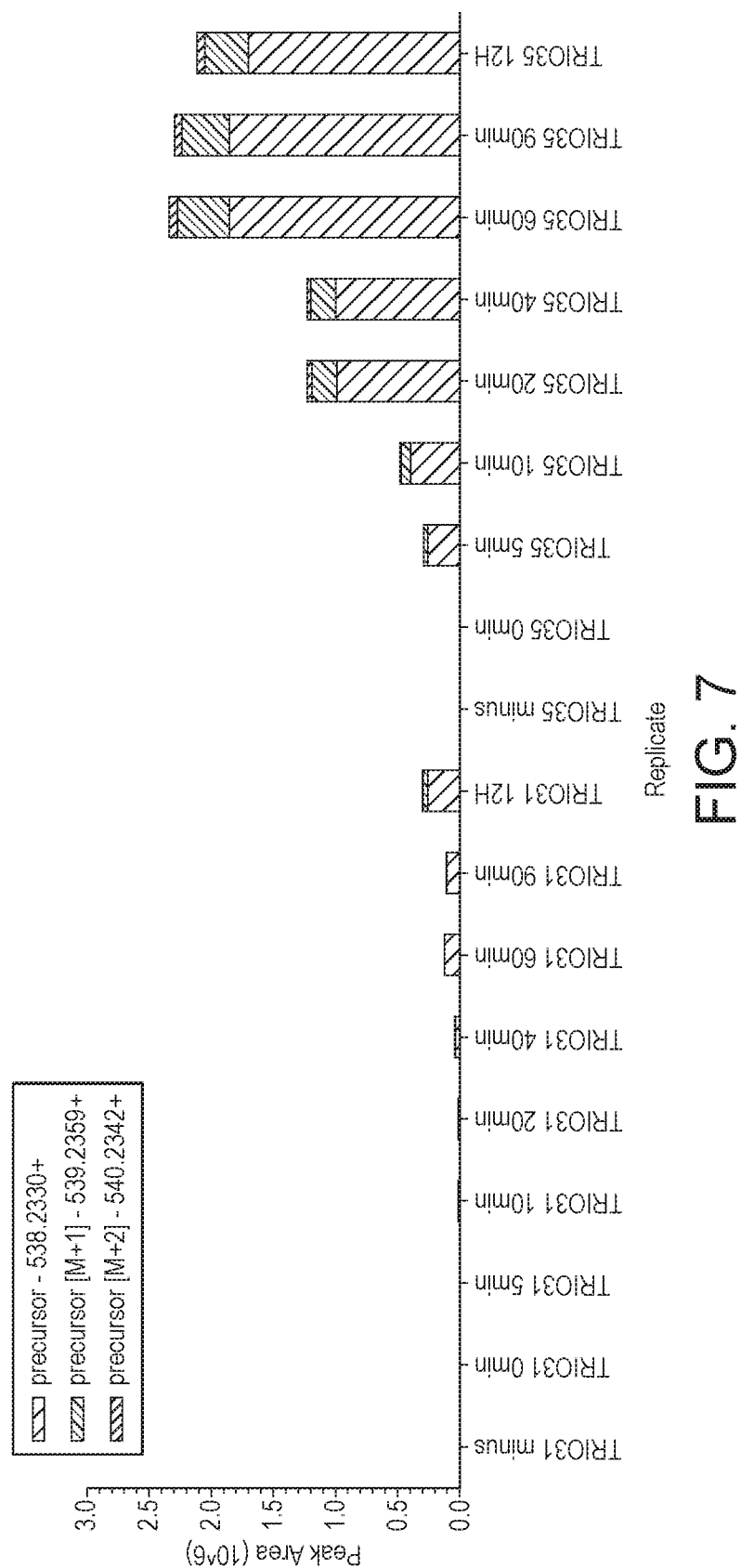
FIG. 7 shows hydrolysis of QPMY. (SEQ ID NO: 28)

The present results show that TRI031 and TRI035 can hydrolyze the peptide WHWLQLKPGQPMY (SEQ ID NO:26) (FIG. 5) to KPGQPMY (SEQ ID NO:27) (FIG. 6) and further down to QPMY (FIG. 7). That is in contrast to what has been described previously for Aspergillus oryzae PepN 2 (A. M. Blinkovsky et al., Biochimica et Biophysica Acta, 1480 (2000) 171-181, where it was claimed that the Aspergillus oryzae PepN 2 does not hydrolyze any of the X-Pro bonds examined including those of the peptide WHWLQLKPGQPMY (SEQ ID NO:26).) However, we also find that their enzyme cleaves the peptide down to QPMY (SEQ ID NO:28) (FIG. 7).

Data Acquisition:

Capillary LC-MS/MS analyses were performed using an Agilent 1100 LC system (Agilent Technologies) interfaced to a LTQ Orbitrap Classic hybrid mass spectrometer (Thermo Scientific, Bremen, Germany). Samples were loaded onto a 15 cm Phenomenix Jupiter 4µ Proteo 90A, C4 analytical column. Separation was performed at a flow rate of 16 µL/min using a 10 min gradient of 0-40% Solvent B $H_2O/CH_3CN/HCOOH$ (50/950/0.65 v/v/v) into the ION-MAX® ion source (Thermo Scientific, San Jose). The LTQ Orbitrap Classic instrument was operated in a data-dependent MS/MS mode. The peptide masses were measured by the Orbitrap (MS scans were obtained with a resolution of 60 000 at m/z 400), and up to 2 of the most intense peptide m/z were selected and subjected to fragmentation using CID in the linear ion trap (LTQ). Dynamic exclusion was enabled with a list size of 500 masses, duration of 40 s, and an exclusion mass width of ±10 ppm relative to masses on the list.

Figure 8:
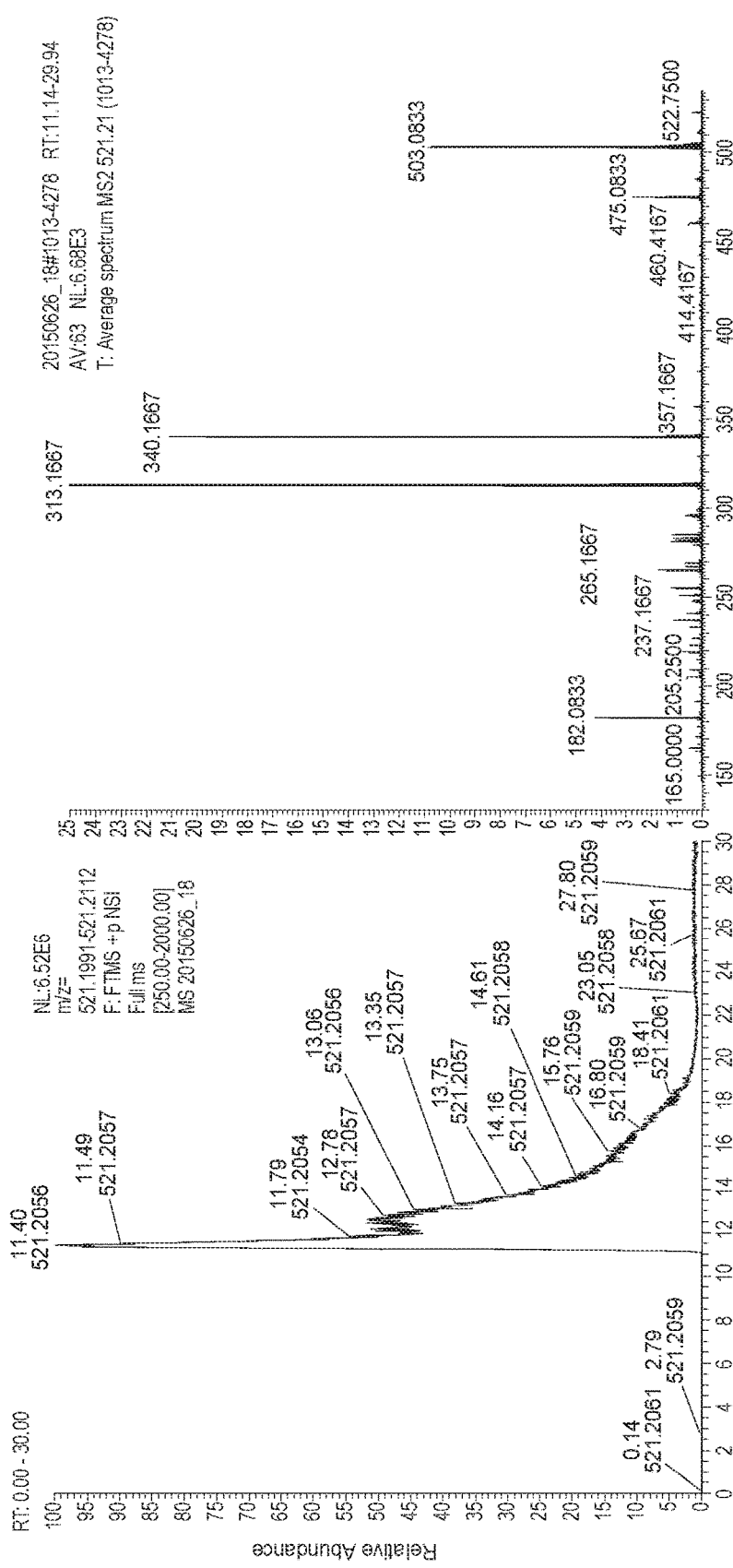
FIG. 8 shows peptide sequences of the substrate as well as cleavage products were typed into Skyline and intensities were calculated in each sample.

Label Free Quantification:

The RAW files were accessed with the program Skyline 2.6.0.7176 (MacLean, B., et al., "Skyline: an open source document editor for creating and analyzing targeted proteomics experiments", Bioinformatics, 2010, 26(7): p. 966-8) which uses the MS1 intensities to build chromatograms (Schilling, B., et al., "Platform-independent and label-free quantitation of proteomic data using MS1 extracted ion chromatograms in skyline: application to protein acetylation and phosphorylation", Mol Cell Proteomics, 2012. 11(5): p. 202-14). The precursor isotopic import filter was set to a count of three, (M, M+1, and M+2) at a resolution of 60,000 and the most intense charge state was used. Peptide sequences of the substrate as well as cleavage products were typed into Skyline and intensities were calculated in each sample. Figures were directly copied from the program (See FIG. 8).

Example 6: Comparison of the Degree of Hydrolyses of the PepN 2 from A. clavatus to the PepN from A. oryzae and L. helveticus ATCC 12046

Enzyme activities of PepN 1 Lactobacillus helveticus ATCC® 12046, PepN 1 Aspergillus oryzae and from PepN 2 from Aspergillus clavatus (TRI035) were determined according to Stressler, Eisele et al. (2013, infra). PepN 1 from L. helveticus was expressed and purified as described by Stressler, Eisele et al. (2013, infra).

PepN 1 from A. oryzae was purified from FLAVOURZYME® 500L (Sigma-Aldrich, Schnelldorf, Germany) after desalting on $PD_{10}$ columns equilibrated in 20 mM Bis-Tris, pH 6.5. The sample was purified by anion exchange chromatography, on a Source Q15, XK26/15 (SQ15) column (GE-Lifesciences, USA) and equilibrated with 20 mM Bis/Tris, pH 6.5 (buffer A). The sample (30 mL) was loaded to the column at a flow rate of 7 mL/min. the column was washed with buffer A and bound proteins were eluted with a linier gradient of 0-0.5 M NaCl in 20 mM Bis/Tris, pH 6.5 (50 min). During the entire run, fractions of approx. 13 mL were collected and kept on ice. Fractions with the highest aminopeptidase activity were combined, desalted on PD10 in 20 mM Bis-Tris, pH 6.0 and subjected to a second run on a Poros Q20 HR26/10, XK26/10 column (GE-Lifesciences, USA) equilibrated with 20 mM Bis/Tris, pH 6.0 (buffer A). The PepN1 sample was loaded to the column at a flow rate of 4 ml/min. the column was washed with buffer A and bound proteins were eluted with a linier gradient of 0-0.25 M NaCl in 20 mM Bis/Tris, pH 6.0 (30 min). During the entire run, fractions of approx. 8 mL were collected and kept on ice. The purified PepN 1 from *A. oryzae* was found to have a molecular weight of about 40 kDa according to SDS-PAGE electrophoresis.

The PepN 1 and 2 aminopeptidases were standardized to the activity range of 2.5-200 nkat*mL$^{-1}$. For protein hydrolyses, 1% (w/w$_{WPI}$) FOODPRO® Alkaline Protease (DuPont, Brabrand, Denmark) and 1% (w/w$_{WPI}$) FOODPRO® PNL (DuPont, Brabrand, Denmark) were added to the whey protein isolate suspension (WPI; LACPRODAN® 9224, Arla Ingredients, Viby, Denmark) with an initial pH of 7.0. Following the endopeptidases addition, the WPI was mixed and 200 µL were transferred to each well of a 96-well microtiter plate. Subsequently, 5 µL of PepN solution were added as indicated in the Table 2. The hydrolysis was conducted at 50° C. without pH control and terminated after 18 hr by addition of 20 µL of 2 M TCA. Prior to the determination of the DH (Nielsen, Petersen et al., 2001, infra), all samples were filtered 0.22 µm.

It was found that PepN 2 from *A. clavatus* achieved high DH than PepN 1 from *A. oryzae* at all dosages and higher DH than PepN 1 from *L. helveticus* at the four highest activity dosages tested. And at the two highest dosages PepN 2 from *A. clavatus* produced at least 25% higher DH than the PepN 1 aminopeptidases.

TABLE 2

Comparison of the degree of hydrolyses of the PepN 2 from
*A. clavatus* to the PepN 1 from *L. helveticus* and *A. oryzae*

PepN dosage [nkat/mL] in stock solution

| 0 | 2.5 | 5 | 10 | 25 | 50 | 75 | 100 | 200 | |
|---|-----|---|----|----|----|----|-----|-----|---|
| Degree of hydrolysis [%] | | | | | | | | | |
| 14 | 14 | 15 | 16 | 16 | 18 | 16 | 21 | 19 | PepN 1: *A. oryzae* |
| 13 | 18 | 18 | 20 | 23 | 23 | 24 | 28 | 27 | PepN 1: *L. helveticus* |
| 14 | 15 | 17 | 17 | 20 | 24 | 26 | 35 | 36 | PepN 2: *A. clavatus* |

Example 7: Influence of Sodium Chloride Concentration on Glutamic Acid Liberation in Soy and Gluten Hydrolyses Sodium chloride is frequently applied in the food industry to reduce the microbial contamination risk in protein hydrolyses. Pre-hydrolysed 10% (w/w) soy (SUPRO® 760, DuPont, Brabrand, Denmark) and gluten (Sigma-Aldrich, Schnelldorf, Germany) was prepared by addition of 1% (w/w$_{protein}$) FOODPRO® Alkaline Protease (DuPont, Brabrand, Denmark) and 1% (w/w$_{protein}$) FOODPRO® PNL (DuPont, Brabrand, Denmark). The hydrolyses were performed at 50° C. at pH 7.0 (without pH control) for 18 hr (heat inactivation after 18 hr; 90° C.; 10 min). Subsequently, the hydrolyses were divided in sodium chloride containing (185 mM) and non-salt containing hydrolyses. 150 µL of each pre-hydrolysed protein suspension was combined with differently standardized *Aspergillus clavatus* PepN 2 as indicated in Table 3. The hydrolyses were conducted at 50° C. without pH control and terminated after 18 hr by addition of 20 µL of 2 M TCA. Prior to the determination of the DH (Nielsen, Petersen et al. 2001, infra), all samples were filtered 0.22 µm. As shown in Table 3, the addition of 185 mM NaCl had no influence on the determined degree of hydrolysis in soy and gluten hydrolyses.

TABLE 3

Influence of 185 mM NaCl on the degree of hydrolyses in soy and gluten hydrolyses
Protein

| | SOY | | | | Gluten | | | | | |
|---|---|---|---|---|---|---|---|---|---|---|
| | Protein concentration [mg/mL] | | | | | | | | | |
| water | 0.2 | 0.3 | 0.4 | 0.5 | 0.1 | 0.2 | 0.25 | 0.3 | 0.4 | 0.5 |
| | Degree of hydrolysis | | | | | | | | | |
| 1 | 1 | 11 | 12 | 12 | 12 | 14 | 16 | 17 | 16 | 17 | 18 | reference |
| 1 | 1 | 10 | 11 | 11 | 12 | 14 | 15 | 15 | 16 | 17 | 18 | 185 mM NaCl |

Nielsen, P. M., et al. (2001), *Journal of Food Science* 66(5): 642-646.

Stressler, T., et al. (2013), *PLoS ONE* 8(7).

Example 8: Product Inhibition of PepN2 TRI031 and TRI035 vs. TRI063 (*A. oryzae*)

In this assay enzyme activity is determined by hydrolysis of the substrate H-Ala-nitroanilide (pNA). The absorbance of released pNA is determined over time at a wavelength of 405 nm using a microtiter plate reader.

As materials buffer 20 mM CPB buffer (20 mM of Na-citrate, Na-phosphate and Na-borate) pH 9.0 was used. Enzyme samples of PepN 2 TRI031 and TRI035 were used. 20 mg H-Ala-pNA substrate (BACHEM, L-1070) was solubilized in 1 mL DMSO (Dimethyl Sulphoxide; Sigma cat # D2650). 96 well plates Costar assay plate 9017 (Corning Inc) were applied and read in a VERSAMAX® reader from Molecular Devices. For the inhibition studies 10 mL of a 20 mg/mL solution were made of each of the amino acids: lysine, histidine, leucine, tryptophan, proline, glycine, serine, asparagine, threonine, aspartic acid, glutamic acid. Tryptophan and proline were dissolved in DMSO. All other amino acids were dissolved in buffer. The final inhibitor mix was made by combining 500 µL of each amino acid solution.

A 96 well plate was placed on ice and 180 µL buffer, 15 µL diluted enzyme and 20 µL inhibitor mix were added to wells in the plate and mixed. Each plate contained all four enzymes at inhibitor mix concentrations of 0.017, 0.085, 0.128, 0.170, 0.426, 0.851, 1.702, 2.553 mg/mL. The reaction was started by adding 20 µL substrate. Only one substrate concentration was used per plate. After initiating the reaction, the plate was, as quickly as possible, placed in the microplate reader, set to 30° C., and absorbance at 405 nm was measured with 30 sec intervals for 30 min. Six plates were run with one substrate concentrations on each plate (either 0.017, 0.170, 0.426, 0.851, 1.702, 2.553 mg/mL). For determination of the apparent inhibition constant (Ki), data was exported to GraphPad Prism, which fitted Michaelis-Menten curves for each inhibitor concentration and based on this calculated Ki in mg/ml. The unit was converted to mM by using an average inhibitor molecular weight of 133.9 g/mol. Apparent Ki values for product inhibition and respective standard deviations (SD) for the different enzymes are listed in Table 4.

TABLE 4

|  | Ki (mM) | SD |
| --- | --- | --- |
| TRI031 | 5.67 | 0.85 |
| TRI035 | 3.06 | 0.59 |
| TRI063 (*A. oryzae*) | 1.20 | 0.36 |

From Table 4 it is seen that PepN 2 TRI031 and TRI035 have the highest apparent Ki values for product inhibition, meaning that they are less inhibited by product compared to TRI063 from *A. oryzae*.

Example 9: PepN2 and PepN1 Activity on Glu-pNA and Gln-pNA Substrates

H-Glu-Nitroanilid (pNA) and H-Gln-Nitroanilid (pNA) were used as substrates and the release of p-Nitroanilid (pNA) was measured by absorbance at 405 nm. As buffer 20 mM CPB-Buffer (20 mM Citric acid, 20 mM Na-phosphate, 20 mM Boric acid) pH 9.0 was used. 10 mg H-Glu-pNA and H-Gln-pNA (from BACHEM or Schafer N; Copenhagen, Denmark) were dissolved in 1 ml of DMSO (Dimethyl Sulphoxide from SIGMA; cat # D2650).

For running the assay 80 µL buffer, 10 µL H-Glu-pNA or H-Gln-pNA substrate and 10 uL appropriately diluted PepN 2 was incubated in Costar assay plate 9017 (Corning Inc.) at 45° C. and measured at 405 nm every 30 sec for 30 min in a VERSAMAX® microplate reader (Molecular Devices) running with SoftMaxPro 5.4.1 software. Activity was determined as the maximal slope of the linear part of the curve determined over 10 time points.

The assay was run for purified samples of PepN 2 TRI031 and TRI035 as well as purified PepN 1 *L. helveticus* (Stressler, Eisele et al., supra) and non-purified PepN 1 *A. sojae* (COROLASE® LAP, AB Enzymes) which all had comparable activity on Ala-pNA or Leu-pNA (run as described for Ala-pNA in Example H, but without inhibitor). As shown in Table 5 the two PepN 2 aminopeptidases showed activity on Glu- and Gln-pNA in contrast to the two PepN 1 enzymes that showed no significant activity. This indicates that PepN 2 aminopeptidases are much more effective in Glu and Gln release than PepN 1 aminopeptidases.

TABLE 5

Activity of PepN 2 and PepN 1 on Glu-pNA and Gln-pNA substrates

|  | Vmax (mU/min) | |
| --- | --- | --- |
|  | Glu-pNA | Gln-pNA |
| PepN 2 TRI031 | 50.8 | 75.9 |
| PepN 2 TRI035 | 20.1 | 98.7 |
| PepN 1 *L. helveticus* | 0.02 | 0 |
| PepN 1 Corolase LAP | 0 | 0 |

Example 10—Hydrolysis of Peptide with Proline in Position 2

The peptide library XPAAAR (X being all amino acids except cysteine) (SEQ ID NO:133) was hydrolysed with enzyme samples of TRI032, TRI035, TRI063 (*A. oryzae*) as well as COROLASE® LAP. The peptide library XPAAAR (1 mg/mL) (SEQ ID NO:133) was incubated with 1 ug/mL of the aminopeptidase in 3×20 mM CPB-Buffer (20 mM Citric acid, 20 mM Phosphate, 20 mM Boric acid) at 55° C. 50 µL aliquots were stopped with 50 ul 5% TFA at the indicated time points and subjected to LC-MS analysis.

Data Acquisition:

Capillary LC-MS/MS analyses were performed using an Agilent 1100 LC system (Agilent Technologies) interfaced to a LTQ Orbitrap Classic hybrid mass spectrometer (Thermo Scientific, Bremen, Germany). Samples were loaded onto a 15 cm Phenomenex Jupiter 4µ Proteo 90A, C4 analytical column. Separation was performed at a flow rate of 16 µL/min using a 10 min gradient of 0-40% Solvent B $H_2O/CH_3CN/HCOOH$ (50/950/0.65 v/v/v) into the ION-MAX® ion source (Thermo Scientific, San Jose). The LTQ Orbitrap Classic instrument was operated in a data-dependent MS/MS mode. The peptide masses were measured by the Orbitrap (MS scans were obtained with a resolution of 60 000 at m/z 400), and up to 2 of the most intense peptide m/z were selected and subjected to fragmentation using CID in the linear ion trap (LTQ). Dynamic exclusion was enabled with a list size of 500 masses, duration of 40 s, and an exclusion mass width of ±10 ppm relative to masses on the list.

Figure 10:
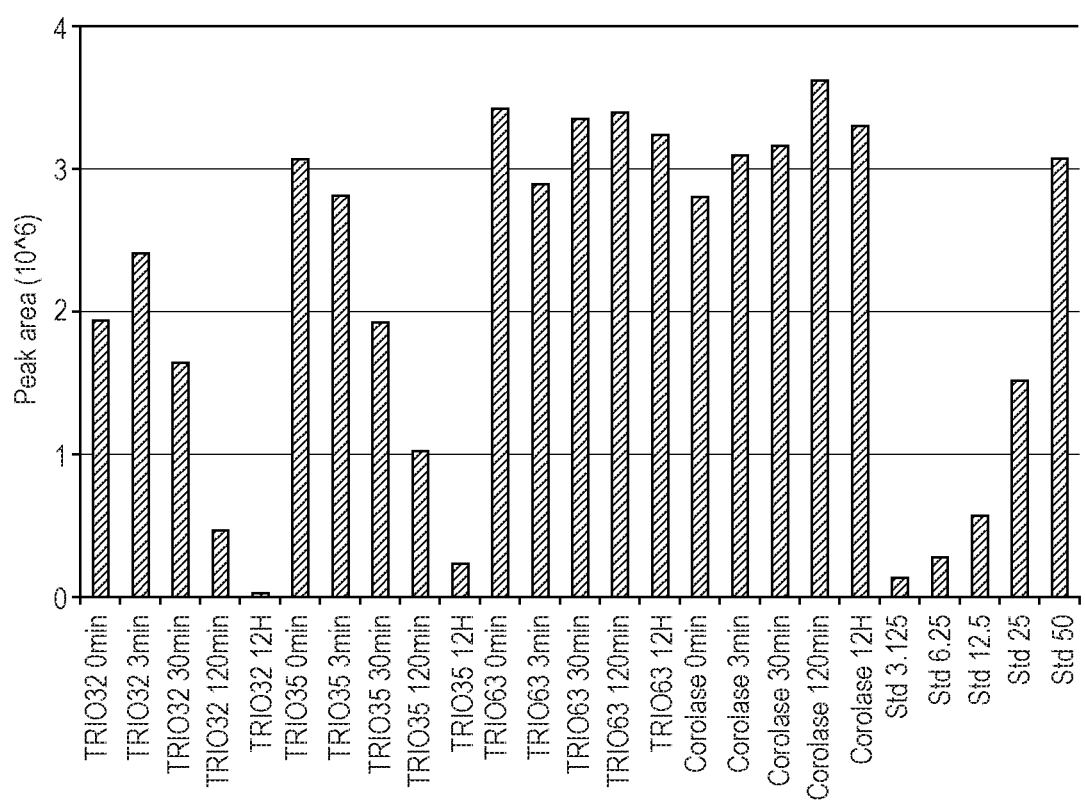
FIG. 10 Hydrolysis of TPAAAR (SEQ ID NO: 29) by TRI032, TRI035, TRI063 (*A. oryzae*) as well as COROLASE® LAP (fungal exo-peptidase.

Label free quantification: The RAW files were accessed with the program Skyline 2.6.0.7176 (MacLean, B., et al., supra) which uses the MS1 intensities to build chromatograms (Schilling, B., et al., supra). The precursor isotopic import filter was set to a count of three, (M, M+1, and M+2) at a resolution of 60,000 and the most intense charge state was used. Peptide sequences of the substrate as well as cleavage products were typed into Skyline and intensities were calculated in each sample. FIG. 10 was generated on the basis the sum of the peak areas of the three isotopes (M, M+1, and M+2). A substrate standard curve (with serial 2 fold increases in concentration from Std 3.125 to Std 50) was included and shows a linear relationship between substrate concentration and peak area.

LC-MS results (FIG. 10) show that TRI032 and TRI035 can hydrolyze the peptide TPAAAR over time to less than half the concentration within 2 hr incubation, whereas TRI063 (*A. oryzae*) and COROLASE® LAP show no hydrolysis of TPAAAR (SEQ ID NO:29 within 12 hr.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The invention claimed is:

1. A method for the production of a protein hydrolysate comprising subjecting a proteinaceous substrate, wherein the substrate is selected from the group consisting of casein, whey protein isolate, soy protein isolate and gluten, to a purified polypeptide having aminopeptidase activity, selected from the group consisting of:
   (a) a polypeptide having an amino acid sequence comprising the amino acid sequence of SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 8; and
   (b) a fragment of (a), wherein the fragment has aminopeptidase activity.

2. The method of claim 1, further comprising subjecting said proteinaceous substrate to an endopeptidase.

3. The method of claim 2, wherein the hydrolysate is enriched in Leu, Gly, Glu, Ser, Asp, Asn, Pro, Cys, Ala, and/or Gln.

4. The method of claim 2, wherein the hydrolysate is enriched in Glu and/or Gln.

5. A method for obtaining from a proteinaceous substrate a protein hydrolysate enriched in free glutamic acid and/or peptide bound glutamic acid residues, comprising subjecting the substrate to a deamidation process and a purified polypeptide having aminopeptidase activity, selected from the group consisting of:
   (a) a polypeptide having an amino acid sequence comprising the amino acid sequence of SEQ ID NO: 1, or SEQ ID NO: 2, or SEQ ID NO: 3, or SEQ ID NO: 4, or SEQ ID NO: 5, or SEQ ID NO: 6, or SEQ ID NO: 7, or SEQ ID NO: 8; and
   (b) a fragment of (a), wherein the fragment has aminopeptidase activity.

6. The method of claim 5, further comprising subjecting the substrate to one or more unspecific acting endo- and/or exo-peptidase enzymes.

* * * * *

UNITED STATES PATENT AND TRADEMARK OFFICE
CERTIFICATE OF CORRECTION

| | |
|---|---|
| PATENT NO. | : 11,473,073 B2 |
| APPLICATION NO. | : 15/574323 |
| DATED | : October 18, 2022 |
| INVENTOR(S) | : Karsten Matthias Kragh et al. |

It is certified that error appears in the above-identified patent and that said Letters Patent is hereby corrected as shown below:

On the Title Page

Item (72) Inventors: --Svend Haaning, Stjaer (DK)-- should be inserted.

Signed and Sealed this
Second Day of May, 2023

Katherine Kelly Vidal
*Director of the United States Patent and Trademark Office*